US008372398B2

(12) United States Patent
 Silence

(10) Patent No.: US 8,372,398 B2
(45) Date of Patent: *Feb. 12, 2013

(54) SINGLE DOMAIN VHH ANTIBODIES AGAINST VON WILLEBRAND FACTOR

(75) Inventor: Karen Silence, Overijse (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/822,729

(22) Filed: Jun. 24, 2010

(65) Prior Publication Data

US 2010/0330084 A1    Dec. 30, 2010

Related U.S. Application Data

(63) Continuation of application No. 11/920,793, filed as application No. PCT/EP2006/004773 on May 19, 2006, now Pat. No. 7,807,162.

(60) Provisional application No. 60/683,474, filed on May 20, 2005.

(51) Int. Cl.
 *A61K 39/395* (2006.01)

(52) U.S. Cl. ............... 424/133.1; 424/134.1; 424/145.1; 424/185.1; 514/13.5; 514/13.7; 514/14.9; 530/387.3; 530/388.25

(58) Field of Classification Search .......... None
 See application file for complete search history.

(56) References Cited

U.S. PATENT DOCUMENTS

| | | | |
|---|---|---|---|
| 5,238,919 | A | 8/1993 | Zimmerman et al. |
| 5,670,132 | A | 9/1997 | Griffiths et al. |
| 5,916,805 | A | 6/1999 | Nagano et al. |
| 5,976,532 | A | 11/1999 | Coller et al. |
| 6,228,360 | B1 | 5/2001 | Co et al. |
| 6,251,393 | B1 | 6/2001 | Handin et al. |
| 6,280,731 | B1 | 8/2001 | Nagano et al. |
| 6,419,934 | B1 | 7/2002 | Tobinick |
| 6,517,829 | B1 | 2/2003 | Frenken et al. |
| 6,759,518 | B1 | 7/2004 | Kontermann et al. |
| 6,793,920 | B2 | 9/2004 | Nagano et al. |
| 7,311,913 | B2 | 12/2007 | Co et al. |
| 7,771,724 | B2 | 8/2010 | Huizinga et al. |
| 7,807,162 | B2 * | 10/2010 | Silence ........ 424/133.1 |
| 7,939,277 | B2 | 5/2011 | De Groot et al. |
| 2001/0024647 | A1 | 9/2001 | Handin et al. |
| 2002/0028204 | A1 | 3/2002 | Nagano et al. |
| 2002/0058033 | A1 | 5/2002 | Raisch et al. |
| 2003/0092892 | A1 | 5/2003 | Frenken et al. |
| 2005/0054001 | A1 * | 3/2005 | Muyldermans ........ 435/7.1 |
| 2005/0136056 | A1 | 6/2005 | Kageyama et al. |
| 2005/0192224 | A1 | 9/2005 | Huizinga et al. |
| 2006/0149041 | A1 | 7/2006 | Silence |
| 2006/0183702 | A1 | 8/2006 | Diener et al. |
| 2006/0286066 | A1 | 12/2006 | Basran |
| 2008/0096223 | A1 | 4/2008 | De Groot et al. |
| 2010/0022452 | A1 | 1/2010 | Silence |
| 2011/0158996 | A1 | 6/2011 | Holz et al. |

FOREIGN PATENT DOCUMENTS

| | | |
|---|---|---|
| EP | 0295645 A2 | 12/1988 |
| EP | 0368684 A1 | 5/1990 |
| EP | 0795608 A1 | 9/1997 |
| EP | 0952218 | 10/1999 |
| EP | 1002861 A1 | 5/2000 |
| EP | 03447005.4 | 1/2003 |
| WO | WO-90/10707 A1 | 9/1990 |
| WO | WO-93/11161 A1 | 6/1993 |
| WO | WO-94/04678 A1 | 3/1994 |
| WO | WO-94/13806 A1 | 6/1994 |
| WO | WO-94/25591 A1 | 11/1994 |
| WO | WO-96/17078 A1 | 6/1996 |
| WO | WO-97/38102 A1 | 10/1997 |
| WO | WO-99/09055 A2 | 2/1999 |
| WO | WO-99/23221 A2 | 5/1999 |
| WO | WO-00/24781 A1 | 5/2000 |
| WO | WO-01/02853 A2 | 1/2001 |
| WO | WO-02/051351 A2 | 7/2002 |
| WO | WO-02/057445 A1 | 7/2002 |
| WO | WO 03/035694 A2 | 5/2003 |
| WO | PCT/EP03/06581 | 6/2003 |
| WO | PCT/EP03/07313 | 7/2003 |
| WO | PCT/BE03/00191 | 12/2003 |
| WO | PCT/BE03/00206 | 12/2003 |
| WO | WO-2004/003019 A2 | 1/2004 |
| WO | WO-2004/015425 A1 | 2/2004 |
| WO | WO-2004/041862 A2 | 5/2004 |
| WO | WO-2004/041863 A2 | 5/2004 |
| WO | WO-2004/041865 A2 | 5/2004 |
| WO | WO-2004/041867 A2 | 5/2004 |
| WO | WO-2004/062551 A2 | 7/2004 |
| WO | WO-2005/044858 A1 | 5/2005 |
| WO | WO-2006/074947 A2 | 7/2006 |

(Continued)

OTHER PUBLICATIONS

Ewert et al., Biophysical properties of camelid V(HH) domains compared to those of human V(H)3 domains. Biochemistry. Mar. 19, 2002;41(11):3628-36.

(Continued)

*Primary Examiner* — Michael Szperka

(74) *Attorney, Agent, or Firm* — Wolf, Greenfield & Sacks, P.C.

(57) ABSTRACT

The present invention relates to improved Nanobodies™ against von Willebrand Factor (vWF), as well as to polypeptides comprising or essentially consisting of one or more of such Nanobodies. The invention also relates to nucleic acids encoding such Nanobodies and polypeptides; to methods for preparing such Nanobodies and polypeptides; to host cells expressing or capable of expressing such Nanobodies or polypeptides; to compositions comprising such Nanobodies, polypeptides, nucleic acids or host cells; and to uses of such Nanobodies, such polypeptides, such nucleic acids, such host cells or such compositions, in particular for prophylactic, therapeutic or diagnostic purposes, such as the prophylactic, therapeutic or diagnostic purposes.

12 Claims, 41 Drawing Sheets

FOREIGN PATENT DOCUMENTS

Figure 4:
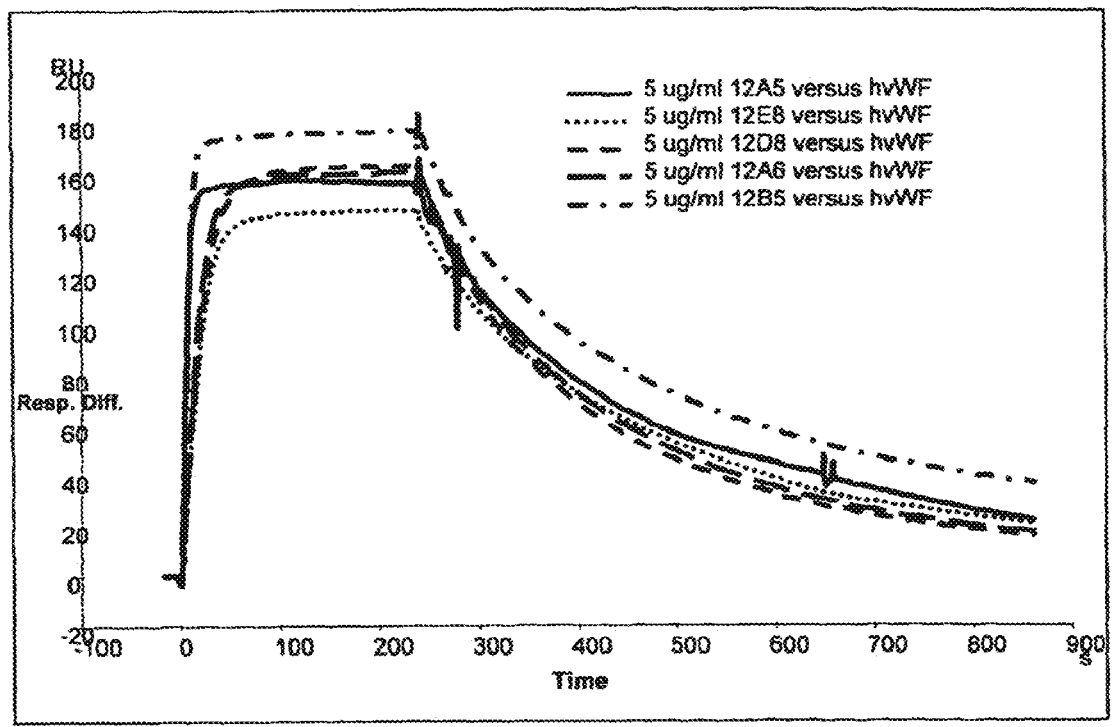

| | | |
|---|---|---|
| WO | WO-2006/122825 A2 | 11/2006 |
| WO | WO-2008/049881 A2 | 5/2008 |

OTHER PUBLICATIONS

[No Author Listed] embolism. Www.wikipedia.org. Accessed Apr. 19, 2010.

[No Author Listed] Immunochemistry. Nankodo Co., Ltd., Jul. 15, 1983 (1st ed.), pp. 35-36.

[No Author Listed] The Merck Manual of Diagnosis and Therapy, 17th Ed. Beers et al, Editors. Merck Research Laboratories, 1999:2057-8.

[No Author Listed] The Merck Manual of Diagnosis and Therapy, 17th Ed. Beers et al, Editors. Merck Research Laboratories, 1999:926-7.

[No Author Listed] Von Willebrand disease. www.wikipedia.org. Accessed Dec. 30, 2008.

Arbabi Gharoudi et al., Selection and identification of single domain antibody fragments from camel heavy-chain antibodies. FEBS Lett. Sep. 15, 1997;414(3):521-6.

Badreldin et al., Gaseous emboli during off-pump surgery with T-graft technique, two different mechanisms. Interact Cardiovasc Thorac Surg. May 2010;10(5):766-9. Epub Feb. 12, 2010.

Berndt et al., The vascular biology of the glycoprotein Ib-IX-V complex. Thromb Haemost. Jul. 2001;86(1):178-88. Review.

Blanco et al., Formation and stability of beta-hairpin structures in polypeptides. Curr Opin Struct Biol. Feb. 1998; 8(1):107-11. Review.

Bonnefoy et al., Shielding the front-strand beta 3 of the von Willebrand factor A1 domain inhibits its binding to platelet glycoprotein Ibalpha. Blood. Feb. 15, 2003;101(4):1375-83. Epub Oct. 10, 2002.

Celikel et al., Crystal structure of the von Willebrand factor A1 domain in complex with the function blocking NMC-4 Fab. Nat Struct Biol. Mar. 1998;5(3):189-94.

Celikel et al., von Willebrand factor conformation and adhesive function is modulated by an internalized water molecule. Nat Struct Biol. Oct. 2000;7(10):881-4.

Chand et al., A two-site, monoclonal antibody-based immunoassay for von Willebrand factor-demonstration that vWF function resides in a conformational epitope. Thromb Haemost. Jun. 30, 1986;55(3):318-24.

Christophe et al., A monoclonal antibody (B724) to von Willebrand factor recognizing an epitope within the A1 disulphide loop (Cys509-Cys695) discriminates between type 2A and type 2B von Willebrand disease. Br J Haematol. May 1995;90(1):195-203.

Conrath et al., Camel single-domain antibodies as modular building units in bispecific and bivalent antibody constructs. J Biol Chem. Mar. 9, 2001;276(10):7346-50. Epub Oct. 25, 2000.

Cortez-Retamozo et al., Efficient tumor targeting by single-domain antibody fragments of camels. Int J Cancer. Mar. 20, 2002;98(3):456-62.

Cruz et al., Mapping the glycoprotein Ib-binding site in the von willebrand factor A1 domain. J Biol Chem. Jun. 23, 2000;275(25)19098-105.

D'Haens et al., Endoscopic and histological healing with infliximab anti-tumor necrosis factor antibodies in Crohn's disease: A European multicenter trial. Gastroenterology. May 1999;116(5):1029-34.

De Mast et al., Thrombocytopenia and release of activated von Willebrand Factor during early *Plasmodium falciparum* malaria. J Infect Dis. Aug. 15, 2007;196(4):622-8. Epub Jul. 10, 2007.

Deffar et al., Nanobodies—The new concept in antibody engineering. Afr J Biotechnol. Jun. 17, 2009;8(12):2645-52.

Dong et al., Novel gain-of-function mutations of platelet glycoprotein IBalpha by valine mutagenesis in the Cys209-Cys248 disulfide loop. Functional analysis under statis and dynamic conditions. J Biol Chem. Sep. 8, 2000;275(36):27663-70.

Dong et al., Tyrosine sulfation of glycoprotein I(b)alpha. Role of electrostatic interactions in von Willebrand factor binding. J Biol Chem. May 18, 2001;276(20):16690-4. Epub Feb. 23, 2001.

Els-Conrath et al., Camel single-domain antibodies as modular building units in bispecific and bivalent antibody constructs. J Biol Chem. Mar. 9, 2001;276(10):7346-50. Epub Oct. 25, 2000.

Emsley et al., Crystal structure of the von Willebrand Factor A1 domain and implications for the binding of platelet glycoprotein Ib. J Biol Chem. Apr. 24, 1998;273(17):10396-401.

Favaloro et al., Development of a simple collagen based ELISA assay aids in the diagnosis of, and permits sensitive discrimination between type I and type II, von Willebrand's disease. Blood Coagul Fibrinolysis. Apr. 1991;2(2):285-91.

Favaloro et al., Discrimination of von Willebrands disease (VWD) subtypes: direct comparison of von Willebrand factor:collagen binding assay (VWF:CBA) with monoclonal antibody (MAB) based VWF-capture systems. Thromb Haemost. Oct. 2000;84(4):541-7.

Favaloro, Detection of von Willebrand disorder and identification of qualitative von Willebrand factor defects. Direct comparison of commercial ELISA-based von Willebrand factor activity options. Am J Clin Pathol. Oct. 2000;114(4):608-18.

Franchini et al., Von Willebrand factor and thrombosis. Ann Hematol. Jul. 2006;85(7):415-23. Epub Mar. 28, 2006. Review.

Fujimura et al., The interaction of botrocetin with normal or variant von Willebrand factor (types IIA and IIB) and its inhibition by monoclonal antibodies that block receptor binding. Thromb Haemost. Oct. 5, 1992;68(4):464-9.

Genbank submission; NIH/NCBI; Accession No. 1AUQ; Emsley et al; Sep. 1, 1997 (last submission).

Genbank submission; NIH/NCBI; Accession No. 1M10_A; Huizinga et al; Sep. 25, 2008 (last submission).

Genbank submission; NIH/NCBI; Accession No. AAA61295; Mancuso et al.; Jan. 14, 1995 (last submission).

Genbank submission; NIH/NCBI; Accession No. AAB34053; Clerc et al.; Jul. 27, 1995 (last submission).

Genbank submission; NIH/NCBI; Accession No. AAB39987; Schulte am Esch II et al.; Jan. 9, 1997 (last submission).

Genbank submission; NIH/NCBI; Accession No. AAB59512; Sadler; Aug. 7, 1995 (last submission).

Genbank submission; NIH/NCBI; Accession No. CAA27972; Bonthron et al.; Jan. 9, 1998 (last submission).

Genbank submission; NIH/NCBI; Accession No. NP_000164; Luo et al; Nov. 16, 2008 (last submission).

Genbank submission; NIH/NCBI; Accession No. NP_000543; Ahmad et al; Nov. 16, 2008 (last submission).

Genbank submission; NIH/NCBI; Accession No. 1SQ0_A; Dumas et al.; Sep. 24, 2008 (last submission).

Goto et al., Characterization of the unique mechanism mediating the shear-dependent binding of soluble von Willebrand factor to platelets. J Biol Chem. Oct. 6, 1995;270(40):23352-61.

Groot et al., The active conformation of von Willebrand factor in patients with thrombotic thrombocytopenic purpura in remission. J Thromb Haemost. Jun. 2009;7(6):962-9.

Groot et al., The presence of active von Willebrand factor under various pathological conditions. Curr Opin Hematol. May 2007;14(3):284-9. Review.

Holliger et al., Retargeting serum immunoglobulin with bispecific diabodies. Nat Biotechnol. Jul. 1997;15(7):632-6.

Hoogenboom et al., Mix and match: building manifold binding sites. Nat Biotechnol. Feb. 1997;15(2):125-6.

Huizinga et al., Structures of glycoprotein Ibalpha and its complex with von Willebrand factor A1 domain. Science. Aug. 16, 2002;297(5584):1176-9.

Hulstein et al., A novel nanobody that detects the gain-of-function phenotype of von Willebrand factor in ADAMTS13 deficiency and von Willebrand disease type 2B. Blood. Nov. 1, 2005 ;106(9):3035-42. Epub Jul. 12, 2005.

Ikeda et al., The role of von Willebrand factor and fibrinogen in platelet aggregation under varying shear stress. J Clin Invest. Apr. 1991;87(4):1234-40.

Ill et al., Design and construction of a hybrid immunoglobulin domain with properties of both heavy and light chain variable regions. Protein Eng. Aug. 1997;10(8):949-57.

Janeway et al., Ch. 3: Structure of the antibody molecule and immunogloblin genes. In Immunobiology: The immune sysyem in health and disease, 3rd Ed. Current Biology, Ltd, 1997;3:1-3:11.

Kageyama et al., Pharmacokinetics and pharmacodynamics of AJW200, a humanized monoclonal antibody to von Willebrand factor, in monkeys. Arterioscler Thromb Vasc Biol. Jan. 2002;22(1):187-92.

Lattuada et al., Mild to moderate reduction of a von Willebrand factor cleaving protease (ADAMTS-13) in pregnant women with HELLP microangiopathic syndrome. Haematologica. Sep. 2003;88(9):1029-34.

López et al., Bernard-Soulier syndrome. Blood. Jun. 15, 1998;91(12):4397-418. Review.

Mallender et al., Construction, expression, and activity of a bivalent bispecific single-chain antibody. J Biol Chem. Jan. 7, 1994;269(1):199-206.

Matsushita et al., Identification of amino acid residues essential for von Willebrand factor binding to platelet glycoprotein Ib. Charged-to-alanine scanning mutagenesis of the A1 domain of human von Willebrand factor. J Biol Chem. Jun. 2, 1995;270(22):13406-14.

Matsushita et al., Localization of von willebrand factor-binding sites for platelet glycoprotein Ib and botrocetin by charged-to-alanine scanning mutagenesis. J Biol Chem. Apr. 14, 2000;275(15)11044-9.

Miller et al.., Mutation in the gene encoding the alpha chain of platelet glycoprotein Ib in platelet-type von Willebrand disease. Proc Natl Acad Sci U S A. Jun. 1, 1991;88(11):4761-5.

Murdock et al., von Willebrand factor activity detected in a monoclonal antibody-based ELISA: an alternative to the ristocetin cofactor platelet agglutination assay for diagnostic use. Thromb Haemost. Oct. 1997;78(4):1272-7.

Muyldermans et al., Single domain camel antibodies: current status. J Biotechnol. Jun. 2001;74(4):277-302. Review.

Neri et al., High-affinity antigen binding by chelating recombinant antibodies (CRAbs). J Mol Biol. Feb. 24, 1995;246(3):367-73.

Nokes et al.,Von Willebrand factor has more than one binding site for platelets. Thromb Res. Jun. 1, 1984 ;34(5):361-6.

Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.

Rudikoff et al., Single amino acid substitution altering antigen-binding specificity. Proc Natl Acad Sci U S A. Mar. 1982;79(6):1979-83.

Ruggeri, Von Willebrand factor, platelets and endothelial cell interactions. J Thromb Haemost. Jul. 2003;1(7):1335-42. Review.

Russell et al., Pseudo-von Willebrand disease: a mutation in the platelet glycoprotein Ib alpha gene associated with a hyperactive surface receptor. Blood. Apr. 1, 1993;81(7):1787-91.

Sadler et al., Molecular mechanism and classification of von Willebrand disease. Thromb Haemost. Jul. 1995;74(1):161-6. Review.

Sadler, Biochemistry and genetics of von Willebrand factor. Annu Rev Biochem. 1998;67:395-424. Review.

Savage et al., Initiation of platelet adhesion by arrest onto fibrinogen or translocation on von Willebrand factor. Cell. Jan. 26, 1996;84(2):289-97.

Silence et al., ALX-0081 NanobodyTM, an Engineered Bivalent Anti-Thrombotic Drug Candidate with Improved Efficacy and Safety as Compared to the Marketed Drugs. Blood. ASH Annual Meeting Abstracts. Nov. 1, 2006; 108(11): Abstract 896.

Tait et al., Phenotype changes resulting in high-affinity binding of von Willebrand factor to recombinant glycoprotein Ib-Ix: analysis of the platelet-type von Willebrand disease mutations. Blood. Sep. 15, 2001;98(6)1 812-8.

Tanha et al., Selection by phage display of llama conventional V(H) fragments with heavy chain antibody V(H)H properties. J Immunol Methods. May 1, 2002;263(1-2):97-109.

Thompson et al., Advances in the pathogenesis and treatment of acute coronary syndromes. J La State Med Soc. May 1999;151(5):272-7. Review. Abstract only.

Triplett, Coagulation and bleeding disorders: review and update. Clin Chem. Aug. 2000;46(8 Pt 2):1260-9. Review.

Tsai et al., Antibodies to von Willebrand factor-cleaving protease in acute thrombotic thrombocytopenic purpura. N Engl J Med. Nov. 26, 1998;339(22)1 585-94.

Valle et al., Infliximab. Expert Opin Pharmacother. Jun. 2001;2(6):1015-25. Review.

Vanhoorelbeke et al., A reliable and reproducible ELISA method to measure ristocetin cofactor activity of von Willebrand factor. Thromb Haemost. Jan. 2000;83(1):107-13.

Varga-Szabo et al., Cell adhesion mechanisms in platelets. Arterioscler Thromb Vasc Biol. Mar. 2008;28(3):403-12. Epub Jan. 3, 2008.

Vasudevan et al., Modeling and functional analysis of the interaction between von Willebrand factor A1 domain and glycoprotein Ibalpha. J Biol Chem. Apr. 28, 2000;275(17)1 2763-8.

Veyradier et al., Laboratory diagnosis of von Willebrand disease. Int J Clin Lab Res. 1998;28(4):201-10. Review.

Vincke et al., General strategy to humanize a camelid single-domain antibody and identification of a universal humanized nanobody scaffold. J. Biol. Chem. 2009;284:3273-3284.

Wu et al., Inhibition of the von Willebrand (VWF)-collagen interaction by an antihuman VWF monoclonal antibody results in abolition of in vivo arterial platelet thrombus formation in baboons. Blood. May 15, 2002;99(10):3623-8.

Ohno et al., Antigen-binding specificities of antibodies are primarily determined by seven residues of VH. Proc Natl Acad Sci U S A. May 1985;82(9):2945-9.

Conway et al., Prognostic value of plasma von Willebrand factor and soluble P-selectin as indices of endothelial damage and platelet activation in 994 patients with nonvalvular atrial fibrillation. Circulation. Jul. 1, 2003;107(25):3141-5. Epub Jun. 9, 2003.

Eto et al., AJvW-2, an anti-vWF monoclonal antibody, inhibits enhanced platelet aggregation induced by high shear stress in platelet-rich plasma from patients with acute coronary syndromes. Arterioscler Thromb Vasc Biol. Apr. 1999;19(4):877-82.

Kageyama et al., Anti-human von willebrand factor monoclonal antibody AJvW-2 prevents thrombus deposition and neointima formation after balloon injury in guinea pigs. Arterioscler Thromb Vasc Biol. Oct. 2000;20(10):2303-8.

Kageyama et al., Anti-human vWF monoclonal antibody, AJvW-2 Fab, inhibits repetitive coronary artery thrombosis without bleeding time prolongation in dogs. Thromb Res. Mar. 1, 2001;101(5):395-404.

Kageyama et al., Anti-thrombotic effects and bleeding risk of AJvW-2, a monoclonal antibody against human von Willebrand factor. Br J Pharmacol. Sep. 1997;122(1):165-71.

Kageyama et al., Effect of a humanized monoclonal antibody to von Willebrand factor in a canine model of coronary arterial thrombosis. Eur J Pharmacol. May 17, 2002;443(1-3):143-9.

Poletti et al., Prevention of arterial thrombosis using a novel heparin with enhanced antiplatelet activity and reduced anticoagulant activity. J Vasc Surg. Sep. 1997;26(3):366-72.

Wang et al., Aspirin and clopidogrel resistance: an emerging clinical entity. Eur Heart J. Mar. 2006;27(6):647-54. Epub Dec. 19, 2005.

Yamamoto et al., Antagonism of vWF inhibits both injury induced arterial and venous thrombosis in the hamster. Thromb Haemost. Jan. 1998;79(1):202-10.

Yamashita et al., Contribution of von Willebrand factor to thrombus formation on neointima of rabbit stenotic iliac artery under high blood-flow velocity. Arterioscler Thromb Vasc Biol. Jun. 1, 2003;23(6):1105-10. Epub May 15, 2003.

Yamashita et al., Increased vascular wall thrombogenicity combined with reduced blood flow promotes occlusive thrombus formation in rabbit femoral artery. Arterioscler Thromb Vasc Biol. Dec. 2004;24(12):2420-4. Epub Oct. 14, 2004.

Ablynx [No Author Listed], "Translational research in the development of Nanobody®-based therapies: vWF programme—a case study. Preclinical and Clinical Development of Therapeutic Antibodies." Ablynx Presentation. PEGS Meeting (Boston); Apr. 7, 2009. Slides 1-27.

Jacobs et al., "Preclinical safety assessment of a new antithrombotic drug, the nanobody® ALX-0681." Ablynx Presentation. Feb. 18, 2010. Abstract 1577. SOT Poster 309.

Meyer et al, Percutaneous transluminal coronary angioplasty in patients with stable and unstable angina pectoris: analysis of early and late results. Am Heart J. Nov. 1983;106(5 Pt 1):973-80.

Patton, Breathing life into protein drugs. Nat Biotechnol. Feb. 1998;16(2):141-3.

Price et al., Tissue factor and tissue factor pathway inhibitor. Anaesthesia. May 2004;59(5):483-92.

Smith et al., Prolonged in vivo residence times of antibody fragments associated with albumin. Bioconjugate Chem. Sep.-Oct. 2001;12(5):750-6.

Vercruysse. "RIPA and RICO predicting efficacy of anti-vWF mediated thrombosis, a Phase I analysis." Ablynx Presentation. Biomarker Congress (Manchester): Feb. 25, 2010. Slides 1-52.

* cited by examiner

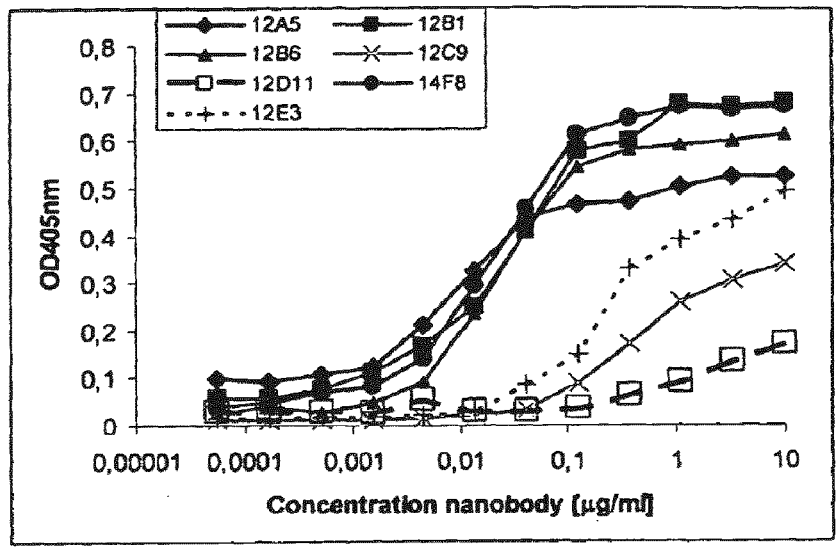

Figure 1

```
12A5    AVQLVESGGGLVQPGGSLRLSCLASGRIFSIGAMGMYRQAPGKQRELVATITSGGSTNYAD
12B4    QVQLVESGGGLVQPGGSLRLSCLASGRIFSIGAMGLYRQAPGKQRELVATITSGGSTNYAD
12E8    AVQLEESGGGLVQPGGSLRLSCLASGRIFSIGAMGLYRQAPGKQRELVATITSGGSTNYAD
12A6    QVQLVESGGGLVQPGGSLRLSCLASGRIFSIGTMGLYRQAPGKQRELVATITSGGSTNYAD
12D8    AVQLVESGGGLVQPGGSLRLSCLASGRIFSIGTMGLYRQAPGKQRELVATITSGGSTNYAD

12A5    PVKGRFTISRDGPKNTVYLQMNSLKPEDTAVYYCYANLKQGSYGYRFNDYWGQGTQVTVSS
12B4    SVKGRFTISRDGPKNTVYLQMNSLKPEDTAVYYCYANLKQGSYGYRFNDYWGQGTQVTVSS
12E8    SVKGRFTISRDGAKNTVYLQMNSLKPEDTAVYYCYANLKQGDYGYRFNDYWGQGTQVTVSS
12A6    SVKGRFTISRDGAKNTVYLQMNSLRPEDTAVYYCYANLKQGDYGYRFNDYWGQGTQVTVSS
12D8    SVKGRFTISRDGAKNTVYLQMNSLRPEDTAVYYCYANLKQGDYGYRFNDYWGQGTQVTVSS
```

Figure 2

```
12B6    QVQLVESGGGLVQAGGALRLSCAASGRTFSYNPMGWFRQAPGKERDVVAAISRTGGSTYYAR
12A2    QVKLEESGGGLVQAGGALRLSCAASGRTFSYNPMGWFRQAPGKERDLVAAISRTGGSTYYPD
12F2    QVKLVESGGGLVQAGGALRLSCAASGRTFSYNPMGWFRQAPGRERDVVAAISRTGGSTYYPD
14H10   QVKLEESGGGLVQAGGALRLSCAASGRTFSYNPMGWFRQAPGKERDVVAAISRTGGSTYYPD

12B6    SVEGRFTISRDNAKRMVYLQMNALKPEDTAVYYCAAAGVRAEDGRVRTLPSEYNFWGQGTQVTVSS
12A2    SVEGRFTISRDNAKRMVYLQMNNLKPEDTAVYYCAAAGVRAEDGRVRTLPSEYTFWGQGTQVTVSS
12F2    SVEGRFTISRDNAKRMVYLQMNNLKPEDTAVYYCAAAGVRAEDGRVRSLPSEYTFWGQGTQVTVSS
14H10   SVEGRFTISRDNAKRMVYLEMNNLKPDDTAVYYCAAAGVRAEDGRVRTLPSEYTFWGQGTQVTVSS
```

Figure 3

| | |
|---|---|
| 12B6 | QVQLVESGGGLVQAGGALRLSCAASGRTFSYNPMGWFRQAPGKERDVVAA |
| 12B6H1 | EVQLVESGGGLVQPGGSLRLSCAASGRTFSYNPMGWFRQAPGKGRDVVAA |
| 12B6H2 | EVQLVESGGGLVQPGGSLRLSCAASGRTFSYNPMGWFRQAPGKGREVVAA |
| 12B6H3 | EVQLVESGGGLVQPGGSLRLSCAASGRTFSYNPMGWFRQAPGKGRDVVAA |
| 12B6H4 | EVQLVESGGGLVQPGGSLRLSCAASGRTFSYNPMGWFRQAPGKGRDVVAA |
| | |
| 12B6 | ISRTGGSTYYARSVEGRFTISRDNAKRMVYLQMNALKPEDTA |
| 12B6H1 | ISRTGGSTYYARSVEGRFTISRDNAKRMVYLQMNSLRAEDTA |
| 12B6H2 | ISRTGGSTYYARSVEGRFTISRDNAKRMVYLQMNSLRAEDTA |
| 12B6H3 | ISRTGGSTYYARSVEGRFTISRDNAKNMVYLQMNSLRAEDTA |
| 12B6H4 | ISRTGGSTYYARSVEGRFTISRDNAKRSVYLQMNSLRAEDTA |
| | |
| 12B6 | VYYCAAAGVRAEDGRVRTLPSEYNFWGQGTQVTVSS |
| 12B6H1 | VYYCAAAGVRAEDGRVRTLPSEYNFWGQGTQVTVSS |
| 12B6H2 | VYYCAAAGVRAEDGRVRTLPSEYNFWGQGTQVTVSS |
| 12B6H3 | VYYCAAAGVRAEDGRVRTLPSEYNFWGQGTQVTVSS |
| 12B6H4 | VYYCAAAGVRAEDGRVRTLPSEYNFWGQGTQVTVSS |

Figure 15

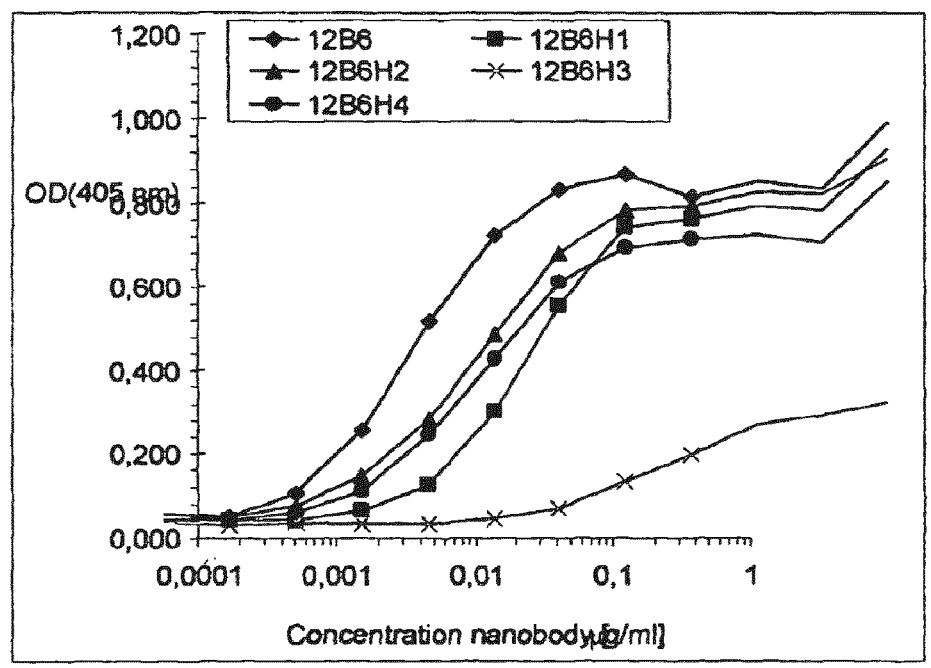

Figure 16

```
12A2      QVKLEESGGGLVQAGGALRLSCAASGRTFSYNPMGWFRQAPGKERDLVAA
12A2H1    EVQLVESGGGLVQPGGSLRLSCAASGRTFSYNPMGWFRQAPGKGRELVAA
12A2H3    EVQLVESGGGLVQPGGSLRLSCAASGRTFSYNPMGWFRQAPGKGRELVAA
12A2H4    EVQLVESGGGLVQPGGSLRLSCAASGRTFSYNPMGWFRQAPGKGRELVAA
12A2H11   EVQLVESGGGLVQPGGSLRLSCAASGFTFSYNPMGWFRQAPGKGRELVAA
12A2H13   EVQLVESGGGLVQPGGSLRLSCAASGFTFSYNPMGWFRQAPGKGRELVAA

12A2      ISRTGGSTYYPDSVEGRFTISRDNAKRMVYLQMNNLKPEDTAVYYCAAA
12A2H1    ISRTGGSTYYPDSVEGRFTISRDNAKRMVYLQMNSLRAEDTAVYYCAAA
12A2H3    ISRTGGSTYYPDSVEGRFTISRDNAKNMVYLQMNSLRAEDTAVYYCAAA
12A2H4    ISRTGGSTYYPDSVEGRFTISRDNAKRSVYLQMNSLRAEDTAVYYCAAA
12A2H11   ISRTGGSTYYPDSVEGRFTISRDNAKRMVYLQMNSLRAEDTAVYYCAAA
12A2H13   ISRTGGSTYYPDSVEGRFTISRDNAKNSVYLQMNSLRAEDTAVYYCAAA

12A2      GVRAEDGRVRTLPSEYTFWGQGTQVTVSS
12A2H1    GVRAEDGRVRTLPSEYTFWGQGTQVTVSS
12A2H3    GVRAEDGRVRTLPSEYTFWGQGTQVTVSS
12A2H4    GVRAEDGRVRTLPSEYTFWGQGTQVTVSS
12A2H11   GVRAEDGRVRTLPSEYTFWGQGTQVTVSS
12A2H13   GVRAEDGRVRTLPSEYTFWGQGTLVTVSS
```

Figure 17

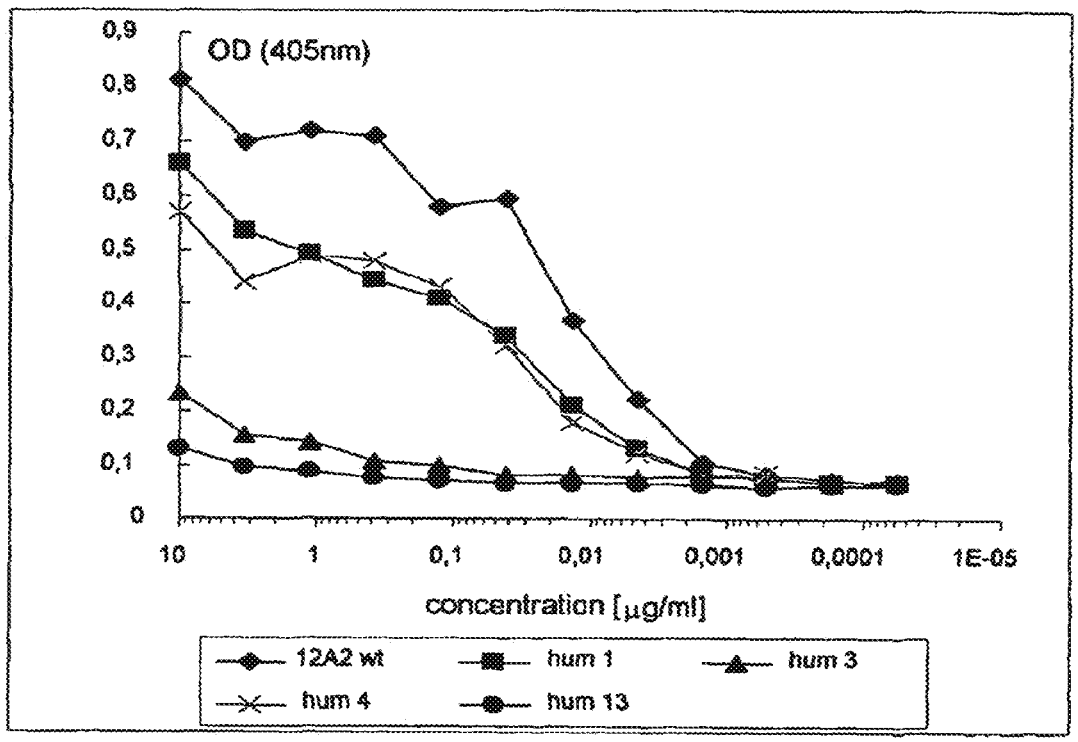

Figure 19

```
12A5      AVQLVESGGGLVQPGGSLRLSCLASGRIFSIGAMGMYRQAPGKQREL
12A5H1    EVQLVESGGGLVQPGGSLRLSCAASGRIFSIGAMGMYRQAPGKGREL
12A5H2    EVQLVESGGGLVQPGGSLRLSCAASGRIFSIGAMGMYRQAPGKGREL
12A5H3    EVQLVESGGGLVQPGGSLRLSCAASGRIFSIGAMGMYRQAPGKGREL

12A5      VATITSGGSTNYADPVKGRFTISRDGPKNTVYLQMNSLKPEDTAVYY
12A5H1    VATITSGGSTNYADPVKGRFTISRDGPKNTVYLQMNSLRAEDTAVYY
12A5H2    VATITSGGSTNYADPVKGRFTISRDGAKNTVYLQMNSLRAEDTAVYY
12A5H3    VATITSGGSTNYADPVKGRFTISRDNAKNTVYLQMNSLRAEDTAVYY

12A5      CYANLKQGSYGYRFNDYWGQGTQVTVSS
12A5H1    CYANLKQGSYGYRFNDYWGQGTQVTVSS
12A5H2    CYANLKQGSYGYRFNDYWGQGTQVTVSS
12A5H3    CYANLKQGSYGYRFNDYWGQGTQVTVSS
```

Figure 20

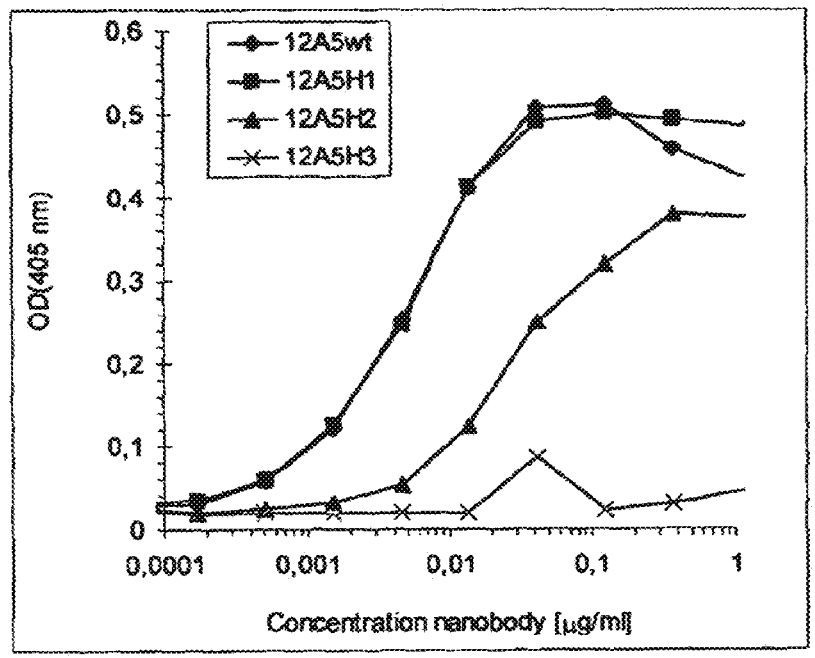

Figure 21

```
12A2H1      EVQLVESGGGLVQPGGSLRLSCAASGRTFSYNPMGWFRQAPGKGRELVA
12A2H4      EVQLVESGGGLVQPGGSLRLSCAASGRTFSYNPMGWFRQAPGKGRELVA
12B6H2      EVQLVESGGGLVQPGGSLRLSCAASGRTFSYNPMGWFRQAPGKGREVVA

12A2H1      AISRTGGSTYYPDSVEGRFTISRDNAKRMVYLQMNSLRAEDTAVYYCAA
12A2H4      AISRTGGSTYYPDSVEGRFTISRDNAKRSVYLQMNSLRAEDTAVYYCAA
12B6H2      AISRTGGSTYYARSVEGRFTISRDNAKRMVYLQMNSLRAEDTAVYYCAA

12A2H1      AGVRAEDGRVRTLPSEYTFWGQGTQVTVSS
12A2H4      AGVRAEDGRVRTLPSEYTFWGQGTQVTVSS
12B6H2      AGVRAEDGRVRTLPSEYNFWGQGTQVTVSS
```

Figure 22

1: marker
2: + NPP
3: no NPP
4: + NPP + EDTA
5: + NPP + PBS
6: + NPP + 10 µg/ml ALX-0081
7: + NPP + 10 µg/ml ALX-0081
8: + NPP + 10 µg/ml ALX-0081
9: marker

SEQUENCE LISTING

<160> NUMBER OF SEQ ID NOS: 303

<210> SEQ ID NO 1
<211> LENGTH: 26
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (11)..(11)
<223> OTHER INFORMATION: Xaa is a Hallmark residue (see Table 2)

<400> SEQUENCE: 1

Gln Val Gln Leu Gln Glu Ser Gly Gly Gly Xaa Val Gln Ala Gly Gly
1               5                   10                  15

Ser Leu Arg Leu Ser Cys Ala Ala Ser Gly
            20                  25

<210> SEQ ID NO 2
<211> LENGTH: 14
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (2)..(2)
<223> OTHER INFORMATION: Xaa is a Hallmark residue
<220> FEATURE:
<221> NAME/KEY: VARIANT
<222> LOCATION: (9)..(9)
<223> OTHER INFORMATION: Xaa is a Hallmark residue
<220> FEATURE:
<221> NAME/KEY: VARIANT
<222> LOCATION: (10)..(10)
<223> OTHER INFORMATION: Xaa is a Hallmark residue
<220> FEATURE:
<221> NAME/KEY: VARIANT
<222> LOCATION: (12)..(12)
<223> OTHER INFORMATION: Xaa is a Hallmark residue

<400> SEQUENCE: 2

Trp Xaa Arg Gln Ala Pro Gly Lys Xaa Xaa Glu Xaa Val Ala
1               5                   10

<210> SEQ ID NO 3
<211> LENGTH: 32
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (21)..(21)
<223> OTHER INFORMATION: Xaa is a Hallmark residue
<220> FEATURE:
<221> NAME/KEY: VARIANT
<222> LOCATION: (22)..(22)
<223> OTHER INFORMATION: Xaa is a Hallmark residue

<400> SEQUENCE: 3

Arg Phe Thr Ile Ser Arg Asp Asn Ala Lys Asn Thr Val Tyr Leu Gln
1               5                   10                  15

Met Asn Ser Leu Xaa Xaa Glu Asp Thr Ala Val Tyr Tyr Cys Ala Ala
            20                  25                  30

<210> SEQ ID NO 4
<211> LENGTH: 11

```
<212> TYPE: PRT
<213> ORGANISM: artificial sequence
<220> FEATURE:
<223> OTHER INFORMATION: synthetic peptide
<220> FEATURE:
<221> NAME/KEY: VARIANT
<222> LOCATION: (1)..(1)
<223> OTHER INFORMATION: Xaa is a Hallmark residue
<220> FEATURE:
<221> NAME/KEY: VARIANT
<222> LOCATION: (2)..(2)
<223> OTHER INFORMATION: Xaa is a Hallmark residue
<220> FEATURE:
<221> NAME/KEY: VARIANT
<222> LOCATION: (6)..(6)
<223> OTHER INFORMATION: Xaa is a Hallmark residue

<400> SEQUENCE: 4

Xaa Xaa Gln Gly Thr Xaa Val Thr Val Ser Ser
1               5                   10

<210> SEQ ID NO 5
<211> LENGTH: 26
<212> TYPE: PRT
<213> ORGANISM: artificial sequence
<220> FEATURE:
<223> OTHER INFORMATION: synthetic peptide

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 6
<211> LENGTH: 14
<212> TYPE: PRT
<213> ORGANISM: artificial sequence
<220> FEATURE:
<223> OTHER INFORMATION: synthetic peptide

<400> SEQUENCE: 6

Trp Phe Arg Gln Ala Pro Gly Lys Glu Arg Glu Leu Val Ala
1               5                   10

<210> SEQ ID NO 7
<211> LENGTH: 14
<212> TYPE: PRT
<213> ORGANISM: artificial sequence
<220> FEATURE:
<223> OTHER INFORMATION: synthetic peptide

<400> SEQUENCE: 7

Trp Phe Arg Gln Ala Pro Gly Lys Glu Arg Glu Phe Val Ala
1               5                   10

<210> SEQ ID NO 8
<211> LENGTH: 13
<212> TYPE: PRT
<213> ORGANISM: artificial sequence
<220> FEATURE:
<223> OTHER INFORMATION: synthetic peptide

<400> SEQUENCE: 8

Trp Phe Arg Gln Ala Pro Gly Lys Glu Arg Glu Gly Ala
1               5                   10

<210> SEQ ID NO 9
<211> LENGTH: 14
```

```
<212> TYPE: PRT
<213> ORGANISM: artificial sequence
<220> FEATURE:
<223> OTHER INFORMATION: synthetic peptide

<400> SEQUENCE: 9

Trp Phe Arg Gln Ala Pro Gly Lys Gln Arg Glu Leu Val Ala
1               5                   10

<210> SEQ ID NO 10
<211> LENGTH: 14
<212> TYPE: PRT
<213> ORGANISM: artificial sequence
<220> FEATURE:
<223> OTHER INFORMATION: synthetic peptide

<400> SEQUENCE: 10

Trp Phe Arg Gln Ala Pro Gly Lys Gln Arg Glu Phe Val Ala
1               5                   10

<210> SEQ ID NO 11
<211> LENGTH: 13
<212> TYPE: PRT
<213> ORGANISM: artificial sequence
<220> FEATURE:
<223> OTHER INFORMATION: synthetic peptide

<400> SEQUENCE: 11

Trp Tyr Arg Gln Ala Pro Gly Lys Gly Leu Glu Trp Ala
1               5                   10

<210> SEQ ID NO 12
<211> LENGTH: 32
<212> TYPE: PRT
<213> ORGANISM: artificial sequence
<220> FEATURE:
<223> OTHER INFORMATION: synthetic peptide

<400> SEQUENCE: 12

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 13
<211> LENGTH: 11
<212> TYPE: PRT
<213> ORGANISM: artificial sequence
<220> FEATURE:
<223> OTHER INFORMATION: synthetic peptide

<400> SEQUENCE: 13

Trp Gly Gln Gly Thr Gln Val Thr Val Ser Ser
1               5                   10

<210> SEQ ID NO 14
<211> LENGTH: 11
<212> TYPE: PRT
<213> ORGANISM: artificial sequence
<220> FEATURE:
<223> OTHER INFORMATION: synthetic peptide

<400> SEQUENCE: 14

Trp Gly Gln Gly Thr Leu Val Thr Val Ser Ser
1               5                   10

<210> SEQ ID NO 15
```

```
<211> LENGTH: 5
<212> TYPE: PRT
<213> ORGANISM: artificial sequence
<220> FEATURE:
<223> OTHER INFORMATION: synthetic peptide

<400> SEQUENCE: 15

Asn Tyr Gly Met Gly
1               5

<210> SEQ ID NO 16
<211> LENGTH: 5
<212> TYPE: PRT
<213> ORGANISM: artificial sequence
<220> FEATURE:
<223> OTHER INFORMATION: synthetic peptide

<400> SEQUENCE: 16

Ser Tyr Thr Leu Gly
1               5

<210> SEQ ID NO 17
<211> LENGTH: 5
<212> TYPE: PRT
<213> ORGANISM: artificial sequence
<220> FEATURE:
<223> OTHER INFORMATION: synthetic peptide

<400> SEQUENCE: 17

Asn Tyr Asn Met Gly
1               5

<210> SEQ ID NO 18
<211> LENGTH: 5
<212> TYPE: PRT
<213> ORGANISM: artificial sequence
<220> FEATURE:
<223> OTHER INFORMATION: synthetic peptide

<400> SEQUENCE: 18

Ser Ser Ala Met Ala
1               5

<210> SEQ ID NO 19
<211> LENGTH: 5
<212> TYPE: PRT
<213> ORGANISM: artificial sequence
<220> FEATURE:
<223> OTHER INFORMATION: synthetic peptide

<400> SEQUENCE: 19

Tyr Tyr Asn Thr Gly
1               5

<210> SEQ ID NO 20
<211> LENGTH: 5
<212> TYPE: PRT
<213> ORGANISM: artificial sequence
<220> FEATURE:
<223> OTHER INFORMATION: synthetic peptide

<400> SEQUENCE: 20

Ile Gly Ala Met Gly
1               5

<210> SEQ ID NO 21
<211> LENGTH: 5
<212> TYPE: PRT
```

```
<213> ORGANISM: artificial sequence
<220> FEATURE:
<223> OTHER INFORMATION: synthetic peptide

<400> SEQUENCE: 21

Ile Gly Thr Met Gly
1               5

<210> SEQ ID NO 22
<211> LENGTH: 5
<212> TYPE: PRT
<213> ORGANISM: artificial sequence
<220> FEATURE:
<223> OTHER INFORMATION: synthetic peptide

<400> SEQUENCE: 22

Tyr Asn Pro Met Gly
1               5

<210> SEQ ID NO 23
<211> LENGTH: 17
<212> TYPE: PRT
<213> ORGANISM: artificial sequence
<220> FEATURE:
<223> OTHER INFORMATION: synthetic peptide

<400> SEQUENCE: 23

Ser Ile Ser Trp Ser Gly Thr Tyr Thr Ala Tyr Ser Asp Asn Val Lys
1               5                   10                  15

Gly

<210> SEQ ID NO 24
<211> LENGTH: 17
<212> TYPE: PRT
<213> ORGANISM: artificial sequence
<220> FEATURE:
<223> OTHER INFORMATION: synthetic peptide

<400> SEQUENCE: 24

Gly Ile Ser Trp Ser Gly Val Ser Thr Asp Tyr Ala Glu Phe Ala Lys
1               5                   10                  15

Gly

<210> SEQ ID NO 25
<211> LENGTH: 18
<212> TYPE: PRT
<213> ORGANISM: artificial sequence
<220> FEATURE:
<223> OTHER INFORMATION: synthetic peptide

<400> SEQUENCE: 25

Thr Ser Ile Ser Trp Ser Gly Ser Tyr Thr Ala Tyr Ala Asp Asn Val
1               5                   10                  15

Lys Gly

<210> SEQ ID NO 26
<211> LENGTH: 17
<212> TYPE: PRT
<213> ORGANISM: artificial sequence
<220> FEATURE:
<223> OTHER INFORMATION: synthetic peptide

<400> SEQUENCE: 26

Ser Ile Ser Trp Ser Gly Met Ser Thr Tyr Tyr Thr Asp Ser Val Lys
1               5                   10                  15
```

Gly

<210> SEQ ID NO 27
<211> LENGTH: 16
<212> TYPE: PRT
<213> ORGANISM: artificial sequence
<220> FEATURE:
<223> OTHER INFORMATION: synthetic peptide

<400> SEQUENCE: 27

Thr Ile Thr Ser Gly Gly Arg Thr Ser Tyr Ala Asp Ser Val Lys Gly
1               5                   10                  15

<210> SEQ ID NO 28
<211> LENGTH: 17
<212> TYPE: PRT
<213> ORGANISM: artificial sequence
<220> FEATURE:
<223> OTHER INFORMATION: synthetic peptide

<400> SEQUENCE: 28

Ala Ile Ser Trp Ser Gly Gly Leu Thr Tyr Tyr Ala Asp Ser Val Lys
1               5                   10                  15

Gly

<210> SEQ ID NO 29
<211> LENGTH: 16
<212> TYPE: PRT
<213> ORGANISM: artificial sequence
<220> FEATURE:
<223> OTHER INFORMATION: synthetic peptide

<400> SEQUENCE: 29

Thr Ile Thr Ser Gly Gly Ser Thr Asn Tyr Ala Asp Pro Val Lys Gly
1               5                   10                  15

<210> SEQ ID NO 30
<211> LENGTH: 16
<212> TYPE: PRT
<213> ORGANISM: artificial sequence
<220> FEATURE:
<223> OTHER INFORMATION: synthetic peptide

<400> SEQUENCE: 30

Thr Ile Thr Ser Gly Gly Ser Thr Asn Tyr Ala Asp Ser Val Lys Gly
1               5                   10                  15

<210> SEQ ID NO 31
<211> LENGTH: 17
<212> TYPE: PRT
<213> ORGANISM: artificial sequence
<220> FEATURE:
<223> OTHER INFORMATION: synthetic peptide

<400> SEQUENCE: 31

Ala Ile Ser Arg Thr Gly Gly Ser Thr Tyr Tyr Ala Arg Ser Val Glu
1               5                   10                  15

Gly

<210> SEQ ID NO 32
<211> LENGTH: 17
<212> TYPE: PRT
<213> ORGANISM: artificial sequence
<220> FEATURE:
<223> OTHER INFORMATION: synthetic peptide

<400> SEQUENCE: 32

-continued

Ala Ile Ser Arg Thr Gly Gly Ser Thr Tyr Tyr Pro Asp Ser Val Glu
1               5                   10                  15
Gly

<210> SEQ ID NO 33
<211> LENGTH: 17
<212> TYPE: PRT
<213> ORGANISM: artificial sequence
<220> FEATURE:
<223> OTHER INFORMATION: synthetic peptide

<400> SEQUENCE: 33

Gln Ser Arg Tyr Arg Ser Asn Tyr Tyr Asp His Asp Asp Lys Tyr Ala
1               5                   10                  15
Tyr

<210> SEQ ID NO 34
<211> LENGTH: 16
<212> TYPE: PRT
<213> ORGANISM: artificial sequence
<220> FEATURE:
<223> OTHER INFORMATION: synthetic peptide

<400> SEQUENCE: 34

Leu Gly Arg Tyr Arg Ser Asn Trp Arg Asn Ile Gly Gln Tyr Asp Tyr
1               5                   10                  15

<210> SEQ ID NO 35
<211> LENGTH: 17
<212> TYPE: PRT
<213> ORGANISM: artificial sequence
<220> FEATURE:
<223> OTHER INFORMATION: synthetic peptide

<400> SEQUENCE: 35

Gln Ser Arg Tyr Ser Ser Asn Tyr Tyr Asp His Asp Asp Lys Tyr Ala
1               5                   10                  15
Tyr

<210> SEQ ID NO 36
<211> LENGTH: 15
<212> TYPE: PRT
<213> ORGANISM: artificial sequence
<220> FEATURE:
<223> OTHER INFORMATION: synthetic peptide

<400> SEQUENCE: 36

Ser Asn Arg Tyr Arg Thr His Thr Thr Gln Ala Met Tyr Asn Tyr
1               5                   10                  15

<210> SEQ ID NO 37
<211> LENGTH: 8
<212> TYPE: PRT
<213> ORGANISM: artificial sequence
<220> FEATURE:
<223> OTHER INFORMATION: synthetic peptide

<400> SEQUENCE: 37

Val Val Asp Gly Lys Arg Ala Pro
1               5

<210> SEQ ID NO 38
<211> LENGTH: 16
<212> TYPE: PRT
<213> ORGANISM: artificial sequence

```
<220> FEATURE:
<223> OTHER INFORMATION: synthetic peptide

<400> SEQUENCE: 38

Asn Arg Arg Gln Lys Thr Val Gln Met Gly Glu Arg Ala Tyr Asp Tyr
1               5                   10                  15

<210> SEQ ID NO 39
<211> LENGTH: 14
<212> TYPE: PRT
<213> ORGANISM: artificial sequence
<220> FEATURE:
<223> OTHER INFORMATION: synthetic peptide

<400> SEQUENCE: 39

Asn Leu Lys Gln Gly Ser Tyr Gly Tyr Arg Phe Asn Asp Tyr
1               5                   10

<210> SEQ ID NO 40
<211> LENGTH: 14
<212> TYPE: PRT
<213> ORGANISM: artificial sequence
<220> FEATURE:
<223> OTHER INFORMATION: synthetic peptide

<400> SEQUENCE: 40

Asn Leu Lys Gln Gly Asp Tyr Gly Tyr Arg Phe Asn Asp Tyr
1               5                   10

<210> SEQ ID NO 41
<211> LENGTH: 19
<212> TYPE: PRT
<213> ORGANISM: artificial sequence
<220> FEATURE:
<223> OTHER INFORMATION: synthetic peptide

<400> SEQUENCE: 41

Ala Gly Val Arg Ala Glu Asp Gly Arg Val Arg Thr Leu Pro Ser Glu
1               5                   10                  15

Tyr Asn Phe

<210> SEQ ID NO 42
<211> LENGTH: 19
<212> TYPE: PRT
<213> ORGANISM: artificial sequence
<220> FEATURE:
<223> OTHER INFORMATION: synthetic peptide

<400> SEQUENCE: 42

Ala Gly Val Arg Ala Glu Asp Gly Arg Val Arg Thr Leu Pro Ser Glu
1               5                   10                  15

Tyr Thr Phe

<210> SEQ ID NO 43
<211> LENGTH: 19
<212> TYPE: PRT
<213> ORGANISM: artificial sequence
<220> FEATURE:
<223> OTHER INFORMATION: synthetic peptide

<400> SEQUENCE: 43

Ala Gly Val Arg Ala Glu Asp Gly Arg Val Arg Ser Leu Pro Ser Glu
1               5                   10                  15

Tyr Thr Phe
```

```
<210> SEQ ID NO 44
<211> LENGTH: 5
<212> TYPE: PRT
<213> ORGANISM: artificial sequence
<220> FEATURE:
<223> OTHER INFORMATION: synthetic peptide

<400> SEQUENCE: 44

Ser Phe Gly Met Ser
1               5

<210> SEQ ID NO 45
<211> LENGTH: 5
<212> TYPE: PRT
<213> ORGANISM: artificial sequence
<220> FEATURE:
<223> OTHER INFORMATION: synthetic peptide

<400> SEQUENCE: 45

Leu Asn Leu Met Gly
1               5

<210> SEQ ID NO 46
<211> LENGTH: 5
<212> TYPE: PRT
<213> ORGANISM: artificial sequence
<220> FEATURE:
<223> OTHER INFORMATION: synthetic peptide

<400> SEQUENCE: 46

Ile Asn Leu Leu Gly
1               5

<210> SEQ ID NO 47
<211> LENGTH: 5
<212> TYPE: PRT
<213> ORGANISM: artificial sequence
<220> FEATURE:
<223> OTHER INFORMATION: synthetic peptide

<400> SEQUENCE: 47

Asn Tyr Trp Met Tyr
1               5

<210> SEQ ID NO 48
<211> LENGTH: 17
<212> TYPE: PRT
<213> ORGANISM: artificial sequence
<220> FEATURE:
<223> OTHER INFORMATION: synthetic peptide

<400> SEQUENCE: 48

Ser Ile Ser Gly Ser Gly Ser Asp Thr Leu Tyr Ala Asp Ser Val Lys
1               5                   10                  15

Gly

<210> SEQ ID NO 49
<211> LENGTH: 16
<212> TYPE: PRT
<213> ORGANISM: artificial sequence
<220> FEATURE:
<223> OTHER INFORMATION: synthetic peptide

<400> SEQUENCE: 49

Thr Ile Thr Val Gly Asp Ser Thr Asn Tyr Ala Asp Ser Val Lys Gly
1               5                   10                  15
```

```
<210> SEQ ID NO 50
<211> LENGTH: 16
<212> TYPE: PRT
<213> ORGANISM: artificial sequence
<220> FEATURE:
<223> OTHER INFORMATION: synthetic peptide

<400> SEQUENCE: 50

Thr Ile Thr Val Gly Asp Ser Thr Ser Tyr Ala Asp Ser Val Lys Gly
1               5                   10                  15

<210> SEQ ID NO 51
<211> LENGTH: 17
<212> TYPE: PRT
<213> ORGANISM: artificial sequence
<220> FEATURE:
<223> OTHER INFORMATION: synthetic peptide

<400> SEQUENCE: 51

Ser Ile Asn Gly Arg Gly Asp Asp Thr Arg Tyr Ala Asp Ser Val Lys
1               5                   10                  15

Gly

<210> SEQ ID NO 52
<211> LENGTH: 17
<212> TYPE: PRT
<213> ORGANISM: artificial sequence
<220> FEATURE:
<223> OTHER INFORMATION: synthetic peptide

<400> SEQUENCE: 52

Ala Ile Ser Ala Asp Ser Ser Thr Lys Asn Tyr Ala Asp Ser Val Lys
1               5                   10                  15

Gly

<210> SEQ ID NO 53
<211> LENGTH: 17
<212> TYPE: PRT
<213> ORGANISM: artificial sequence
<220> FEATURE:
<223> OTHER INFORMATION: synthetic peptide

<400> SEQUENCE: 53

Ala Ile Ser Ala Asp Ser Ser Asp Lys Arg Tyr Ala Asp Ser Val Lys
1               5                   10                  15

Gly

<210> SEQ ID NO 54
<211> LENGTH: 17
<212> TYPE: PRT
<213> ORGANISM: artificial sequence
<220> FEATURE:
<223> OTHER INFORMATION: synthetic peptide

<400> SEQUENCE: 54

Arg Ile Ser Thr Gly Gly Gly Tyr Ser Tyr Tyr Ala Asp Ser Val Lys
1               5                   10                  15

Gly

<210> SEQ ID NO 55
<211> LENGTH: 13
<212> TYPE: PRT
<213> ORGANISM: artificial sequence
<220> FEATURE:
<223> OTHER INFORMATION: synthetic peptide
```

```
<400> SEQUENCE: 55

Asp Arg Glu Ala Gln Val Asp Thr Leu Asp Phe Asp Tyr
1               5                   10

<210> SEQ ID NO 56
<211> LENGTH: 6
<212> TYPE: PRT
<213> ORGANISM: artificial sequence
<220> FEATURE:
<223> OTHER INFORMATION: synthetic peptide

<400> SEQUENCE: 56

Gly Gly Ser Leu Ser Arg
1               5

<210> SEQ ID NO 57
<211> LENGTH: 8
<212> TYPE: PRT
<213> ORGANISM: artificial sequence
<220> FEATURE:
<223> OTHER INFORMATION: synthetic peptide

<400> SEQUENCE: 57

Arg Arg Thr Trp His Ser Glu Leu
1               5

<210> SEQ ID NO 58
<211> LENGTH: 7
<212> TYPE: PRT
<213> ORGANISM: artificial sequence
<220> FEATURE:
<223> OTHER INFORMATION: synthetic peptide

<400> SEQUENCE: 58

Gly Arg Ser Val Ser Arg Ser
1               5

<210> SEQ ID NO 59
<211> LENGTH: 5
<212> TYPE: PRT
<213> ORGANISM: artificial sequence
<220> FEATURE:
<223> OTHER INFORMATION: synthetic peptide

<400> SEQUENCE: 59

Gly Arg Gly Ser Pro
1               5

<210> SEQ ID NO 60
<211> LENGTH: 122
<212> TYPE: PRT
<213> ORGANISM: artificial sequence
<220> FEATURE:
<223> OTHER INFORMATION: synthetic peptide

<400> SEQUENCE: 60

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
                20                  25                  30

Ala Met Gly Met Tyr Arg Gln Ala Pro Gly Lys Gln Arg Glu Leu Val
            35                  40                  45

Ala Thr Ile Thr Ser Gly Gly Ser Thr Asn Tyr Ala Asp Pro Val Lys
        50                  55                  60

Gly Arg Phe Thr Ile Ser Arg Asp Gly Pro Lys Asn Thr Val Tyr Leu
```

```
                65                  70                  75                  80
Gln Met Asn Ser Leu Lys Pro Glu Asp Thr Ala Val Tyr Tyr Cys Tyr
                    85                  90                  95

Ala Asn Leu Lys Gln Gly Ser Tyr Gly Tyr Arg Phe Asn Asp Tyr Trp
                100                 105                 110

Gly Gln Gly Thr Gln Val Thr Val Ser Ser
                115                 120

<210> SEQ ID NO 61
<211> LENGTH: 126
<212> TYPE: PRT
<213> ORGANISM: artificial sequence
<220> FEATURE:
<223> OTHER INFORMATION: synthetic peptide

<400> SEQUENCE: 61

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
                20                  25                  30

Gly Met Gly Trp Phe Arg Gln Ala Pro Gly Lys Glu Arg Glu Phe Val
            35                  40                  45

Thr Ser Ile Ser Trp Ser Gly Thr Tyr Thr Ala Tyr Ser Asp Asn Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gln Ser Arg Tyr Arg Ser Asn Tyr Tyr Asp His Asp Asp Lys
                100                 105                 110

Tyr Ala Tyr Trp Gly Gln Gly Thr Gln Val Thr Val Ser Ser
            115                 120                 125

<210> SEQ ID NO 62
<211> LENGTH: 128
<212> TYPE: PRT
<213> ORGANISM: artificial sequence
<220> FEATURE:
<223> OTHER INFORMATION: synthetic peptide

<400> SEQUENCE: 62

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
                20                  25                  30

Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
                100                 105                 110

Ser Glu Tyr Asn Phe Trp Gly Gln Gly Thr Gln Val Thr Val Ser Ser
            115                 120                 125
```

```
<210> SEQ ID NO 63
<211> LENGTH: 126
<212> TYPE: PRT
<213> ORGANISM: artificial sequence
<220> FEATURE:
<223> OTHER INFORMATION: synthetic peptide

<400> SEQUENCE: 63
```

| Ala | Val | Gln | Leu | Val | Asp | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Glu | Arg | Thr | Thr | Phe | Ser | Ser |
|---|---|---|---|---|---|---|---|---|---|---|---|---|---|---|---|
| | | | 20 | | | | | 25 | | | | | 30 | | |

| Tyr | Thr | Leu | Gly | Trp | Phe | Arg | Gln | Ala | Pro | Gly | Lys | Glu | Arg | Glu | Phe |
|---|---|---|---|---|---|---|---|---|---|---|---|---|---|---|---|
| | | | 35 | | | | | 40 | | | | | 45 | | |

| Val | Gly | Gly | Ile | Ser | Trp | Ser | Gly | Val | Ser | Thr | Asp | Tyr | Ala | Glu | Phe |
|---|---|---|---|---|---|---|---|---|---|---|---|---|---|---|---|
| | 50 | | | | | 55 | | | | | 60 | | | | |

| Ala | Lys | Gly | Arg | Phe | Thr | Ile | Ser | Arg | Asp | His | Ala | Ala | Asn | Thr | Val |
|---|---|---|---|---|---|---|---|---|---|---|---|---|---|---|---|
| 65 | | | | | 70 | | | | | 75 | | | | | 80 |

| Tyr | Leu | Glu | Met | Asn | Ser | Leu | Lys | Pro | Glu | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Ala | Leu | Gly | Arg | Tyr | Arg | Ser | Asn | Trp | Arg | Asn | Ile | Gly | Gln |
|---|---|---|---|---|---|---|---|---|---|---|---|---|---|---|---|
| | | | 100 | | | | | 105 | | | | | 110 | | |

| Tyr | Asp | Tyr | Trp | Gly | Gln | Gly | Thr | Gln | Val | Thr | Val | Ser | Ser |
|---|---|---|---|---|---|---|---|---|---|---|---|---|---|
| | | 115 | | | | | 120 | | | | | 125 | |

```
<210> SEQ ID NO 64
<211> LENGTH: 126
<212> TYPE: PRT
<213> ORGANISM: artificial sequence
<220> FEATURE:
<223> OTHER INFORMATION: synthetic peptide

<400> SEQUENCE: 64
```

| Glu | Val | Gln | Leu | Val | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Arg | Thr | Phe | Asn | Asn | Tyr |
|---|---|---|---|---|---|---|---|---|---|---|---|---|---|---|---|
| | | | 20 | | | | | 25 | | | | | 30 | | |

| Gly | Met | Gly | Trp | Phe | Arg | Gln | Ala | Pro | Gly | Lys | Glu | Arg | Glu | Phe | Val |
|---|---|---|---|---|---|---|---|---|---|---|---|---|---|---|---|
| | | | 35 | | | | | 40 | | | | | 45 | | |

| Thr | Ser | Ile | Ser | Trp | Ser | Gly | Ser | Tyr | Thr | Ala | Tyr | Ala | Asp | Asn | Val |
|---|---|---|---|---|---|---|---|---|---|---|---|---|---|---|---|
| | | | | 50 | | | | | 55 | | | | | 60 | |

| Lys | Gly | Arg | Phe | Thr | Ile | Ser | Arg | Asp | Asn | Ala | Lys | Asn | Thr | Val | Tyr |
|---|---|---|---|---|---|---|---|---|---|---|---|---|---|---|---|
| 65 | | | | | 70 | | | | | 75 | | | | | 80 |

| Leu | Gln | Met | Asp | Ser | Leu | Lys | Pro | Gly | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ala | Gln | Ser | Arg | Tyr | Ser | Ser | Asn | Tyr | Tyr | Asp | His | Asp | Asp | Lys |
|---|---|---|---|---|---|---|---|---|---|---|---|---|---|---|---|
| | | | 100 | | | | | 105 | | | | | 110 | | |

| Tyr | Ala | Tyr | Trp | Gly | Gln | Gly | Thr | Gln | Val | Thr | Val | Ser | Ser |
|---|---|---|---|---|---|---|---|---|---|---|---|---|---|
| | | 115 | | | | | 120 | | | | | 125 | |

```
<210> SEQ ID NO 65
<211> LENGTH: 116
<212> TYPE: PRT
<213> ORGANISM: artificial sequence
<220> FEATURE:
<223> OTHER INFORMATION: synthetic peptide

<400> SEQUENCE: 65
```

| Ala | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

```
Ser Leu Lys Leu Ser Cys Ala Thr Ser Gly Ser Ile Phe Ser Ser Ser
            20                  25                  30

Ala Met Ala Trp Tyr Arg Gln Ala Ser Gly Lys Gln Arg Glu Leu Val
        35                  40                  45

Ala Thr Ile Thr Ser Gly Gly Arg Thr Ser Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Asp Cys Asn
                85                  90                  95

Phe Val Val Asp Gly Lys Arg Ala Pro Trp Gly Gln Gly Thr Gln Val
            100                 105                 110

Thr Val Ser Ser
        115
```

<210> SEQ ID NO 66
<211> LENGTH: 125
<212> TYPE: PRT
<213> ORGANISM: artificial sequence
<220> FEATURE:
<223> OTHER INFORMATION: synthetic peptide

<400> SEQUENCE: 66

```
Ala Val Gln Leu Val Glu Ser Gly Gly Gly Leu Val Gln Ala Gly Glu
1               5                   10                  15

Ser Leu Arg Leu Ser Cys Thr Ser Ser Gly Arg Ala Phe Ser Tyr Tyr
            20                  25                  30

Asn Thr Gly Trp Phe Arg Gln Ala Pro Gly Lys Glu Arg Glu Phe Val
        35                  40                  45

Ala Ala Ile Ser Trp Ser Gly Leu Thr Tyr Tyr Ala Asp Ser Val
    50                  55                  60

Lys Gly Arg Phe Thr Ile Ser Arg Asp Asn Ala Lys Asp Met Val Tyr
65                  70                  75                  80

Leu Gln Met Ala Ser Leu Lys Pro Glu Asp Thr Ala Val Tyr Tyr Cys
                85                  90                  95

Ala Ala Asn Arg Arg Gln Lys Thr Val Gln Met Gly Glu Arg Ala Tyr
            100                 105                 110

Asp Tyr Trp Gly Gln Gly Thr Gln Val Thr Val Ser Ser
            115                 120                 125
```

<210> SEQ ID NO 67
<211> LENGTH: 122
<212> TYPE: PRT
<213> ORGANISM: artificial sequence
<220> FEATURE:
<223> OTHER INFORMATION: synthetic peptide

<400> SEQUENCE: 67

```
Gln Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Leu Tyr Arg Gln Ala Pro Gly Lys Gln Arg Glu Leu Val
        35                  40                  45

Ala Thr Ile Thr Ser Gly Gly Ser Thr Asn Tyr Ala Asp Ser Val Lys
    50                  55                  60

Gly Arg Phe Thr Ile Ser Arg Asp Gly Pro Lys Asn Thr Val Tyr Leu
65                  70                  75                  80
```

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser
        115                 120

<210> SEQ ID NO 68
<211> LENGTH: 122
<212> TYPE: PRT
<213> ORGANISM: artificial sequence
<220> FEATURE:
<223> OTHER INFORMATION: synthetic peptide

<400> SEQUENCE: 68

Ala Val Gln Leu Glu Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Leu Tyr Arg Gln Ala Pro Gly Lys Gln Arg Glu Leu Val
        35                  40                  45

Ala Thr Ile Thr Ser Gly Gly Ser Thr Asn Tyr Ala Asp Ser Val Lys
    50                  55                  60

Gly Arg Phe Thr Ile Ser Arg Asp Gly Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Asp Tyr Gly Tyr Arg Phe Asn Asp Tyr Trp
            100                 105                 110

Gly Gln Gly Thr Gln Val Thr Val Ser Ser
        115                 120

<210> SEQ ID NO 69
<211> LENGTH: 122
<212> TYPE: PRT
<213> ORGANISM: artificial sequence
<220> FEATURE:
<223> OTHER INFORMATION: synthetic peptide

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Thr Met Gly Leu Tyr Arg Gln Ala Pro Gly Lys Gln Arg Glu Leu Val
        35                  40                  45

Ala Thr Ile Thr Ser Gly Gly Ser Thr Asn Tyr Ala Asp Ser Val Lys
    50                  55                  60

Gly Arg Phe Thr Ile Ser Arg Asp Gly Ala Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Ala Asn Leu Lys Gln Gly Asp Tyr Gly Tyr Arg Phe Asn Asp Tyr Trp
            100                 105                 110

Gly Gln Gly Thr Gln Val Thr Val Ser Ser
        115                 120

<210> SEQ ID NO 70
<211> LENGTH: 122

```
<212> TYPE: PRT
<213> ORGANISM: artificial sequence
<220> FEATURE:
<223> OTHER INFORMATION: synthetic peptide

<400> SEQUENCE: 70

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Thr Met Gly Leu Tyr Arg Gln Ala Pro Gly Lys Gln Arg Glu Leu Val
        35                  40                  45

Ala Thr Ile Thr Ser Gly Gly Ser Thr Asn Tyr Ala Asp Ser Val Lys
    50                  55                  60

Gly Arg Phe Thr Ile Ser Arg Asp Gly Ala Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Ala Asn Leu Lys Gln Gly Asp Tyr Tyr Arg Phe Asn Asp Tyr Trp
            100                 105                 110

Gly Gln Gly Thr Gln Val Thr Val Ser Ser
        115                 120

<210> SEQ ID NO 71
<211> LENGTH: 128
<212> TYPE: PRT
<213> ORGANISM: artificial sequence
<220> FEATURE:
<223> OTHER INFORMATION: synthetic peptide

<400> SEQUENCE: 71

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

<210> SEQ ID NO 72
<211> LENGTH: 128
<212> TYPE: PRT
<213> ORGANISM: artificial sequence
<220> FEATURE:
<223> OTHER INFORMATION: synthetic peptide

<400> SEQUENCE: 72

Gln Val Lys Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30
```

Pro Met Gly Trp Phe Arg Gln Ala Pro Gly Arg Glu Arg Asp Val Val
            35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Ser Leu Pro
            100                 105                 110

Ser Glu Tyr Thr Phe Trp Gly Gln Gly Thr Gln Val Thr Val Ser Ser
            115                 120                 125

<210> SEQ ID NO 73
<211> LENGTH: 128
<212> TYPE: PRT
<213> ORGANISM: artificial sequence
<220> FEATURE:
<223> OTHER INFORMATION: synthetic peptide

<400> SEQUENCE: 73

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
            35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Met Val Tyr
65                  70                  75                  80

Leu Glu Met Asn Asn Leu Lys Pro Asp Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

<210> SEQ ID NO 74
<211> LENGTH: 259
<212> TYPE: PRT
<213> ORGANISM: artificial sequence
<220> FEATURE:
<223> OTHER INFORMATION: synthetic peptide

<400> SEQUENCE: 74

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
            35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

```
Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
            195                 200                 205

Met Val Tyr Leu Gln Met Asn Asn Leu Lys Pro Glu Asp Thr Ala Val
            210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 75
<211> LENGTH: 265
<212> TYPE: PRT
<213> ORGANISM: artificial sequence
<220> FEATURE:
<223> OTHER INFORMATION: synthetic peptide

<400> SEQUENCE: 75

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Ser Glu Val Gln Leu Val Glu Ser
            130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Glu Arg Asp Leu Val Ala Ala Ile Ser Arg Thr Gly
            180                 185                 190

Gly Ser Thr Tyr Tyr Pro Asp Ser Val Glu Gly Arg Phe Thr Ile Ser
```

```
                195                 200                 205
Arg Asp Asn Ala Lys Arg Met Val Tyr Leu Gln Met Asn Asn Leu Lys
    210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265

<210> SEQ ID NO 76
<211> LENGTH: 286
<212> TYPE: PRT
<213> ORGANISM: artificial sequence
<220> FEATURE:
<223> OTHER INFORMATION: synthetic peptide

<400> SEQUENCE: 76

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Asn Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Gly Ser Gly Gly Gly Gly Ser Glu Val
145                 150                 155                 160

Gln Leu Val Glu Ser Gly Gly Gly Leu Val Gln Ala Gly Gly Ala Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Glu Arg Asp Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Met Val Tyr Leu Gln
225                 230                 235                 240

Met Asn Asn Leu Lys Pro Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
        275                 280                 285

<210> SEQ ID NO 77
```

```
<211> LENGTH: 247
<212> TYPE: PRT
<213> ORGANISM: artificial sequence
<220> FEATURE:
<223> OTHER INFORMATION: synthetic peptide

<400> SEQUENCE: 77

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Ala Ala Ala Glu Val Gln
        115                 120                 125

Leu Val Glu Ser Gly Gly Gly Leu Val Gln Pro Gly Gly Ser Leu Arg
    130                 135                 140

Leu Ser Cys Leu Ala Ser Gly Arg Ile Phe Ser Ile Gly Ala Met Gly
145                 150                 155                 160

Met Tyr Arg Gln Ala Pro Gly Lys Gln Arg Glu Leu Val Ala Thr Ile
                165                 170                 175

Thr Ser Gly Gly Ser Thr Asn Tyr Ala Asp Pro Val Lys Gly Arg Phe
            180                 185                 190

Thr Ile Ser Arg Asp Gly Pro Lys Asn Thr Val Tyr Leu Gln Met Asn
        195                 200                 205

Ser Leu Lys Pro Glu Asp Thr Ala Val Tyr Tyr Cys Tyr Ala Asn Leu
    210                 215                 220

Lys Gln Gly Ser Tyr Gly Tyr Arg Phe Asn Asp Tyr Trp Gly Gln Gly
225                 230                 235                 240

Thr Gln Val Thr Val Ser Ser
                245

<210> SEQ ID NO 78
<211> LENGTH: 253
<212> TYPE: PRT
<213> ORGANISM: artificial sequence
<220> FEATURE:
<223> OTHER INFORMATION: synthetic peptide

<400> SEQUENCE: 78

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Pro Lys Asn Thr Val Tyr Leu
65                  70                  75                  80
```

```
Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Gly Gly Gly Gly Ser Gly
        115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Leu Ala Ser Gly Arg Ile Phe
145                 150                 155                 160

Ser Ile Gly Ala Met Gly Met Tyr Arg Gln Ala Pro Gly Lys Gln Arg
                165                 170                 175

Glu Leu Val Ala Thr Ile Thr Ser Gly Gly Ser Thr Asn Tyr Ala Asp
            180                 185                 190

Pro Val Lys Gly Arg Phe Thr Ile Ser Arg Asp Gly Pro Lys Asn Thr
        195                 200                 205

Val Tyr Leu Gln Met Asn Ser Leu Lys Pro Glu Asp Thr Ala Val Tyr
    210                 215                 220

Tyr Cys Tyr Ala Asn Leu Lys Gln Gly Ser Tyr Gly Tyr Arg Phe Asn
225                 230                 235                 240

Asp Tyr Trp Gly Gln Gly Thr Gln Val Thr Val Ser Ser
            245                 250

<210> SEQ ID NO 79
<211> LENGTH: 274
<212> TYPE: PRT
<213> ORGANISM: artificial sequence
<220> FEATURE:
<223> OTHER INFORMATION: synthetic peptide

<400> SEQUENCE: 79

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser Ile Gly
            20                  25                  30

Ala Met Gly Met Tyr Arg Gln Ala Pro Gly Lys Gln Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Pro Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser Gly Gly Gly Gly Ser Gly
        115                 120                 125

Gly Gly Ser Gly Gly Gly Gly Ser Gly Gly Gly Gly Ser Gly Gly Gly
130                 135                 140

Gly Gly Ser Gly Gly Gly Ser Glu Val Gln Leu Val Glu Ser Gly Gly
145                 150                 155                 160

Gly Leu Val Gln Pro Gly Gly Ser Leu Arg Leu Ser Cys Leu Ala Ser
                165                 170                 175

Gly Arg Ile Phe Ser Ile Gly Ala Met Gly Met Tyr Arg Gln Ala Pro
            180                 185                 190
```

Pro Gly Lys Gln Arg Glu Leu Val Ala Thr Ile Thr Ser Gly Gly Ser
           195                 200                 205

Thr Asn Tyr Ala Asp Pro Val Lys Gly Arg Phe Thr Ile Ser Arg Asp
210                 215                 220

Gly Pro Lys Asn Thr Val Tyr Leu Gln Met Asn Ser Leu Lys Pro Glu
225                 230                 235                 240

Asp Thr Ala Val Tyr Tyr Cys Tyr Ala Asn Leu Lys Gln Gly Ser Tyr
                245                 250                 255

Gly Tyr Arg Phe Asn Asp Tyr Trp Gly Gln Gly Thr Gln Val Thr Val
            260                 265                 270

Ser Ser

<210> SEQ ID NO 80
<211> LENGTH: 259
<212> TYPE: PRT
<213> ORGANISM: artificial sequence
<220> FEATURE:
<223> OTHER INFORMATION: synthetic peptide

<400> SEQUENCE: 80

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Ala Gly Gly Ala Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Glu Arg
                165                 170                 175

Asp Val Val Ala Ala Ile Ser Arg Thr Gly Gly Ser Thr Tyr Tyr Ala
            180                 185                 190

Arg Ser Val Glu Gly Arg Phe Thr Ile Ser Arg Asp Asn Ala Lys Arg
        195                 200                 205

Met Val Tyr Leu Gln Met Asn Ala Leu Lys Pro Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Asn Phe Trp Gly Gln Gly Thr Gln Val Thr
                245                 250                 255

Val Ser Ser

<210> SEQ ID NO 81
<211> LENGTH: 265

```
<212> TYPE: PRT
<213> ORGANISM: artificial sequence
<220> FEATURE:
<223> OTHER INFORMATION: synthetic peptide

<400> SEQUENCE: 81

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ala Leu Lys Pro Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
130                 135                 140

Gly Gly Gly Leu Val Gln Ala Gly Gly Ala Leu Arg Leu Ser Cys Ala
145                 150                 155                 160

Ala Ser Gly Arg Thr Phe Ser Tyr Asn Pro Met Gly Trp Phe Arg Gln
            165                 170                 175

Ala Pro Gly Lys Glu Arg Asp Val Val Ala Ala Ile Ser Arg Thr Gly
        180                 185                 190

Gly Ser Thr Tyr Tyr Ala Arg Ser Val Glu Gly Arg Phe Thr Ile Ser
            195                 200                 205

Arg Asp Asn Ala Lys Arg Met Val Tyr Leu Gln Met Asn Ala Leu Lys
        210                 215                 220

Pro Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Asn Phe Trp Gly
                245                 250                 255

Gln Gly Thr Gln Val Thr Val Ser Ser
            260                 265

<210> SEQ ID NO 82
<211> LENGTH: 286
<212> TYPE: PRT
<213> ORGANISM: artificial sequence
<220> FEATURE:
<223> OTHER INFORMATION: synthetic peptide

<400> SEQUENCE: 82

Gln Val Gln Leu Val Glu Ser Gly Gly Gly Leu Val Gln Ala Gly Gly
1               5                   10                  15

Ala Leu Arg Leu Ser Cys Ala Ala Ser Gly Arg Thr Phe Ser Tyr Asn
            20                  25                  30

Pro Met Gly Trp Phe Arg Gln Ala Pro Gly Lys Glu Arg Asp Val Val
        35                  40                  45

Ala Ala Ile Ser Arg Thr Gly Gly Ser Thr Tyr Tyr Ala Arg Ser Val
    50                  55                  60
```

-continued

```
Glu Gly Arg Phe Thr Ile Ser Arg Asp Asn Ala Lys Arg Met Val Tyr
 65                  70                  75                  80

Leu Gln Met Asn Ala Leu Lys Pro Glu Asp Thr Ala Val Tyr Tyr Cys
                 85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

Gly Gly Gly Gly Ser Gly Gly Gly Ser Gly Gly Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Ala Gly Gly Ala Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Glu Arg Asp Val Ala Ala
        195                 200                 205

Ile Ser Arg Thr Gly Gly Ser Thr Tyr Tyr Ala Arg Ser Val Glu Gly
    210                 215                 220

Arg Phe Thr Ile Ser Arg Asp Asn Ala Lys Arg Met Val Tyr Leu Gln
225                 230                 235                 240

Met Asn Ala Leu Lys Pro Glu Asp Thr Ala Val Tyr Tyr Cys Ala Ala
                245                 250                 255

Ala Gly Val Arg Ala Glu Asp Gly Arg Val Arg Thr Leu Pro Ser Glu
            260                 265                 270

Tyr Asn Phe Trp Gly Gln Gly Thr Gln Val Thr Val Ser Ser
        275                 280                 285

<210> SEQ ID NO 83
<211> LENGTH: 3
<212> TYPE: PRT
<213> ORGANISM: artificial sequence
<220> FEATURE:
<223> OTHER INFORMATION: synthetic peptide

<400> SEQUENCE: 83

Ala Ala Ala
1

<210> SEQ ID NO 84
<211> LENGTH: 9
<212> TYPE: PRT
<213> ORGANISM: artificial sequence
<220> FEATURE:
<223> OTHER INFORMATION: synthetic peptide

<400> SEQUENCE: 84

Gly Gly Gly Gly Ser Gly Gly Gly Ser
1               5

<210> SEQ ID NO 85
<211> LENGTH: 30
<212> TYPE: PRT
<213> ORGANISM: artificial sequence
<220> FEATURE:
<223> OTHER INFORMATION: synthetic peptide

<400> SEQUENCE: 85

Gly Gly Gly Gly Ser Gly Gly Gly Gly Ser Gly Gly Gly Gly Ser Gly
1               5                   10                  15
```

Gly Gly Gly Ser Gly Gly Gly Ser Gly Gly Gly Ser
            20              25              30

<210> SEQ ID NO 86
<211> LENGTH: 128
<212> TYPE: PRT
<213> ORGANISM: artificial sequence
<220> FEATURE:
<223> OTHER INFORMATION: synthetic peptide

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

<210> SEQ ID NO 87
<211> LENGTH: 128
<212> TYPE: PRT
<213> ORGANISM: artificial sequence
<220> FEATURE:
<223> OTHER INFORMATION: synthetic peptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

<210> SEQ ID NO 88
<211> LENGTH: 128
<212> TYPE: PRT
<213> ORGANISM: artificial sequence
<220> FEATURE:
<223> OTHER INFORMATION: synthetic peptide

```
<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Asn Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

<210> SEQ ID NO 89
<211> LENGTH: 128
<212> TYPE: PRT
<213> ORGANISM: artificial sequence
<220> FEATURE:
<223> OTHER INFORMATION: synthetic peptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Asp Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
        115                 120                 125

<210> SEQ ID NO 90
<211> LENGTH: 128
<212> TYPE: PRT
<213> ORGANISM: artificial sequence
<220> FEATURE:
<223> OTHER INFORMATION: synthetic peptide

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
```

```
                50                  55                  60
Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Thr Phe Trp Gly Gln Gly Thr Gln Val Thr Val Ser Ser
                115                 120                 125

<210> SEQ ID NO 91
<211> LENGTH: 128
<212> TYPE: PRT
<213> ORGANISM: artificial sequence
<220> FEATURE:
<223> OTHER INFORMATION: synthetic peptide

<400> SEQUENCE: 91

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Tyr Asn
                20                  25                  30

Pro Met Gly Trp Phe Arg Gln Ala Pro Gly Lys Gly Arg Glu Leu Val
             35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Asn Met Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Thr Phe Trp Gly Gln Gly Thr Gln Val Thr Val Ser Ser
                115                 120                 125

<210> SEQ ID NO 92
<211> LENGTH: 128
<212> TYPE: PRT
<213> ORGANISM: artificial sequence
<220> FEATURE:
<223> OTHER INFORMATION: synthetic peptide

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Tyr Asn
                20                  25                  30

Pro Met Gly Trp Phe Arg Gln Ala Pro Gly Lys Gly Arg Glu Leu Val
             35                  40                  45

Ala Ala Ile Ser Arg Thr Gly Gly Ser Thr Tyr Tyr Pro Asp Ser Val
 50                  55                  60

Glu Gly Arg Phe Thr Ile Ser Arg Asp Asn Ala Lys Arg Ser Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
                100                 105                 110

Ser Glu Tyr Thr Phe Trp Gly Gln Gly Thr Gln Val Thr Val Ser Ser
```

<210> SEQ ID NO 93
<211> LENGTH: 128
<212> TYPE: PRT
<213> ORGANISM: artificial sequence
<220> FEATURE:
<223> OTHER INFORMATION: synthetic peptide

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

<210> SEQ ID NO 94
<211> LENGTH: 128
<212> TYPE: PRT
<213> ORGANISM: artificial sequence
<220> FEATURE:
<223> OTHER INFORMATION: synthetic peptide

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Leu Val Thr Val Ser Ser
        115                 120                 125

<210> SEQ ID NO 95
<211> LENGTH: 122
<212> TYPE: PRT
<213> ORGANISM: artificial sequence
<220> FEATURE:
<223> OTHER INFORMATION: synthetic peptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Ile Gly
            20                  25                  30

Ala Met Gly Met Tyr Arg Gln Ala Pro Gly Lys Gly Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Pro Lys Asn Thr Val Tyr Leu
65                  70                  75                  80

Gln Met Asn Ser Leu Arg Ala Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser
            115                 120

<210> SEQ ID NO 96
<211> LENGTH: 122
<212> TYPE: PRT
<213> ORGANISM: artificial sequence
<220> FEATURE:
<223> OTHER INFORMATION: synthetic peptide

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Ile Gly
            20                  25                  30

Ala Met Gly Met Tyr Arg Gln Ala Pro Gly Lys Gly Arg Glu Leu Val
        35                  40                  45

Ala Thr Ile Thr Ser Gly Gly Ser Thr Asn Tyr Ala Asp Pro Val Lys
    50                  55                  60

Gly Arg Phe Thr Ile Ser Arg Asp Gly Ala Lys Asn Thr Val Tyr Leu
65                  70                  75                  80

Gln Met Asn Ser Leu Arg Ala Glu Asp Thr Ala Val Tyr Tyr Cys Tyr
                85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser
            115                 120

<210> SEQ ID NO 97
<211> LENGTH: 122
<212> TYPE: PRT
<213> ORGANISM: artificial sequence
<220> FEATURE:
<223> OTHER INFORMATION: synthetic peptide

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Ile Gly
            20                  25                  30

Ala Met Gly Met Tyr Arg Gln Ala Pro Gly Lys Gly Arg Glu Leu Val
        35                  40                  45

Ala Thr Ile Thr Ser Gly Gly Ser Thr Asn Tyr Ala Asp Pro Val Lys
    50                  55                  60

```
Gly Arg Phe Thr Ile Ser Arg Asp Asn Ala Lys Asn Thr Val Tyr Leu
 65                  70                  75                  80

Gln Met Asn Ser Leu Arg Ala Glu Asp Thr Ala Val Tyr Tyr Cys Tyr
                 85                  90                  95

Ala Asn Leu Lys Gln Gly Ser Tyr Gly Tyr Arg Phe Asn Asp Tyr Trp
            100                 105                 110

Gly Gln Gly Thr Gln Val Thr Val Ser Ser
        115                 120

<210> SEQ ID NO 98
<211> LENGTH: 259
<212> TYPE: PRT
<213> ORGANISM: artificial sequence
<220> FEATURE:
<223> OTHER INFORMATION: synthetic peptide

<400> SEQUENCE: 98

Glu Val Gln Leu Val Glu Ser Gly Gly Gly Leu Val Gln Pro Gly Gly
  1               5                  10                  15

Ser Leu Arg Leu Ser Cys Ala Ala Ser Gly Arg Thr Phe Ser Tyr Asn
             20                  25                  30

Pro Met Gly Trp Phe Arg Gln Ala Pro Gly Lys Gly Arg Glu Leu Val
         35                  40                  45

Ala Ala Ile Ser Arg Thr Gly Gly Ser Thr Tyr Tyr Pro Asp Ser Val
     50                  55                  60

Glu Gly Arg Phe Thr Ile Ser Arg Asp Asn Ala Lys Arg Met Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Met Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 99
<211> LENGTH: 259
<212> TYPE: PRT
<213> ORGANISM: artificial sequence
<220> FEATURE:
<223> OTHER INFORMATION: synthetic peptide
```

-continued

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Asp Ser Val Glu Gly Arg Phe Thr Ile Ser Arg Asp Asn Ala Lys Arg
        195                 200                 205

Ser Val Tyr Leu Gln Met Asn Ser Leu Arg Ala Glu Asp Thr Ala Val
    210                 215                 220

Tyr Tyr Cys Ala Ala Ala Gly Val Arg Ala Glu Asp Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 100
<211> LENGTH: 259
<212> TYPE: PRT
<213> ORGANISM: artificial sequence
<220> FEATURE:
<223> OTHER INFORMATION: synthetic peptide

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

```
Ala Ala Ala Gly Val Arg Ala Glu Asp Gly Arg Val Arg Thr Leu Pro
            100                 105                 110

Ser Glu Tyr Asn Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
        130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Val Val Ala Ala Ile Ser Arg Thr Gly Gly Ser Thr Tyr Tyr Ala
            180                 185                 190

Arg Ser Val Glu Gly Arg Phe Thr Ile Ser Arg Asp Asn Ala Lys Arg
            195                 200                 205

Met Val Tyr Leu Gln Met Asn Ser Leu Arg Ala Glu Asp Thr Ala Val
        210                 215                 220

Tyr Tyr Cys Ala Ala Ala Gly Val Arg Ala Glu Asp Gly Arg Val Arg
225                 230                 235                 240

Thr Leu Pro Ser Glu Tyr Asn Phe Trp Gly Gln Gly Thr Gln Val Thr
                245                 250                 255

Val Ser Ser

<210> SEQ ID NO 101
<211> LENGTH: 265
<212> TYPE: PRT
<213> ORGANISM: artificial sequence
<220> FEATURE:
<223> OTHER INFORMATION: synthetic peptide

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Glu Val Gln Leu Val Glu Ser
        130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
            180                 185                 190

Gly Ser Thr Tyr Tyr Pro Asp Ser Val Glu Gly Arg Phe Thr Ile Ser
            195                 200                 205
```

Arg Asp Asn Ala Lys Arg Met Val Tyr Leu Gln Met Asn Ser Leu Arg
    210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265

<210> SEQ ID NO 102
<211> LENGTH: 265
<212> TYPE: PRT
<213> ORGANISM: artificial sequence
<220> FEATURE:
<223> OTHER INFORMATION: synthetic peptide

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Ser Thr Tyr Tyr Pro Asp Ser Val
50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Glu Val Gln Leu Val Glu Ser
130                 135                 140

Gly Gly Gly Leu Val Gln Pro Gly Gly Ser Leu Arg Leu Ser Cys Ala
145                 150                 155                 160

Ala Ser Gly Arg Thr Phe Ser Tyr Asn Pro Met Gly Trp Phe Arg Gln
                165                 170                 175

Ala Pro Gly Lys Gly Arg Glu Leu Val Ala Ala Ile Ser Arg Thr Gly
            180                 185                 190

Gly Ser Thr Tyr Tyr Pro Asp Ser Val Glu Gly Arg Phe Thr Ile Ser
        195                 200                 205

Arg Asp Asn Ala Lys Arg Ser Val Tyr Leu Gln Met Asn Ser Leu Arg
    210                 215                 220

Ala Glu Asp Thr Ala Val Tyr Tyr Cys Ala Ala Ala Gly Val Arg Ala
225                 230                 235                 240

Glu Asp Gly Arg Val Arg Thr Leu Pro Ser Glu Tyr Thr Phe Trp Gly
                245                 250                 255

Gln Gly Thr Gln Val Thr Val Ser Ser
            260                 265

<210> SEQ ID NO 103
<211> LENGTH: 265
<212> TYPE: PRT
<213> ORGANISM: artificial sequence
<220> FEATURE:

<223> OTHER INFORMATION: synthetic peptide

<400> SEQUENCE: 103

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Ser Tyr Asn
            20                  25                  30
Pro Met Gly Trp Phe Arg Gln Ala Pro Gly Lys Gly Arg Glu Val Val
        35                  40                  45
Ala Ala Ile Ser Arg Thr Gly Gly Ser Thr Tyr Tyr Ala Arg Ser Val
    50                  55                  60
Glu Gly Arg Phe Thr Ile Ser Arg Asp Asn Ala Lys Arg Met Val Tyr
65                  70                  75                  80
Leu Gln Met Asn Ser Leu Arg Ala Glu Asp Thr Ala Val Tyr Tyr Cys
                85                  90                  95
Ala Ala Ala Gly Val Arg Ala Glu Asp Gly Arg Val Arg Thr Leu Pro
            100                 105                 110
Ser Glu Tyr Asn Phe Trp Gly Gln Gly Thr Gln Val Thr Val Ser Ser
        115                 120                 125
Gly Gly Gly Gly Ser Gly Gly Gly Ser Glu Val Gln Leu Val Glu Ser
    130                 135                 140
Gly Gly Gly Leu Val Gln Pro Gly Gly Ser Leu Arg Leu Ser Cys Ala
145                 150                 155                 160
Ala Ser Gly Arg Thr Phe Ser Tyr Asn Pro Met Gly Trp Phe Arg Gln
                165                 170                 175
Ala Pro Gly Lys Gly Arg Glu Val Val Ala Ala Ile Ser Arg Thr Gly
            180                 185                 190
Gly Ser Thr Tyr Tyr Ala Arg Ser Val Glu Gly Arg Phe Thr Ile Ser
        195                 200                 205
Arg Asp Asn Ala Lys Arg Met Val Tyr Leu Gln Met Asn Ser Leu Arg
    210                 215                 220
Ala Glu Asp Thr Ala Val Tyr Tyr Cys Ala Ala Ala Gly Val Arg Ala
225                 230                 235                 240
Glu Asp Gly Arg Val Arg Thr Leu Pro Ser Glu Tyr Asn Phe Trp Gly
                245                 250                 255
Gln Gly Thr Gln Val Thr Val Ser Ser
            260                 265
```

<210> SEQ ID NO 104
<211> LENGTH: 286
<212> TYPE: PRT
<213> ORGANISM: artificial sequence
<220> FEATURE:
<223> OTHER INFORMATION: synthetic peptide

<400> SEQUENCE: 104

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Arg Thr Phe Ser Tyr Asn
            20                  25                  30
Pro Met Gly Trp Phe Arg Gln Ala Pro Gly Lys Gly Arg Glu Leu Val
        35                  40                  45
Ala Ala Ile Ser Arg Thr Gly Gly Ser Thr Tyr Tyr Pro Asp Ser Val
    50                  55                  60
Glu Gly Arg Phe Thr Ile Ser Arg Asp Asn Ala Lys Arg Met Val Tyr
65                  70                  75                  80
```

```
Leu Gln Met Asn Ser Leu Arg Ala Glu Asp Thr Ala Val Tyr Tyr Cys
                 85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
                165                 170                 175

Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Met Val Tyr Leu Gln
225                 230                 235                 240

Met Asn Ser Leu Arg Ala Glu Asp Thr Ala Val Tyr Cys Ala Ala
                245                 250                 255

Ala Gly Val Arg Ala Glu Asp Gly Arg Val Arg Thr Leu Pro Ser Glu
            260                 265                 270

Tyr Thr Phe Trp Gly Gln Gly Thr Gln Val Thr Val Ser Ser
        275                 280                 285

<210> SEQ ID NO 105
<211> LENGTH: 286
<212> TYPE: PRT
<213> ORGANISM: artificial sequence
<220> FEATURE:
<223> OTHER INFORMATION: synthetic peptide

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Asp Ser Val
    50                  55                  60

Glu Gly Arg Phe Thr Ile Ser Arg Asp Asn Ala Lys Arg Ser Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Asp Gly Arg Val Arg Thr Leu Pro
            100                 105                 110

Ser Glu Tyr Thr Phe Trp Gly Gln Gly Thr Gln Val Thr Val Ser Ser
        115                 120                 125

Gly Gly Gly Gly Ser Gly Gly Gly Ser Gly Gly Gly Ser Gly
    130                 135                 140

Gly Gly Gly Ser Gly Gly Gly Ser Gly Gly Gly Ser Glu Val
145                 150                 155                 160

Gln Leu Val Glu Ser Gly Gly Leu Val Gln Pro Gly Gly Ser Leu
```

```
                165                 170                 175
Arg Leu Ser Cys Ala Ala Ser Gly Arg Thr Phe Ser Tyr Asn Pro Met
            180                 185                 190

Gly Trp Phe Arg Gln Ala Pro Gly Lys Gly Arg Glu Leu Val Ala Ala
        195                 200                 205

Ile Ser Arg Thr Gly Gly Ser Thr Tyr Tyr Pro Asp Ser Val Glu Gly
    210                 215                 220

Arg Phe Thr Ile Ser Arg Asp Asn Ala Lys Arg Ser Val Tyr Leu Gln
225                 230                 235                 240

Met Asn Ser Leu Arg Ala Glu Asp Thr Ala Val Tyr Tyr Cys Ala Ala
            245                 250                 255

Ala Gly Val Arg Ala Glu Asp Gly Arg Val Arg Thr Leu Pro Ser Glu
        260                 265                 270

Tyr Thr Phe Trp Gly Gln Gly Thr Gln Val Thr Val Ser Ser
    275                 280                 285

<210> SEQ ID NO 106
<211> LENGTH: 286
<212> TYPE: PRT
<213> ORGANISM: artificial sequence
<220> FEATURE:
<223> OTHER INFORMATION: synthetic peptide

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Val Val
        35                  40                  45

Ala Ala Ile Ser Arg Thr Gly Gly Ser Thr Tyr Tyr Ala Arg Ser Val
    50                  55                  60

Glu Gly Arg Phe Thr Ile Ser Arg Asp Asn Ala Lys Arg Met Val Tyr
65                  70                  75                  80

Leu Gln Met Asn Ser Leu Arg Ala Glu Asp Thr Ala Val Tyr Tyr Cys
            85                  90                  95

Ala Ala Ala Gly Val Arg Ala Glu Asp Gly Arg Val Arg Thr Leu Pro
        100                 105                 110

Ser Glu Tyr Asn Phe Trp Gly Gln Gly Thr Gln Val Thr Val Ser Ser
    115                 120                 125

Gly Gly Gly Gly Ser Gly Gly Gly Ser Gly Gly Gly Gly Ser Gly
130                 135                 140

Gly Gly Ser Gly Gly Gly Ser Gly Gly Gly Ser Glu Val
145                 150                 155                 160

Gln Leu Val Glu Ser Gly Gly Gly Leu Val Gln Pro Gly Gly Ser Leu
            165                 170                 175

Arg Leu Ser Cys Ala Ala Ser Gly Arg Thr Phe Ser Tyr Asn Pro Met
        180                 185                 190

Gly Trp Phe Arg Gln Ala Pro Gly Lys Gly Arg Glu Val Val Ala Ala
    195                 200                 205

Ile Ser Arg Thr Gly Gly Ser Thr Tyr Tyr Ala Arg Ser Val Glu Gly
    210                 215                 220

Arg Phe Thr Ile Ser Arg Asp Asn Ala Lys Arg Met Val Tyr Leu Gln
225                 230                 235                 240

Met Asn Ser Leu Arg Ala Glu Asp Thr Ala Val Tyr Tyr Cys Ala Ala
            245                 250                 255
```

```
Ala Gly Val Arg Ala Glu Asp Gly Arg Val Arg Thr Leu Pro Ser Glu
            260                 265                 270

Tyr Asn Phe Trp Gly Gln Gly Thr Gln Val Thr Val Ser Ser
            275                 280                 285

<210> SEQ ID NO 107
<211> LENGTH: 117
<212> TYPE: PRT
<213> ORGANISM: artificial sequence
<220> FEATURE:
<223> OTHER INFORMATION: synthetic peptide

<400> SEQUENCE: 107

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
            20                  25                  30

Leu Met Gly Trp Tyr Arg Gln Gly Pro Gly Asn Glu Arg Glu Leu Val
        35                  40                  45

Ala Thr Cys Ile Thr Val Gly Asp Ser Thr Asn Tyr Ala Asp Ser Val
    50                  55                  60

Lys Gly Arg Phe Thr Ile Ser Met Asp Tyr Thr Lys Gln Thr Val Tyr
65                  70                  75                  80

Leu His Met Asn Ser Leu Arg Pro Glu Asp Thr Gly Leu Tyr Tyr Cys
                85                  90                  95

Lys Ile Arg Arg Thr Trp His Ser Glu Leu Trp Gly Gln Gly Thr Gln
            100                 105                 110

Val Thr Val Ser Ser
        115

<210> SEQ ID NO 108
<211> LENGTH: 116
<212> TYPE: PRT
<213> ORGANISM: artificial sequence
<220> FEATURE:
<223> OTHER INFORMATION: synthetic peptide

<400> SEQUENCE: 108

Glu Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Trp Asp Ile Asn
            20                  25                  30

Leu Leu Gly Trp Tyr Arg Gln Gly Pro Gly Asn Glu Arg Glu Leu Val
        35                  40                  45

Ala Thr Ile Thr Val Gly Asp Ser Thr Ser Tyr Ala Asp Ser Val Lys
    50                  55                  60

Gly Arg Phe Thr Ile Ser Arg Asp Tyr Asp Lys Asn Thr Leu Tyr Leu
65                  70                  75                  80

Gln Met Asn Ser Leu Arg Pro Glu Asp Thr Gly Leu Tyr Tyr Cys Lys
                85                  90                  95

Ile Arg Arg Thr Trp His Ser Glu Leu Trp Gly Gln Gly Thr Gln Val
            100                 105                 110

Thr Val Ser Ser
        115

<210> SEQ ID NO 109
<211> LENGTH: 115
<212> TYPE: PRT
<213> ORGANISM: artificial sequence
```

```
<220> FEATURE:
<223> OTHER INFORMATION: synthetic peptide

<400> SEQUENCE: 109

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gly Gly Thr Gln Val Thr
            100                 105                 110

Val Ser Ser
        115

<210> SEQ ID NO 110
<211> LENGTH: 116
<212> TYPE: PRT
<213> ORGANISM: artificial sequence
<220> FEATURE:
<223> OTHER INFORMATION: synthetic peptide

<400> SEQUENCE: 110

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly Ser Phe
            20                  25                  30

Gly Met Ser Trp Val Arg Gln Tyr Pro Gly Lys Glu Pro Glu Trp Val
        35                  40                  45

Ser Ser Ile Asn Gly Arg Gly Asp Asp Thr Arg Tyr Ala Asp Ser Val
    50                  55                  60

Lys Gly Arg Phe Ser Ile Ser Arg Asp Asn Ala Lys Asn Thr Leu Tyr
65                  70                  75                  80

Leu Gln Met Asn Ser Leu Lys Pro Glu Asp Thr Ala Glu Tyr Tyr Cys
                85                  90                  95

Thr Ile Gly Arg Ser Val Ser Arg Ser Arg Thr Gln Gly Thr Gln Val
            100                 105                 110

Thr Val Ser Ser
        115

<210> SEQ ID NO 111
<211> LENGTH: 114
<212> TYPE: PRT
<213> ORGANISM: artificial sequence
<220> FEATURE:
<223> OTHER INFORMATION: synthetic peptide

<400> SEQUENCE: 111

Ala Val Gln Leu Val Glu Ser Gly Gly Gly Leu Val Gln Pro Gly Gly
1               5                   10                  15

Ser Leu Arg Leu Thr Cys Thr Ala Ser Gly Phe Thr Phe Arg Ser Phe
            20                  25                  30

Gly Met Ser Trp Val Arg Gln Ala Pro Gly Lys Asp Gln Glu Trp Val
```

```
              35                  40                  45
Ser Ala Ile Ser Ala Asp Ser Ser Thr Lys Asn Tyr Ala Asp Ser Val
 50                  55                  60

Lys Gly Arg Phe Thr Ile Ser Arg Asp Asn Ala Lys Lys Met Leu Tyr
 65                  70                  75                  80

Leu Glu Met Asn Ser Leu Lys Pro Glu Asp Thr Ala Val Tyr Tyr Cys
                 85                  90                  95

Val Ile Gly Arg Gly Ser Pro Ser Pro Gly Thr Gln Val Thr Val
                100                 105                 110

Ser Ser

<210> SEQ ID NO 112
<211> LENGTH: 114
<212> TYPE: PRT
<213> ORGANISM: artificial sequence
<220> FEATURE:
<223> OTHER INFORMATION: synthetic peptide

<400> SEQUENCE: 112

Gln Val Gln Leu Ala Glu Ser Gly Gly Gly Leu Val Gln Pro Gly Gly
 1               5                  10                  15

Ser Leu Arg Leu Thr Cys Thr Ala Ser Gly Phe Thr Phe Gly Ser Phe
                20                  25                  30

Gly Met Ser Trp Val Arg Gln Ala Pro Gly Glu Gly Leu Glu Trp Val
             35                  40                  45

Ser Ala Ile Ser Ala Asp Ser Ser Asp Lys Arg Tyr Ala Asp Ser Val
 50                  55                  60

Lys Gly Arg Phe Thr Ile Ser Arg Asp Asn Ala Lys Lys Met Leu Tyr
 65                  70                  75                  80

Leu Glu Met Asn Ser Leu Lys Ser Glu Asp Thr Ala Val Tyr Tyr Cys
                 85                  90                  95

Val Ile Gly Arg Gly Ser Pro Ala Ser Gln Gly Thr Gln Val Thr Val
                100                 105                 110

Ser Ser

<210> SEQ ID NO 113
<211> LENGTH: 123
<212> TYPE: PRT
<213> ORGANISM: artificial sequence
<220> FEATURE:
<223> OTHER INFORMATION: synthetic peptide

<400> SEQUENCE: 113

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Trp Met Tyr Trp Val Arg Val Ala Pro Gly Lys Gly Leu Glu Arg Ile
             35                  40                  45

Ser Arg Asp Ile Ser Thr Gly Gly Gly Tyr Ser Tyr Tyr Ala Asp Ser
 50                  55                  60

Val Lys Gly Arg Phe Thr Ile Ser Arg Asp Asn Ala Lys Asn Thr Leu
 65                  70                  75                  80

Tyr Leu Gln Met Asn Ser Leu Lys Pro Glu Asp Thr Ala Leu Tyr Tyr
                 85                  90                  95

Cys Ala Lys Asp Arg Glu Ala Gln Val Asp Thr Leu Asp Phe Asp Tyr
                100                 105                 110
```

-continued

Arg Gly Gln Gly Thr Gln Val Thr Val Ser Ser
            115                 120

<210> SEQ ID NO 114
<211> LENGTH: 115
<212> TYPE: PRT
<213> ORGANISM: artificial sequence
<220> FEATURE:
<223> OTHER INFORMATION: synthetic peptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 115
<211> LENGTH: 115
<212> TYPE: PRT
<213> ORGANISM: artificial sequence
<220> FEATURE:
<223> OTHER INFORMATION: synthetic peptide

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 116
<211> LENGTH: 115
<212> TYPE: PRT
<213> ORGANISM: artificial sequence
<220> FEATURE:
<223> OTHER INFORMATION: synthetic peptide

<400> SEQUENCE: 116

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Lys Pro Glu Asp Thr Ala Val Tyr Tyr Cys
                 85                  90                  95

Thr Ile Gly Gly Ser Leu Ser Arg Ser Ser Gly Gly Thr Gln Val Thr
             100                 105                 110

Val Ser Ser
        115

<210> SEQ ID NO 117
<211> LENGTH: 115
<212> TYPE: PRT
<213> ORGANISM: artificial sequence
<220> FEATURE:
<223> OTHER INFORMATION: synthetic peptide

<400> SEQUENCE: 117

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Gly Gln Gly Thr Leu Val Thr
             100                 105                 110

Val Ser Ser
        115

<210> SEQ ID NO 118
<211> LENGTH: 115
<212> TYPE: PRT
<213> ORGANISM: artificial sequence
<220> FEATURE:
<223> OTHER INFORMATION: synthetic peptide

<400> SEQUENCE: 118

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Lys Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 119
<211> LENGTH: 115
<212> TYPE: PRT
<213> ORGANISM: artificial sequence
<220> FEATURE:
<223> OTHER INFORMATION: synthetic peptide

<400> SEQUENCE: 119

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 120
<211> LENGTH: 115
<212> TYPE: PRT
<213> ORGANISM: artificial sequence
<220> FEATURE:
<223> OTHER INFORMATION: synthetic peptide

<400> SEQUENCE: 120

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115
```

```
<210> SEQ ID NO 121
<211> LENGTH: 115
<212> TYPE: PRT
<213> ORGANISM: artificial sequence
<220> FEATURE:
<223> OTHER INFORMATION: synthetic peptide

<400> SEQUENCE: 121

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 122
<211> LENGTH: 30
<212> TYPE: PRT
<213> ORGANISM: artificial sequence
<220> FEATURE:
<223> OTHER INFORMATION: synthetic peptide

<400> SEQUENCE: 122

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser
            20                  25                  30

<210> SEQ ID NO 123
<211> LENGTH: 30
<212> TYPE: PRT
<213> ORGANISM: artificial sequence
<220> FEATURE:
<223> OTHER INFORMATION: synthetic peptide

<400> SEQUENCE: 123

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 124
<211> LENGTH: 30
<212> TYPE: PRT
<213> ORGANISM: artificial sequence
<220> FEATURE:
<223> OTHER INFORMATION: synthetic peptide

<400> SEQUENCE: 124

Gln Val Gln Leu Val Glu Ser Gly Gly Gly Leu Val Gln Ala Gly Gly
1               5                   10                  15
```

Ala Leu Arg Leu Ser Cys Ala Ala Ser Gly Arg Thr Phe Ser
            20                  25                  30

<210> SEQ ID NO 125
<211> LENGTH: 30
<212> TYPE: PRT
<213> ORGANISM: artificial sequence
<220> FEATURE:
<223> OTHER INFORMATION: synthetic peptide

<400> SEQUENCE: 125

Ala Val Gln Leu Val Asp Ser Gly Gly Gly Leu Val Gln Ala Gly Gly
1               5                   10                  15

Ser Leu Arg Leu Ser Cys Thr Ala Ser Glu Arg Thr Thr Phe
            20                  25                  30

<210> SEQ ID NO 126
<211> LENGTH: 30
<212> TYPE: PRT
<213> ORGANISM: artificial sequence
<220> FEATURE:
<223> OTHER INFORMATION: synthetic peptide

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 127
<211> LENGTH: 30
<212> TYPE: PRT
<213> ORGANISM: artificial sequence
<220> FEATURE:
<223> OTHER INFORMATION: synthetic peptide

<400> SEQUENCE: 127

Ala Val Gln Leu Val Glu Ser Gly Gly Gly Leu Val Gln Pro Gly Gly
1               5                   10                  15

Ser Leu Lys Leu Ser Cys Ala Thr Ser Gly Ser Ile Phe Ser
            20                  25                  30

<210> SEQ ID NO 128
<211> LENGTH: 30
<212> TYPE: PRT
<213> ORGANISM: artificial sequence
<220> FEATURE:
<223> OTHER INFORMATION: synthetic peptide

<400> SEQUENCE: 128

Ala Val Gln Leu Val Glu Ser Gly Gly Gly Leu Val Gln Ala Gly Glu
1               5                   10                  15

Ser Leu Arg Leu Ser Cys Thr Ser Ser Gly Arg Ala Phe Ser
            20                  25                  30

<210> SEQ ID NO 129
<211> LENGTH: 30
<212> TYPE: PRT
<213> ORGANISM: artificial sequence
<220> FEATURE:
<223> OTHER INFORMATION: synthetic peptide

<400> SEQUENCE: 129

Gln Val Gln Leu Val Glu Ser Gly Gly Gly Leu Val Gln Pro Gly Gly
1               5                   10                  15

```
Ser Leu Arg Leu Ser Cys Leu Ala Ser Gly Arg Ile Phe Ser
            20                  25                  30

<210> SEQ ID NO 130
<211> LENGTH: 30
<212> TYPE: PRT
<213> ORGANISM: artificial sequence
<220> FEATURE:
<223> OTHER INFORMATION: synthetic peptide

<400> SEQUENCE: 130

Ala Val Gln Leu Glu Glu Ser Gly Gly Gly Leu Val Gln Pro Gly Gly
1               5                   10                  15

Ser Leu Arg Leu Ser Cys Leu Ala Ser Gly Arg Ile Phe Ser
            20                  25                  30

<210> SEQ ID NO 131
<211> LENGTH: 30
<212> TYPE: PRT
<213> ORGANISM: artificial sequence
<220> FEATURE:
<223> OTHER INFORMATION: synthetic peptide

<400> SEQUENCE: 131

Gln Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser
            20                  25                  30

<210> SEQ ID NO 132
<211> LENGTH: 30
<212> TYPE: PRT
<213> ORGANISM: artificial sequence
<220> FEATURE:
<223> OTHER INFORMATION: synthetic peptide

<400> SEQUENCE: 132

Ala Val Gln Leu Val Glu Ser Gly Gly Gly Leu Val Gln Pro Gly Gly
1               5                   10                  15

Ser Leu Arg Leu Ser Cys Leu Ala Ser Gly Arg Ile Phe Ser
            20                  25                  30

<210> SEQ ID NO 133
<211> LENGTH: 30
<212> TYPE: PRT
<213> ORGANISM: artificial sequence
<220> FEATURE:
<223> OTHER INFORMATION: synthetic peptide

<400> SEQUENCE: 133

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser
            20                  25                  30

<210> SEQ ID NO 134
<211> LENGTH: 30
<212> TYPE: PRT
<213> ORGANISM: artificial sequence
<220> FEATURE:
<223> OTHER INFORMATION: synthetic peptide

<400> SEQUENCE: 134

Gln Val Lys Leu Val Glu Ser Gly Gly Gly Leu Val Gln Ala Gly Gly
1               5                   10                  15
```

Ala Leu Arg Leu Ser Cys Ala Ala Ser Gly Arg Thr Phe Ser
            20                  25                  30

<210> SEQ ID NO 135
<211> LENGTH: 30
<212> TYPE: PRT
<213> ORGANISM: artificial sequence
<220> FEATURE:
<223> OTHER INFORMATION: synthetic peptide

<400> SEQUENCE: 135

Gln Val Lys Leu Glu Glu Ser Gly Gly Gly Leu Val Gln Ala Gly Gly
1               5                   10                  15

Ala Leu Arg Leu Ser Cys Ala Ala Ser Gly Arg Thr Phe Ser
            20                  25                  30

<210> SEQ ID NO 136
<211> LENGTH: 30
<212> TYPE: PRT
<213> ORGANISM: artificial sequence
<220> FEATURE:
<223> OTHER INFORMATION: synthetic peptide

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 137
<211> LENGTH: 30
<212> TYPE: PRT
<213> ORGANISM: artificial sequence
<220> FEATURE:
<223> OTHER INFORMATION: synthetic peptide

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 138
<211> LENGTH: 30
<212> TYPE: PRT
<213> ORGANISM: artificial sequence
<220> FEATURE:
<223> OTHER INFORMATION: synthetic peptide

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 139
<211> LENGTH: 30
<212> TYPE: PRT
<213> ORGANISM: artificial sequence
<220> FEATURE:
<223> OTHER INFORMATION: synthetic peptide

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 140
<211> LENGTH: 30
<212> TYPE: PRT
<213> ORGANISM: artificial sequence
<220> FEATURE:
<223> OTHER INFORMATION: synthetic peptide

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 141
<211> LENGTH: 30
<212> TYPE: PRT
<213> ORGANISM: artificial sequence
<220> FEATURE:
<223> OTHER INFORMATION: synthetic peptide

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 142
<211> LENGTH: 30
<212> TYPE: PRT
<213> ORGANISM: artificial sequence
<220> FEATURE:
<223> OTHER INFORMATION: synthetic peptide

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 143
<211> LENGTH: 30
<212> TYPE: PRT
<213> ORGANISM: artificial sequence
<220> FEATURE:
<223> OTHER INFORMATION: synthetic peptide

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 144
<211> LENGTH: 30
<212> TYPE: PRT
<213> ORGANISM: artificial sequence
<220> FEATURE:
<223> OTHER INFORMATION: synthetic peptide

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 145
<211> LENGTH: 30
<212> TYPE: PRT
<213> ORGANISM: artificial sequence
<220> FEATURE:
<223> OTHER INFORMATION: synthetic peptide

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser
            20                  25                  30

<210> SEQ ID NO 146
<211> LENGTH: 30
<212> TYPE: PRT
<213> ORGANISM: artificial sequence
<220> FEATURE:
<223> OTHER INFORMATION: synthetic peptide

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser
            20                  25                  30

<210> SEQ ID NO 147
<211> LENGTH: 30
<212> TYPE: PRT
<213> ORGANISM: artificial sequence
<220> FEATURE:
<223> OTHER INFORMATION: synthetic peptide

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser
            20                  25                  30

<210> SEQ ID NO 148
<211> LENGTH: 5
<212> TYPE: PRT
<213> ORGANISM: artificial sequence
<220> FEATURE:
<223> OTHER INFORMATION: synthetic peptide

<400> SEQUENCE: 148

Ile Gly Ala Met Gly
1               5

<210> SEQ ID NO 149
<211> LENGTH: 5
<212> TYPE: PRT
<213> ORGANISM: artificial sequence
<220> FEATURE:
<223> OTHER INFORMATION: synthetic peptide

<400> SEQUENCE: 149

Asn Tyr Gly Met Gly
1               5

<210> SEQ ID NO 150
<211> LENGTH: 5

```
<212> TYPE: PRT
<213> ORGANISM: artificial sequence
<220> FEATURE:
<223> OTHER INFORMATION: synthetic peptide

<400> SEQUENCE: 150

Tyr Asn Pro Met Gly
1               5

<210> SEQ ID NO 151
<211> LENGTH: 6
<212> TYPE: PRT
<213> ORGANISM: artificial sequence
<220> FEATURE:
<223> OTHER INFORMATION: synthetic peptide

<400> SEQUENCE: 151

Ser Ser Tyr Thr Leu Gly
1               5

<210> SEQ ID NO 152
<211> LENGTH: 5
<212> TYPE: PRT
<213> ORGANISM: artificial sequence
<220> FEATURE:
<223> OTHER INFORMATION: synthetic peptide

<400> SEQUENCE: 152

Asn Tyr Gly Met Gly
1               5

<210> SEQ ID NO 153
<211> LENGTH: 5
<212> TYPE: PRT
<213> ORGANISM: artificial sequence
<220> FEATURE:
<223> OTHER INFORMATION: synthetic peptide

<400> SEQUENCE: 153

Ser Ser Ala Met Ala
1               5

<210> SEQ ID NO 154
<211> LENGTH: 5
<212> TYPE: PRT
<213> ORGANISM: artificial sequence
<220> FEATURE:
<223> OTHER INFORMATION: synthetic peptide

<400> SEQUENCE: 154

Tyr Tyr Asn Thr Gly
1               5

<210> SEQ ID NO 155
<211> LENGTH: 5
<212> TYPE: PRT
<213> ORGANISM: artificial sequence
<220> FEATURE:
<223> OTHER INFORMATION: synthetic peptide

<400> SEQUENCE: 155

Ile Gly Ala Met Gly
1               5

<210> SEQ ID NO 156
<211> LENGTH: 5
<212> TYPE: PRT
<213> ORGANISM: artificial sequence
```

<220> FEATURE:
<223> OTHER INFORMATION: synthetic peptide

<400> SEQUENCE: 156

Ile Gly Ala Met Gly
1               5

<210> SEQ ID NO 157
<211> LENGTH: 5
<212> TYPE: PRT
<213> ORGANISM: artificial sequence
<220> FEATURE:
<223> OTHER INFORMATION: synthetic peptide

<400> SEQUENCE: 157

Ile Gly Thr Met Gly
1               5

<210> SEQ ID NO 158
<211> LENGTH: 5
<212> TYPE: PRT
<213> ORGANISM: artificial sequence
<220> FEATURE:
<223> OTHER INFORMATION: synthetic peptide

<400> SEQUENCE: 158

Ile Gly Thr Met Gly
1               5

<210> SEQ ID NO 159
<211> LENGTH: 5
<212> TYPE: PRT
<213> ORGANISM: artificial sequence
<220> FEATURE:
<223> OTHER INFORMATION: synthetic peptide

<400> SEQUENCE: 159

Tyr Asn Pro Met Gly
1               5

<210> SEQ ID NO 160
<211> LENGTH: 5
<212> TYPE: PRT
<213> ORGANISM: artificial sequence
<220> FEATURE:
<223> OTHER INFORMATION: synthetic peptide

<400> SEQUENCE: 160

Tyr Asn Pro Met Gly
1               5

<210> SEQ ID NO 161
<211> LENGTH: 5
<212> TYPE: PRT
<213> ORGANISM: artificial sequence
<220> FEATURE:
<223> OTHER INFORMATION: synthetic peptide

<400> SEQUENCE: 161

Tyr Asn Pro Met Gly
1               5

<210> SEQ ID NO 162
<211> LENGTH: 5
<212> TYPE: PRT
<213> ORGANISM: artificial sequence
<220> FEATURE:
<223> OTHER INFORMATION: synthetic peptide

<400> SEQUENCE: 162

Tyr Asn Pro Met Gly
1               5

<210> SEQ ID NO 163
<211> LENGTH: 5
<212> TYPE: PRT
<213> ORGANISM: artificial sequence
<220> FEATURE:
<223> OTHER INFORMATION: synthetic peptide

<400> SEQUENCE: 163

Tyr Asn Pro Met Gly
1               5

<210> SEQ ID NO 164
<211> LENGTH: 5
<212> TYPE: PRT
<213> ORGANISM: artificial sequence
<220> FEATURE:
<223> OTHER INFORMATION: synthetic peptide

<400> SEQUENCE: 164

Tyr Asn Pro Met Gly
1               5

<210> SEQ ID NO 165
<211> LENGTH: 5
<212> TYPE: PRT
<213> ORGANISM: artificial sequence
<220> FEATURE:
<223> OTHER INFORMATION: synthetic peptide

<400> SEQUENCE: 165

Tyr Asn Pro Met Gly
1               5

<210> SEQ ID NO 166
<211> LENGTH: 5
<212> TYPE: PRT
<213> ORGANISM: artificial sequence
<220> FEATURE:
<223> OTHER INFORMATION: synthetic peptide

<400> SEQUENCE: 166

Tyr Asn Pro Met Gly
1               5

<210> SEQ ID NO 167
<211> LENGTH: 5
<212> TYPE: PRT
<213> ORGANISM: artificial sequence
<220> FEATURE:
<223> OTHER INFORMATION: synthetic peptide

<400> SEQUENCE: 167

Tyr Asn Pro Met Gly
1               5

<210> SEQ ID NO 168
<211> LENGTH: 5
<212> TYPE: PRT
<213> ORGANISM: artificial sequence
<220> FEATURE:
<223> OTHER INFORMATION: synthetic peptide

<400> SEQUENCE: 168

Tyr Asn Pro Met Gly
1               5

<210> SEQ ID NO 169
<211> LENGTH: 5
<212> TYPE: PRT
<213> ORGANISM: artificial sequence
<220> FEATURE:
<223> OTHER INFORMATION: synthetic peptide

<400> SEQUENCE: 169

Tyr Asn Pro Met Gly
1               5

<210> SEQ ID NO 170
<211> LENGTH: 5
<212> TYPE: PRT
<213> ORGANISM: artificial sequence
<220> FEATURE:
<223> OTHER INFORMATION: synthetic peptide

<400> SEQUENCE: 170

Tyr Asn Pro Met Gly
1               5

<210> SEQ ID NO 171
<211> LENGTH: 5
<212> TYPE: PRT
<213> ORGANISM: artificial sequence
<220> FEATURE:
<223> OTHER INFORMATION: synthetic peptide

<400> SEQUENCE: 171

Ile Gly Ala Met Gly
1               5

<210> SEQ ID NO 172
<211> LENGTH: 5
<212> TYPE: PRT
<213> ORGANISM: artificial sequence
<220> FEATURE:
<223> OTHER INFORMATION: synthetic peptide

<400> SEQUENCE: 172

Ile Gly Ala Met Gly
1               5

<210> SEQ ID NO 173
<211> LENGTH: 5
<212> TYPE: PRT
<213> ORGANISM: artificial sequence
<220> FEATURE:
<223> OTHER INFORMATION: synthetic peptide

<400> SEQUENCE: 173

Ile Gly Ala Met Gly
1               5

<210> SEQ ID NO 174
<211> LENGTH: 14
<212> TYPE: PRT
<213> ORGANISM: artificial sequence
<220> FEATURE:
<223> OTHER INFORMATION: synthetic peptide

<400> SEQUENCE: 174

Met Tyr Arg Gln Ala Pro Gly Lys Gln Arg Glu Leu Val Ala

```
1               5                   10
```

<210> SEQ ID NO 175
<211> LENGTH: 14
<212> TYPE: PRT
<213> ORGANISM: artificial sequence
<220> FEATURE:
<223> OTHER INFORMATION: synthetic peptide

<400> SEQUENCE: 175

```
Trp Phe Arg Gln Ala Pro Gly Lys Glu Arg Glu Phe Val Thr
1               5                   10
```

<210> SEQ ID NO 176
<211> LENGTH: 14
<212> TYPE: PRT
<213> ORGANISM: artificial sequence
<220> FEATURE:
<223> OTHER INFORMATION: synthetic peptide

<400> SEQUENCE: 176

```
Trp Phe Arg Gln Ala Pro Gly Lys Glu Arg Asp Val Val Ala
1               5                   10
```

<210> SEQ ID NO 177
<211> LENGTH: 14
<212> TYPE: PRT
<213> ORGANISM: artificial sequence
<220> FEATURE:
<223> OTHER INFORMATION: synthetic peptide

<400> SEQUENCE: 177

```
Trp Phe Arg Gln Ala Pro Gly Lys Glu Arg Glu Phe Val Gly
1               5                   10
```

<210> SEQ ID NO 178
<211> LENGTH: 14
<212> TYPE: PRT
<213> ORGANISM: artificial sequence
<220> FEATURE:
<223> OTHER INFORMATION: synthetic peptide

<400> SEQUENCE: 178

```
Trp Phe Arg Gln Ala Pro Gly Lys Glu Arg Glu Phe Val Thr
1               5                   10
```

<210> SEQ ID NO 179
<211> LENGTH: 14
<212> TYPE: PRT
<213> ORGANISM: artificial sequence
<220> FEATURE:
<223> OTHER INFORMATION: synthetic peptide

<400> SEQUENCE: 179

```
Trp Tyr Arg Gln Ala Ser Gly Lys Gln Arg Glu Leu Val Ala
1               5                   10
```

<210> SEQ ID NO 180
<211> LENGTH: 14
<212> TYPE: PRT
<213> ORGANISM: artificial sequence
<220> FEATURE:
<223> OTHER INFORMATION: synthetic peptide

<400> SEQUENCE: 180

```
Trp Phe Arg Gln Ala Pro Gly Lys Glu Arg Glu Phe Val Ala
1               5                   10
```

```
<210> SEQ ID NO 181
<211> LENGTH: 14
<212> TYPE: PRT
<213> ORGANISM: artificial sequence
<220> FEATURE:
<223> OTHER INFORMATION: synthetic peptide

<400> SEQUENCE: 181

Leu Tyr Arg Gln Ala Pro Gly Lys Gln Arg Glu Leu Val Ala
1               5                   10

<210> SEQ ID NO 182
<211> LENGTH: 14
<212> TYPE: PRT
<213> ORGANISM: artificial sequence
<220> FEATURE:
<223> OTHER INFORMATION: synthetic peptide

<400> SEQUENCE: 182

Leu Tyr Arg Gln Ala Pro Gly Lys Gln Arg Glu Leu Val Ala
1               5                   10

<210> SEQ ID NO 183
<211> LENGTH: 14
<212> TYPE: PRT
<213> ORGANISM: artificial sequence
<220> FEATURE:
<223> OTHER INFORMATION: synthetic peptide

<400> SEQUENCE: 183

Leu Tyr Arg Gln Ala Pro Gly Lys Gln Arg Glu Leu Val Ala
1               5                   10

<210> SEQ ID NO 184
<211> LENGTH: 14
<212> TYPE: PRT
<213> ORGANISM: artificial sequence
<220> FEATURE:
<223> OTHER INFORMATION: synthetic peptide

<400> SEQUENCE: 184

Leu Tyr Arg Gln Ala Pro Gly Lys Gln Arg Glu Leu Val Ala
1               5                   10

<210> SEQ ID NO 185
<211> LENGTH: 14
<212> TYPE: PRT
<213> ORGANISM: artificial sequence
<220> FEATURE:
<223> OTHER INFORMATION: synthetic peptide

<400> SEQUENCE: 185

Trp Phe Arg Gln Ala Pro Gly Lys Glu Arg Asp Leu Val Ala
1               5                   10

<210> SEQ ID NO 186
<211> LENGTH: 14
<212> TYPE: PRT
<213> ORGANISM: artificial sequence
<220> FEATURE:
<223> OTHER INFORMATION: synthetic peptide

<400> SEQUENCE: 186

Trp Phe Arg Gln Ala Pro Gly Arg Glu Arg Asp Val Val Ala
1               5                   10

<210> SEQ ID NO 187
```

```
<211> LENGTH: 14
<212> TYPE: PRT
<213> ORGANISM: artificial sequence
<220> FEATURE:
<223> OTHER INFORMATION: synthetic peptide

<400> SEQUENCE: 187

Trp Phe Arg Gln Ala Pro Gly Lys Glu Arg Asp Val Val Ala
1               5                   10

<210> SEQ ID NO 188
<211> LENGTH: 14
<212> TYPE: PRT
<213> ORGANISM: artificial sequence
<220> FEATURE:
<223> OTHER INFORMATION: synthetic peptide

<400> SEQUENCE: 188

Trp Phe Arg Gln Ala Pro Gly Lys Gly Arg Asp Val Val Ala
1               5                   10

<210> SEQ ID NO 189
<211> LENGTH: 14
<212> TYPE: PRT
<213> ORGANISM: artificial sequence
<220> FEATURE:
<223> OTHER INFORMATION: synthetic peptide

<400> SEQUENCE: 189

Trp Phe Arg Gln Ala Pro Gly Lys Gly Arg Glu Val Val Ala
1               5                   10

<210> SEQ ID NO 190
<211> LENGTH: 14
<212> TYPE: PRT
<213> ORGANISM: artificial sequence
<220> FEATURE:
<223> OTHER INFORMATION: synthetic peptide

<400> SEQUENCE: 190

Trp Phe Arg Gln Ala Pro Gly Lys Gly Arg Asp Val Val Ala
1               5                   10

<210> SEQ ID NO 191
<211> LENGTH: 14
<212> TYPE: PRT
<213> ORGANISM: artificial sequence
<220> FEATURE:
<223> OTHER INFORMATION: synthetic peptide

<400> SEQUENCE: 191

Trp Phe Arg Gln Ala Pro Gly Lys Gly Arg Asp Val Val Ala
1               5                   10

<210> SEQ ID NO 192
<211> LENGTH: 14
<212> TYPE: PRT
<213> ORGANISM: artificial sequence
<220> FEATURE:
<223> OTHER INFORMATION: synthetic peptide

<400> SEQUENCE: 192

Trp Phe Arg Gln Ala Pro Gly Lys Gly Arg Glu Leu Val Ala
1               5                   10

<210> SEQ ID NO 193
<211> LENGTH: 14
<212> TYPE: PRT
```

```
<213> ORGANISM: artificial sequence
<220> FEATURE:
<223> OTHER INFORMATION: synthetic peptide

<400> SEQUENCE: 193

Trp Phe Arg Gln Ala Pro Gly Lys Gly Arg Glu Leu Val Ala
1               5                   10

<210> SEQ ID NO 194
<211> LENGTH: 14
<212> TYPE: PRT
<213> ORGANISM: artificial sequence
<220> FEATURE:
<223> OTHER INFORMATION: synthetic peptide

<400> SEQUENCE: 194

Trp Phe Arg Gln Ala Pro Gly Lys Gly Arg Glu Leu Val Ala
1               5                   10

<210> SEQ ID NO 195
<211> LENGTH: 14
<212> TYPE: PRT
<213> ORGANISM: artificial sequence
<220> FEATURE:
<223> OTHER INFORMATION: synthetic peptide

<400> SEQUENCE: 195

Trp Phe Arg Gln Ala Pro Gly Lys Gly Arg Glu Leu Val Ala
1               5                   10

<210> SEQ ID NO 196
<211> LENGTH: 14
<212> TYPE: PRT
<213> ORGANISM: artificial sequence
<220> FEATURE:
<223> OTHER INFORMATION: synthetic peptide

<400> SEQUENCE: 196

Trp Phe Arg Gln Ala Pro Gly Lys Gly Arg Glu Leu Val Ala
1               5                   10

<210> SEQ ID NO 197
<211> LENGTH: 14
<212> TYPE: PRT
<213> ORGANISM: artificial sequence
<220> FEATURE:
<223> OTHER INFORMATION: synthetic peptide

<400> SEQUENCE: 197

Met Tyr Arg Gln Ala Pro Gly Lys Gly Arg Glu Leu Val Ala
1               5                   10

<210> SEQ ID NO 198
<211> LENGTH: 14
<212> TYPE: PRT
<213> ORGANISM: artificial sequence
<220> FEATURE:
<223> OTHER INFORMATION: synthetic peptide

<400> SEQUENCE: 198

Met Tyr Arg Gln Ala Pro Gly Lys Gly Arg Glu Leu Val Ala
1               5                   10

<210> SEQ ID NO 199
<211> LENGTH: 14
<212> TYPE: PRT
<213> ORGANISM: artificial sequence
<220> FEATURE:
```

<223> OTHER INFORMATION: synthetic peptide

<400> SEQUENCE: 199

Met Tyr Arg Gln Ala Pro Gly Lys Gly Arg Glu Leu Val Ala
1               5                   10

<210> SEQ ID NO 200
<211> LENGTH: 16
<212> TYPE: PRT
<213> ORGANISM: artificial sequence
<220> FEATURE:
<223> OTHER INFORMATION: synthetic peptide

<400> SEQUENCE: 200

Thr Ile Thr Ser Gly Gly Ser Thr Asn Tyr Ala Asp Pro Val Lys Gly
1               5                   10                  15

<210> SEQ ID NO 201
<211> LENGTH: 17
<212> TYPE: PRT
<213> ORGANISM: artificial sequence
<220> FEATURE:
<223> OTHER INFORMATION: synthetic peptide

<400> SEQUENCE: 201

Ser Ile Ser Trp Ser Gly Thr Tyr Thr Ala Tyr Ser Asp Asn Val Lys
1               5                   10                  15

Gly

<210> SEQ ID NO 202
<211> LENGTH: 17
<212> TYPE: PRT
<213> ORGANISM: artificial sequence
<220> FEATURE:
<223> OTHER INFORMATION: synthetic peptide

<400> SEQUENCE: 202

Ala Ile Ser Arg Thr Gly Gly Ser Thr Tyr Tyr Ala Arg Ser Val Glu
1               5                   10                  15

Gly

<210> SEQ ID NO 203
<211> LENGTH: 17
<212> TYPE: PRT
<213> ORGANISM: artificial sequence
<220> FEATURE:
<223> OTHER INFORMATION: synthetic peptide

<400> SEQUENCE: 203

Gly Ile Ser Trp Ser Gly Val Ser Thr Asp Tyr Ala Glu Phe Ala Lys
1               5                   10                  15

Gly

<210> SEQ ID NO 204
<211> LENGTH: 17
<212> TYPE: PRT
<213> ORGANISM: artificial sequence
<220> FEATURE:
<223> OTHER INFORMATION: synthetic peptide

<400> SEQUENCE: 204

Ser Ile Ser Trp Ser Gly Ser Tyr Thr Ala Tyr Ala Asp Asn Val Lys
1               5                   10                  15

Gly

```
<210> SEQ ID NO 205
<211> LENGTH: 16
<212> TYPE: PRT
<213> ORGANISM: artificial sequence
<220> FEATURE:
<223> OTHER INFORMATION: synthetic peptide

<400> SEQUENCE: 205

Thr Ile Thr Ser Gly Gly Arg Thr Ser Tyr Ala Asp Ser Val Lys Gly
1               5                   10                  15

<210> SEQ ID NO 206
<211> LENGTH: 17
<212> TYPE: PRT
<213> ORGANISM: artificial sequence
<220> FEATURE:
<223> OTHER INFORMATION: synthetic peptide

<400> SEQUENCE: 206

Ala Ile Ser Trp Ser Gly Gly Leu Thr Tyr Tyr Ala Asp Ser Val Lys
1               5                   10                  15

Gly

<210> SEQ ID NO 207
<211> LENGTH: 16
<212> TYPE: PRT
<213> ORGANISM: artificial sequence
<220> FEATURE:
<223> OTHER INFORMATION: synthetic peptide

<400> SEQUENCE: 207

Thr Ile Thr Ser Gly Gly Ser Thr Asn Tyr Ala Asp Ser Val Lys Gly
1               5                   10                  15

<210> SEQ ID NO 208
<211> LENGTH: 16
<212> TYPE: PRT
<213> ORGANISM: artificial sequence
<220> FEATURE:
<223> OTHER INFORMATION: synthetic peptide

<400> SEQUENCE: 208

Thr Ile Thr Ser Gly Gly Ser Thr Asn Tyr Ala Asp Ser Val Lys Gly
1               5                   10                  15

<210> SEQ ID NO 209
<211> LENGTH: 16
<212> TYPE: PRT
<213> ORGANISM: artificial sequence
<220> FEATURE:
<223> OTHER INFORMATION: synthetic peptide

<400> SEQUENCE: 209

Thr Ile Thr Ser Gly Gly Ser Thr Asn Tyr Ala Asp Ser Val Lys Gly
1               5                   10                  15

<210> SEQ ID NO 210
<211> LENGTH: 16
<212> TYPE: PRT
<213> ORGANISM: artificial sequence
<220> FEATURE:
<223> OTHER INFORMATION: synthetic peptide

<400> SEQUENCE: 210

Thr Ile Thr Ser Gly Gly Ser Thr Asn Tyr Ala Asp Ser Val Lys Gly
1               5                   10                  15
```

```
<210> SEQ ID NO 211
<211> LENGTH: 17
<212> TYPE: PRT
<213> ORGANISM: artificial sequence
<220> FEATURE:
<223> OTHER INFORMATION: synthetic peptide

<400> SEQUENCE: 211

Ala Ile Ser Arg Thr Gly Gly Ser Thr Tyr Tyr Pro Asp Ser Val Glu
1               5                   10                  15

Gly

<210> SEQ ID NO 212
<211> LENGTH: 17
<212> TYPE: PRT
<213> ORGANISM: artificial sequence
<220> FEATURE:
<223> OTHER INFORMATION: synthetic peptide

<400> SEQUENCE: 212

Ala Ile Ser Arg Thr Gly Gly Ser Thr Tyr Tyr Pro Asp Ser Val Glu
1               5                   10                  15

Gly

<210> SEQ ID NO 213
<211> LENGTH: 17
<212> TYPE: PRT
<213> ORGANISM: artificial sequence
<220> FEATURE:
<223> OTHER INFORMATION: synthetic peptide

<400> SEQUENCE: 213

Ala Ile Ser Arg Thr Gly Gly Ser Thr Tyr Tyr Pro Asp Ser Val Glu
1               5                   10                  15

Gly

<210> SEQ ID NO 214
<211> LENGTH: 17
<212> TYPE: PRT
<213> ORGANISM: artificial sequence
<220> FEATURE:
<223> OTHER INFORMATION: synthetic peptide

<400> SEQUENCE: 214

Ala Ile Ser Arg Thr Gly Gly Ser Thr Tyr Tyr Ala Arg Ser Val Glu
1               5                   10                  15

Gly

<210> SEQ ID NO 215
<211> LENGTH: 17
<212> TYPE: PRT
<213> ORGANISM: artificial sequence
<220> FEATURE:
<223> OTHER INFORMATION: synthetic peptide

<400> SEQUENCE: 215

Ala Ile Ser Arg Thr Gly Gly Ser Thr Tyr Tyr Ala Arg Ser Val Glu
1               5                   10                  15

Gly

<210> SEQ ID NO 216
<211> LENGTH: 17
<212> TYPE: PRT
<213> ORGANISM: artificial sequence
```

```
<220> FEATURE:
<223> OTHER INFORMATION: synthetic peptide

<400> SEQUENCE: 216

Ala Ile Ser Arg Thr Gly Gly Ser Thr Tyr Tyr Ala Arg Ser Val Glu
1               5                   10                  15

Gly

<210> SEQ ID NO 217
<211> LENGTH: 17
<212> TYPE: PRT
<213> ORGANISM: artificial sequence
<220> FEATURE:
<223> OTHER INFORMATION: synthetic peptide

<400> SEQUENCE: 217

Ala Ile Ser Arg Thr Gly Gly Ser Thr Tyr Tyr Ala Arg Ser Val Glu
1               5                   10                  15

Gly

<210> SEQ ID NO 218
<211> LENGTH: 17
<212> TYPE: PRT
<213> ORGANISM: artificial sequence
<220> FEATURE:
<223> OTHER INFORMATION: synthetic peptide

<400> SEQUENCE: 218

Ala Ile Ser Arg Thr Gly Gly Ser Thr Tyr Tyr Pro Asp Ser Val Glu
1               5                   10                  15

Gly

<210> SEQ ID NO 219
<211> LENGTH: 17
<212> TYPE: PRT
<213> ORGANISM: artificial sequence
<220> FEATURE:
<223> OTHER INFORMATION: synthetic peptide

<400> SEQUENCE: 219

Ala Ile Ser Arg Thr Gly Gly Ser Thr Tyr Tyr Pro Asp Ser Val Glu
1               5                   10                  15

Gly

<210> SEQ ID NO 220
<211> LENGTH: 17
<212> TYPE: PRT
<213> ORGANISM: artificial sequence
<220> FEATURE:
<223> OTHER INFORMATION: synthetic peptide

<400> SEQUENCE: 220

Ala Ile Ser Arg Thr Gly Gly Ser Thr Tyr Tyr Pro Asp Ser Val Glu
1               5                   10                  15

Gly

<210> SEQ ID NO 221
<211> LENGTH: 17
<212> TYPE: PRT
<213> ORGANISM: artificial sequence
<220> FEATURE:
<223> OTHER INFORMATION: synthetic peptide

<400> SEQUENCE: 221
```

```
Ala Ile Ser Arg Thr Gly Gly Ser Thr Tyr Tyr Pro Asp Ser Val Glu
1               5                   10                  15

Gly

<210> SEQ ID NO 222
<211> LENGTH: 17
<212> TYPE: PRT
<213> ORGANISM: artificial sequence
<220> FEATURE:
<223> OTHER INFORMATION: synthetic peptide

<400> SEQUENCE: 222

Ala Ile Ser Arg Thr Gly Gly Ser Thr Tyr Tyr Pro Asp Ser Val Glu
1               5                   10                  15

Gly

<210> SEQ ID NO 223
<211> LENGTH: 16
<212> TYPE: PRT
<213> ORGANISM: artificial sequence
<220> FEATURE:
<223> OTHER INFORMATION: synthetic peptide

<400> SEQUENCE: 223

Thr Ile Thr Ser Gly Gly Ser Thr Asn Tyr Ala Asp Pro Val Lys Gly
1               5                   10                  15

<210> SEQ ID NO 224
<211> LENGTH: 16
<212> TYPE: PRT
<213> ORGANISM: artificial sequence
<220> FEATURE:
<223> OTHER INFORMATION: synthetic peptide

<400> SEQUENCE: 224

Thr Ile Thr Ser Gly Gly Ser Thr Asn Tyr Ala Asp Pro Val Lys Gly
1               5                   10                  15

<210> SEQ ID NO 225
<211> LENGTH: 16
<212> TYPE: PRT
<213> ORGANISM: artificial sequence
<220> FEATURE:
<223> OTHER INFORMATION: synthetic peptide

<400> SEQUENCE: 225

Thr Ile Thr Ser Gly Gly Ser Thr Asn Tyr Ala Asp Pro Val Lys Gly
1               5                   10                  15

<210> SEQ ID NO 226
<211> LENGTH: 32
<212> TYPE: PRT
<213> ORGANISM: artificial sequence
<220> FEATURE:
<223> OTHER INFORMATION: synthetic peptide

<400> SEQUENCE: 226

Arg Phe Thr Ile Ser Arg Asp Gly Pro Lys Asn Thr Val Tyr Leu Gln
1               5                   10                  15

Met Asn Ser Leu Lys Pro Glu Asp Thr Ala Val Tyr Tyr Cys Tyr Ala
                20                  25                  30

<210> SEQ ID NO 227
<211> LENGTH: 32
<212> TYPE: PRT
<213> ORGANISM: artificial sequence
```

```
<220> FEATURE:
<223> OTHER INFORMATION: synthetic peptide

<400> SEQUENCE: 227

Arg Phe Thr Ile Ser Arg Asp Asn Ala Lys Asn Thr Val Tyr Leu Gln
1               5                   10                  15

Met Asp Ser Leu Lys Pro Glu Asp Thr Ala Val Tyr Tyr Cys Ala Ala
            20                  25                  30

<210> SEQ ID NO 228
<211> LENGTH: 32
<212> TYPE: PRT
<213> ORGANISM: artificial sequence
<220> FEATURE:
<223> OTHER INFORMATION: synthetic peptide

<400> SEQUENCE: 228

Arg Phe Thr Ile Ser Arg Asp Asn Ala Lys Arg Met Val Tyr Leu Gln
1               5                   10                  15

Met Asn Ala Leu Lys Pro Glu Asp Thr Ala Val Tyr Tyr Cys Ala Ala
            20                  25                  30

<210> SEQ ID NO 229
<211> LENGTH: 32
<212> TYPE: PRT
<213> ORGANISM: artificial sequence
<220> FEATURE:
<223> OTHER INFORMATION: synthetic peptide

<400> SEQUENCE: 229

Arg Phe Thr Ile Ser Arg Asp His Ala Ala Asn Thr Val Tyr Leu Glu
1               5                   10                  15

Met Asn Ser Leu Lys Pro Glu Asp Thr Ala Val Tyr Tyr Cys Ala Ala
            20                  25                  30

<210> SEQ ID NO 230
<211> LENGTH: 32
<212> TYPE: PRT
<213> ORGANISM: artificial sequence
<220> FEATURE:
<223> OTHER INFORMATION: synthetic peptide

<400> SEQUENCE: 230

Arg Phe Thr Ile Ser Arg Asp Asn Ala Lys Asn Thr Val Tyr Leu Gln
1               5                   10                  15

Met Ser Ser Leu Lys Pro Gly Asp Thr Ala Val Tyr Tyr Cys Ala Ala
            20                  25                  30

<210> SEQ ID NO 231
<211> LENGTH: 32
<212> TYPE: PRT
<213> ORGANISM: artificial sequence
<220> FEATURE:
<223> OTHER INFORMATION: synthetic peptide

<400> SEQUENCE: 231

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Asp Cys Asn Phe
            20                  25                  30

<210> SEQ ID NO 232
<211> LENGTH: 32
<212> TYPE: PRT
<213> ORGANISM: artificial sequence
```

```
<220> FEATURE:
<223> OTHER INFORMATION: synthetic peptide

<400> SEQUENCE: 232

Arg Phe Thr Ile Ser Arg Asp Asn Ala Lys Asp Met Val Tyr Leu Gln
1               5                   10                  15
Met Ala Ser Leu Lys Pro Glu Asp Thr Ala Val Tyr Tyr Cys Ala Ala
            20                  25                  30

<210> SEQ ID NO 233
<211> LENGTH: 32
<212> TYPE: PRT
<213> ORGANISM: artificial sequence
<220> FEATURE:
<223> OTHER INFORMATION: synthetic peptide

<400> SEQUENCE: 233

Arg Phe Thr Ile Ser Arg Asp Gly Pro Lys Asn Thr Val Tyr Leu Gln
1               5                   10                  15
Met Asn Ser Leu Lys Pro Glu Asp Thr Ala Val Tyr Tyr Cys Tyr Ala
            20                  25                  30

<210> SEQ ID NO 234
<211> LENGTH: 32
<212> TYPE: PRT
<213> ORGANISM: artificial sequence
<220> FEATURE:
<223> OTHER INFORMATION: synthetic peptide

<400> SEQUENCE: 234

Arg Phe Thr Ile Ser Arg Asp Gly Ala Lys Asn Thr Val Tyr Leu Gln
1               5                   10                  15
Met Asn Ser Leu Lys Pro Glu Asp Thr Ala Val Tyr Tyr Cys Tyr Ala
            20                  25                  30

<210> SEQ ID NO 235
<211> LENGTH: 32
<212> TYPE: PRT
<213> ORGANISM: artificial sequence
<220> FEATURE:
<223> OTHER INFORMATION: synthetic peptide

<400> SEQUENCE: 235

Arg Phe Thr Ile Ser Arg Asp Gly Ala Lys Asn Thr Val Tyr Leu Gln
1               5                   10                  15
Met Asn Ser Leu Arg Pro Glu Asp Thr Ala Val Tyr Tyr Cys Tyr Ala
            20                  25                  30

<210> SEQ ID NO 236
<211> LENGTH: 32
<212> TYPE: PRT
<213> ORGANISM: artificial sequence
<220> FEATURE:
<223> OTHER INFORMATION: synthetic peptide

<400> SEQUENCE: 236

Arg Phe Thr Ile Ser Arg Asp Gly Ala Lys Asn Thr Val Tyr Leu Gln
1               5                   10                  15
Met Asn Ser Leu Arg Pro Glu Asp Thr Ala Val Tyr Tyr Cys Tyr Ala
            20                  25                  30

<210> SEQ ID NO 237
<211> LENGTH: 32
<212> TYPE: PRT
<213> ORGANISM: artificial sequence
```

```
<220> FEATURE:
<223> OTHER INFORMATION: synthetic peptide

<400> SEQUENCE: 237

Arg Phe Thr Ile Ser Arg Asp Asn Ala Lys Arg Met Val Tyr Leu Gln
1               5                   10                  15

Met Asn Asn Leu Lys Pro Glu Asp Thr Ala Val Tyr Tyr Cys Ala Ala
            20                  25                  30

<210> SEQ ID NO 238
<211> LENGTH: 32
<212> TYPE: PRT
<213> ORGANISM: artificial sequence
<220> FEATURE:
<223> OTHER INFORMATION: synthetic peptide

<400> SEQUENCE: 238

Arg Phe Thr Ile Ser Arg Asp Asn Ala Lys Arg Met Val Tyr Leu Gln
1               5                   10                  15

Met Asn Asn Leu Lys Pro Glu Asp Thr Ala Val Tyr Tyr Cys Ala Ala
            20                  25                  30

<210> SEQ ID NO 239
<211> LENGTH: 32
<212> TYPE: PRT
<213> ORGANISM: artificial sequence
<220> FEATURE:
<223> OTHER INFORMATION: synthetic peptide

<400> SEQUENCE: 239

Arg Phe Thr Ile Ser Arg Asp Asn Ala Lys Arg Met Val Tyr Leu Glu
1               5                   10                  15

Met Asn Asn Leu Lys Pro Asp Asp Thr Ala Val Tyr Tyr Cys Ala Ala
            20                  25                  30

<210> SEQ ID NO 240
<211> LENGTH: 32
<212> TYPE: PRT
<213> ORGANISM: artificial sequence
<220> FEATURE:
<223> OTHER INFORMATION: synthetic peptide

<400> SEQUENCE: 240

Arg Phe Thr Ile Ser Arg Asp Asn Ala Lys Arg Met Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 241
<211> LENGTH: 32
<212> TYPE: PRT
<213> ORGANISM: artificial sequence
<220> FEATURE:
<223> OTHER INFORMATION: synthetic peptide

<400> SEQUENCE: 241

Arg Phe Thr Ile Ser Arg Asp Asn Ala Lys Arg Met Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 242
<211> LENGTH: 32
<212> TYPE: PRT
<213> ORGANISM: artificial sequence
```

-continued

```
<220> FEATURE:
<223> OTHER INFORMATION: synthetic peptide

<400> SEQUENCE: 242

Arg Phe Thr Ile Ser Arg Asp Asn Ala Lys Asn Met Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 243
<211> LENGTH: 32
<212> TYPE: PRT
<213> ORGANISM: artificial sequence
<220> FEATURE:
<223> OTHER INFORMATION: synthetic peptide

<400> SEQUENCE: 243

Arg Phe Thr Ile Ser Arg Asp Asn Ala Lys Arg Ser Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 244
<211> LENGTH: 32
<212> TYPE: PRT
<213> ORGANISM: artificial sequence
<220> FEATURE:
<223> OTHER INFORMATION: synthetic peptide

<400> SEQUENCE: 244

Arg Phe Thr Ile Ser Arg Asp Asn Ala Lys Arg Met Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 245
<211> LENGTH: 32
<212> TYPE: PRT
<213> ORGANISM: artificial sequence
<220> FEATURE:
<223> OTHER INFORMATION: synthetic peptide

<400> SEQUENCE: 245

Arg Phe Thr Ile Ser Arg Asp Asn Ala Lys Asn Met Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 246
<211> LENGTH: 32
<212> TYPE: PRT
<213> ORGANISM: artificial sequence
<220> FEATURE:
<223> OTHER INFORMATION: synthetic peptide

<400> SEQUENCE: 246

Arg Phe Thr Ile Ser Arg Asp Asn Ala Lys Arg Ser Val Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 247
<211> LENGTH: 32
<212> TYPE: PRT
<213> ORGANISM: artificial sequence
```

<220> FEATURE:
<223> OTHER INFORMATION: synthetic peptide

<400> SEQUENCE: 247

```
Arg Phe Thr Ile Ser Arg Asp Asn Ala Lys Arg Met Val Tyr Leu Gln
1               5                   10                  15

Met Asn Ser Leu Arg Ala Glu Asp Thr Ala Val Tyr Tyr Cys Ala Ala
            20                  25                  30
```

<210> SEQ ID NO 248
<211> LENGTH: 32
<212> TYPE: PRT
<213> ORGANISM: artificial sequence
<220> FEATURE:
<223> OTHER INFORMATION: synthetic peptide

<400> SEQUENCE: 248

```
Arg Phe Thr Ile Ser Arg Asp Asn Ala Lys Asn Ser Val Tyr Leu Gln
1               5                   10                  15

Met Asn Ser Leu Arg Ala Glu Asp Thr Ala Val Tyr Tyr Cys Ala Ala
            20                  25                  30
```

<210> SEQ ID NO 249
<211> LENGTH: 32
<212> TYPE: PRT
<213> ORGANISM: artificial sequence
<220> FEATURE:
<223> OTHER INFORMATION: synthetic peptide

<400> SEQUENCE: 249

```
Arg Phe Thr Ile Ser Arg Asp Gly Pro Lys Asn Thr Val Tyr Leu Gln
1               5                   10                  15

Met Asn Ser Leu Arg Ala Glu Asp Thr Ala Val Tyr Tyr Cys Tyr Ala
            20                  25                  30
```

<210> SEQ ID NO 250
<211> LENGTH: 32
<212> TYPE: PRT
<213> ORGANISM: artificial sequence
<220> FEATURE:
<223> OTHER INFORMATION: synthetic peptide

<400> SEQUENCE: 250

```
Arg Phe Thr Ile Ser Arg Asp Gly Ala Lys Asn Thr Val Tyr Leu Gln
1               5                   10                  15

Met Asn Ser Leu Arg Ala Glu Asp Thr Ala Val Tyr Tyr Cys Tyr Ala
            20                  25                  30
```

<210> SEQ ID NO 251
<211> LENGTH: 32
<212> TYPE: PRT
<213> ORGANISM: artificial sequence
<220> FEATURE:
<223> OTHER INFORMATION: synthetic peptide

<400> SEQUENCE: 251

```
Arg Phe Thr Ile Ser Arg Asp Asn Ala Lys Asn Thr Val Tyr Leu Gln
1               5                   10                  15

Met Asn Ser Leu Arg Ala Glu Asp Thr Ala Val Tyr Tyr Cys Tyr Ala
            20                  25                  30
```

<210> SEQ ID NO 252
<211> LENGTH: 14
<212> TYPE: PRT
<213> ORGANISM: artificial sequence

```
<220> FEATURE:
<223> OTHER INFORMATION: synthetic peptide

<400> SEQUENCE: 252

Asn Leu Lys Gln Gly Ser Tyr Gly Tyr Arg Phe Asn Asp Tyr
1               5                   10

<210> SEQ ID NO 253
<211> LENGTH: 17
<212> TYPE: PRT
<213> ORGANISM: artificial sequence
<220> FEATURE:
<223> OTHER INFORMATION: synthetic peptide

<400> SEQUENCE: 253

Gln Ser Arg Tyr Arg Ser Asn Tyr Tyr Asp His Asp Asp Lys Tyr Ala
1               5                   10                  15
Tyr

<210> SEQ ID NO 254
<211> LENGTH: 19
<212> TYPE: PRT
<213> ORGANISM: artificial sequence
<220> FEATURE:
<223> OTHER INFORMATION: synthetic peptide

<400> SEQUENCE: 254

Ala Gly Val Arg Ala Glu Asp Gly Arg Val Arg Thr Leu Pro Ser Glu
1               5                   10                  15
Tyr Asn Phe

<210> SEQ ID NO 255
<211> LENGTH: 16
<212> TYPE: PRT
<213> ORGANISM: artificial sequence
<220> FEATURE:
<223> OTHER INFORMATION: synthetic peptide

<400> SEQUENCE: 255

Leu Gly Arg Tyr Arg Ser Asn Trp Arg Asn Ile Gly Gln Tyr Asp Tyr
1               5                   10                  15

<210> SEQ ID NO 256
<211> LENGTH: 17
<212> TYPE: PRT
<213> ORGANISM: artificial sequence
<220> FEATURE:
<223> OTHER INFORMATION: synthetic peptide

<400> SEQUENCE: 256

Gln Ser Arg Tyr Ser Ser Asn Tyr Tyr Asp His Asp Asp Lys Tyr Ala
1               5                   10                  15
Tyr

<210> SEQ ID NO 257
<211> LENGTH: 8
<212> TYPE: PRT
<213> ORGANISM: artificial sequence
<220> FEATURE:
<223> OTHER INFORMATION: synthetic peptide

<400> SEQUENCE: 257

Val Val Asp Gly Lys Arg Ala Pro
1               5
```

```
<210> SEQ ID NO 258
<211> LENGTH: 16
<212> TYPE: PRT
<213> ORGANISM: artificial sequence
<220> FEATURE:
<223> OTHER INFORMATION: synthetic peptide

<400> SEQUENCE: 258

Asn Arg Arg Gln Lys Thr Val Gln Met Gly Glu Arg Ala Tyr Asp Tyr
1               5                   10                  15

<210> SEQ ID NO 259
<211> LENGTH: 14
<212> TYPE: PRT
<213> ORGANISM: artificial sequence
<220> FEATURE:
<223> OTHER INFORMATION: synthetic peptide

<400> SEQUENCE: 259

Asn Leu Lys Gln Gly Ser Tyr Gly Tyr Arg Phe Asn Asp Tyr
1               5                   10

<210> SEQ ID NO 260
<211> LENGTH: 14
<212> TYPE: PRT
<213> ORGANISM: artificial sequence
<220> FEATURE:
<223> OTHER INFORMATION: synthetic peptide

<400> SEQUENCE: 260

Asn Leu Lys Gln Gly Asp Tyr Gly Tyr Arg Phe Asn Asp Tyr
1               5                   10

<210> SEQ ID NO 261
<211> LENGTH: 14
<212> TYPE: PRT
<213> ORGANISM: artificial sequence
<220> FEATURE:
<223> OTHER INFORMATION: synthetic peptide

<400> SEQUENCE: 261

Asn Leu Lys Gln Gly Asp Tyr Gly Tyr Arg Phe Asn Asp Tyr
1               5                   10

<210> SEQ ID NO 262
<211> LENGTH: 14
<212> TYPE: PRT
<213> ORGANISM: artificial sequence
<220> FEATURE:
<223> OTHER INFORMATION: synthetic peptide

<400> SEQUENCE: 262

Asn Leu Lys Gln Gly Asp Tyr Gly Tyr Arg Phe Asn Asp Tyr
1               5                   10

<210> SEQ ID NO 263
<211> LENGTH: 19
<212> TYPE: PRT
<213> ORGANISM: artificial sequence
<220> FEATURE:
<223> OTHER INFORMATION: synthetic peptide

<400> SEQUENCE: 263

Ala Gly Val Arg Ala Glu Asp Gly Arg Val Arg Thr Leu Pro Ser Glu
1               5                   10                  15

Tyr Thr Phe
```

```
<210> SEQ ID NO 264
<211> LENGTH: 19
<212> TYPE: PRT
<213> ORGANISM: artificial sequence
<220> FEATURE:
<223> OTHER INFORMATION: synthetic peptide

<400> SEQUENCE: 264

Ala Gly Val Arg Ala Glu Asp Gly Arg Val Arg Ser Leu Pro Ser Glu
1               5                   10                  15

Tyr Thr Phe

<210> SEQ ID NO 265
<211> LENGTH: 19
<212> TYPE: PRT
<213> ORGANISM: artificial sequence
<220> FEATURE:
<223> OTHER INFORMATION: synthetic peptide

<400> SEQUENCE: 265

Ala Gly Val Arg Ala Glu Asp Gly Arg Val Arg Thr Leu Pro Ser Glu
1               5                   10                  15

Tyr Thr Phe

<210> SEQ ID NO 266
<211> LENGTH: 19
<212> TYPE: PRT
<213> ORGANISM: artificial sequence
<220> FEATURE:
<223> OTHER INFORMATION: synthetic peptide

<400> SEQUENCE: 266

Ala Gly Val Arg Ala Glu Asp Gly Arg Val Arg Thr Leu Pro Ser Glu
1               5                   10                  15

Tyr Asn Phe

<210> SEQ ID NO 267
<211> LENGTH: 19
<212> TYPE: PRT
<213> ORGANISM: artificial sequence
<220> FEATURE:
<223> OTHER INFORMATION: synthetic peptide

<400> SEQUENCE: 267

Ala Gly Val Arg Ala Glu Asp Gly Arg Val Arg Thr Leu Pro Ser Glu
1               5                   10                  15

Tyr Asn Phe

<210> SEQ ID NO 268
<211> LENGTH: 19
<212> TYPE: PRT
<213> ORGANISM: artificial sequence
<220> FEATURE:
<223> OTHER INFORMATION: synthetic peptide

<400> SEQUENCE: 268

Ala Gly Val Arg Ala Glu Asp Gly Arg Val Arg Thr Leu Pro Ser Glu
1               5                   10                  15

Tyr Asn Phe

<210> SEQ ID NO 269
<211> LENGTH: 19
<212> TYPE: PRT
<213> ORGANISM: artificial sequence
<220> FEATURE:
```

<223> OTHER INFORMATION: synthetic peptide

<400> SEQUENCE: 269

Ala Gly Val Arg Ala Glu Asp Gly Arg Val Arg Thr Leu Pro Ser Glu
1               5                   10                  15

Tyr Asn Phe

<210> SEQ ID NO 270
<211> LENGTH: 19
<212> TYPE: PRT
<213> ORGANISM: artificial sequence
<220> FEATURE:
<223> OTHER INFORMATION: synthetic peptide

<400> SEQUENCE: 270

Ala Gly Val Arg Ala Glu Asp Gly Arg Val Arg Thr Leu Pro Ser Glu
1               5                   10                  15

Tyr Thr Phe

<210> SEQ ID NO 271
<211> LENGTH: 19
<212> TYPE: PRT
<213> ORGANISM: artificial sequence
<220> FEATURE:
<223> OTHER INFORMATION: synthetic peptide

<400> SEQUENCE: 271

Ala Gly Val Arg Ala Glu Asp Gly Arg Val Arg Thr Leu Pro Ser Glu
1               5                   10                  15

Tyr Thr Phe

<210> SEQ ID NO 272
<211> LENGTH: 19
<212> TYPE: PRT
<213> ORGANISM: artificial sequence
<220> FEATURE:
<223> OTHER INFORMATION: synthetic peptide

<400> SEQUENCE: 272

Ala Gly Val Arg Ala Glu Asp Gly Arg Val Arg Thr Leu Pro Ser Glu
1               5                   10                  15

Tyr Thr Phe

<210> SEQ ID NO 273
<211> LENGTH: 19
<212> TYPE: PRT
<213> ORGANISM: artificial sequence
<220> FEATURE:
<223> OTHER INFORMATION: synthetic peptide

<400> SEQUENCE: 273

Ala Gly Val Arg Ala Glu Asp Gly Arg Val Arg Thr Leu Pro Ser Glu
1               5                   10                  15

Tyr Thr Phe

<210> SEQ ID NO 274
<211> LENGTH: 19
<212> TYPE: PRT
<213> ORGANISM: artificial sequence
<220> FEATURE:
<223> OTHER INFORMATION: synthetic peptide

<400> SEQUENCE: 274

Ala Gly Val Arg Ala Glu Asp Gly Arg Val Arg Thr Leu Pro Ser Glu

<210> SEQ ID NO 275
<211> LENGTH: 14
<212> TYPE: PRT
<213> ORGANISM: artificial sequence
<220> FEATURE:
<223> OTHER INFORMATION: synthetic peptide

<400> SEQUENCE: 275

Asn Leu Lys Gln Gly Ser Tyr Gly Tyr Arg Phe Asn Asp Tyr
1               5                   10

<210> SEQ ID NO 276
<211> LENGTH: 14
<212> TYPE: PRT
<213> ORGANISM: artificial sequence
<220> FEATURE:
<223> OTHER INFORMATION: synthetic peptide

<400> SEQUENCE: 276

Asn Leu Lys Gln Gly Ser Tyr Gly Tyr Arg Phe Asn Asp Tyr
1               5                   10

<210> SEQ ID NO 277
<211> LENGTH: 14
<212> TYPE: PRT
<213> ORGANISM: artificial sequence
<220> FEATURE:
<223> OTHER INFORMATION: synthetic peptide

<400> SEQUENCE: 277

Asn Leu Lys Gln Gly Ser Tyr Gly Tyr Arg Phe Asn Asp Tyr
1               5                   10

<210> SEQ ID NO 278
<211> LENGTH: 11
<212> TYPE: PRT
<213> ORGANISM: artificial sequence
<220> FEATURE:
<223> OTHER INFORMATION: synthetic peptide

<400> SEQUENCE: 278

Trp Gly Gln Gly Thr Gln Val Thr Val Ser Ser
1               5                   10

<210> SEQ ID NO 279
<211> LENGTH: 11
<212> TYPE: PRT
<213> ORGANISM: artificial sequence
<220> FEATURE:
<223> OTHER INFORMATION: synthetic peptide

<400> SEQUENCE: 279

Trp Gly Gln Gly Thr Gln Val Thr Val Ser Ser
1               5                   10

<210> SEQ ID NO 280
<211> LENGTH: 11
<212> TYPE: PRT
<213> ORGANISM: artificial sequence
<220> FEATURE:
<223> OTHER INFORMATION: synthetic peptide

<400> SEQUENCE: 280

Trp Gly Gln Gly Thr Gln Val Thr Val Ser Ser

```
1               5                   10
```

<210> SEQ ID NO 281
<211> LENGTH: 11
<212> TYPE: PRT
<213> ORGANISM: artificial sequence
<220> FEATURE:
<223> OTHER INFORMATION: synthetic peptide

<400> SEQUENCE: 281

```
Trp Gly Gln Gly Thr Gln Val Thr Val Ser Ser
1               5                   10
```

<210> SEQ ID NO 282
<211> LENGTH: 11
<212> TYPE: PRT
<213> ORGANISM: artificial sequence
<220> FEATURE:
<223> OTHER INFORMATION: synthetic peptide

<400> SEQUENCE: 282

```
Trp Gly Gln Gly Thr Gln Val Thr Val Ser Ser
1               5                   10
```

<210> SEQ ID NO 283
<211> LENGTH: 11
<212> TYPE: PRT
<213> ORGANISM: artificial sequence
<220> FEATURE:
<223> OTHER INFORMATION: synthetic peptide

<400> SEQUENCE: 283

```
Trp Gly Gln Gly Thr Gln Val Thr Val Ser Ser
1               5                   10
```

<210> SEQ ID NO 284
<211> LENGTH: 11
<212> TYPE: PRT
<213> ORGANISM: artificial sequence
<220> FEATURE:
<223> OTHER INFORMATION: synthetic peptide

<400> SEQUENCE: 284

```
Trp Gly Gln Gly Thr Gln Val Thr Val Ser Ser
1               5                   10
```

<210> SEQ ID NO 285
<211> LENGTH: 11
<212> TYPE: PRT
<213> ORGANISM: artificial sequence
<220> FEATURE:
<223> OTHER INFORMATION: synthetic peptide

<400> SEQUENCE: 285

```
Trp Gly Gln Gly Thr Gln Val Thr Val Ser Ser
1               5                   10
```

<210> SEQ ID NO 286
<211> LENGTH: 11
<212> TYPE: PRT
<213> ORGANISM: artificial sequence
<220> FEATURE:
<223> OTHER INFORMATION: synthetic peptide

<400> SEQUENCE: 286

```
Trp Gly Gln Gly Thr Gln Val Thr Val Ser Ser
1               5                   10
```

<210> SEQ ID NO 287
<211> LENGTH: 11
<212> TYPE: PRT
<213> ORGANISM: artificial sequence
<220> FEATURE:
<223> OTHER INFORMATION: synthetic peptide

<400> SEQUENCE: 287

Trp Gly Gln Gly Thr Gln Val Thr Val Ser Ser
1               5                   10

<210> SEQ ID NO 288
<211> LENGTH: 11
<212> TYPE: PRT
<213> ORGANISM: artificial sequence
<220> FEATURE:
<223> OTHER INFORMATION: synthetic peptide

<400> SEQUENCE: 288

Trp Gly Gln Gly Thr Gln Val Thr Val Ser Ser
1               5                   10

<210> SEQ ID NO 289
<211> LENGTH: 11
<212> TYPE: PRT
<213> ORGANISM: artificial sequence
<220> FEATURE:
<223> OTHER INFORMATION: synthetic peptide

<400> SEQUENCE: 289

Trp Gly Gln Gly Thr Gln Val Thr Val Ser Ser
1               5                   10

<210> SEQ ID NO 290
<211> LENGTH: 11
<212> TYPE: PRT
<213> ORGANISM: artificial sequence
<220> FEATURE:
<223> OTHER INFORMATION: synthetic peptide

<400> SEQUENCE: 290

Trp Gly Gln Gly Thr Gln Val Thr Val Ser Ser
1               5                   10

<210> SEQ ID NO 291
<211> LENGTH: 11
<212> TYPE: PRT
<213> ORGANISM: artificial sequence
<220> FEATURE:
<223> OTHER INFORMATION: synthetic peptide

<400> SEQUENCE: 291

Trp Gly Gln Gly Thr Gln Val Thr Val Ser Ser
1               5                   10

<210> SEQ ID NO 292
<211> LENGTH: 11
<212> TYPE: PRT
<213> ORGANISM: artificial sequence
<220> FEATURE:
<223> OTHER INFORMATION: synthetic peptide

<400> SEQUENCE: 292

Trp Gly Gln Gly Thr Gln Val Thr Val Ser Ser
1               5                   10

<210> SEQ ID NO 293

```
<211> LENGTH: 11
<212> TYPE: PRT
<213> ORGANISM: artificial sequence
<220> FEATURE:
<223> OTHER INFORMATION: synthetic peptide

<400> SEQUENCE: 293

Trp Gly Gln Gly Thr Gln Val Thr Val Ser Ser
1               5                   10

<210> SEQ ID NO 294
<211> LENGTH: 11
<212> TYPE: PRT
<213> ORGANISM: artificial sequence
<220> FEATURE:
<223> OTHER INFORMATION: synthetic peptide

<400> SEQUENCE: 294

Trp Gly Gln Gly Thr Gln Val Thr Val Ser Ser
1               5                   10

<210> SEQ ID NO 295
<211> LENGTH: 11
<212> TYPE: PRT
<213> ORGANISM: artificial sequence
<220> FEATURE:
<223> OTHER INFORMATION: synthetic peptide

<400> SEQUENCE: 295

Trp Gly Gln Gly Thr Gln Val Thr Val Ser Ser
1               5                   10

<210> SEQ ID NO 296
<211> LENGTH: 11
<212> TYPE: PRT
<213> ORGANISM: artificial sequence
<220> FEATURE:
<223> OTHER INFORMATION: synthetic peptide

<400> SEQUENCE: 296

Trp Gly Gln Gly Thr Gln Val Thr Val Ser Ser
1               5                   10

<210> SEQ ID NO 297
<211> LENGTH: 11
<212> TYPE: PRT
<213> ORGANISM: artificial sequence
<220> FEATURE:
<223> OTHER INFORMATION: synthetic peptide

<400> SEQUENCE: 297

Trp Gly Gln Gly Thr Gln Val Thr Val Ser Ser
1               5                   10

<210> SEQ ID NO 298
<211> LENGTH: 11
<212> TYPE: PRT
<213> ORGANISM: artificial sequence
<220> FEATURE:
<223> OTHER INFORMATION: synthetic peptide

<400> SEQUENCE: 298

Trp Gly Gln Gly Thr Gln Val Thr Val Ser Ser
1               5                   10

<210> SEQ ID NO 299
<211> LENGTH: 11
<212> TYPE: PRT
```

```
-continued

<213> ORGANISM: artificial sequence
<220> FEATURE:
<223> OTHER INFORMATION: synthetic peptide

<400> SEQUENCE: 299

Trp Gly Gln Gly Thr Gln Val Thr Val Ser Ser
1               5                   10

<210> SEQ ID NO 300
<211> LENGTH: 11
<212> TYPE: PRT
<213> ORGANISM: artificial sequence
<220> FEATURE:
<223> OTHER INFORMATION: synthetic peptide

<400> SEQUENCE: 300

Trp Gly Gln Gly Thr Leu Val Thr Val Ser Ser
1               5                   10

<210> SEQ ID NO 301
<211> LENGTH: 11
<212> TYPE: PRT
<213> ORGANISM: artificial sequence
<220> FEATURE:
<223> OTHER INFORMATION: synthetic peptide

<400> SEQUENCE: 301

Trp Gly Gln Gly Thr Gln Val Thr Val Ser Ser
1               5                   10

<210> SEQ ID NO 302
<211> LENGTH: 11
<212> TYPE: PRT
<213> ORGANISM: artificial sequence
<220> FEATURE:
<223> OTHER INFORMATION: synthetic peptide

<400> SEQUENCE: 302

Trp Gly Gln Gly Thr Gln Val Thr Val Ser Ser
1               5                   10

<210> SEQ ID NO 303
<211> LENGTH: 11
<212> TYPE: PRT
<213> ORGANISM: artificial sequence
<220> FEATURE:
<223> OTHER INFORMATION: synthetic peptide

<400> SEQUENCE: 303

Trp Gly Gln Gly Thr Gln Val Thr Val Ser Ser
1               5                   10
```

SINGLE DOMAIN VHH ANTIBODIES AGAINST VON WILLEBRAND FACTOR

RELATED APPLICATIONS

This application is a continuation of U.S. application Ser. No. 11/920,793, filed Nov. 20, 2007, now U.S. Pat. No. 7,807, 162 which is a national stage filing under 35 U.S.C. §371 of international application PCT/EP2006/004773, filed May 19, 2006, and claims the benefit under 35 U.S.C. §119(e) of U.S. provisional application Ser. No. 60/683,474, filed May 20, 2005.

The present invention relates to improved Nanobodies™ against von Willebrand Factor (vWF), as well as to polypeptides comprising or essentially consisting of one or more of such Nanobodies. [Note: Nanobody™, Nanobodies™ and Nanoclone™ are trademarks of Ablynx N.V.]

The invention also relates to nucleic acids encoding such Nanobodies and polypeptides; to methods for preparing such Nanobodies and polypeptides; to host cells expressing or capable of expressing such Nanobodies or polypeptides; to compositions comprising such Nanobodies, polypeptides, nucleic acids or host cells; and to uses of such Nanobodies, such polypeptides, such nucleic acids, such host cells or such compositions, in particular for prophylactic, therapeutic or diagnostic purposes, such as the prophylactic, therapeutic or diagnostic purposes mentioned below.

Other aspects, embodiments, advantages and applications of the invention will become clear from the further description hereinbelow.

WO 04/062551 of Applicant relates to Nanobodies against Von Willebrand Factor (vWF) and to the preparation and use thereof, in particular for the prevention and/or treatment of diseases and disorders relating to platelet-mediated aggregation.

The anti-vWF Nanobodies according to WO 04/062551 may be humanized and may be monovalent or multivalent, the latter of which leads to increased affinity for vWF. The anti-vWF Nanobodies according to WO 04/062551 may also be multispecific, and may in particular be in the form of a multispecific construct comprising two or more Nanobodies against vWF and a further Nanobody directed against a serum protein such as human serum albumin, which leads to an increased half-life in vivo.

The anti-vWF Nanobodies described in WO 04/062551 may be directed against any epitope or conformation of vWF (such as the A1 domain or A3 domain), but are preferably directed against the A1 domain, and in particular against the activated conformation of the A1 domain.

WO 04/062551 also describes the preparation of the anti-vWF Nanobodies, nucleotide sequences encoding the anti-vWF Nanobodies, as well as pharmaceutical compositions comprising the anti-vWF Nanobodies.

The anti-vWF Nanobodies and compositions described in WO 04/062551 may be used for the prevention and treatment of diseases and disorders related to platelet-mediated aggregation, such as the formation of a non-occlusive thrombus, the formation of an occlusive thrombus, arterial thrombus formation, acute coronary occlusion, peripheral arterial occlusive disease, restenosis and disorders arising from coronary bypass graft, coronary artery valve replacement and coronary interventions such angioplasty, stenting or atherectomy, hyperplasia after angioplasty, atherectomy or arterial stenting, occlusive syndrome in a vascular system or lack of patency of diseased arteries, thrombotic thrombocytopenic purpura (TTP), transient cerebral ischemic attack, unstable or stable angina pectoris, cerebral infarction, HELLP syndrome, carotid endarterectomy, carotid artery stenosis, critical limb ischaemia, cardioembolism, peripheral vascular disease, restenosis and myocardial infarction.

The pharmaceutical compositions described in WO 04/062551 may be suitable for intravenous, subcutaneous, oral, sublingual, topical, nasal, vaginal or rectal administration, or for administration by inhalation; and may also comprise a trombolytic agent, such as staphylokinase, tissue plasminogen activator, streptokinase, single chain streptokinase, urokinase and acyl plasminogen streptokinase complex. The anti-vWF Nanobodies described in WO 04/062551 may also be used for diagnostic purposes (optionally in the form of a kit-of-parts) or in coatings for medical devices such as stents It is a general object of the present invention to provide Nanobodies against vWF, in particular against human vWF.

In particular, it is an object of the present invention to provide Nanobodies against vWF, in particular against human vWF, and to provide proteins or polypeptides comprising the same, that are suitable for therapeutic and/or diagnostic use, and in particular for the prevention, treatment and/or diagnosis of one or more diseases and disorders associated with and/or mediated by vWF such as those mentioned above, and/or that can be used in the preparation of a pharmaceutical composition for the prevention and/or treatment of one or more diseases associated with and/or mediated by vWF, such as those mentioned above.

More in particular, it is an object of the invention to provide Nanobodies against vWF, and to provide proteins and polypeptides comprising the same, that are either an alternative to the Nanobodies and polypeptides against vWF described in WO 04/062551 and/or that have one or more improved properties or characteristics, compared to the Nanobodies and polypeptides against vWF described in WO 04/062551.

More in particular, it is an object of the invention to provide Nanobodies against vWF, and to provide proteins or polypeptides comprising the same, that are improved compared to the Nanobodies and polypeptides against vWF described in WO 04/062551 with respect to one or more of the following properties or characteristics:

- increased affinity for vWF, either in a monovalent format, in a multivalent format (for example in a bivalent format) and/or in a multispecific format (for example one of the multispecific formats described in WO 04/062551 or hereinbelow);
- better suitability for formatting in a multivalent format (for example in a bivalent format);
- better suitability for formatting in a multispecific format (for example one of the multispecific formats described in WO 04/062551 or hereinbelow);
- improved suitability or susceptibility for "humanizing" substitutions (as defined herein); and/or
- less immunogenicity, either in a monovalent format, in a multivalent format (for example in a bivalent format) and/or in a multispecific format (for example one of the multispecific formats described in WO 04/062551 or hereinbelow) in a monovalent format;
- increased stability, either in a monovalent format, in a multivalent format (for example in a bivalent format) and/or in a multispecific format (for example one of the multispecific formats described in WO 04/062551 or hereinbelow) in a monovalent format;
- increased specificity towards vWF, either in a monovalent format, in a multivalent format (for example in a bivalent format) and/or in a multispecific format (for example one of the multispecific formats described in WO 04/062551 or hereinbelow) in a monovalent format;

decreased or where desired increased cross-reactivity with vWF from different species;
and/or
one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described in WO 04/062551 or hereinbelow).

These objects are achieved by the Nanobodies against vWF and by the polypeptides described herein. The Nanobodies against vWF and polypeptides described herein are in particular directed against human vWF, but it is included within the scope of the invention that some of the anti-vWF Nanobodies and polypeptides of the invention may show cross-reactivity with vWF from other vertebrate animals, in particular from other warm-blooded animals, more in particular from other mammals, and in particular from other species of primates, such as the baboons used in the Examples below. However, as with anti-vWF Nanobodies described in WO 04/062551, the present invention in its broadest sense is not particularly limited to or defined by a specific epitope, domain or confirmation of vWF against which the Nanobodies and polypeptides of the invention are directed. However, it is generally assumed and preferred that the Nanobodies and polypeptides of the invention are directed against the A1 domain of vWF, either in its activated or non-activated confirmation.

Thus, in a first aspect, the invention relates to a Nanobody (as defined herein), against vWF, which consist of 4 framework regions (FR1 to FR4 respectively) and 3 complementarity determining regions (CDR1 to CDR3 respectively), in which:
i) CDR1 comprises or essentially consists of an amino acid sequence chosen from the group consisting of:

```
NYGMG    [SEQ ID NO: 15]
SYTLG    [SEQ ID NO: 16]
NYNMG    [SEQ ID NO: 17]
SSAMA    [SEQ ID NO: 18]
YYNTG    [SEQ ID NO: 19]
IGAMG    [SEQ ID NO: 20]
IGTMG    [SEQ ID NO: 21]
YNPMG    [SEQ ID NO: 22]
``` or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 2 or only 1 "amino acid difference(s)" (as defined herein) with one of the above amino acid sequences, in which:

(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and in which:
ii) CDR2 comprises or essentially consist of an amino acid sequence chosen from the group consisting of:

```
SISWSGTYTAYSDNVKG    [SEQ ID NO: 23]
GISWSGVSTDYAEFAKG    [SEQ ID NO: 24]
TSISWSGSYTAYADNVKG   [SEQ ID NO: 25]
SISWSGMSTYYTDSVKG    [SEQ ID NO: 26]
TITSGGRTSYADSVKG     [SEQ ID NO: 27]
AISWSGGLTYYADSVKG    [SEQ ID NO: 28]
TITSGGSTNYADPVKG     [SEQ ID NO: 29]
TITSGGSTNYADSVKG     [SEQ ID NO: 30]
AISRTGGSTYYARSVEG    [SEQ ID NO: 31]
AISRTGGSTYYPDSVEG    [SEQ ID NO: 32]
``` or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and in which:
iii) CDR3 comprises or essentially consists of an amino acid sequence chosen from the group consisting of:

```
QSRYRSNYYDHDDKYAY    [SEQ ID NO: 33]
LGRYRSNWRNIGQYDY     [SEQ ID NO: 34]
QSRYSSNYYDHDDKYAY    [SEQ ID NO: 35]
SNRYRTHTTQAMYNY      [SEQ ID NO: 36]
VVDGKRAP             [SEQ ID NO: 37]
NRRQKTVQMGERAYDY     [SEQ ID NO: 38]
NLKQGSYGYRFNDY       [SEQ ID NO: 39]
```

NLKQGDYGYRFNDY       [SEQ ID NO: 40]

AGVRAEDGRVRTLPSEYNF  [SEQ ID NO: 41]

AGVRAEDGRVRTLPSEYTF  [SEQ ID NO: 42]

AGVRAEDGRVRSLPSEYTF  [SEQ ID NO: 43]

or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s).

In another aspect, the invention relates to a Nanobody (as defined herein), against vWF, which consist of 4 framework regions (FR1 to FR4 respectively) and 3 complementarity determining regions (CDR1 to CDR3 respectively), in which:
i) CDR1 is an amino acid sequence chosen from the group consisting of:

NYGMG  [SEQ ID NO: 15]

SYTLG  [SEQ ID NO: 16]

NYNMG  [SEQ ID NO: 17]

SSAMA  [SEQ ID NO: 18]

YYNTG  [SEQ ID NO: 19]

IGAMG  [SEQ ID NO: 20]

IGTMG  [SEQ ID NO: 21]

YNPMG  [SEQ ID NO: 22]

or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and in which:
ii) CDR2 is an amino acid sequence chosen from the group consisting of:

SISWSGTYTAYSDNVKG   [SEQ ID NO: 23]

GISWSGVSTDYAEFAKG   [SEQ ID NO: 24]

TSISWSGSYTAYADNVKG  [SEQ ID NO: 25]

SISWSGMSTYYTDSVKG   [SEQ ID NO: 26]

TITSGGRTSYADSVKG    [SEQ ID NO: 27]

AISWSGGLTYYADSVKG   [SEQ ID NO: 28]

TITSGGSTNYADPVKG    [SEQ ID NO: 29]

TITSGGSTNYADSVKG    [SEQ ID NO: 30]

AISRTGGSTYYARSVEG   [SEQ ID NO: 31]

AISRTGGSTYYPDSVEG   [SEQ ID NO: 32]

or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s);
and in which:
iii) CDR3 is an amino acid sequence chosen from the group consisting of:

QSRYRSNYYDHDDKYAY   [SEQ ID NO: 33]

LGRYRSNWRNIGQYDY    [SEQ ID NO: 34]

QSRYSSNYYDHDDKYAY   [SEQ ID NO: 35]

SNRYRTHTTQAMYNY     [SEQ ID NO: 36]

VVDGKRAP            [SEQ ID NO: 37]

NRRQKTVQMGERAYDY    [SEQ ID NO: 38]

```
            -continued
NLKQGSYGYRFNDY            [SEQ ID NO: 39]

NLKQGDYGYRFNDY            [SEQ ID NO: 40]

AGVRAEDGRVRTLPSEYNF       [SEQ ID NO: 41]

AGVRAEDGRVRTLPSEYTF       [SEQ ID NO: 42]

AGVRAEDGRVRSLPSEYTF       [SEQ ID NO: 43]
``` or from the group consisting of amino acid sequences that have at least 80%, preferably at least 90%, more preferably at least 95%, even more preferably at least 99% sequence identity (as defined herein) with one of the above amino acid sequences; in which
  (1) any amino acid substitution is preferably a conservative amino acid substitution (as defined herein); and/or
  (2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
  (1) any amino acid substitution is preferably a conservative amino acid substitution (as defined herein); and/or
  (2) said amino acid sequence preferably only contains amino acid substitutions, and no amino acid deletions or insertions, compared to the above amino acid sequence(s).

The Nanobodies against vWF as described above and as further described hereinbelow are also referred to herein as Nanobodies of the invention.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

In another aspect, the invention relates to a Nanobody against vWF, which consist of 4 framework regions (FR1 to FR4 respectively) and 3 complementarity determining regions (CDR1 to CDR3 respectively), which is chosen from the group consisting of Nanobodies with the one of the following combinations of CDR1, CDR2 and CDR3, respectively:

```
CDR1: NYGMG;                  [SEQ ID NO: 15]

CDR2: SISWSGTYTAYSDNVKG;      [SEQ ID NO: 23]

CDR3: QSRYRSNYYDHDDKYAY;      [SEQ ID NO: 33]

CDR1: SYTLG;                  [SEQ ID NO: 16]

CDR2: GISWSGVSTDYAEFAKG;      [SEQ ID NO: 24]

CDR3: LGRYRSNWRNIGQYDY;       [SEQ ID NO: 34]

CDR1: NYGMG;                  [SEQ ID NO: 15]

CDR2: TSISWSGSYTAYADNVKG;     [SEQ ID NO: 25]

CDR3: QSRYSSNYYDHDDKYAY       [SEQ ID NO: 35]

CDR1: NYNMG;                  [SEQ ID NO: 17]
```

```
            -continued
CDR2: SISWSGMSTYYTDSVKG;      [SEQ ID NO: 26]

CDR3: SNRYRTHTTQAMYNY         [SEQ ID NO: 36]

CDR1: SSAMA;                  [SEQ ID NO: 18]

CDR2: TITSGGRTSYADSVKG;       [SEQ ID NO: 27]

CDR3: VVDGKRAP;               [SEQ ID NO: 37]

CDR1: YYNTG;                  [SEQ ID NO: 19]

CDR2: AISWSGGLTYYADSVKG;      [SEQ ID NO: 28]

CDR3: NRRQKTVQMGERAYDY        [SEQ ID NO: 38]

CDR1: IGAMG;                  [SEQ ID NO: 20]

CDR2: TITSGGSTNYADPVKG;       [SEQ ID NO: 29]

CDR3: NLKQGSYGYRFNDY          [SEQ ID NO: 39]

CDR1: IGAMG;                  [SEQ ID NO: 20]

CDR2: TITSGGSTNYADSVKG;       [SEQ ID NO: 30]

CDR3: NLKQGSYGYRFNDY          [SEQ ID NO: 39]

CDR1: IGAMG;                  [SEQ ID NO: 20]

CDR2: TITSGGSTNYADSVKG;       [SEQ ID NO: 30]

CDR3: NLKQGDYGYRFNDY          [SEQ ID NO: 40]

CDR1: IGTMG;                  SEQ ID NO: 21

CDR2: TITSGGSTNYADSVKG;       [SEQ ID NO: 30]

CDR3: NLKQGDYGYRFNDY          [SEQ ID NO: 40]

CDR1: YNPMG;                  [SEQ ID NO: 22]

CDR2: AISRTGGSTYYARSVEG;      [SEQ ID NO: 31]

CDR3: AGVRAEDGRVRTLPSEYNF     [SEQ ID NO: 41]

CDR1: YNPMG;                  [SEQ ID NO: 22]

CDR2: AISRTGGSTYYPDSVEG;      [SEQ ID NO: 32]

CDR3: AGVRAEDGRVRTLPSEYTF     [SEQ ID NO: 42]

CDR1: YNPMG;                  [SEQ ID NO: 22]

CDR2: AISRTGGSTYYPDSVEG;      [SEQ ID NO: 32]

CDR3: AGVRAEDGRVRSLPSEYTF     [SEQ ID NO: 43]
```

In the Nanobodies of the invention that comprise the combinations of CDR's mentioned above, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which
  (1) any amino acid substitution is preferably a conservative amino acid substitution (as defined herein); and/or
  (2) said amino acid sequence preferably only contains amino acid substitutions, and no amino acid deletions or insertions, compared to the above amino acid sequence(s);
and/or chosen from the group consisting of amino acid sequences that have 3, 2 or only 1 (as indicated in the preceding paragraph) "amino acid difference(s)" (as defined herein)

with the mentioned CDR(s) one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequence(s).

However, of the Nanobodies of the invention that comprise the combinations of CDR's mentioned above, Nanobodies comprising one or more of the CDR's listed above are particularly preferred; Nanobodies comprising two or more of the CDR's listed above are more particularly preferred; and Nanobodies comprising three of the CDR's listed above are most particularly preferred.

TABLE I

Preferred combinations of CDR's, of CDR's and framework sequences, and of CDR's and humanized FR's

| CLONE | ID | FR1 | ID | CDR1 | FR2 | ID | CDR1 | ID | FR3 | ID | CDR3 | ID | FR4 |
|---|---|---|---|---|---|---|---|---|---|---|---|---|---|
| 12A5 | 122 | AVQLVESGGG LVQPGGSLRL SCLASGRIFS | 148 | IGAMG | MYRQAPGK QRELVA | 174 | 200 | TITSGGSTNY ADPVKG | 226 | RFTISRDGPKNTVYLQ MNSLKPEDTAVYYCYA | 252 | NLKQGSY GYRFNDY | 278 | WGQGT QVTVSS |
| 12B1 | 123 | QVQLVESGGG LVQAGGSLRL SCAASGRTFS | 149 | NYGMG | WFRQAPGK EREFVT | 175 | 201 | SISWSGTYT AYSDNVKG | 227 | RFTISRDNAKNTVYLQ MDSLKPEDTAVYYCAA | 253 | QSRYRSNYYD HDDKYAY | 279 | WGQGT QVTVSS |
| 12B6 | 124 | QVQLVESGGG LVQAGGALRL SCAASGRTFS | 150 | YNPMG | WFRQAPGK ERDVVA | 176 | 202 | AISRTGGST YYARSVEG | 228 | RFTISRDNAKRMVYLQ MNALKPEDTAVYYCAA | 254 | AGVRAEDGR VRTLPSEYNF | 280 | WGQGT QVTVSS |
| 12D11 | 125 | AVQLVDSGGG LVQAGGSLRL SCTASERTTF | 151 | SSYTLG | WFRQAPGK EREFVG | 177 | 203 | GISWSGVST DYAEFAKG | 229 | RFTISRDHAANTVYLE MNSLKPEDTAVYYCAA | 255 | LGRYRSNWR NIGQYDY | 281 | WGQGT QVTVSS |
| 12-E3 | 126 | EVQLVESGGG LVQAGGSLRL SCAASGRTFN | 152 | NYGMG | WFRQAPGK EREFVT | 178 | 204 | SISWSGSYT AYADNVKG | 230 | RFTISRDNAKNTVYLQ MDSLKPGDTAVYYCAA | 256 | QSRYSSNYY DHDDKYAY | 282 | WGQGT QVTVSS |
| 12C9 | 127 | AVQLVESGGG LVQPGGSLKL SCATSGSIFS | 153 | SSAMA | WYRQASGK QRELVA | 179 | 205 | TITSGGRTSY ADSVKG | 231 | RFTISRDNAKNTVYLQ MNSLKPEDTAVYDCNF | 257 | VVDGKRAP QVTVSS | 283 | WGQGT |
| 14F8 | 128 | AVQLVESGGG LVQAGESLRL SCTSSGRAFS | 154 | YYNTG | WFRQAPGK EREFVA | 180 | 206 | AISWSGGLT YYADSVKG | 232 | RFTISRDNAKDMVYLQ MASLKPEDTAVYYCAA | 258 | NRRQKTVQM GERAYDY | 284 | WGQGT QVTVSS |
| 12B4 | 129 | QVQLVESGGG LVQPGGSLRL SCLASGRIFS | 155 | IGAMG | LYRQAPGK QRELVA | 181 | 207 | TITSGGSTNY ADSVKG | 233 | RFTISRDGPKNTVYLQ MNSLKPEDTAVYYCYA | 259 | NLKQGSY GYRFN DY | 285 | WGQGT QVTVSS |
| 12-E8 | 130 | AVQLEESGGG LVQPGGSLRL SCLASGRIFS | 156 | IGAMG | LYRQAPGK QRELVA | 182 | 208 | TITSGGSTNY ADSVKG | 234 | RFTISRDGAKNTVYLQ MNSLKPEDTAVYYCYA | 260 | NLKQGDYG YRFN DY | 286 | WGQGT QVTVSS |
| 12A6 | 131 | QVQLVESGGG LVQPGGSLRL SCLASGRIFS | 157 | IGTMG | LYRQAPGK QRELVA | 183 | 209 | TITSGGSTNY ADSVKG | 235 | RFTISRDGAKNTVYLQ MNSLRPEDTAVYYCYA | 261 | NLKQGDYG YRFN DY | 287 | WGQGT QVTVSS |
| 12D8 | 132 | AVQLVESGGG LVQPGGSLRL SCLASGRIFS | 158 | IGTMG | LYRQAPGK QRELVA | 184 | 210 | TITSGGSTNY ADSVKG | 236 | RFTISRDGAKNTVYLQ MNSLRPEDTAVYYCYA | 262 | NLKQGDY GYRFNDY | 288 | WGQGT QVTVSS |
| 12A2 | 133 | QVKLEESGGG LVQAGGALRL SCAASGRTFS | 159 | YNPMG | WFRQAPGK ERDLVA | 185 | 211 | AISRTGGST YYPDSVEG | 237 | RFTISRDNAKRMVYLQ MNNLKPEDTAVYYCAA | 263 | AGVRAEDGR VRTLPSEYTF | 289 | WGQGT QVTVSS |
| 12F2 | 134 | QVKLVESGGG LVQAGGALRL SCAASGRTFS | 160 | YNPMG | WFRQAPGR ERDVVA | 186 | 212 | AISRTGGST YYPDSVEG | 238 | RFTISRDNAKRMVYLQ MNNLKPEDTAVYYCAA | 264 | AGVRAEDGR VRSLPSEYTF | 290 | WGQGT QVTVSS |
| 14H10 | 135 | QVKLEESGGG LVQAGGALRL SCAASGRTFS | 161 | YNPMG | WFRQAPGK ERDVVA | 187 | 213 | AISRTGGST YYPDSVEG | 239 | RFTISRDNAKRMVYLE MNNLKPDDTAVYYCAA | 265 | AGVRAEDG RVRTLPSEYTF | 291 | WGQGT QVTVSS |
| 12B6H1 | 136 | EVQLVESGGG LVQPGGSLRL SCAASGRTFS | 162 | YNPMG | WFRQAPGK GRDVVA | 188 | 214 | AISRTGGST YYARSVEG | 240 | RFTISRDNAKRMVYLQ MNSLRAEDTAVYYCAA | 266 | AGVRAEDGRVR TLPSEYNF | 292 | WGQGT QVTVSS |
| 12B6H2 | 137 | EVQLVESGGG LVQPGGSLRL SCAASGRTFS | 163 | YNPMG | WFRQAPGK GREVVA | 189 | 215 | AISRTGGST YYARSVEG | 241 | RFTISRDNAKRMVYLQ MNSLRAEDTAVYYCAA | 267 | AGVRAEDGRV RTLPSEYNF | 293 | WGQGT QVTVSS |

TABLE I-continued

Preferred combinations of CDR's, of CDR's and framework sequences, and of CDR's and humanized FR's

| CLONE | ID FR1 | ID CDR1 | FR2 | ID CDR1 | ID FR3 | CDR3 | ID FR4 |
|---|---|---|---|---|---|---|---|
| 12B6H3 | 138 EVQLVESGGG LVQPGGSLRL SCAASGRTFS | 164 YNPMG | 190 WFRQAPGK GRDVVA | 216 AISRTGGST YYARSVEG | 242 RFTISRDNAKNMVYLQ MNSLRAEDTAVYYCAA | 268 AGVRAEDGRV RTLPSEYNF | 294 WGQGT QVTVSS |
| 12B6H4 | 139 EVQLVESGGG LVQPGGSLRL SCAASGRTFS | 165 YNPMG | 191 WFRQAPGK GRDVVA | 217 AISRTGGST YYARSVEG | 243 RFTISRDNAKRSVYLQ MNSLRAEDTAVYYCAA | 269 AGVRAEDGRV RTLPSEYNF | 295 WGQGT QVTVSS |
| 12A2H1 | 140 EVQLVESGGG LVQPGGSLRL SCAASGRTFS | 166 YNPMG | 192 WFRQAPGK GRELVA | 218 AISRTGGST YYPDSVEG | 244 RFTISRDNAKRMVYLQ MNSLRAEDTAVYYCAA | 270 AGVRAEDGRV RTLPSEYTF | 296 WGQGT QVTVSS |
| 12A2H3 | 141 EVQLVESGGG LVQPGGSLRL SCAASGRTFS | 167 YNPMG | 193 WFRQAPGK GRELVA | 219 AISRTGGST YYPDSVEG | 245 RFTISRDNAKNMVYLQ MNSLRAEDTAVYYCAA | 271 AGVRAEDGRV RTLPSEYTF | 297 WGQGT QVTVSS |
| 12A2H4 | 142 EVQLVESGGG LVQPGGSLRL SCAASGRTFS | 168 YNPMG | 194 WFRQAPGK GRELVA | 220 AISRTGGST YYPDSVEG | 246 RFTISRDNAKRSVYLQ MNSLRAEDTAVYYCAA | 272 AGVRAEDGRV RTLPSEYTF | 298 WGQGT QVTVSS |
| 12A2H11 | 143 EVQLVESGGG LVQPGGSLRL SCAASGFTFS | 169 YNPMG | 195 WFRQAPGK GRELVA | 221 AISRTGGST YYPDSVEG | 247 RFTISRDNAKRMVYLQ MNSLRAEDTAVYYCAA | 273 AGVRAEDGRV RTLPSEYTF | 299 WGQGT QVTVSS |
| 12A2H13 | 144 EVQLVESGGG LVQPGGSLRL SCAASGFTFS | 170 YNPMG | 196 WFRQAPGK GRELVA | 222 AISRTGGST YYPDSVEG | 248 RFTISRDNAKNSVYLQ MNSLRAEDTAVYYCAA | 274 AGVRAEDGRV RTLPSEYTF | 300 WGQGT LVTVSS |
| 12A5H1 | 145 EVQLVESGGG LVQPGGSLRL SCAASGRIFS | 171 IGAMG | 197 MYRQAPGK GRELVA | 223 TITSGGSTNY ADPVKG | 249 RFTISRDGPKNTVYLQ MNSLRAEDTAVYYCYA | 275 NLKQGSYGYR FNDY | 301 WGQGT QVTVSS |
| 12A5H2 | 146 EVQLVESGGG LVQPGGSLRL SCAASGRIFS | 172 IGAMG | 198 MYRQAPGK GRELVA | 224 TITSGGSTNY ADPVKG | 250 RFTISRDGAKNTVYLQ MNSLRAEDTAVYYCYA | 276 NLKQGSYGY RFNDY | 302 WGQGT QVTVSS |
| 12A5H3 | 147 EVQLVESGGG LVQPGGSLRL SCAASGRIFS | 173 IGAMG | 199 MYRQAPGK GRELVA | 225 TITSGGSTNY ADPVKG | 251 RFTISRDNAKNTVYLQ MNSLRAEDTAVYYCYA | 277 NLKQGSYGY RFNDY | 303 WGQGT QVTVSS |

Thus, in the Nanobodies of the invention, at least one of the CDR1, CDR2 and CDR3 sequences present is suitably chosen from the group consisting of the CDR1, CDR2 and CDR3 sequences, respectively, listed in Table I; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table I; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table I. In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively.

In particular, in the Nanobodies of the invention, at least the CDR3 sequence present is suitably chosen from the group consisting of the CDR3 sequences listed in Table I or from the group of CDR3 sequences that have at least 80%, preferably at least 90%, more preferably at least 95%, even more preferably at least 99% sequence identity with at least one of the CDR3 sequences listed in Table I; and/or from the group consisting of the CDR3 sequences that have 3, 2 or only 1 amino acid difference(s) with at least one of the CDR3 sequences listed in Table I.

Preferably, in the Nanobodies of the invention, at least two of the CDR1, CDR2 and CDR3 sequences present are suitably chosen from the group consisting of the CDR1, CDR2 and CDR3 sequences, respectively, listed in Table I or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table I; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table I.

In particular, in the Nanobodies of the invention, at least the CDR3 sequence present is suitably chosen from the group consisting of the CDR3 sequences listed in Table I or from the group of CDR3 sequences that have at least 80%, preferably at least 90%, more preferably at least 95%, even more preferably at least 99% sequence identity with at least one of the CDR3 sequences listed in Table I, respectively; and at least one of the CDR1 and CDR2 sequences present is suitably chosen from the group consisting of the CDR1 and CDR2 sequences, respectively, listed in Table I or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table I; and/or from the group consisting of the CDR1 and CDR2 sequences, respectively, that have 3, 2 or only 1 amino acid difference(s) with at least one of the CDR1 and CDR2 sequences, respectively, listed in Table I.

Most preferably, in the Nanobodies of the invention, all three CDR1, CDR2 and CDR3 sequences present are suitably chosen from the group consisting of the CDR1, CDR2 and CDR3 sequences, respectively, listed in Table I or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table I; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table I.

Even more preferably, in the Nanobodies of the invention, at least one of the CDR1, CDR2 and CDR3 sequences present is suitably chosen from the group consisting of the CDR1, CDR2 and CDR3 sequences, respectively, listed in Table I. Preferably, in this embodiment, at least one or preferably both of the other two CDR sequences present are suitably chosen from CDR sequences that that have at least 80%, preferably at least 90%, more preferably at least 95%, even more preferably at least 99% sequence identity with at least one of the corresponding CDR sequences, respectively, listed in Table I; and/or from the group consisting of the CDR sequences that have 3, 2 or only 1 amino acid difference(s) with at least one of the corresponding sequences, respectively, listed in Table I.

In particular, in the Nanobodies of the invention, at least the CDR3 sequence present is suitably chosen from the group consisting of the CDR3 listed in Table I. Preferably, in this embodiment, at least one and preferably both of the CDR1 and CDR2 sequences present are suitably chosen from the groups of CDR1 and CDR2 sequences, respectively, that that have at least 80%, preferably at least 90%, more preferably at least 95%, even more preferably at least 99% sequence identity with the CDR1 and CDR2 sequences, respectively, listed in listed in Table I; and/or from the group consisting of the CDR1 and CDR2 sequences, respectively, that have 3, 2 or only 1 amino acid difference(s) with at least one of the CDR1 and CDR2 sequences, respectively, listed in Table I.

Even more preferably, in the Nanobodies of the invention, at least two of the CDR1, CDR2 and CDR3 sequences present are suitably chosen from the group consisting of the CDR1, CDR2 and CDR3 sequences, respectively, listed in Table I. Preferably, in this embodiment, the remaining CDR sequence present are suitably chosen from the group of CDR sequences that that have at least 80%, preferably at least 90%, more preferably at least 95%, even more preferably at least 99% sequence identity with at least one of the corresponding CDR sequences listed in Table I; and/or from the group consisting of CDR sequences that have 3, 2 or only 1 amino acid difference(s) with at least one of the corresponding sequences listed in Table I.

In particular, in the Nanobodies of the invention, at least the CDR3 sequence is suitably chosen from the group consisting of the CDR3 sequences listed in Table I, and either the CDR1 sequence or the CDR2 sequence is suitably chosen from the group consisting of the CDR1 and CDR2 sequences, respectively, listed in Table I. Preferably, in this embodiment, the remaining CDR sequence present are suitably chosen from the group of CDR sequences that that have at least 80%, preferably at least 90%, more preferably at least 95%, even more preferably at least 99% sequence identity with at least one of the corresponding CDR sequences listed in Table I; and/or from the group consisting of CDR sequences that have 3, 2 or only 1 amino acid difference(s) with the corresponding CDR sequences listed in Table I.

Even more preferably, in the Nanobodies of the invention, all three CDR1, CDR2 and CDR3 sequences present are suitably chosen from the group consisting of the CDR1, CDR2 and CDR3 sequences, respectively, listed in Table I.

Also, generally, the combinations of CDR's listed in Table I (i.e. those mentioned on the same line in Table I) are preferred. Thus, it is generally preferred that, when a CDR in a Nanobody of the invention is a CDR sequence mentioned in Table I or is suitably chosen from the group of CDR sequences that have at least 80%, preferably at least 90%, more preferably at least 95%, even more preferably at least 99% sequence identity with a CDR sequence listed in Table I; and/or from the group consisting of CDR sequences that have 3, 2 or only 1 amino acid difference(s) with a CDR sequence listed in Table I, that at least one and preferably both of the other CDR's are suitably chosen from the CDR sequences that belong to the same combination in Table I (i.e. mentioned on the same line in Table I) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table I.

Thus, by means of non-limiting examples, a Nanobody of the invention can for example comprise a CDR1 sequence that has more than 80% sequence identity with one of the CDR1 sequences mentioned in Table I, a CDR2 sequence that has 3, 2 or 1 amino acid difference with one of the CDR2 sequences mentioned in Table I (but belonging to a different combination), and a CDR3 sequence.

Some preferred Nanobodies of the invention may for example comprise: (1) a CDR1 sequence that has more than 80% sequence identity with one of the CDR1 sequences mentioned in Table I; a CDR2 sequence that has 3, 2 or 1 amino acid difference with one of the CDR2 sequences mentioned in Table I (but belonging to a different combination); and a CDR3 sequence that has more than 80% sequence identity with one of the CDR3 sequences mentioned in Table I (but belonging to a different combination); or (2) a CDR1 sequence that has more than 80% sequence identity with one of the CDR1 sequences mentioned in Table I; a CDR2 sequence, and one of the CDR3 sequences listed in Table I; or (3) a CDR1 sequence; a CDR2 sequence that has more than 80% sequence identity with one of the CDR2 sequence listed in Table I; and a CDR3 sequence that has 3, 2 or 1 amino acid differences with the CDR3 sequence mentioned in Table I that belongs to the same combination as the CDR2 sequence.

Some particularly preferred Nanobodies of the invention may for example comprise: (1) a CDR1 sequence that has more than 80% sequence identity with one of the CDR1 sequences mentioned in Table I; a CDR2 sequence that has 3, 2 or 1 amino acid difference with the CDR2 sequence mentioned in Table I that belongs to the same combination; and a CDR3 sequence that has more than 80% sequence identity with the CDR3 sequence mentioned in Table I that belongs to the same combination; (2) a CDR1 sequence; a CDR 2 listed in Table I and a CDR3 sequence listed in Table I (in which the CDR2 sequence and CDR3 sequence may belong to different combinations).

Some even more preferred Nanobodies of the invention may for example comprise: (1) a CDR1 sequence that has more than 80% sequence identity with one of the CDR1 sequences mentioned in Table I; the CDR2 sequence listed in Table I that belongs to the same combination; and a CDR3 sequence mentioned in Table I that belongs to a different combination; or (2) a CDR1 sequence mentioned in Table I; a CDR2 sequence that has 3, 2 or 1 amino acid differences with the CDR2 sequence mentioned in Table I that belongs to the same combination; and more than 80% sequence identity with the CDR3 sequence listed in Table I that belongs to same different combination.

Particularly preferred Nanobodies of the invention may for example comprise a CDR1 sequence mentioned in Table I, a CDR2 sequence that has more than 80% sequence identity with the CDR2 sequence mentioned in Table I that belongs to the same combination; and the CDR3 sequence mentioned in Table I that belongs to the same.

In the most preferred in the Nanobodies of the invention, the CDR1, CDR2 and CDR3 sequences present are suitably chosen from the one of the combinations of CDR1, CDR2 and CDR3 sequences, respectively, listed in Table I.

Preferably, when a CDR sequence is suitably chosen from the group of CDR sequences that have at least 80%, preferably at least 90%, more preferably at least 95%, even more preferably at least 99% sequence identity (as defined herein) with one of the CDR sequences listed in Table I; and/or when a CDR sequence is suitably chosen from the group consisting of CDR sequences that have 3, 2 or only 1 amino acid difference(s) with one of the CDR sequences listed in Table I:
  i) any amino acid substitution is preferably a conservative amino acid substitution (as defined herein); and/or
  ii) said amino acid sequence preferably only contains amino acid substitutions, and no amino acid deletions or insertions, compared to the CDR sequence listed in Table I.

According to a non-limiting but preferred embodiment of the invention, the CDR sequences in the Nanobodies of the invention are as defined above and are also such that the Nanobody of the invention binds to vWF with an dissociation constant ($K_D$) of $10^{-5}$ to $10^{-12}$ moles/liter (M) or less, and preferably $10^{-7}$ to $10^{-12}$ moles/liter (M) or less and more preferably $10^{-8}$ to $10^{-12}$ moles/liter (M), and/or with an association constant ($K_A$) of at least $10^7$ M$^{-1}$, preferably at least $10^8$ M$^{-1}$, more preferably at least $10^9$ M$^{-1}$, such as at least 1012 M$^{-1}$; and in particular with a $K_D$ less than 500 nM, preferably less than 200 nM, more preferably less than 10 nM, such as less than 500 µM. The $K_D$ and $K_A$ values of the Nanobody of the invention against vWF can be determined in a manner known per se, for example using the assay described herein. More generally, the Nanobodies described herein preferably have a dissociation constant with respect to vWF that is as described in this paragraph.

In another aspect, the invention relates to a Nanobody with an amino acid sequence that is chosen from the group consisting of SEQ ID NO's: 60 to 73 and SEQ ID NO's: 86 to 97 or from the group consisting of from amino acid sequences that have more than 80%, preferably more than 90%, more preferably more than 95%, such as 99% or more "sequence identity" (as defined herein) with one or more of the amino acid sequences of SEQ ID NO's: 60 to 73 and SEQ ID NO's: 86 to 97, which amino acid sequences most preferably have framework sequences that are as further defined below under the general description of the framework sequences of Nanobodies.

According to a specific, but non-limiting embodiment, the latter amino acid sequences have been "humanized", as further described below.

Most preferably, the Nanobodies of the invention are chosen from the group consisting of SEQ ID NO's: 60 to 73 and SEQ ID NO's: 86 to 97, of which the "humanized" Nanobodies of SEQ ID NO's: 86 to 97 may be particularly preferred.

Nanobodies that are particular preferred according to the invention is Nanobody 12B6 (SEQ ID NO: 62) and homologues and variants thereof, and in particular humanized variants thereof. Some particularly preferred, but non-limiting homologues and (humanized) variants are for example Nanobodies 12A2 (SEQ ID NO: 71); 12F2 (SEQ ID NO: 72); 14H10 (SEQ ID NO: 73) and humanized variants thereof, such as 12B6H1 (SEQ ID NO: 86); 12B6H2 (SEQ ID NO: 87); 12B6H3 (SEQ ID NO: 88); 12B6H4 (SEQ ID NO: 89); 12A2H1 (SEQ ID NO: 90); 12A2H3 (SEQ ID NO: 91); 12A2H4 (SEQ ID NO: 92); 12A2H11 (SEQ ID NO: 93) and 12A2H13 (SEQ ID NO: 94).

Particularly preferred in the invention is Nanobody 12A2 (SEQ ID NO: 71) and homologues and variants thereof, and in particular humanized variants thereof. Some particularly preferred, but non-limiting homologues and (humanized) variants are for example Nanobodies 12A2H1 (SEQ ID NO: 90); 12A2H3 (SEQ ID NO: 91); 12A2H4 (SEQ ID NO: 92); 12A2H11 (SEQ ID NO: 93) and 12A2H13 (SEQ ID NO: 94), of which Nanobody 12A2H1 (SEQ ID NO: 90) is in particular preferred.

Thus, one preferred but non-limiting aspect of the invention relates to a Nanobody against Von Willebrand Factor (vWF), said Nanobody consisting of 4 framework regions (FR1 to FR4 respectively) and 3 complementarity determining regions (CDR1 to CDR3 respectively), in which:
  a) CDR1 comprises or essentially consists of:
    the amino acid sequence YNPMG [SEQ ID NO: 22]; or
    an amino acid sequences that has 2 or only 1 amino acid difference(s) with the amino acid sequence YNPMG [SEQ ID NO: 22];
  and
  b) CDR2 comprises or essentially consists of:
    the amino acid sequence AISRTGGSTYYPDSVEG [SEQ ID NO: 32]; or
    an amino acid sequence that has at least 80%, preferably at least 90%, more preferably at least 95%, even more preferably at least 99% sequence identity with the amino acid sequence AISRTGGSTYYPDSVEG [SEQ ID NO: 32]; or
    an amino acid sequences that has 2 or only 1 amino acid difference(s) with the amino acid sequence AISRTGGSTYYPDSVEG [SEQ ID NO: 32];
  and
  c) CDR3 comprises or essentially consists of:
    the amino acid sequence AGVRAEDGRVRTLPSEYTF [SEQ ID NO: 42]; or
    an amino acid sequence that has at least 80%, preferably at least 90%, more preferably at least 95%, even more preferably at least 99% sequence identity with the amino acid sequence AGVRAEDGRVRTLPSEYTF [SEQ ID NO: 42]; or
    an amino acid sequences that has only 1 amino acid difference with the amino acid sequence AGVRAEDGRVRTLPSEYTF [SEQ ID NO: 42].

In particular, the invention relates to such a Nanobody, in which:
  CDR1 comprises or essentially consists of the amino acid sequence YNPMG [SEQ ID NO: 22];

or in which:
CDR2 comprises or essentially consists of the amino acid sequence AISRTGGSTYYPDSVEG [SEQ ID NO: 32];
or in which
CDR3 comprises or essentially consists of the amino acid sequence AGVRAEDGRVRTLPSEYTF [SEQ ID NO: 42].

For example, the invention relates to such Nanobodies, in which:
CDR1 comprises or essentially consists of the amino acid sequence YNPMG [SEQ ID NO: 22]; and CDR3 comprises or essentially consists of the amino acid sequence AGVRAEDGRVRTLPSEYTF [SEQ ID NO: 42];
or in which:
CDR1 comprises or essentially consists of the amino acid sequence YNPMG [SEQ ID NO: 22]; and CDR2 comprises or essentially consists of the amino acid sequence AISRTGGSTYYPDSVEG [SEQ ID NO: 32];
or in which:
CDR2 comprises or essentially consists of the amino acid sequence AISRTGGSTYYPDSVEG [SEQ ID NO: 32]; and CDR3 comprises or essentially consists of the amino acid sequence AGVRAEDGRVRTLPSEYTF [SEQ ID NO: 42]

In one aspect, the invention relates to such a Nanobody, in which CDR1 comprises or essentially consists of the amino acid sequence YNPMG [SEQ ID NO: 22]; and CDR3 comprises or essentially consists of the amino acid sequence AGVRAEDGRVRTLPSEYTF [SEQ ID NO: 42].

The invention also relates to humanized variants of such a Nanobody. Some preferred, but non-limiting humanizing substitutions will be described herein, or will be clear to the skilled person by comparing the corresponding non-humanized and humanized Nanobodies disclosed herein. Some particularly useful humanizing substitutions are one or more of those present in the humanized variants of 12A2 (as will be clear to the skilled person from a comparison of the sequences of 12A2H1 (SEQ ID NO: 90) with the corresponding humanized sequences of 12A2H3 (SEQ ID NO: 91); 12A2H4 (SEQ ID NO: 92); 12A2H11 (SEQ ID NO: 93) and 12A2H13 (SEQ ID NO: 94).

Another one preferred but non-limiting aspect of the invention relates to a Nanobody against Von Willebrand Factor (vWF), said Nanobody consisting of 4 framework regions (FR1 to FR4 respectively) and 3 complementarity determining regions (CDR1 to CDR3 respectively), in which:
d) CDR1 is:
the amino acid sequence YNPMG [SEQ ID NO: 22]; or
an amino acid sequences that has 2 or only 1 amino acid difference(s) with the amino acid sequence YNPMG [SEQ ID NO: 22];
and
e) CDR2 is:
the amino acid sequence AISRTGGSTYYPDSVEG [SEQ ID NO: 32]; or
an amino acid sequence that has at least 80%, preferably at least 90%, more preferably at least 95%, even more preferably at least 99% sequence identity with the amino acid sequence AISRTGGSTYYPDSVEG [SEQ ID NO: 32]; or
an amino acid sequences that has 2 or only 1 amino acid difference(s) with the amino acid sequence AISRTGGSTYYPDSVEG [SEQ ID NO: 32];
and
f) CDR3 is:
the amino acid sequence AGVRAEDGRVRTLPSEYTF [SEQ ID NO: 42]; or
an amino acid sequence that has at least 80%, preferably at least 90%, more preferably at least 95%, even more preferably at least 99% sequence identity with the amino acid sequence AGVRAEDGRVRTLPSEYTF [SEQ ID NO: 42]; or
an amino acid sequences that has only 1 amino acid difference with the amino acid sequence AGVRAEDGRVRTLPSEYTF [SEQ ID NO: 42].

In particular, the invention relates to such a Nanobody, in which:
CDR1 is the amino acid sequence YNPMG [SEQ ID NO: 22];
or in which:
CDR2 is the amino acid sequence AISRTGGSTYYPDSVEG [SEQ ID NO: 32];
or in which
CDR3 is the amino acid sequence AGVRAEDGRVRTLPSEYTF [SEQ ID NO: 42].

For example, the invention relates to such Nanobodies, in which:
CDR1 is the amino acid sequence YNPMG [SEQ ID NO: 22]; and CDR3 is the amino acid sequence AGVRAEDGRVRTLPSEYTF [SEQ ID NO: 42];
or in which:
CDR1 is the amino acid sequence YNPMG [SEQ ID NO: 22]; and CDR2 is the amino acid sequence AISRTGGSTYYPDSVEG [SEQ ID NO: 32];
or in which:
CDR2 is the amino acid sequence AISRTGGSTYYPDSVEG [SEQ ID NO: 32]; and CDR3 is the amino acid sequence AGVRAEDGRVRTLPSEYTF [SEQ ID NO: 42]

In one aspect, the invention relates to such a Nanobody, in which CDR1 is the amino acid sequence YNPMG [SEQ ID NO: 22]; and CDR3 is the amino acid sequence AGVRAEDGRVRTLPSEYTF [SEQ ID NO: 42].

The invention also relates to humanized variants of such a Nanobody. Some preferred, but non-limiting humanizing substitutions will be described herein, or will be clear to the skilled person by comparing the corresponding non-humanized and humanized Nanobodies disclosed herein. Some particularly useful humanizing substitutions are one or more of those present in the humanized variants of 12A2 (as will be clear to the skilled person from a comparison of the sequences of 12A2H1 (SEQ ID NO: 90) with the corresponding humanized sequences of 12A2H3 (SEQ ID NO: 91); 12A2H4 (SEQ ID NO: 92); 12A2H11 (SEQ ID NO: 93) and 12A2H13 (SEQ ID NO: 94).

The Nanobodies described herein may be GLEW-class Nanobodies, "103 P, R or S"-class Nanobodies or "KERE-class Nanobodies" (all as described herein). In particular, the Nanobodies described herein may be KERE-class Nanobodies, although the invention is not limited thereto.

In another aspect, the invention relates to a Nanobody which has at least 80%, or at least 90%, or at least 95%, or at least 99% sequence identity (as defined herein) with at least one of the Nanobodies from the group consisting of SEQ ID NO's 60-73 and SEQ ID NO's 86-97.

In particular, the invention relates to a Nanobody which has at least 80%, or at least 90%, or at least 95%, or at least 99% sequence identity (as defined herein) with at least one of the Nanobodies 12B6 (SEQ ID NO: 62); 12A2 (SEQ ID NO: 71); 12F2 (SEQ ID NO: 72); 14H10 (SEQ ID NO: 73); 12B6H1 (SEQ ID NO: 86); 12B6H2 (SEQ ID NO: 87); 12B6H3 (SEQ ID NO: 88); 12B6H4 (SEQ ID NO: 89); 12A2H1 (SEQ ID NO: 90); 12A2H3 (SEQ ID NO: 91); 12A2H4 (SEQ ID NO: 92); 12A2H11 (SEQ ID NO: 93) and/or 12A2H13 (SEQ ID NO: 94).

More in particular, the invention relates to a Nanobody which has at least 80%, or at least 90%, or at least 95%, or at least 99% sequence identity (as defined herein) with at least one of the Nanobodies 12A2 (SEQ ID NO: 71); 12A2H1 (SEQ ID NO: 90); 12A2H3 (SEQ ID NO: 91); 12A2H4 (SEQ ID NO: 92); 12A2H11 (SEQ ID NO: 93) and/or 12A2H113 (SEQ ID NO: 94).

Even more in particular, the invention relates to a Nanobody which has at least 80%, or at least 90%, or at least 95%, or at least 99% sequence identity (as defined herein) with the Nanobody 12A2H1 (SEQ ID NO: 90).

The invention also relates to humanized variants of such Nanobodies. Some preferred, but non-limiting humanizing substitutions will be described herein, or will be clear to the skilled person by comparing the corresponding non-humanized and humanized Nanobodies disclosed herein. Some particularly useful humanizing substitutions are one or more of those present in the humanized variants of 12A2 (as will be clear to the skilled person from a comparison of the sequences of 12A2H1 (SEQ ID NO: 90) with the corresponding humanized sequences of 12A2H3 (SEQ ID NO: 91); 12A2H4 (SEQ ID NO: 92); 12A2H11 (SEQ ID NO: 93) and 12A2H13 (SEQ ID NO: 94).

The invention also relates to a Nanobody that is chosen from the group consisting of the Nanobodies of SEQ ID NO's 60-73 and SEQ ID NO's 86-97.

In particular, the invention relates to a Nanobody that is chosen from the group consisting of the Nanobodies 12B6 (SEQ ID NO: 62); 12A2 (SEQ ID NO: 71); 12F2 (SEQ ID NO: 72); 14H10 (SEQ ID NO: 73); 12B6H1 (SEQ ID NO: 86); 12B6H2 (SEQ ID NO: 87); 12B6H3 (SEQ ID NO: 88); 12B6H4 (SEQ ID NO: 89); 12A2H1 (SEQ ID NO: 90); 12A2H3 (SEQ ID NO: 91); 12A2H4 (SEQ ID NO: 92); 12A2H11 (SEQ ID NO: 93) and/or 12A2H13 (SEQ ID NO: 94).

More in particular, the invention relates to a Nanobody that is chosen from the group consisting of the Nanobodies 12A2 (SEQ ID NO: 71); 12A2H1 (SEQ ID NO: 90); 12A2H3 (SEQ ID NO: 91); 12A2H4 (SEQ ID NO: 92); 12A2H11 (SEQ ID NO: 93) and/or 12A2H13 (SEQ ID NO: 94). A particularly useful Nanobody is Nanobody 12A2H1 (SEQ ID NO:90).

The Nanobodies described herein preferably have framework sequences that are as further described herein. Some particularly preferred framework sequences (FR1, FR2, FR3 and FR4, respectively) are those of Nanobody 12A2 and its humanized variants; and framework sequences that have at least 80%, preferably at least 90%, more preferably at least 95%, even more preferably at least 99% sequence identity (as defined herein) with one of said framework sequences; and/or from the group consisting of amino acid sequences that have 3, 2 or only 1 "amino acid difference(s)" (as defined herein) with one of said framework sequences (in which any amino acid substitution is preferably a conservative amino acid substitution; and/or in which said amino acid sequence preferably contains amino acid substitutions and no more than 3 amino acid deletions or no more than 3 amino acid insertions). Nanobodies against vWF with such framework sequences form a further aspect of the invention.

In particular, the invention relates to a Nanobody against vWF, in which FR1 is SEQ ID NO: 140; FR2 is SEQ ID NO: 192; FR3 is SEQ ID NO: 244; and FR4 is SEQ ID NO: 296; or framework sequences that have at least 80%, preferably at least 90%, more preferably at least 95%, even more preferably at least 99% sequence identity (as defined herein) with one of said framework sequences; and/or from the group consisting of amino acid sequences that have 3, 2 or only 1 "amino acid difference(s)" (as defined herein) with one of said framework sequences (in which any amino acid substitution is preferably a conservative amino acid substitution; and/or in which said amino acid sequence preferably contains amino acid substitutions and no more than 3 amino acid deletions or no more than 3 amino acid insertions).

More in particular, the invention relates to a Nanobody against vWF, in which FR1 is SEQ ID NO: 140; FR2 is SEQ ID NO: 192; FR3 is SEQ ID 244; and FR4 is SEQ ID NO: 296.

In another aspect, the invention relates to a polypeptide that comprises or essentially consists of at least one Nanobody against vWF as defined herein. Such polypeptides are also referred to herein as "polypeptides of the invention" and may be as further described hereinbelow and/or as generally described in WO 02/062551 for the Nanobodies disclosed therein, and may for example be multivalent polypeptides or multispecific polypeptides, again as further described hereinbelow.

Preferably, a polypeptide of the invention is either bivalent or trivalent (i.e. comprising two or three Nanobodies of the invention, respectively, optionally linked via one or two linkers as defined herein, respectively) or a multispecific polypeptide, comprising one or two, and preferably two, Nanobodies of the invention and at least one Nanobody directed against a serum protein, and in particular against a human serum protein, such as against human serum albumin.

In one preferred, but non-limiting embodiments, the Nanobodies of the invention present in the polypeptides of the invention are chosen from the group consisting of SEQ ID NO's: 60 to 73 and SEQ ID NO's: 86 to 97, and in particular from the "humanized" Nanobodies of SEQ ID NO's 86 to 97. The Nanobodies against human serum albumin present in the polypeptides of the invention are preferably as defined herein, and are more preferably chosen from the group consisting of SEQ ID NO's: 107 to 121, and in particular from the "humanized" Nanobodies against human serum albumin of SEQ ID NO's 114-121.

Some preferred, but non-limiting examples of polypeptides of the invention are the polypeptides of SEQ ID NO's: 74 to 82 and the polypeptides of SEQ ID NO's 98-106. Other polypeptides of the invention may for example be chosen from the group consisting of amino acid sequences that have more than 80%, preferably more than 90%, more preferably more than 95%, such as 99% or more "sequence identity" (as defined herein) with one or more of the amino acid sequences of SEQ ID NO's: 74 to 82 and/or SEQ ID NO's 98 to 106, in which the Nanobodies comprised within said amino acid sequences are preferably as defined herein.

According to one aspect of the invention, the Nanobodies, proteins and polypeptides described herein have essentially no influence on the cleavage of ULvWF by ADAMTS-13. In particular, when the Nanobodies, proteins and polypeptides described herein are used at the doses described herein, the cleavage of ULvWF by ADAMTS-13 (either in vivo upon administration and/or as measured using a suitable assay, such as the assay described herein), essentially does not reduce or inhibit the cleavage of ULvWF by ADAMTS-13, i.e. by not more than 50%, preferably not more than 20%, even more preferably not more than 10%, such as less than 5% or essentially not at all). Thus, one further aspect of the invention relates to a Nanobody, protein or polypeptide, and in particular a Nanobody, protein or polypeptide as described herein, that essentially does not reduce or inhibit the cleavage of ULvWF by ADAMTS-13.

In another aspect, the invention relates to a nucleic acid that encodes a Nanobody of the invention and/or a polypeptide of the invention. Such a nucleic acid will also be referred to below as a "nucleic acid of the invention" and may for example be in the form of a genetic construct, as defined herein.

In another aspect, the invention relates to host or host cell that expresses or is capable of expressing a Nanobody of the invention and/or a polypeptide of the invention; and/or that contains a nucleic acid encoding a Nanobody of the invention and/or a polypeptide of the invention. Such a host or a host cell may also be analogous to the hosts and host cells described in WO 02/062551, but expressing or capable of expressing a Nanobody of the invention and/or a polypeptide of the invention and/or containing a nucleic acid as described herein.

The invention further relates to a product or composition containing or comprising a Nanobody of the invention, a polypeptide of the invention; and/or a nucleic acid of the invention. Such a product or composition may for example be a pharmaceutical composition (as described below) or a product or composition for diagnostic use (as also described below). Such a product or composition may also be analogous to the products and compositions described in WO 02/062551, but containing or comprising a Nanobody of the invention, a polypeptide of the invention or a nucleic acid of the invention.

The invention further relates to methods for preparing or generating the Nanobodies, polypeptides, nucleic acids, host cells, products and compositions as described herein, which methods are as further described below. Also, generally, the Nanobodies, polypeptides, nucleic acids, host cells, products and compositions described herein may also be prepared and used in a manner analogous to the manner described in WO 02/062551.

The invention further relates to applications and uses of the above Nanobodies, polypeptides, nucleic acids, host cells, products and compositions described herein, which applications and uses include, but are not limited to, the applications and uses described hereinbelow and/or the further uses and applications for Nanobodies against vWF and/or for polypeptides containing the same in WO 02/062551.

Other aspects, embodiments, advantages and applications of the invention will become clear from the further description hereinbelow.

DETAILED DESCRIPTION OF THE INVENTION

The above and other aspects and embodiments of the invention will become clear from the further description hereinbelow, in which:

a) Unless indicated or defined otherwise, all terms used have their usual meaning in the art, which will be clear to the skilled person. Reference is for example made to the standard handbooks, such as Sambrook et al, "*Molecular Cloning: A Laboratory Manual*" (2nd. Ed.), Vols. 1-3, Cold Spring Harbor Laboratory Press (1989); F. Ausubel et al, eds., "*Current protocols in molecular biology*", Green Publishing and Wiley Interscience, New York (1987); Roitt et al., "*Immunology*" (6th. Ed.), Mosby/Elsevier, Edinburgh (2001); and Janeway et al., "*Immunobiology*" (6th Ed.), Garland Science Publishing/Churchill Livingstone, New York (2005), as well as to the general background art cited above;

b) Unless indicated otherwise, the term "immunoglobulin sequence"—whether it used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acid sequences or nucleotide sequences encoding the same, unless the context requires a more limited interpretation;

c) Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein;

d) Amino acid residues will be indicated according to the standard three-letter or one-letter amino acid code, as mentioned in Table 1;

TABLE 1

| one-letter and three-letter amino acid code | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine[4] | His | H |
| | Aspartate | Asp | D |
| | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residu can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

f) For the purposes of comparing two or more amino acid sequences, the percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of nucleotides in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-2 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, *Biochemistry* 13: 211, 1974 and *Adv. Enzymol.*, 47: 45-149, 1978, and on the analysis of hydrophobicity patterns in proteins developed by Eisenberg et al., *Proc. Nad. Acad. Sci. USA* 81: 140-144, 1984; Kyte & Doolittle; J. *Molec. Biol.* 157: 105-132, 1981, and Goldman et al., *Ann. Rev. Biophys. Chem.* 15: 321-353, 1986, all incorporated herein in their entirety by reference. Information on the primary, secondary and tertiary structure of Nanobodies given in the description below and in the general background art cited above. Also, for this purpose, the crystal structure of a $V_{HH}$ domain from a llama is for example given by Desmyter et al., *Nature Structural Biology*, Vol. 3, 9, 803 (1996); Spinelli et al., *Natural Structural Biology* (1996); 3, 752-757; and Decanniere et al., Structure, Vol. 7, 4, 361 (1999);

g) amino acid sequences and nucleic acid sequences are said to be "exactly the same" if they have 100% sequence identity (as defined herein) over their entire length;

h) when comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

i) a nucleic acid sequence or amino acid sequence is considered to be "(in) essentially isolated form"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gelelectrophoresis;

j) The term "domain" as used herein generally refers to a globular region of an antibody chain, and in particular to a globular region of a heavy chain antibody, or to a polypeptide that essentially consists of such a globular region. Usually, such a domain will comprise peptide loops (for example 3 or 4 peptide loops) stabilized, for example, as a sheet or by disulfide bonds.

k) The term 'antigenic determinant' refers to the epitope on the antigen recognized by the antigen-binding molecule (such as a Nanobody or a polypeptide of the invention) and more in particular by the antigen-binding site of said molecule. The terms "antigenic determinant" and "epitope" may also be used interchangeably herein.

l) An amino acid sequence (such as a Nanobody, an antibody, a polypeptide of the invention, or generally an antigen binding protein or polypeptide or a fragment thereof) that can bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

m) The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the Nanobodies and/or polypeptides of the invention) will bind with a dissociation constant (KD) of $10^{-5}$ to $10^{-12}$ moles/liter (M) or less, and preferably $10^{-7}$ to $10^{-12}$ moles/liter (M) or less and more preferably $10^{-8}$ to $10^{-12}$ moles/liter, and/or with an association constant ($K_A$) of at least $10^7$ $M^{-1}$, preferably at least $10^8$ $M^{-1}$, more preferably at least $10^9$ M-1, such as at least $10^{12}$ $M^{-1}$. Any $K_D$ value greater than $10^{-4}$ M is generally considered to indicate non-specific binding. Preferably, a Nanobody or polypeptide of the invention will bind to the desired antigen with an $K_D$ less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

n) as further described hereinbelow, the amino acid sequence and structure of a Nanobody can be considered—without however being limited thereto—to be comprised of four framework regions or "FR's", which are referred to in the art and hereinbelow as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively;

o) as also further describe hereinbelow, the total number of amino acid residues in a Nanobody can be in the region of 110-120, is preferably 112-115, and is most preferably 113. It should however be noted that parts, fragments or analogs (as further described hereinbelow) of a Nanobody are not particularly limited as to their length and/or size, as long as such parts, fragments or analogs meet the further requirements outlined hereinbelow and are also preferably suitable for the purposes described herein;

p) the amino acid residues of a Nanobody are numbered according to the general numbering for $V_H$ domains given by Kabat et al. ("*Sequence of proteins of immunological interest*", US Public Health Services, NIH Bethesda, Md., Publication No. 91), as applied to $V_{HH}$ domains from Camelids in the article of Riechmann and Muyldermans, referred to above (see for example FIG. 2 of said reference). According to this numbering, FR1 of a Nanobody comprises the amino acid residues at positions 1-30, CDR1 of a Nanobody comprises the amino acid residues at positions 31-36, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and visa versa, position 36 according to the Kabat numbering corresponds to the start of FR2 and visa versa, position 66 according to the Kabat numbering corresponds to the start of FR3 and visa versa, and position 103 according to the Kabat numbering corresponds to the start of FR4 and visa versa.].

Alternative methods for numbering the amino acid residues of $V_H$ domains, which methods can also be applied in an analogous manner to $V_{HH}$ domains from Camelids and to Nanobodies, are the method described by Chothia et al. (*Nature* 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise; and q) the Figures, Sequence Listing and the Experimental Part/ Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and applicant; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by applicant and the further published patent applications by applicant; Hamers-Casterman et al., Nature 1993 Jun. 3; 363 (6428): 446-8; Davies and Riechmann, FEBS Lett. 1994 Feb. 21; 339(3): 285-90; Muyldermans et al., Protein Eng. 1994 September; 7(9): 1129-3; Davies and Riechmann, Biotechnology (NY) 1995 May; 13(5): 475-9; Gharoudi et al., 9th Forum of Applied Biotechnology, Med. Fac. Landbouw Univ. Gent. 1995; 60/4a part I: 2097-2100; Davies and Riechmann, Protein Eng. 1996 June; 9(6): 531-7; Desmyter et al., Nat Struct Biol. 1996 September; 3(9): 803-11; Sheriff et al., Nat Struct Biol. 1996 September; 3(9): 733-6; Spinelli et al., Nat Struct Biol. 1996 September; 3(9): 752-7; Arbabi Ghahroudi et al., FEBS Lett. 1997 Sep. 15; 414(3): 521-6; Vu et al., Mol. Immunol. 1997 November-December; 34(16-17): 1121-31; Atarhouch et al., Journal of Carnel Practice and Research 1997; 4: 177-182; Nguyen et al., J. Mol. Biol. 1998 Jan. 23; 275(3): 413-8; Lauwereys et al., EMBO J. 1998 Jul. 1; 17(13): 3512-20; Frenken et al., Res Immunol. 1998 July-August; 149(6):589-99; Transue et al., Proteins 1998 Sep. 1; 32(4): 515-22; Muyldermans and Lauwereys, J. Mol. Recognit. 1999 March-April; 12 (2): 131-40; van der Linden et al., Biochim. Biophys. Acta 1999 Apr. 12; 1431(1): 37-46; Decanniere et al., Structure Fold. Des. 1999 Apr. 15; 7(4): 361-70; Ngyuen et al., Mol. Immunol. 1999 June; 36(8): 515-24; Woolven et al., Immunogenetics 1999 October; 50 (1-2): 98-101; Riechmann and Muyldermans, J. Immunol. Methods 1999 Dec. 10; 231 (1-2): 25-38; Spinelli et al., Biochemistry 2000 Feb. 15; 39(6): 1217-22; Frenken et al., J. Biotechnol. 2000 Feb. 28; 78(1): 11-21; Nguyen et al., EMBO J. 2000 Mar. 1; 19(5): 921-30; van der Linden et al., J. Immunol. Methods 2000 Jun. 23; 240 (1-2): 185-95; Decanniere et al., J. Mol. Biol. 2000 Jun. 30; 300 (1): 83-91; van der Linden et al., J. Biotechnol. 2000 Jul. 14; 80(3): 261-70; Harmsen et al., Mol. Immunol. 2000 August; 37(10): 579-90; Perez et al., Biochemistry 2001 Jan. 9; 40(1): 74-83; Conrath et al., J. Biol. Chem. 2001 Mar. 9; 276 (10): 7346-50; Muyldermans et al., Trends Biochem Sci. 2001 April; 26(4):230-5; Muyldermans S., J. Biotechnol. 2001 June; 74 (4): 277-302; Desmyter et al., J. Biol. Chem. 2001 Jul. 13; 276 (28): 26285-90; Spinelli et al., J. Mol. Biol. 2001 Aug. 3; 311 (1): 123-9; Conrath et al., Antimicrob Agents Chemother. 2001 October; 45 (10): 2807-12; Decanniere et al., J. Mol. Biol. 2001 Oct. 26; 313(3): 473-8; Nguyen et al., Adv Immunol. 2001; 79: 261-96; Muruganandam et al., FASEB J. 2002 February; 16 (2): 240-2; Ewert et al., Biochemistry 2002 Mar. 19; 41 (11): 3628-36; Dumoulin et al., Protein Sci. 2002 March; 11 (3): 500-15; Cortez-Retamozo et al., Int. J. Cancer. 2002 Mar. 20; 98 (3): 456-62; Su et al., Mol. Biol. Evol. 2002 March; 19 (3): 205-15; van der Vaart J M., Methods Mol. Biol. 2002; 178: 359-66; Vranken et al., Biochemistry 2002 Jul. 9; 41 (27): 8570-9; Nguyen et al., Immunogenetics 2002 April; 54 (1): 39-47; Renisio et al., Proteins 2002 Jun. 1; 47 (4): 546-55; Desmyter et al., J. Biol. Chem. 2002 Jun. 28; 277 (26): 23645-50; Ledeboer et al., J. Dairy Sci. 2002 June; 85 (6): 1376-82; De Genst et al., J. Biol. Chem. 2002 Aug. 16; 277 (33): 29897-907; Ferrat et al., Biochem. J. 2002 Sep. 1; 366 (Pt 2): 415-22; Thomassen et al., Enzyme and Microbial Technol. 2002; 30: 273-8; Harmsen et al., Appl. Microbiol. Biotechnol. 2002 December; 60 (4): 449-54; Jobling et al., Nat. Biotechnol. 2003 January; 21 (1): 77-80; Conrath et al., Dev. Comp. Immunol. 2003 February; 27 (2): 87-103; Pleschberger et al., Bioconjug. Chem. 2003 March-April; 14 (2): 440-8; Lah et al., J. Biol. Chem. 2003 Apr. 18; 278 (16): 14101-11; Nguyen et al., Immunology. 2003 May; 109 (1): 93-101; Joosten et al., Microb. Cell Fact. 2003 Jan. 30; 2 (1): 1; Li et al., Proteins 2003 Jul. 1; 52 (1): 47-50; Loris et al., Biol. Chem. 2003 Jul. 25; 278 (30): 28252-7; van Koningsbruggen et al., J. Immunol. Methods. 2003 August; 279 (1-2): 149-61; Dumoulin et al., Nature. 2003 Aug. 14; 424 (6950): 783-8; Bond et al., J. Mol. Biol. 2003 Sep. 19; 332 (3): 643-55; Yau et al., J. Immunol. Methods. 2003 Oct. 1; 281 (1-2): 161-75; Dekker et al., J. Virol. 2003 November; 77 (22): 12132-9; Meddeb-Mouelhi et al., Toxicon. 2003 December; 42 (7): 785-91; Verheesen et al., Biochim. Biophys. Acta 2003 Dec. 5; 1624 (1-3): 21-8; Zhang et al., J Mol Biol. 2004 Jan. 2; 335 (1): 49-56; Stijlemans et al., J Biol. Chem. 2004 Jan. 9; 279 (2): 1256-61; Cortez-Retamozo et al., Cancer Res. 2004 Apr. 15; 64 (8): 2853-7; Spinelli et al., FEBS Lett. 2004 Apr. 23; 564 (1-2): 35-40; Pleschberger et al., Bioconjug. Chem. 2004 May-June; 15 (3): 664-71; Nicaise et al., Protein Sci. 2004 July; 13 (7): 1882-91; Omidfar et al., Tumour Biol. 2004 July-August; 25 (4): 179-87; Omidfar et al., Tumour Biol. 2004 September-December; 25(5-6): 296-305; Szynol et al., Antimicrob Agents Chemother. 2004 September; 48(9):3390-5; Saerens et al., J. Biol. Chem. 2004 Dec. 10; 279 (50): 51965-72; De Genst et al., J. Biol. Chem. 2004 Dec. 17; 279 (51): 53593-601; Dolk et al., Appl. Environ. Microbiol. 2005 January; 71(1): 442-50; Joosten et al., Appl Microbiol Biotechnol. 2005 January; 66(4): 384-92; Dumoulin et al., J. Mol. Biol. 2005 Feb. 25; 346 (3): 773-88; Yau et al., J Immunol Methods. 2005 February; 297 (1-2): 213-24; De Genst et al., J. Biol. Chem. 2005 Apr. 8; 280 (14): 14114-21; Huang et al., Eur. J. Hum. Genet. 2005 Apr. 13; Dolk et al., Proteins. 2005 May 15; 59 (3): 555-64; Bond et al., J. Mol. Biol. 2005 May 6; 348(3):699-709; Zarebski et al., J. Mol. Biol. 2005 Apr. 21; [E-publication ahead of print].

As mentioned above, the invention generally relates to Nanobodies directed against vWF, as well as to polypeptides comprising or essentially consisting of one or more of such Nanobodies, that can be used for the prophylactic, therapeutic and/or diagnostic purposes described below and in WO 04/062551.

As also mentioned above and further described below, the invention further relates to nucleic acids encoding such Nanobodies and polypeptides, to methods for preparing such Nanobodies and polypeptides, to host cells expressing or capable of expressing such Nanobodies or polypeptides, to uses of such Nanobodies, polypeptides, nucleic acids or host cells, and to compositions comprising such Nanobodies, polypeptides, nucleic acids or host cells.

Generally, it should be noted that the term Nanobody as used herein in its broadest sense is not limited to a specific biological source or to a specific method of preparation. For example, as will be discussed in more detail below, the Nanobodies of the invention can be obtained (1) by isolating the $V_{HH}$ domain of a naturally occurring heavy chain antibody; (2) by expression of a nucleotide sequence encoding a naturally occurring $V_{HH}$ domain; (3) by "humanization" (as described below) of a naturally occurring $V_{HH}$ domain or by expression of a nucleic acid encoding a such humanized $V_{HH}$ domain; (4) by "camelization" (as described below) of a naturally occurring $V_H$ domain from any animal species, in particular a species of mammal, such as from a human being, or by expression of a nucleic acid encoding such a camelized $V_H$ domain; (5) by "camelisation" of a "domain antibody" or "Dab" as described by Ward et al (supra), or by expression of a nucleic acid encoding such a camelized $V_H$ domain; (6) using synthetic or semi-synthetic techniques for preparing proteins, polypeptides or other amino acid sequences; (7) by preparing a nucleic acid encoding a Nanobody using techniques for nucleic acid synthesis, followed by expression of the nucleic acid thus obtained; and/or (8) by any combination of the foregoing. Suitable methods and techniques for performing the foregoing will be clear to the skilled person based on the disclosure herein and for example include the methods and techniques described in more detail hereinbelow.

However, according to a specific embodiment, the Nanobodies of the invention do not have an amino acid sequence that is exactly the same as (i.e. as a degree of sequence identity of 100% with) the amino acid sequence of a naturally occurring $V_H$ domain, such as the amino acid sequence of a naturally occurring $V_H$ domain from a mammal, and in particular from a human being.

One particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description below and the prior art on humanization referred to herein. Again, it should be noted that such humanized Nanobodies of the invention can be obtained in any suitable manner known per se (i.e. as indicated under points (1)-(8) above) and thus are not strictly limited to polypeptides that have been obtained using a polypeptide that comprises a naturally occurring $V_{HH}$ domain as a starting material.

Another particularly preferred class of Nanobodies of the invention comprises Nanobodies with an amino acid sequence that corresponds to the amino acid sequence of a naturally occurring $V_H$ domain that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description below. Reference is also made to WO 94/04678. Such camelization may preferentially occur at amino acid positions which are present at the $V_H$-$V_L$ interface and at the so-called Camelidae hallmark residues (see for example also WO 94/04678), as also mentioned below. Preferably, the $V_H$ domain or sequence that is used as a starting material or starting point for generating or designing the camelized Nanobody is preferably a $V_H$ sequence from a mammal, more preferably the $V_H$ sequence of a human being. However, it should be noted that such camelized Nanobodies of the invention can be obtained in any suitable manner known per se (i.e. as indicated under points (1)-(8) above) and thus are not strictly limited to polypeptides that have been obtained using a polypeptide that comprises a naturally occurring $V_H$ domain as a starting material.

For example, again as further described below, both "humanization" and "camelization" can be performed by providing a nucleotide sequence that encodes such a naturally occurring $V_{HH}$ domain or $V_H$ domain, respectively, and then changing, in a manner known per se, one or more codons in said nucleotide sequence such that the new nucleotide sequence encodes a humanized or camelized Nanobody of the invention, respectively, and then expressing the nucleotide sequence thus obtained in a manner known per se so as to provide the desired Nanobody of the invention. Alternatively, based on the amino acid sequence of a naturally occurring $V_{HH}$ domain or $V_H$ domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized Nanobody of the invention, respectively, can be designed and then synthesized de novo using techniques for nucleic acid synthesis known per se, after which the nucleotide sequence thus obtained can be expressed in a manner known per se so as to provide the desired Nanobody of the invention.

Other suitable ways and techniques for obtaining Nanobodies of the invention and/or nucleotide sequences and/or nucleic acids encoding the same, starting from (the amino acid sequence of) naturally occurring $V_H$ domains or preferably $V_{HH}$ domains and/or from nucleotide sequences and/or nucleic acid sequences encoding the same will be clear from the skilled person, and may for example comprising combining one or more amino acid sequences and/or nucleotide sequences from naturally occurring $V_H$ domains (such as one or more FR's and/or CDR's) with one or more one or more amino acid sequences and/or nucleotide sequences from naturally occurring $V_{HH}$ domains (such an one or more FR's or CDR's), in a suitable manner so as to provide (a nucleotide sequence or nucleic acid encoding) a Nanobody of the invention.

According to one preferred, but non-limiting aspect of the aspect of the invention, a Nanobody in its broadest sense can be generally defined as a polypeptide comprising:

a) an amino acid sequence that is comprised of four framework regions/sequences interrupted by three complementarity determining regions/sequences, in which the amino acid residue at position 108 according to the Kabat numbering is Q;

and/or:

b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;

and/or:

c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which i) the amino acid residue at position 108 according to the Kabat numbering is Q;

and/or in which:

ii) the amino acid residue at position 44 according to the Kabat numbering is E and in which the amino acid residue at position 45 according to the Kabat numbering is an R;

and/or in which:

iii) the amino acid residue at position 103 according to the Kabat numbering is chosen from the group consisting of P, R and S, and is in particular chosen from the group consisting of R and S;

and in which:

iv) CDR 1 is an amino acid sequence that is chosen from the group consisting of the following amino acid sequences:

```
NYGMG        [SEQ ID NO: 15]
SYTLG        [SEQ ID NO: 16]
NYNMG        [SEQ ID NO: 17]
SSAMA        [SEQ ID NO: 18]
YYNTG        [SEQ ID NO: 19]
IGAMG        [SEQ ID NO: 20]
IGTMG        [SEQ ID NO: 21]
YNPMG        [SEQ ID NO: 22]
``` or from the group consisting of amino acid sequences that have at least 80%, preferably at least 90%, more preferably at least 95%, even more preferably at least 99% sequence identity (as defined herein) with one of the above amino acid sequences; in which (1) any amino acid substitution is preferably a conservative amino acid substitution (as defined herein); and/or (2) said amino acid sequence preferably only contains amino acid substitutions, and no amino acid deletions or insertions, compared to the above amino acid sequence(s);

and/or from the group consisting of amino acid sequences that have 2 or only 1 "amino acid difference(s)" (as defined herein) with one of the above amino acid sequences, in which:

(1) any amino acid substitution is preferably a conservative amino acid substitution (as defined herein); and/or (2) said amino acid sequence preferably only contains amino acid substitutions, and no amino acid deletions or insertions, compared to the above amino acid sequence(s);

and in which:

v) CDR 2 is an amino acid sequence that is chosen from the group consisting of the following amino acid sequences:

```
SISWSGTYTAYSDNVKG    [SEQ ID NO: 23]
GISWSGVSTDYAEFAKG    [SEQ ID NO: 24]
TSISWSGSYTAYADNVKG   [SEQ ID NO: 25]
SISWSGMSTYYTDSVKG    [SEQ ID NO: 26]
TITSGGRTSYADSVKG     [SEQ ID NO: 27]
AISWSGGLTYYADSVKG    [SEQ ID NO: 28]
TITSGGSTNYADPVKG     [SEQ ID NO: 29]
TITSGGSTNYADSVKG     [SEQ ID NO: 30]
AISRTGGSTYYARSVEG    [SEQ ID NO: 31]
AISRTGGSTYYPDSVEG    [SEQ ID NO: 32]
``` or from the group consisting of amino acid sequences that have at least 80%, preferably at least 90%, more preferably at least 95%, even more preferably at least 99% sequence identity (as defined herein) with one of the above amino acid sequences; in which (1) any amino acid substitution is preferably a conservative amino acid substitution (as defined herein); and/or (2) said amino acid sequence preferably only contains amino acid substitutions, and no amino acid deletions or insertions, compared to the above amino acid sequence(s);

and/or from the group consisting of amino acid sequences that have 3, 2 or only 1 "amino acid difference(s)" (as defined herein) with one of the above amino acid sequences, in which:

(1) any amino acid substitution is preferably a conservative amino acid substitution (as defined herein); and/or (2) said amino acid sequence preferably only contains amino acid substitutions, and no amino acid deletions or insertions, compared to the above amino acid sequence(s);

and in which:

vi) CDR 3 is an amino acid sequence that is chosen from the group consisting of the following amino acid sequences:

```
QSRYRSNYYDHDDKYAY      [SEQ ID NO: 33]
LGRYRSNWRNIGQYDY       [SEQ ID NO: 34]
QSRYSSNYYDHDDKYAY      [SEQ ID NO: 35]
SNRYRTHTTQAMYNY        [SEQ ID NO: 36]
VVDGKRAP               [SEQ ID NO: 37]
NRRQKTVQMGERAYDY       [SEQ ID NO: 38]
NLKQGSYGYRFNDY         [SEQ ID NO: 39]
NLKQGDYGYRFNDY         [SEQ ID NO: 40]
AGVRAEDGRVRTLPSEYNF    [SEQ ID NO: 41]
AGVRAEDGRVRTLPSEYTF    [SEQ ID NO: 42]
AGVRAEDGRVRSLPSEYTF    [SEQ ID NO: 43]
``` or from the group consisting of amino acid sequences that have at least 80%, preferably at least 90%, more preferably at least 95%, even more preferably at least 99% sequence identity (as defined herein) with one of the above amino acid sequences; in which (1) any amino acid substitution is preferably a conservative amino acid substitution (as defined herein); and/or (2) said amino acid sequence preferably only contains amino acid substitutions, and no amino acid deletions or insertions, compared to the above amino acid sequence(s);

and/or from the group consisting of amino acid sequences that have 3, 2 or only 1 "amino acid difference(s)" (as defined herein) with one of the above amino acid sequences, in which:

(1) any amino acid substitution is preferably a conservative amino acid substitution (as defined herein); and/or (2) said amino acid sequence preferably only contains amino acid substitutions, and no amino acid deletions or insertions, compared to the above amino acid sequence(s).

Preferably, in the Nanobodies of the invention:

when CDR1 is chosen from the group consisting of (1) NYGMG [SEQ ID NO: 15]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) SISWSG-TYTAYSDNVKG [SEQ ID NO: 23]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) QSRYRSNYYDHDDKYAY [SEQ ID NO: 33]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) SYTLG [SEQ ID NO: 16]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) GISWSGVST-DYAEFAKG [SEQ ID NO: 24]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) LGRYRSNRNIGQYDY [SEQ ID NO: 34]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) NYGMG [SEQ ID NO: 15]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) TSISWSG-SYTAYADNVKG [SEQ ID NO: 25]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) QSRYSSNYYDHDDKYAY [SEQ ID NO: 35]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) NYNMG [SEQ ID NO: 15]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) SISWSGM-STYYTDSVKG [SEQ ID NO: 26]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) SNRYRTHTTQAMYNY [SEQ ID NO: 36]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) SSAMA [SEQ ID NO: 18]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) TITSGGRTSY-ADSVKG [SEQ ID NO: 27]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) VVDGKRAP [SEQ ID NO: 37]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence;

when CDR1 is chosen from the group consisting of (1) YYNTG [SEQ ID NO: 19]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) AISWSG-GLTYYADSVKG [SEQ ID NO: 28]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) NRRQKTVQMGERAYDY [SEQ ID NO: 38]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) IGAMG [SEQ ID NO: 20]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) TITSGGSTNYADPVKG [SEQ ID NO: 29]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) NLKQGSYGYRFNDY [SEQ ID NO: 39]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence;

when CDR1 is chosen from the group consisting of (1) IGAMG [SEQ ID NO: 20]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) TITSGGSTNYADSVKG [SEQ ID NO: 30]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) NLKQGSYGYRFNDY [SEQ ID NO: 39]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) IGAMG [SEQ ID NO: 20]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) TITSGGSTNYADSVKG [SEQ ID NO: 30]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) NLKQGDYGYRFNDY [SEQ ID NO: 40]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) IGTMG [SEQ ID NO: 21]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) TITSGGSTNYADSVKG [SEQ ID NO: 30]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) NLKQGDYGYRFNDY [SEQ ID NO: 40]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) YNPMG [SEQ ID NO: 22]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) AISRTGGSTYYARSVEG [SEQ ID NO: 31]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) AGVRAEDGRVRTLPSEYNF [SEQ ID NO: 41]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) YNPMG [SEQ ID NO: 22]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) AIS-RTGGSTYYPDSVEG [SEQ ID NO: 32]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) AGVRAEDGRVRTLPSEYTF [SEQ ID NO: 42]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence;

when CDR1 is chosen from the group consisting of (1) YNPMG [SEQ ID NO: 22]; (2) amino acid sequences that have at least 80%, preferably at least 90%, more preferably at least 95%, even more preferably at least 99% sequence identity (as defined herein) with said amino acid sequence; and (3) amino acid sequences that have 2 or only 1 "amino acid difference(s)" (as defined herein) with said amino acid sequence; then CDR2 is chosen from the group consisting of (1) AIS-RTGGSTYYPDSVEG [SEQ ID NO: 32]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; and CDR3 is chosen from the group consisting of (1) AGVRAEDGRVRSLPSEYTF [SEQ ID NO: 43]; (2) amino acid sequences that have at least 80%, preferably at least 90%, more preferably at least 95%, even more preferably at least 99% sequence identity (as defined herein) with said amino acid sequence; and (3) amino acid sequences that have 3, 2 or only 1 "amino acid difference(s)" (as defined herein) with said amino acid sequence; in which (1) any amino acid substitution is preferably a conservative amino acid substitution (as defined herein); and/or (2) said amino acid sequence preferably only contains amino acid substitutions, and no amino acid deletions or insertions, compared to the above amino acid sequence(s).

In particular, a Nanobody against vWF according to the invention may have the structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which i) the amino acid residue at position 108 according to the Kabat numbering is Q;

and/or in which:

ii) the amino acid residue at position 44 according to the Kabat numbering is E and in which the amino acid residue at position 45 according to the Kabat numbering is an R;

and/or in which:

iii) the amino acid residue at position 103 according to the Kabat numbering is chosen from the group consisting of P, R and S, and is in particular chosen from the group consisting of R and S;

and in which:

iv) CDR 1 is an amino acid sequence that is chosen from the group consisting of the following amino acid sequences:

| | |
|---|---|
| NYGMG | [SEQ ID NO: 15] |
| SYTLG | [SEQ ID NO: 16] |
| NYNMG | [SEQ ID NO: 17] |
| SSAMA | [SEQ ID NO: 18] |
| YYNTG | [SEQ ID NO: 19] |
| IGAMG | [SEQ ID NO: 20] |
| IGTMG | [SEQ ID NO: 21] |
| YNPMG | [SEQ ID NO: 22] | and in which:

v) CDR 2 is an amino acid sequence that is chosen from the group consisting of the following amino acid sequences:

| | |
|---|---|
| SISWSGTYTAYSDNVKG | [SEQ ID NO: 23] |
| GISWSGVSTDYAEFAKG | [SEQ ID NO: 24] |
| TSISWSGSYTAYADNVKG | [SEQ ID NO: 25] |
| SISWSGMSTYYTDSVKG | [SEQ ID NO: 26] |
| TITSGGRTSYADSVKG | [SEQ ID NO: 27] |
| AISWSGGLTYYADSVKG | [SEQ ID NO: 28] |
| TITSGGSTNYADPVKG | [SEQ ID NO: 29] |
| TITSGGSTNYADSVKG | [SEQ ID NO: 30] |
| AISRTGGSTYYARSVEG | [SEQ ID NO: 31] |
| AISRTGGSTYYPDSVEG | [SEQ ID NO: 32] | and in which:

vi) CDR 3 is an amino acid sequence that is chosen from the group consisting of the following amino acid sequences:

| | |
|---|---|
| QSRYRSNYYDHDDKYAY | [SEQ ID NO: 33] |
| LGRYRSNWRNIGQYDY | [SEQ ID NO: 34] |
| QSRYSSNYYDHDDKYAY | [SEQ ID NO: 35] |
| SNRYRTHTTQAMYNY | [SEQ ID NO: 36] |
| VVDGKRAP | [SEQ ID NO: 37] |

-continued

| | |
|---|---|
| NRRQKTVQMGERAYDY | [SEQ ID NO: 38] |
| NLKQGSYGYRFNDY | [SEQ ID NO: 39] |
| NLKQGDYGYRFNDY | [SEQ ID NO: 40] |
| AGVRAEDGRVRTLPSEYNF | [SEQ ID NO: 41] |
| AGVRAEDGRVRTLPSEYTF | [SEQ ID NO: 42] |
| AGVRAEDGRVRSLPSEYTF | [SEQ ID NO: 43] |

Preferably, in the Nanobodies of the invention according to the latter aspect:

When CDR1 is: NYGMG [SEQ ID NO: 15]; then CDR2 is: SISWSGTYTAYSDNVKG [SEQ ID NO: 23]; and CDR3 is: QSRYRSNYYDHDDKYAY [SEQ ID NO: 33]

When CDR1 is: SYTLG [SEQ ID NO: 16]; then CDR2 is: GISWSGVSTDYAEFAKG [SEQ ID NO: 24]; and CDR3 is: LGRYRSNRNIGQYDY [SEQ ID NO: 34]

When CDR1 is: NYGMG [SEQ ID NO: 15]; then CDR2 is: TSISWSGSYTAYADNVKG [SEQ ID NO: 25]; and CDR3 is: QSRYSSNYYDHDDKYAY [SEQ ID NO: 35]

When CDR1 is: NYNMG [SEQ ID NO: 17]; then CDR2 is: SISWSGMSTYYTDSVKG [SEQ ID NO: 26]; and CDR3 is: SNRYRTHTTQAMYNY [SEQ ID NO: 36]

When CDR1 is: SSAMA [SEQ ID NO: 18]; then CDR2 is: TITSGGRTSYADSVKG [SEQ ID NO: 27]; and CDR3 is: VVDGKRAP [SEQ ID NO: 37]

When CDR1 is: YYNTG [SEQ ID NO: 19]; then CDR2 is: AISWSGGLTYYADSVKG [SEQ ID NO: 28]; and CDR3 is: NRRQKTVQMGERAYDY [SEQ ID NO: 38]

When CDR1 is: IGAMG [SEQ ID NO: 20]; then CDR2 is: TITSGGSTNYADPVKG [SEQ ID NO: 29]; and CDR3 is: NLKQGSYGYRFNDY [SEQ ID NO: 39]

When CDR1 is: IGAMG [SEQ ID NO: 20]; then CDR2 is: TITSGGSTNYADSVKG [SEQ ID NO: 30]; and CDR3 is: NLKQGSYGYRFNDY [SEQ ID NO: 39]

When CDR1 is: IGAMG [SEQ ID NO: 20]; then CDR2 is: TITSGGSTNYADSVKG [SEQ ID NO: 30]; and CDR3 is: NLKQGDYGYRFNDY [SEQ ID NO: 40]

When CDR1 is: IGTMG [SEQ ID NO: 21]; then CDR2 is: TITSGGSTNYADSVKG [SEQ ID NO: 30]; and CDR3 is: NLKQGDYGYRFNDY [SEQ ID NO: 40]

When CDR1 is: YNPMG [SEQ ID NO: 22]; then CDR2 is: AISRTGGSTYYARSVEG [SEQ ID NO: 31]; and CDR3 is: AGVRAEDGRVRTLPSEYNF [SEQ ID NO: 41]

When CDR1 is: YNPMG [SEQ ID NO: 22]; and CDR2 is: AISRTGGSTYYPDSVEG [SEQ ID NO: 32]; and CDR3 is: AGVRAEDGRVRTLPSEYTF [SEQ ID NO: 42]

When CDR1 is: YNPMG [SEQ ID NO: 22]; CDR2: AISRTGGSTYYPDSVEG [SEQ ID NO: 32]; and CDR3 is: AGVRAEDGRVRSLPSEYTF [SEQ ID NO: 43]

In particular, according to one preferred, but non-limiting aspect of the aspect of the invention, a Nanobody can generally be defined as a polypeptide comprising an amino acid sequence that is comprised of four framework regions/sequences interrupted by three complementarity determining regions/sequences, in which;

a-1) the amino acid residue at position 44 according to the Kabat numbering is chosen from the group consisting of G, E, D, G, Q, R, S, L; and is preferably chosen from the group consisting of G, E or Q; and a-2) the amino acid residue at position 45 according to the Kabat numbering is chosen from the group consisting of L, R or C; and is preferably chosen from the group consisting of L or R; and a-3) the amino acid residue at position 103 according to the Kabat numbering is chosen from the group consisting of W, R or S; and is preferably W or R, and is most preferably W;

a-4) the amino acid residue at position 108 according to the Kabat numbering is Q;

or in which:

b-1) the amino acid residue at position 44 according to the Kabat numbering is chosen from the group consisting of E and Q; and b-2) the amino acid residue at position 45 according to the Kabat numbering is R; and b-3) the amino acid residue at position 103 according to the Kabat numbering is chosen from the group consisting of W, R and S; and is preferably W;

b-4) the amino acid residue at position 108 according to the Kabat numbering is chosen from the group consisting of Q and L; and is preferably Q;

or in which:

c-1) the amino acid residue at position 44 according to the Kabat numbering is chosen from the group consisting of G, E, D, Q, R, S and L; and is preferably chosen from the group consisting of G, E and Q; and c-2) the amino acid residue at position 45 according to the Kabat numbering is chosen from the group consisting of L, R and C; and is preferably chosen from the group consisting of L and R; and c-3) the amino acid residue at position 103 according to the Kabat numbering is chosen from the group consisting of P, R and S; and is in particular chosen from the group consisting of R and S; and c-4) the amino acid residue at position 108 according to the Kabat numbering is chosen from the group consisting of Q and L; is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residue at position 44 according to the Kabat numbering is chosen from the group consisting of G, E, D, G, Q, R, S, L; and is preferably chosen from the group consisting of G, E or Q;

and in which:

ii) the amino acid residue at position 45 according to the Kabat numbering is chosen from the group consisting of L, R or C; and is preferably chosen from the group consisting of L or R;

and in which:

iii) the amino acid residue at position 103 according to the Kabat numbering is chosen from the group consisting of W, R or S; and is preferably W or R, and is most preferably W;

and in which iv) the amino acid residue at position 108 according to the Kabat numbering is Q;

and in which:

v) CDR1, CDR2 and CDR3 are as defined herein, and are preferably as defined according to one of the preferred definitions above, and are more preferably as defined according to one of the more preferred definitions above.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residue at position 44 according to the Kabat numbering is chosen from the group consisting of E and Q; and in which:
ii) the amino acid residue at position 45 according to the Kabat numbering is R; and in which:
iii) the amino acid residue at position 103 according to the Kabat numbering is chosen from the group consisting of W, R and S; and is preferably W; and in which:
iv) the amino acid residue at position 108 according to the Kabat numbering is Q; and in which:
vi) CDR1, CDR2 and CDR3 are as defined herein, and are preferably as defined according to one of the preferred definitions above, and are more preferably as defined according to one of the more preferred definitions above.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residue at position 44 according to the Kabat numbering is chosen from the group consisting of G, E, D, Q, R, S and L; and is preferably chosen from the group consisting of G, E and Q; and in which:
ii) the amino acid residue at position 45 according to the Kabat numbering is chosen from the group consisting of L, R and C; and is preferably chosen from the group consisting of L and R; and in which:
iii) the amino acid residue at position 103 according to the Kabat numbering is chosen from the group consisting of P, R and S; and is in particular chosen from the group consisting of R and S; and in which:
iv) the amino acid residue at position 108 according to the Kabat numbering is chosen from the group consisting of Q and L; is preferably Q; and in which:
v) CDR1, CDR2 and CDR3 are as defined herein, and are preferably as defined according to one of the preferred definitions above, and are more preferably as defined according to one of the more preferred definitions above.

Two particularly preferred, but non-limiting groups of the Nanobodies of the invention are those according to a) above; according to a-1) to a-4) above; according to b) above; according to b-1) to b-4) above; according to c) above; and/or according to c-1) to c-4) above, in which;
a) the amino acid residues at positions 44-47 according to the Kabat numbering form the sequence GLEW (or a GLEW-like sequence as defined herein) and the amino acid residue at position 108 is Q;

or in which:
b) the amino acid residues at positions 43-46 according to the Kabat numbering form the sequence KERE or KQRE (or a KERE-like sequence) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residues at positions 44-47 according to the Kabat numbering form the sequence GLEW (or a GLEW-like sequence as defined herein) and the amino acid residue at position 108 is Q; and in which:
ii) CDR1, CDR2 and CDR3 are as defined herein, and are preferably as defined according to one of the preferred definitions above, and are more preferably as defined according to one of the more preferred definitions above.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residues at positions 43-46 according to the Kabat numbering form the sequence KERE or KQRE (or a KERE-like sequence) and the amino acid residue at position 108 is Q or L, and is preferably Q; and in which:
ii) CDR1, CDR2 and CDR3 are as defined herein, and are preferably as defined according to one of the preferred definitions above, and are more preferably as defined according to one of the more preferred definitions above.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, V or F, and is most preferably F.

Thus, without being limited hereto in any way, on the basis of the amino acid residues present on the positions mentioned above, the Nanobodies of the invention can generally be classified is on the basis of the following three groups:
a) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table 2 below;
b) The "KERE-group": Nanobodies with the amino acid sequence KERE or KQRE or at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103;

c) The "103 P, R, S-group": Nanobodies with a P R or S at position 103. These Nanobodies can have either the amino acid sequence GLEW at positions 44-47 of the Kabat numbering or the amino acid sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Thus, in another preferred, but non-limiting aspect, a Nanobody of the invention may be a Nanobody belonging to the GLEW-group (as defined herein), and in which CDR1, CDR2 and CDR3 are as defined herein, and are preferably as defined according to one of the preferred definitions above, and are more preferably as defined according to one of the more preferred definitions above.

In another preferred, but non-limiting aspect, a Nanobody of the invention may be a Nanobody belonging to the KERE-group (as defined herein), and in which CDR1, CDR2 and CDR3 are as defined herein, and are preferably as defined according to one of the preferred definitions above, and are more preferably as defined according to one of the more preferred definitions above.

Thus, in another preferred, but non-limiting aspect, a Nanobody of the invention may be a Nanobody belonging to the 103 P, R, S-group (as defined herein), and in which CDR1, CDR2 and CDR3 are as defined herein, and are preferably as defined according to one of the preferred definitions above, and are more preferably as defined according to one of the more preferred definitions above.

Also, more generally and in addition to the 108Q, 43E/44R and 103P,R,S residues mentioned above, the Nanobodies of the invention can contain, at one or more positions that, in a conventional $V_H$ domain, would form (part of) the $V_H/V_L$ interface, contain one or more amino acid residues that are more highly charged than the amino acid residues that naturally occur at the same position(s) in the corresponding naturally occurring $V_H$ or $V_{HH}$ domain, and in particular one or more charged amino acid residues (as mentioned in Table 1).

Such substitutions include, but are not limited to the GLEW-like sequences mentioned in Table 2 below; as well as the substitutions that are described in the International Application WO 00/29004 for so-called "microbodies", e.g. a Q at position 108 and KLEW at positions 44-47.

In the Nanobodies of the invention, the amino acid residue at position 83 is chosen from the group consisting of L, M, S, V and W; and is preferably L.

Also, in the Nanobodies of the invention, the amino acid residue at position 83 is chosen from the group consisting of R, K, N, E, I and Q; and is most preferably either K or E (for Nanobodies corresponding to naturally occurring $V_{HH}$ domains) or R (for "humanized" Nanobodies, as described below). The amino acid residue at position 84 is chosen from the group consisting of P, A, R, S, D and V, and is most preferably P (for Nanobodies corresponding to naturally occurring $V_{HH}$ domains) or R (for "humanized" Nanobodies, as described below).

Furthermore, in the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human VH domain, VH3, are summarized in Table 2.

Some especially preferred combinations of these Hallmark Residues as occur in naturally occurring $V_{HH}$ domains are mentioned in Table 3. For comparison, the corresponding amino acid residues of the human $V_H3$ called DP-47 have been indicated in italics.

TABLE 2

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | F$^{(1)}$, Y, H, I or V, preferably F$^{(1)}$ or Y |
| 44$^{(8)}$ | G | G$^{(2)}$, E$^{(3)}$, D, Q, R, S, L; preferably G$^{(2)}$, E$^{(3)}$ or Q; most preferably G$^{(2)}$ or E$^{(3)}$. |
| 45$^{(8)}$ | L | L$^{(2)}$, R$^{(3)}$, C, I, L, P, Q, V; preferably L$^{(2)}$ or R$^{(3)}$ |
| 47$^{(8)}$ | W, Y | W$^{(2)}$, L$^{(1)}$ or F$^{(1)}$, A, G, I, M, R, S or Y; preferably W$^{(2)}$, L$^{(1)}$, F$^{(1)}$ or R |
| 83 | R or K; usually R | R, K$^{(5)}$, N, E$^{(5)}$, I, M or Q; preferably K or R; most preferably K |
| 84 | A, T, D; predominantly A | P$^{(5)}$, A, L, R, S, D, V; preferably P |
| 103 | W | W$^{(4)}$, P$^{(6)}$, R$^{(6)}$, S; preferably W |
| 104 | G | G or D; preferably G |
| 108 | L, M or T; predominantly L | Q, L$^{(7)}$ or R; preferably Q or L$^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring $V_{HH}$ domains.
$^{(6)}$In particular, but not exclusively, in combination with GLEW at positions 44-47.
$^{(7)}$With the proviso that when positions 44-47 are GLEW, position 108 is always Q.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE 3

Some preferred combinations of Hallmark Residues in naturally occurring Nanobodies. For humanization of these combinations, reference is made to the specification.

| | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
| | L | F | E | R | F | E | P | W | G | Q |
| | L | F | E | R | F | K | P | W | G | Q |
| | L | Y | Q | R | L | K | P | W | G | Q |
| | L | F | L | R | V | K | P | Q | G | Q |
| | L | F | Q | R | L | K | P | W | G | Q |
| | L | F | E | R | F | K | P | W | G | Q |
| "GLEW" group | L | V | G | L | W | K | S | W | G | Q |
| | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables 4-7 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering Chothia (supra) that the residues at these positions already form part of CDR1.)

In Tables 4-7, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

TABLE 4

Non-limiting examples of amino acid residues in FR1
(for the footnotes, see the footnotes to Table 2)

Amino acid residue(s):

| Pos. | Human $V_H3$ | Camelid $V_{HH}$'s |
|---|---|---|
| 1 | E, Q | Q, A, E, D, H, R |
| 2 | V | V, A, E, G, L, M, Q |
| 3 | Q | Q, K, E, H, P, R, Y |
| 4 | L | L, F, P, R, V |
| 5 | V, L | Q, E, L, V, M, P, A, I |
| 6 | E | E, D, Q, A, H |
| 7 | S, T | S, F, H |
| 8 | G, R | G, A, R |
| 9 | G | G, E |
| 10 | G, V | G, D, R, A, E, N, T, V |
| 11 | Hallmark residue: L, M, S, V, W, F, N, P, T, Y; preferably L | |
| 12 | V, I | V, A, G, M |
| 13 | Q, K, R | Q, E, K, D, G, A, H, L, N, P, R, T |
| 14 | P | A, Q, A, G, P, T, V, E, F, I, N, S |
| 15 | G | G |
| 16 | G, R | G, A, E, D, N, P, R, S, V, W |
| 17 | S | S, F, T, N, P, A, C |
| 18 | L | L, V, M, Q, R |
| 19 | R, K | R, K, L, N, S, T, A, F, G, I, M, Q |
| 20 | L | L, F, I, V, M, S |
| 21 | S | S, F, T, G, H, P, A |
| 22 | C | C |
| 23 | A, T | A, D, P, S, T, V, E, G, I, L, Q, R |
| 24 | A | A, I, S, T, V, C, E, F, G, L, N, P, Q, Y |
| 25 | S | S, A, F, P, T, L, V |
| 26 | G | G, D, E, R, S, V, A, I, M, P, T |
| 27 | F | S, F, R, L, P, G, N, A, D, E, H, I, K, M, Q, T, V, Y |
| 28 | T | N, T, E, D, S, I, R, A, G, R, F, Y, L, M, P, V |
| 29 | F, V | F, L, D, S, I, G, V, A, E, P, T, Y |
| 30 | S, D, G | N, S, E, G, A, D, M, T, H, I, P, R, V, W |

TABLE 5

Non-limiting examples of amino acid residues in FR2
(for the footnotes, see the footnotes to Table 2)

Amino acid residue(s):

| Pos. | Human $V_H3$ | Camelid $V_{HH}$'s |
|---|---|---|
| 36 | W | W |
| 37 | Hallmark residue: F[1], Y, H, I, A, L, P, S or V preferably F[1] or Y | |
| 38 | R | R |
| 39 | Q | Q, H, P, R, A, D, G, L, E |
| 40 | A | A, F, G, P, T, V, I, L, N, R, S, Y |
| 41 | P, S, T | P, A, L, S, I, Q, T |

TABLE 5-continued

Non-limiting examples of amino acid residues in FR2
(for the footnotes, see the footnotes to Table 2)

Amino acid residue(s):

| Pos. | Human $V_H3$ | Camelid $V_{HH}$'s |
|---|---|---|
| 42 | G | G, E, D, R, T, V |
| 43 | K | K, D, E, N, Q, R, T, V, A, L, M, S |
| 44 | Hallmark residue: G[2], E[3], D, Q, R, S, L, A, F, K, M, N, P, V, W, Y; preferably G[2], E[3] or Q; most preferably G[2] or E[3]. | |
| 45 | Hallmark residue: L[2], R[3], C, I, L, P, Q, V, D, E, G, H, K, T; preferably L[2] or R[3] | |
| 46 | E, V | E, D, K, Q, V, A, G, N |
| 47 | Hallmark residue: W[2], L[1] or F[1], A, G, I, M, R, S, D, E, H, K, Q, T, V or Y; preferably W[2], L[1], F[1] or R | |
| 48 | V | V, I, L, A, C, E, F, G, H, M, P, Q, R, S, T, V, W, Y |
| 49 | S, A, G | A, S, A, G, T, V, D, E, I, L, Q, R, Y |

TABLE 6

Non-limiting examples of amino acid residues in FR3
(for the footnotes, see the footnotes to Table 2)

Amino acid residue(s):

| Pos. | Human $V_H3$ | Camelid $V_{HH}$'s |
|---|---|---|
| 66 | R | R |
| 67 | F | F, L, V, A, D, I, S, Y |
| 68 | T | T, A, S, D, F, G, I, K, N |
| 69 | I | I, M, V, A, F, L, R, S, T |
| 70 | S | S, A, F, E, G, K, P, T, V |
| 71 | R | R, G, I, K, Q, S, T, W, A, F, L, M, N |
| 72 | D, E | D, E, G, N, V, A, H, I, L, Q, S, T |
| 73 | N, D, G | N, D, F, I, K, S, T, Y, A, G, H, L, M, R, V |
| 74 | A, S | A, D, G, N, P, S, T, F, H, I, L, R, V, Y |
| 75 | K | K, A, E, K, L, N, Q, R, D, G, I, M, S, T, V, W |
| 76 | N, S | N, D, K, R, S, T, Y, E, G, H, I, Q |
| 77 | S, T, I | T, A, E, I, M, S, K, L, N, R, V |
| 78 | L, A | V, L, A, F, G, I, M, E, N, Q, R, S, T, W |
| 79 | Y, H | Y, A, D, F, H, S, T, C, E, I, L, N, V, W |
| 80 | L | L, F, V, M |
| 81 | Q | Q, E, R, T, G, H, I, K, L, M, N |
| 82 | M | M, I, L, V, G, P, T |
| 82a | N, G | N, D, G, H, S, T, A, E, I, K, R, V |
| 82b | S | S, N, D, G, R, A, C, E, F, I, K, M, P, T, V |
| 82c | L | L, P, M, T, V |
| 83 | Hallmark residue: R, K[5], N, E[5], I, M, A, D, G, L, Q, S, T or Q; preferably K or R; most preferably K | |
| 84 | Hallmark residue: P[5], A, L, R, S, D, V, F, G, H, N, T, Y; preferably P | |
| 85 | E, G | E, D, G, Q, A, N, R, V, Y |
| 86 | D | D, E, F, Y |
| 87 | T, M | T, S, A, C, M |
| 88 | A | A, G, S, D, L, N, P |
| 89 | V, L | V, A, D, I, L, M, N, R, T, E, F, S |
| 90 | Y | Y, F, E, H, N |
| 91 | Y, H | Y, D, F, H, L, S, T, V, C, I, N, R, W |
| 92 | C | C |
| 93 | A, K, T | A, N, G, H, K, R, S, T, V, Y, E, F, I, L, M, Q |
| 94 | K, R, T | A, V, C, F, G, I, L, R, S, D, E, K, M, N, P, Q, T, W, Y T or K; |

TABLE 7

Non-limiting examples of amino acid residues in FR4
(for the footnotes, see the footnotes to Table 2)

| Pos. | Human V$_H$3 | Camelid V$_{HH}$'s |
|---|---|---|
| 103 | Hallmark residue: W[(4)], P[(6)], R[(6)], S, F, G, K, L, N, Q, V, Y; preferably W | |
| 104 | Hallmark residue: G, A, R, S, T or D; preferably G | |
| 105 | Q, R | Q, E, K, P, R, G, H, L, S, V |
| 106 | G | G |
| 107 | T | T, A, I, N, P |
| 108 | Hallmark residue: Q, L[(7)], E, H, N, P, T or R; preferably Q or L[(7)] | |
| 109 | V | V |
| 110 | T | T, I, A |
| 111 | V | V, A, I, G |
| 112 | S | S, F, A, L, P, T, Y |
| 113 | S | S, A, L, P, F, T |

Thus, in another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the Hallmark residues are as defined herein;
and in which:
ii) CDR1, CDR2 and CDR3 are as defined herein, and are preferably as defined according to one of the preferred definitions above, and are more preferably as defined according to one of the more preferred definitions above.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
and in which
i) FR1 is chosen from the group consisting of the amino acid sequence:

[1] QVQLQESGGGXVQAGGSLRLSCAASG [26]    [SEQ ID NO: 1]

or from the group consisting of amino acid sequences that have at least 80%, preferably at least 90%, more preferably at least 95%, even more preferably at least 99% sequence identity (as defined herein) with the above amino acid sequence; in which
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 4; and/or
(2) said amino acid sequence preferably only contains amino acid substitutions, and no amino acid deletions or insertions, compared to the above amino acid sequence(s);
and in which:
ii) FR2 is chosen from the group consisting of the amino acid sequence:

[36] WXRQAPGKXXEXVA [49]    [SEQ ID NO: 2]

or from the group consisting of amino acid sequences that have at least 80%, preferably at least 90%, more preferably at least 95%, even more preferably at least 99% sequence identity (as defined herein) with the above amino acid sequence; in which
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 5; and/or
(2) said amino acid sequence preferably only contains amino acid substitutions, and no amino acid deletions or insertions, compared to the above amino acid sequence(s);
and in which:
iii) FR3 is chosen from the group consisting of the amino acid sequence:

[SEQ ID NO: 3]
[66] RFTISRDNAKNTVYLQMNSLXXEDTAVYYCAA [94]

or from the group consisting of amino acid sequences that have at least 80%, preferably at least 90%, more preferably at least 95%, even more preferably at least 99% sequence identity (as defined herein) with the above amino acid sequence; in which
(1) any amino acid substitution at any position other than a Hallmark position is preferably either a conservative amino acid substitution (as defined herein) and/or an amino acid substitution as defined in Table 6; and/or
(2) said amino acid sequence preferably only contains amino acid substitutions, and no amino acid deletions or insertions, compared to the above amino acid sequence(s);
and/or from the group consisting of amino acid sequences that have 3, 2 or only 1 "amino acid difference(s)" (as defined herein) with one of the above amino acid sequences, in which:
(1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to the above amino acid sequence(s);

and in which:

iv) FR4 is chosen from the group consisting of the amino acid sequence:

[103] XXQGTXVTVSS [113]       [SEQ ID NO: 4]

or from the group consisting of amino acid sequences that have at least 80%, preferably at least 90%, more preferably at least 95%, even more preferably at least 99% sequence identity (as defined herein) with the above amino acid sequence; in which
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s);

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s);

and in which:

v) CDR1, CDR2 and CDR3 are as defined herein, and are preferably as defined according to one of the preferred definitions above, and are more preferably as defined according to one of the more preferred definitions above;

in which the Hallmark Residues are indicated by "X" and are as defined hereinabove and in which the numbers between brackets refer to the amino acid positions according to the Kabat numbering.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which: and in which i) FR1 is chosen from the group consisting of the amino acid sequence:

[1] QVQLQESGGGLVQAGGSLRLSCAASG [26]   [SEQ ID NO: 5]

or from the group consisting of amino acid sequences that have at least 80%, preferably at least 90%, more preferably at least 95%, even more preferably at least 99% sequence identity (as defined herein) with the above amino acid sequence; in which
  (1) any amino acid substitution at any position other than a Hallmark position is preferably either a conservative amino acid substitution (as defined herein) and/or an amino acid substitution as defined in Table 4; and/or
  (2) said amino acid sequence preferably only contains amino acid substitutions, and no amino acid deletions or insertions, compared to the above amino acid sequence(s); and
  (3) the Hallmark residue at position is as indicated in the sequence above;

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 4; and/or
  (2) said amino acid sequence preferably only contains amino acid substitutions, and no amino acid deletions or insertions, compared to the above amino acid sequence(s); and
  (3) the Hallmark residue at position is as indicated in the sequence above;

and in which:

ii) FR2 is chosen from the group consisting of the amino acid sequences:

[36] WFRQAPGKERELVA [49]       [SEQ ID NO: 6]

[36] WFRQAPGKEREFVA [49]       [SEQ ID NO: 7]

[36] WFRQAPGKEREGA [49]        [SEQ ID NO: 8]

[36] WFRQAPGKQRELVA [49]       [SEQ ID NO: 9]

[36] WFRQAPGKQREFVA [49]       [SEQ ID NO: 10]

[36] WYRQAPGKGLEWA [49]        [SEQ ID NO: 11]

or from the group consisting of amino acid sequences that have at least 80%, preferably at least 90%, more preferably at least 95%, even more preferably at least 99% sequence identity (as defined herein) with one of the above amino acid sequences; in which
  (1) any amino acid substitution at any position other than a Hallmark position is preferably either a conservative amino acid substitution (as defined herein) and/or an amino acid substitution as defined in Table 5; and/or
  (2) said amino acid sequence preferably only contains amino acid substitutions, and no amino acid deletions or insertions, compared to the above amino acid sequence(s); and
  (3) the Hallmark residues at positions 37, 44, 45 and 47 are as indicated in each of the sequences above;

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 5; and/or
  (2) said amino acid sequence preferably only contains amino acid substitutions, and no amino acid deletions or insertions, compared to the above amino acid sequence(s); and
  (3) the Hallmark residues at positions 37, 44, 45 and 47 are as indicated in each of the sequences above;

and in which:

iii) FR3 is chosen from the group consisting of the amino acid sequence:

[66] RFTISRDNAKNTVYLQMNSLKPEDTAVYYCAA [94]   [SEQ ID NO: 12]

or from the group consisting of amino acid sequences that have at least 80%, preferably at least 90%, more preferably at least 95%, even more preferably at least 99% sequence identity (as defined herein) with the above amino acid sequence; in which
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s); and
  (3) the Hallmark residues at positions 83 and 84 are as indicated in each of the sequences above;

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s); and
  (3) the Hallmark residues at positions 83 and 84 are as indicated in each of the sequences above;

and in which:

iv) FR4 is chosen from the group consisting of the amino acid sequences:

[103] WGQGTQVTVSS [113]    [SEQ ID NO: 13]

[103] WGQGTLVTVSS [113]    [SEQ ID NO: 14]

or from the group consisting of amino acid sequences that have at least 80%, preferably at least 90%, more preferably at least 95%, even more preferably at least 99% sequence identity (as defined herein) with one of the above amino acid sequence; in which
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s); and
  (3) the Hallmark residues at positions 103, 104 and 108 are as indicated in each of the sequences above;

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s); and
  (3) the Hallmark residues at positions 103, 104 and 108 are as indicated in each of the sequences above;

and in which:

v) CDR1, CDR2 and CDR3 are as defined herein, and are preferably as defined according to one of the preferred definitions above, and are more preferably as defined according to one of the more preferred definitions above.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which and in which i) FR1 is chosen from the group consisting of the amino acid sequence:

[1] QVQLQESGGGLVQAGGSLRLSCAASG [26]    [SEQ ID NO: 5]

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 4; and/or
  (2) said amino acid sequence preferably only contains amino acid substitutions, and no amino acid deletions or insertions, compared to the above amino acid sequence(s); and
  (3) the Hallmark residue at position is as indicated in the sequence above;

and in which:

ii) FR2 is chosen from the group consisting of the amino acid sequences:

[36] WFRQAPGKEREL**VA [49]    [SEQ ID NO: 6]

[36] WFRQAPGKEREF**VA [49]    [SEQ ID NO: 7]

[36] WFRQAPGKEREG**A [49]    [SEQ ID NO: 8]

[36] WFRQAPGKQREL**VA [49]    [SEQ ID NO: 9]

[36] WFRQAPGKQREF**VA [49]    [SEQ ID NO: 10]

and/or from the group consisting of amino acid sequences that have 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 5; and/or
  (2) said amino acid sequence preferably only contains amino acid substitutions, and no amino acid deletions or insertions, compared to the above amino acid sequence(s); and
  (3) the Hallmark residues at positions 37, 44, 45 and 47 are as indicated in each of the sequences above;

and in which:
iii) FR3 is chosen from the group consisting of the amino acid sequence:

[SEQ ID NO: 12]
[66] RFTISRDNAKNTVYLQMNSLKPEDTAVYYCAA [94]

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s); and
  (3) the Hallmark residues at positions 83 and 84 are as indicated in each of the sequences above;

and in which:
iv) FR4 is chosen from the group consisting of the amino acid sequences:

[103] WGQGTQVTVSS [113]    [SEQ ID NO: 13]

[103] WGQGTLVTVSS [113]    [SEQ ID NO: 14]

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 7; and/or
  (2) said amino acid sequence preferably only contains amino acid substitutions, and no amino acid deletions or insertions, compared to the above amino acid sequence(s); and
  (3) the Hallmark residues at positions 103, 104 and 108 are as indicated in each of the sequences above;

and in which:
v) CDR1, CDR2 and CDR3 are as defined herein, and are preferably as defined according to one of the preferred definitions above, and are more preferably as defined according to one of the more preferred definitions above.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
and in which
i) FR1 is chosen from the group consisting of the amino acid sequence:

[1] QVQLQESGGGLVQAGGSLRLSCAASG [26]    [SEQ ID NO: 5]

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 4; and/or
  (2) said amino acid sequence preferably only contains amino acid substitutions, and no amino acid deletions or insertions, compared to the above amino acid sequence(s); and
  (3) the Hallmark residue at position is as indicated in the sequence above;

and in which:
ii) FR2 is chosen from the group consisting of the amino acid sequence:

[36] WYRQAPGKGLEWA [49]    [SEQ ID NO: 11]

and/or from the group consisting of amino acid sequences that have 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 5; and/or
  (2) said amino acid sequence preferably only contains amino acid substitutions, and no amino acid deletions or insertions, compared to the above amino acid sequence(s); and
  (3) the Hallmark residues at positions 37, 44, 45 and 47 are as indicated in each of the sequences above;

and in which:
iii) FR3 is chosen from the group consisting of the amino acid sequence:

[SEQ ID NO: 12]
[66] RFTISRDNAKNTVYLQMNSLKPEDTAVYYCAA [94]

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 6; and/or
  (2) said amino acid sequence preferably only contains amino acid substitutions, and no amino acid deletions or insertions, compared to the above amino acid sequence(s); and
  (3) the Hallmark residues at positions 83 and 84 are as indicated in each of the sequences above;

and in which:
iv) FR4 is chosen from the group consisting of the amino acid sequence:

[103] WGQGTQVTVSS [113]    [SEQ ID NO: 13]

and/or from the group consisting of amino acid sequences that have 3, 2 or only 1 "amino acid difference(s)" (as defined herein) with one of the above amino acid sequences, in which:
  (1) any amino acid substitution at any position other than a Hallmark position is preferably either a conservative amino acid substitution (as defined herein) and/or an amino acid substitution as defined in Table 7; and/or (2) said amino acid sequence preferably only contains amino acid substitutions, and no amino acid deletions or insertions, compared to the above amino acid sequence(s); and (3) the Hallmark residues at positions 103, 104 and 108 are as indicated in each of the sequences above;

and in which:

v) CDR1, CDR2 and CDR3 are as defined herein, and are preferably as defined according to one of the preferred definitions above, and are more preferably as defined according to one of the more preferred definitions above.

In another preferred, but not limiting aspect, a Nanobody of the invention can have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

and in which i) FR1 is chosen from the group consisting of the FR1 sequences present in the Nanobodies of SEQ ID NO's 60 to 73 and SEQ ID NO's 86 to 97, and in particular in the humanized Nanobodies of SEQ ID NO's 86 to 97, or from the group consisting of amino acid sequences that have at least 80%, preferably at least 90%, more preferably at least 95%, even more preferably at least 99% sequence identity (as defined herein) with one of said FR1 sequences; in which (1) any amino acid substitution at any position other than a Hallmark position is preferably either a conservative amino acid substitution (as defined herein) and/or an amino acid substitution as defined in Table 4; and/or (2) said amino acid sequence preferably only contains amino acid substitutions, and no amino acid deletions or insertions, compared to said FR1 sequence; and (3) the Hallmark residue at position is as indicated in said FR1 sequence;

and/or from the group consisting of amino acid sequences that have 3, 2 or only 1 "amino acid difference(s)" (as defined herein) with one of said FR1 sequences, in which:

(1) any amino acid substitution at any position other than a Hallmark position is preferably either a conservative amino acid substitution (as defined herein) and/or an amino acid substitution as defined in Table 4; and/or (2) said amino acid sequence preferably only contains amino acid substitutions, and no amino acid deletions or insertions, compared to said FR1 sequence; and (3) the Hallmark residue at position is as indicated in said FR1 sequence;

and in which:

ii) FR2 is chosen from the group consisting of the FR2 sequences present in the Nanobodies of SEQ ID NO's 60 to 73 and SEQ ID NO's 86 to 97, and in particular in the humanized Nanobodies of SEQ ID NO's 86 to 97, or from the group consisting of amino acid sequences that have at least 80%, preferably at least 90%, more preferably at least 95%, even more preferably at least 99% sequence identity (as defined herein) with one of said FR2 sequences; in which (1) any amino acid substitution at any position other than a Hallmark position is preferably either a conservative amino acid substitution (as defined herein) and/or an amino acid substitution as defined in Table 5; and/or (2) said amino acid sequence preferably only contains amino acid substitutions, and no amino acid deletions or insertions, compared to said FR2 sequence; and (3) the Hallmark residues at positions 37, 44, 45 and 47 are as indicated in said FR2 sequence;

and/or from the group consisting of amino acid sequences that have 3, 2 or only 1 "amino acid difference(s)" (as defined herein) with one of said FR2 sequences, in which:

(1) any amino acid substitution at any position other than a Hallmark position is preferably either a conservative amino acid substitution (as defined herein) and/or an amino acid substitution as defined in Table 5; and/or (2) said amino acid sequence preferably only contains amino acid substitutions, and no amino acid deletions or insertions, compared to said FR2 sequence; and (3) the Hallmark residues at positions 37, 44, 45 and 47 are as indicated in said FR2 sequence;

and in which:

iii) FR3 is chosen from the group consisting of the FR3 sequences present in the Nanobodies of SEQ ID NO's 60 to 73 and SEQ ID NO's 86 to 97, and in particular in the humanized Nanobodies of SEQ ID NO's 86-97, or from the group consisting of amino acid sequences that have at least 80%, preferably at least 90%, more preferably at least 95%, even more preferably at least 99% sequence identity (as defined herein) with one of said FR3 sequences; in which (1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to said FR3 sequence; and (3) the Hallmark residues at positions 83 and 84 are as indicated in said FR3 sequence;

and/or from the group consisting of amino acid sequences that have 3, 2 or only 1 "amino acid difference(s)" (as defined herein) with one of said FR3 sequences, in which:

(1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to said FR3 sequence; and (3) the Hallmark residues at positions 83 and 84 are as indicated in said FR3 sequence;

and in which:

iv) FR4 is chosen from the group consisting of the FR4 sequences present in the Nanobodies of SEQ ID NO's 60 to 73 and SEQ ID NO's 86 to 97, and in particular in the humanized Nanobodies of SEQ ID NO's 86 to 97, or from the group consisting of amino acid sequences that have at least 80%, preferably at least 90%, more preferably at least 95%, even more preferably at least 99% sequence identity (as defined herein) with one of said FR4 sequences; in which (1) any amino acid substitution at any position other than a Hallmark position is preferably either a conservative amino acid substitution (as defined herein) and/or an amino acid substitution as defined in Table 6; and/or (2) said amino acid sequence preferably only contains amino acid substitutions, and no amino acid deletions or insertions, compared to said FR4 sequence; and (3) the Hallmark residues at positions 103, 104 and 108 are as indicated in said FR3 sequence;

and/or from the group consisting of amino acid sequences that have 3, 2 or only 1 "amino acid difference(s)" (as defined herein) with one of said FR4 sequences, in which:
(1) any amino acid substitution at any position other than a Hallmark position is preferably either a conservative amino acid substitution (as defined herein) and/or an amino acid substitution as defined in Table 6; and/or
(2) said amino acid sequence preferably only contains amino acid substitutions, and no amino acid deletions or insertions, compared to said FR4 sequence; and
(3) the Hallmark residues at positions 103, 104 and 108 are as indicated in said FR4 sequence;

and in which:

v) CDR1, CDR2 and CDR3 are as defined herein, and are preferably as defined according to one of the preferred definitions above, and are more preferably as defined according to one of the more preferred definitions above.

Some particularly preferred Nanobodies of the invention can be chosen from the group consisting of the amino acid sequences of SEQ ID NO's 60 to 73 and SEQ ID NO's 86 to 97, and in particular in the humanized Nanobodies of SEQ ID NO's 86 to 97 or from the group consisting of amino acid sequences that have at least 80%, preferably at least 90%, more preferably at least 95%, even more preferably at least 99% sequence identity (as defined herein) with one of the amino acid sequences of SEQ ID NO's 60 to 73 and SEQ ID NO's 86 to 97 (and preferably of SEQ ID NO's 86 to 97); in which
(1) the Hallmark residues can be as indicated in Table 2 above;
(2) any amino acid substitution at any position other than a Hallmark position is preferably either a conservative amino acid substitution (as defined herein) and/or an amino acid substitution as defined in Tables 4-7; and/or
(3) said amino acid sequence preferably only contains amino acid substitutions, and no amino acid deletions or insertions, compared to the above amino acid sequence(s).

Some even more particularly preferred Nanobodies of the invention can be chosen from the group consisting of the amino acid sequences of SEQ ID NO's 60 to 73 and SEQ ID NO's 86 to 97, and in particular in the humanized Nanobodies of SEQ ID NO's 86 to 97 or from the group consisting of amino acid sequences that have at least 80%, preferably at least 90%, more preferably at least 95%, even more preferably at least 99% sequence identity (as defined herein) with one of the amino acid sequences of SEQ ID NO's 60 to 73 and SEQ ID NO's 86 to 97 (and preferably of SEQ ID NO's 86 to 97); in which
(1) the Hallmark residues are as indicated in the pertinent sequence chosen from SEQ ID NO's 60 to 73 and SEQ ID NO's 86 to 97 (and preferably from SEQ ID NO's 86 to 97);
(2) any amino acid substitution at any position other than a Hallmark position is preferably either a conservative amino acid substitution (as defined herein) and/or an amino acid substitution as defined in Tables 4-7; and/or
(3) said amino acid sequence preferably only contains amino acid substitutions, and no amino acid deletions or insertions, compared to the pertinent sequence chosen from SEQ ID NO's 60 to 73 and SEQ ID NO's 86 to 97 (and preferably from SEQ ID NO's 86 to 97).

Some of the most preferred Nanobodies of the invention can be chosen from the group consisting of the amino acid sequences of SEQ ID NO's 60 to 73 and SEQ ID NO's 86 to 97, and in particular from the humanized Nanobodies of SEQ ID NO's 86 to 97.

As will be clear from the above, the term Nanobodies of the invention as used herein in its broadest sense also comprises natural or synthetic mutants, variants, alleles, analogs and orthologs (hereinbelow collectively referred to as "analogs") of the Nanobodies mentioned in the SEQ ID NO's 60 to 73 and SEQ ID NO's 86 to 97.

Generally, such analogs can for example comprise homologous sequences, functional portions, or a functional portion of a homologous sequence (as further defined below) of a Nanobody. Generally, in such analogs, each amino acid residue (other than the Hallmark Residue) in each of the framework regions can be replaced by any other amino acid residue, provided that the total degree of sequence identity of the framework regions remains as defined herein. Preferably, however, in such analogs:

one or amino acid residues in the above framework sequences are replaced by one or more amino acid residues that naturally occur at the same position in a naturally occurring $V_{HH}$ domain. Some examples of such substitutions are mentioned in Tables 4-7 above;

and/or:

one or amino acid residues in the above framework sequences are replaced by one or more amino acid residues that can be considered a "conservative" amino acid substitution, as described hereinabove;

and/or:

one or amino acid residues in the above framework sequences are replaced by one or more amino acid residues that naturally occur at the same position in a naturally occurring $V_H$ domain of a human being. This is generally referred to as "humanization" of the naturally occurring $V_{HH}$/Nanobody in general and of said position in particular, and will be discussed in more detail hereinbelow;

and:

positions for which only one amino acid residue is mentioned for both the $V_H$ domain and the $V_{HH}$ domain in Tables 4-7 above are preferably not replaced.

Also, although generally less preferred, in such analogs, one or more amino acid residues may be deleted from the framework regions and/or inserted into the framework regions (optionally in addition to one or more amino acid substitutions as mentioned above), provided that the total degree of sequence identity of the framework regions remains as defined herein. The Hallmark residues should not be deleted. Also, most preferably, amino acid residues for which only one amino acid residue is mentioned for both the $V_H$ domain and the $V_{HH}$ domain in Tables 4-7 above are preferably not deleted.

Preferably, such analogs should be such that they still can bind to, have affinity for and/or have specificity for vWF, i.e. with an affinity and/or a specificity which is at least 10%, preferably at least 50%, more preferably at least 70%, even more preferably at least 80%, such as at least 90%, at least 95%, at least 99% or more, of the affinity and/or specificity of at least one of the Nanobodies of SEQ ID No's 60 to 73 and SEQ ID NO's 86 to 97, as determined using a suitable assay, for example an assay to determine binding of the analog to vWF, and in particular one of the assays as used in the Examples below.

Generally, such analogs can for example be obtained by providing a nucleic acid that encodes a naturally occurring $V_{HH}$ domain, changing the codons for the one or more amino acid residues that are to be humanized into the codons for the corresponding human amino acid residue(s), expressing the nucleic acid/nucleotide sequence thus obtained in a suitable host or expression system; and optionally isolating and/or purifying the analog thus obtained to provide said analog in essentially isolated form (as defined hereinabove). This can generally be performed using methods and techniques known per se, which will be clear to the skilled person, for example from the handbooks and references cited herein and/or from the further description hereinbelow. Alternatively, and for example, a nucleic acid encoding an analog can be synthesized in a manner known per se (for example using an automated apparatus for synthesizing nucleic acid sequences with a predefined amino acid sequence) and can be expressed in a suitable host or expression system, upon which the analog thus obtained can optionally be isolated and/or purified so as to provide said analog in essentially isolated form (as defined hereinabove). Another way to provide the analogs involves chemical synthesis of the pertinent amino acid sequence using techniques for peptide synthesis known per se, such as those mentioned hereinbelow.

It will be also generally be clear to the skilled person that Nanobodies (including analogs thereof) can also be prepared starting from human $V_H$ sequences (i.e. amino acid sequences or the corresponding nucleotide sequences), such as for example human $V_H3$ sequences such as DP-47, DP-51 or DP-29, by changing one or more amino acid residues in the amino acid sequence of said human $V_H$ domain, so as to provide an amino acid sequence that has (a) a Q at position 108; and/or (b) E at position 44 and/or R at position 45, and preferably E at position 44 and R at position 45; and/or (c) P, R or S at position 103, as described above. Again, this can generally be performed using the various methods and techniques referred to in the previous paragraph, using an amino acid sequence and/or nucleotide sequence for a human $V_H$ domain as a starting point.

The term Nanobodies as used herein in its broadest sense also comprises parts or fragments of the Nanobodies (including analogs) of the invention as defined herein, which can again be as further described below.

Generally, parts or fragments of the Nanobodies and/or analogs have amino acid sequences in which, compared to the amino acid sequence of the corresponding full length Nanobody or analog, one or more of the amino acid residues at the N-terminal end, one or more amino acid residues at the C-terminal end, one or more contiguous internal amino acid residues, or any combination thereof, have been deleted and/or removed. It is also possible to combine one or more of such parts or fragments to provide a Nanobody of the invention.

Preferably, the amino acid sequence of a Nanobody that comprises one or more parts or fragments of a full length Nanobody and/or analog should have a degree of sequence identity of at least 50%, preferably at least 60%, more preferably at least 70%, such as at least 80%, at least 90% or at least 95%, with the amino acid sequence of the corresponding full length Nanobody.

Also, the amino acid sequence of a Nanobody that comprises one or more parts or fragments of a full length Nanobody and/or analog is preferably such that is comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length Nanobody.

Generally, such parts or fragments of the Nanobodies of the invention will have amino acid sequences in which, compared to the amino acid sequence of the corresponding full length Nanobody of the invention, one or more of the amino acid residues at the N-terminal end, one or more amino acid residues at the C-terminal end, one or more contiguous internal amino acid residues, or any combination thereof, have been deleted and/or removed. It is also possible to combine one or more of such parts or fragments to provide a Nanobody of the invention.

According to one preferred embodiment, a fragment as used herein comprises at least one of the CDR's present in a full-sized Nanobody of the invention, preferably at least two of the CDR's present in a full-sized Nanobody of the invention, more preferably at least CDR2 and CDR3 present in a full-sized Nanobody of the invention, such as for example all three CDR's present in a full-sized Nanobody of the invention.

According to another particularly preferred, but non-limiting embodiment, such a part or fragment comprises at least FR3, CDR3 and FR4 of the corresponding full length Nanobody of the invention, i.e. as for example described in the International application WO 03/050531 (Lasters et al.).

Preferably, such parts or fragments should be such that they still can bind to, have affinity for and/or have specificity for vWF, i.e. with an affinity and/or a specificity which is at least 10%, preferably at least 50%, more preferably at least 70%, even more preferably at least 80%, such as at least 90%, at least 95%, at least 99% or more, of the affinity and/or specificity of the corresponding full-sized Nanobody of the invention, for example an assay to determine binding of the analog to vWF, and in particular one of the assays as used in the Examples below.

From the description hereinabove, it will be clear that the amino acid sequences of the Nanobodies used herein differ at least one amino acid position in at least one of the framework regions from the amino acid sequences of naturally occurring $V_H$ domains, such as the amino acid sequences of naturally occurring $V_H$ domains of antibodies from human beings. In particular, it will be clear that the amino acid sequences of the Nanobodies used herein differ at least one of the Hallmark Residues from amino acid sequences of naturally occurring $V_H$ domains, such as the amino acid sequences of naturally occurring $V_H$ domains from antibodies from Camelids and/or human beings.

Thus, according to one specific embodiment, a Nanobody of the invention has an amino acid sequence that differs at least one amino acid position in one of the framework regions from the amino acid sequence of a naturally occurring $V_H$ domain. According to a more specific, but non-limiting embodiment of the invention, a Nanobody of the invention has an amino acid sequence that differs at least one of the Hallmark residues from the amino acid sequence of a naturally occurring $V_H$ domain.

From the description hereinabove, it will also be clear that the amino acid sequences of the some of the Nanobodies of the invention, such as the humanized Nanobodies of the invention, will differ at least one amino acid position in at least one of the framework regions (i.e. either at the position of a Hallmark residue or at another position) from the amino acid sequences of naturally occurring $V_{HH}$ domains. Thus, according to one specific, but non-limiting embodiment, a Nanobody of the invention has an amino acid sequence that differs at at least one amino acid position in one of the framework regions from the amino acid sequence of a naturally occurring $V_{HH}$ domain. According to a more specific, but non-limiting embodiment of the invention, a Nanobody of the invention has an amino acid sequence that differs at least one of the Hallmark residues from the amino acid sequence of a naturally occurring $V_{HH}$ domain.

As mentioned above, the invention also relates to proteins or polypeptides comprising at least one $V_{HH}$ domain (i.e. as identified using the methods of the invention) or at least one Nanobody based thereon.

According to one non-limiting embodiment of the invention, such a polypeptide of the invention essentially consists of a Nanobody. By "essentially consist of" is meant that the amino acid sequence of the polypeptide of the invention either is exactly the same as the amino acid sequence of a Nanobody (as mentioned above) or corresponds to the amino acid sequence of a Nanobody in which a limited number of amino acid residues, such as 1-10 amino acid residues and preferably 1-6 amino acid residues, such as 1, 2, 3, 4, 5 or 6 amino acid residues, have been added to the amino terminal end, to the carboxy terminal end, or both to the amino terminal end and to the carboxy terminal end of the amino acid sequence of the Nanobody.

Said amino acid residues may or may not change, alter or otherwise influence the (biological) properties of the Nanobody and may or may not add further functionality to the Nanobody. For example, said amino acid residues may:

a) form a "tag", i.e. an amino acid sequence or residue that allows or facilitates the purification of the Nanobody, for example using affinity techniques directed against said sequence or residue. Thereafter, said sequence or residue may be removed (e.g. by chemical or enzymatical cleavage) to provide the nucleotide sequence of the invention (for this purpose, the sequence or residue may optionally be linked to the amino acid sequence of the invention via a cleavable linker sequence). Some preferred, but non-limiting examples of such residues are multiple histidine residues and glutatione residues, b) can be a N-terminal Met residue, for example as result of expression in a heterologous host cell or host organism.

c) may be one or more amino acid residues that can be provided with functional groups and/or that have been functionalized, in a manner known per se. For example, as is known in the art, amino acid residues such as lysine and in particular cysteine allow for the attachment of PEG groups, which may mask surface site on a protein and thus for example decrease immunogenicity, improve half-life in plasma and stabilize against proteolytic cleavage;

d) increase the half-life in serum of a Nanobody or polypeptide of the invention. Amino acid sequences that can be attached to and/or fused with therapeutic proteins in order to increase their half-life in vivo are well know to the skilled person and include human serum proteins or fragments thereof (such as human serum albumin or a part or fragment thereof), or even Fc portions of antibodies (in particular of human antibodies). Also, as already described herein, such an amino acid sequence for increasing the half-life may be an amino acid sequence directed against a serum protein, such as a Nanobody directed against a serum protein, for example against human serum albumin.

With regard to pegylation, its should be noted that generally, the invention also encompasses any Nanobody of the invention and/or polypeptide of the invention that has been pegylated at one or more amino acid positions, preferably in such a way that said pegylation either (1) increases the half-life in vivo; (2) reduces immunogenicity; (3) provides one or more further beneficial properties known per se for pegylation; (4) does not essentially affect the affinity of the Nanobody and/or polypeptide for vWF (e.g. does not reduce said affinity by more than 90%, preferably not by more than 50%, and more preferably not by more than 10%, as determined by a suitable assay, such as those described in the Examples below); and/or (4) does not affect any of the other desired properties of the Nanobodies and/or polypeptides of the invention. Suitable PEG-groups and methods for attaching them, either specifically or non-specifically, will be clear to the skilled person. Suitable kits and reagents for such pegylation can for example be obtained from Nektar (CA, USA).

According to one non-limiting embodiment, one or more amino acid residues can be added to, inserted in and/or substituted in the amino acid sequence of a Nanobody or polypeptide of the invention, so as to provide one or more specific amino acid residues for attachment of a PEG-group.

The invention also encompasses any Nanobody of the invention and/or polypeptide of the invention that has been glycosylated at one or more amino acid positions, usually depending upon the host used to express the Nanobody or polypeptide of the invention (as further described below).

According to one non-limiting embodiment, one or more amino acid residues can be added to, inserted in and/or substituted in the amino acid sequence of a Nanobody or polypeptide of the invention, so as to provide one or more specific amino acid residues and/or a site that can be glycosylated by the host organism used. By means of a preferred, but non-limiting example, the N-residue on position 50 within CDR2 of a Nanobody of the invention can for example be replaced by a Q, D or S residue so as to provide a glycosylation site, e.g. for glycosylation by *Pichia*.

According to another embodiment, a polypeptide of the invention can comprise a the amino acid sequence of a Nanobody, which is fused at its amino terminal end, at its carboxy terminal end, or both at its amino terminal end and at its carboxy terminal end with at least one further amino acid sequence.

Again, said further amino acid sequence(s) may or may not change, alter or otherwise influence the (biological) properties of the Nanobody and may or may not add further functionality to the Nanobody.

For example, according to one preferred, but non-limiting embodiment, said further amino acid sequence may comprise at least one further Nanobody, so as to provide a polypeptide of the invention that comprises at least two, such as three, four or five, Nanobodies, in which said Nanobodies may optionally be linked via one or more linker sequences (as defined herein).

Polypeptides of the invention comprising two or more Nanobodies will also referred to herein as "multivalent" polypeptides. For example a "bivalent" polypeptide of the Invention comprises two Nanobodies, optionally linked via a linker sequence, whereas a "trivalent" polypeptide of the invention comprises three Nanobodies, optionally linked via two linker sequences; etc.

In a multivalent polypeptide of the invention, the two or more Nanobodies may be the same or different. For example, the two or more Nanobodies in a multivalent polypeptide of the invention:
  may be directed against the same antigen, i.e. against the same parts or epitopes of said antigen or against two or more different parts or epitopes of said antigen; and/or:
  may be directed against the different antigens;
or a combination thereof.

Thus, a bivalent polypeptide of the invention for example:
  may comprise two identical Nanobodies;
  may comprise a first Nanobody directed against a first part or epitope of an antigen and a second Nanobody directed against the same part or epitope of said antigen or against another part or epitope of said antigen;
  or may comprise a first Nanobody directed against a first antigen and a second Nanobody directed against a second antigen different from said first antigen;

whereas a trivalent Polypeptide of the Invention for example:
- may comprises three identical or different Nanobodies directed against the same or different parts or epitopes of the same antigen;
- may comprise two identical or different Nanobodies directed against the same or different parts or epitopes on a first antigen and a third Nanobody directed against a second antigen different from said first antigen; or
- may comprise a first Nanobody directed against a first antigen, a second Nanobody directed against a second antigen different from said first antigen, and a third Nanobody directed against a third antigen different from said first and second antigen, Polypeptides of the invention that contain at least two Nanobodies, in which at least one Nanobody is directed against a first antigen and at least one Nanobody is directed against a second Nanobody different from the first antigen, will also be referred to as "multispecific" Nanobodies. Thus, a "bispecific" Nanobody is a Nanobody that comprises at least one Nanobody directed against a first antigen and at least one further Nanobody directed against a second antigen, whereas a "trispecific" Nanobody is a Nanobody that comprises at least one Nanobody directed against a first antigen, at least one further Nanobody directed against a second antigen, and at least one further Nanobody directed against a third antigen; etc.

Accordingly, in their simplest form, a bispecific polypeptide of the invention is a bivalent polypeptide of the invention (as defined herein), comprising a first Nanobody directed against a first antigen and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against a first antigen, a second Nanobody directed against a second antigen and a third Nanobody directed against a third antigen, in which said first, second and third Nanobody may optionally be linked via one or more, and in particular one and more in particular two, linker sequences.

However, as will be clear from the description hereinabove, the invention is not limited thereto, in the sense that a multispecific polypeptide of the invention may comprise any number of Nanobodies directed against two or more different antigens.

For multivalent and multispecific polypeptides containing one or more $V_{HH}$ domains and their preparation, reference is also made to Conrath et al., *J. Biol. Chem.*, Vol. 276, 10. 7346-7350, as well as to EP 0 822 985.

Linkers for use in multivalent and multispecific polypeptides will be clear to the skilled person, and for example include gly-ser linkers, for example of the type $(gly_x ser_y)_z$, such as (for example $(gly_4 ser)_3$ or $(gly_3 ser_2)_3$, as described in WO 99/42077, hinge like regions such as the hinge regions of naturally occurring heavy chain antibodies or similar sequences. For other suitable linkers, reference is also made to the general background art cited above. Some particularly preferred linkers are given in SEQ ID NO's 83 to 85, in which the linkers of SEQ ID NO's 84 and 85 are particularly preferred.

Linkers can also provide some functionality for the multivalent or multispecific polypeptide. For example, linkers containing one or more charged amino acid residues (see Table 1 above) can provide improved hydrophilic properties, whereas linkers that form or contain small epitopes or tags can be used for the purposes of detection, identification and/or purification.

As also further described herein, a multispecific polypeptide of the invention directed against a desired antigen and against at least one serum protein, such as the serum proteins mentioned hereinbelow, and in particular against human serum albumin, may show increased half-life in serum, compared to the corresponding monovalent Nanobody.

As mentioned hereinabove, the methods described herein are particularly suited for generating such multivalent of multispecific polypeptides of the invention.

In a polypeptide of the invention, the at least one Nanobody may also be linked to a conventional $V_H$ domain or to a natural or synthetic analog of a $V_H$ domain, optionally via a linker sequence.

In a polypeptide of the invention, the at least one Nanobody may also be linked to a $V_L$ domain or to a natural or synthetic analog of a $V_L$ domain, optionally via a linker sequence, so as to provide a polypeptide of the invention that is in the form analogous to a conventional scFv fragment, but containing a Nanobody instead of a $V_H$ domain.

In a polypeptide of the invention, the at least one Nanobody may also be linked to one or more of a CH1, CH2 and/or CH3 domain, optionally via a linker sequence. For instance, a Nanobody linked to a suitable CH1 domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by a Nanobody. Such fragments may also be heterospecific or bispecific, i.e. directed against two or more antigens. A Nanobody linked to suitable CH2 and CH3 domains, for example derived from Camelids, could be used to form a monospecific or bispecific heavy chain antibody. Finally, a Nanobody linked to suitable CH1, CH2 and CH3 domains, for example derived from a human being, could be used—together with suitable light chains—to form an antibody that is analogous to a conventional 4-chain antibody, but in which one or both of the conventional $V_H$ domains have been replaced by a Nanobody.

Also, in addition to the one or more Nanobodies, Polypeptides of the Invention can also contain functional groups, moieties or residues, for example therapeutically active substances, such as those mentioned below, and/or markers or labels, such as fluorescent markers, isotopes, etc., as further described hereinbelow.

The Nanobodies of the invention, the polypeptides of the invention, and nucleic acids encoding the same, can be prepared in a manner known per se, and will be clear to the skilled person from the further description herein. Some preferred, but non-limiting methods for preparing the Nanobodies, polypeptides and nucleic acids include the methods and techniques mentioned above and/or further described hereinbelow.

As will be clear to the skilled person, one particularly useful method for preparing a Nanobody and/or a polypeptide of the invention generally comprises the steps of:
- the expression, in a suitable host cell or host organism (also referred to herein as a "host of the invention") or in another suitable expression system of a nucleic acid that encodes said Nanobody or polypeptide of the invention (also referred to herein as a "nucleic acid of the invention"), optionally followed by:
- isolating and/or purifying the Nanobody or polypeptide of the invention thus obtained.

In particular, such a method may comprise the steps of:
- cultivating and/or maintaining a host of the invention under conditions that are such that said host of the invention expresses and/or produces at least one Nanobody and/or polypeptide of the invention; optionally followed by:

isolating and/or purifying the Nanobody or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined hereinabove.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring GPCR as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to hereinbelow. Such genetic constructs comprising at least one nucleic acid of the invention will also be referred to herein as "genetic constricts of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises a) at least one nucleic acid of the invention; operably connected to
b) one or more regulatory elements, such as a promoter and optionally a suitable terminator;
c) and optionally also
d) one or more further elements of genetic constructs known per se;

in which the terms "regulatory element", "promoter", "terminator" and "operably connected" have their usual meaning in the art (as further described below); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in bacterial cells, such as those mentioned hereinbelow and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycine or ampicilline), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 6,207,410, U.S. Pat. No. 5,693,492 and EP 1 085 089. Other examples will be clear to the skilled person. Reference is also made to the general background art cited above and the further references cited hereinbelow.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned below.

The nucleic acids of the invention and/or the genetic constructs of the invention may be used to transform a host cell or host organism, i.e. for expression and/or production of the Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; f *Yarrowia*, for example of *Yarrowia lipolytica*;
- an amphibian cell or cell line, such as *Xenopus oocytes*;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example derived a cell or cell line derived from a human, from the mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The Nanobodies and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patent by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-)introduced into the body of the patient. All this can be performed using gene therapy vectors, techniques and delivery systems which are well known to the skilled person, for Culver, K. W., "Gene Therapy", 1994, p. xii, Mary Ann Liebert, Inc., Publishers, New York, N.Y.). Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ.

Res. 77 (1995), 1077-1086; Onodera, Blood 91; (1998), 30-36; Verma, Gene Ther. 5 (1998), 692-699; Nabel, Ann. N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580, 859; 1 U.S. Pat. No. 5,589,5466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the Nanobodies in a cell, they may also be expressed as so-called or as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

For production, the Nanobodies and polypeptides of the invention can for example also be produced in the milk of transgenic mammals, for example in the milk of rabbits, cows, goats or sheep (see for example U.S. Pat. No. 6,741, 957, U.S. Pat. No. 6,304,489 and U.S. Pat. No. 6,849,992 for general techniques for introducing transgenes into mammals), in plants or parts of plants including but not limited to their leaves, flowers, fruits, seed, roots or turbers (for example in tobacco, maize, soybean or alfalfa) or in for example pupae of the silkworm *Bombix mori*.

Furthermore, the Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, Polypeptides of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast are usually leads to a glycosylation pattern that differs from human glycosylation. Nevertheless, it should be understood that all the foregoing host cells and expression systems can be used in the invention, depending on the desired Nanobody or protein to be obtained.

Thus, according to one non-limiting embodiment of the invention, the Nanobody or polypeptide of the invention is glycosylated. According to another non-limiting embodiment of the invention, the Nanobody or polypeptide of the invention is non-glycosylated.

According to one preferred, but non-limiting embodiment of the invention, the Nanobody or polypeptide of the invention is produced in a bacterial cell, in particular a bacterial cell suitable for large scale pharmaceutical production, such as cells of the strains mentioned above.

According to another preferred, but non-limiting embodiment of the invention, the Nanobody or polypeptide of the invention is produced in a yeast cell, in particular a yeast cell suitable for large scale pharmaceutical production, such as cells of the species mentioned above.

According to yet another preferred, but non-limiting embodiment of the invention, the Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the Nanobodies and the proteins of the invention, the Nanobodies and proteins of the invention can be produced either intracellularly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic hosts cells are used, extracellular production is usually preferred since this considerably facilitates the further isolation and downstream processing of the Nanobodies and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular a Nanobody or a polypeptide of the invention, can be used.

Thus, according to one non-limiting embodiment of the invention, the Nanobody or polypeptide of the invention is a Nanobody or polypeptide that has been produced intracellularly and that has been isolated from the host cell, and in particular from a bacterial cell or from an inclusion body in a bacterial cell. According to another non-limiting embodiment of the invention, the Nanobody or polypeptide of the invention is a Nanobody or polypeptide that has been produced extracellularly, and that has been isolated from the medium in which the host cell is cultivated.

Some preferred, but non-limiting promoters for use with these host cells include,
for expression in *E. coli*: lac promoter (and derivatives thereof such as the lacUV5 promoter); arabinose promoter; left—(PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;
for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase); PGK1 (phosphoglycerate kinase), PYK1 (pyruvate kinase); regulated: GAL1,10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);
for expression in *Pichia pastoris*: the AOX1 promoter (alcohol oxidase I)
for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:
vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUC-Tag (ATCC 37460) and 1ZD35 (ATCC 37565), as well as viral-based expression systems, such as those based on adenovirus;
vectors for expression in bacterials cells: pET vectors (Novagen) and pQE vectors (Qiagen);
vectors for expression in yeast or other fungal cells: pYES2 (Invitrogen) and *Pichia* expression vectors (Invitrogen);
vectors for expression in insect cells: pBlueBacII (Invitrogen) and other baculovirus vectors
vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:
for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal
for use in yeast: α-mating factor prepro-sequence, phosphatase (phoI), invertase (Suc), etc.;
for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence of the invention may (first) be generated in an immature form (as mentioned above), which may then be subjected to post-translational modification, depending on the host cell/host organism used. Also, the amino acid sequence of the invention may be glycosylated, again depending on the host cell/host organism used.

The amino acid sequence of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence of the invention) and/or preparative immunological techniques (i.e. using antibodies against the amino acid sequence to be isolated).

Generally, for pharmaceutical use, the polypeptides of the invention may be formulated as a pharmaceutical preparation comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described hereinbelow.

Thus, in a further aspect, the invention relates to a pharmaceutical composition that contains at least one Nanobody of the invention or at least one polypeptide of the invention and at least one suitable carrier (i.e. a carrier suitable for veterinary use), and optionally one or more further active substances.

One embodiment of the present invention is a polypeptide construct comprising: at least one Nanobody of the invention, i.e. directed against any of vWF, vWF A1 domain, A1 domain of activated vWF, vWF A3 domain.

Another embodiment of the present invention is a polypeptide construct as described above, wherein the Nanobody of the invention directed against the A1 domain of activated vWF specifically recognizes the activated vWF conformation at the site of thrombus formation but does not bind to circulating unactivated forms of vWF.

The Nanobodies of the invention may also be directed against a fragment of vWF, vWF A1 domain, A1 domain of activated vWF, vWF A3 domain, such as a fragment capable of eliciting an immune response. A target is also a fragment of vWF, vWF A1 domain, A1 domain of activated vWF, vWF A3 domain, capable of binding to a Nanobody of the invention raised against the 'parent' full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of $1 \times 10-6$ M or better.

A fragment as used herein also refers to optional insertions, deletions and substitutions of one or more amino acids which do not substantially alter the ability of the target to bind to a Nanobody of the invention raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A Nanobody of the invention directed against a target generally means Nanobody of the invention that it is capable of binding to its target with an affinity of better than $10^{-6}$ M.

Another embodiment of the present invention is a polypeptide construct as described above wherein at least one Nanobody of the invention is a humanised sequence.

Another embodiment of the present invention is a polypeptide construct as described above wherein at least one Nanobody of the invention is a Camelidae $V_{HH}$ antibody.

Another embodiment of the present invention is a polypeptide construct as described above, wherein said Nanobody of the invention is an homologous sequence, a functional portion, or a functional portion of an homologous sequence of the full length Nanobody of the invention.

Another embodiment of the present invention is a polypeptide construct as described above, wherein said polypeptide construct is a homologous sequence of said polypeptide construct, a functional portion thereof, of an homologous sequence of a functional portion thereof.

Another embodiment of the present invention is a polypeptide construct as described above, further comprising at least one Nanobody of the invention directed against one or more serum proteins, in particular one or more human serum proteins.

Another embodiment of the present invention is a polypeptide construct as described above wherein said at least one (human) serum protein is any of (human) serum albumin, (human) serum immunoglobulins, (human) thyroxine-binding protein, (human) transferrine, or (human) fibrinogen or a fragment thereof.

According to a specific, but non-limiting aspect of the invention, the polypeptides of the invention contain, besides the one or more Nanobodies of the invention, at least one Nanobody against human serum albumin. Although these Nanobodies against human serum albumin may be as generally described in W04/062551 or in the further references cited therein, according to a particularly preferred, but non-limiting embodiment, said Nanobody against human serum albumin consists of 4 framework regions (FR1 to FR4 respectively) and 3 complementarity determining regions (CDR1 to CDR3 respectively), in which:

i) CDR1 is an amino acid sequence chosen from the group consisting of:

| | |
|---|---|
| SFGMS | [SEQ ID NO: 44] |
| LNLMG | [SEQ ID NO: 45] |
| INLLG | [SEQ ID NO: 46] |
| NYWMY; | [SEQ ID NO: 47] | and/or from the group consisting of amino acid sequences that have 2 or only 1 "amino acid difference(s)" (as defined herein) with one of the above amino acid sequences, in which:

(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;

and in which:

ii) CDR2 is an amino acid sequence chosen from the group consisting of:

```
SISGSGSDTLYADSVKG    [SEQ ID NO: 48]
TITVGDSTNYADSVKG     [SEQ ID NO: 49]
TITVGDSTSYADSVKG     [SEQ ID NO: 50]
SINGRGDDTRYADSVKG    [SEQ ID NO: 51]
AISADSSTKNYADSVKG    [SEQ ID NO: 52]
AISADSSDKRYADSVKG    [SEQ ID NO: 53]
RISTGGGYSYYADSVKG    [SEQ ID NO: 54]
``` or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;

and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;

and in which:

iii) CDR3 is an amino acid sequence chosen from the group consisting of:

```
DREAQVDTLDFDY        [SEQ ID NO: 55]
``` or from the group consisting of amino acid sequences that have at least 80%, preferably at least 90%, more preferably at least 95%, even more preferably at least 99% sequence identity (as defined herein) with one of the above amino acid sequences; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;

and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;

or from the group consisting of:

```
GGSLSR      [SEQ ID NO: 56]
RRTWHSEL    [SEQ ID NO: 57]
GRSVSRS     [SEQ ID NO: 58]
GRGSP       [SEQ ID NO: 59]
``` and/or from the group consisting of amino acid sequences that have 3, 2 or only 1 "amino acid difference(s)" (as defined herein) with one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences.

In another aspect, the invention relates to a Nanobody against vWF, which consist of 4 framework regions (FR1 to FR4 respectively) and 3 complementarity determining regions (CDR1 to CDR3 respectively), which is chosen from the group consisting of Nanobodies with the one of the following combinations of CDR1, CDR2 and CDR3, respectively:

```
CDR1: SFGMS;              [SEQ ID NO: 44]
CDR2: SISGSGSDTLYADSVKG;  [SEQ ID NO: 48]
CDR3: GGSLSR;             [SEQ ID NO: 56]
CDR1: LNLMG;              [SEQ ID NO: 45]
CDR2: TITVGDSTNYADSVKG;   [SEQ ID NO: 49]
CDR3: RRTWHSEL;           [SEQ ID NO: 57]
CDR1: INLLG;              [SEQ ID NO: 46]
CDR2: TITVGDSTSYADSVKG;   [SEQ ID NO: 50]
CDR3: RRTWHSEL;           [SEQ ID NO: 57]
CDR1: SFGMS;              [SEQ ID NO: 44]
CDR2: SINGRGDDTRYADSVKG;  [SEQ ID NO: 51]
CDR3: GRSVSRS;            [SEQ ID NO: 58]
CDR1: SFGMS;              [SEQ ID NO: 44]
CDR2: AISADSSDKRYADSVKG;  [SEQ ID NO: 53]
CDR3: GRGSP;              [SEQ ID NO: 59]
CDR1: SFGMS;              [SEQ ID NO: 44]
CDR2: AISADSSDKRYADSVKG;  [SEQ ID NO: 53]
CDR3: GRGSP;              [SEQ ID NO: 59]
CDR1: NYWMY;              [SEQ ID NO: 47]
```

-continued

```
CDR2: RISTGGGYSYYADSVKG;   [SEQ ID NO: 54]

CDR3: DREAQVDTLDFDY.       [SEQ ID NO: 55]
```

In the Nanobodies of the invention that comprise the combinations of CDR's mentioned above, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences;
and/or chosen from the group consisting of amino acid sequences that have 3, 2 or only 1 (as indicated in the preceding paragraph) "amino acid difference(s)" (as defined herein) with the mentioned CDR(s) one of the above amino acid sequences, in which:
(1) any amino acid substitution is preferably a conservative amino acid substitution (as defined herein); and/or
(2) said amino acid sequence preferably only contains amino acid substitutions, and no amino acid deletions or insertions, compared to the above amino acid sequences.

However, of the Nanobodies of the invention that comprise the combinations of CDR's mentioned above, Nanobodies comprising one or more of the CDR's listed above are particularly preferred; Nanobodies comprising two or more of the CDR's listed above are more particularly preferred; and Nanobodies comprising three of the CDR's listed above are most particularly preferred.

In these Nanobodies against human serum albumin, the Framework regions FR1 to FR4 are preferably as defined hereinabove for the Nanobodies of the invention.

Particularly preferred Nanobodies against human serum albumin are chosen from the group consisting of SEQ ID NO's: 107-121. These correspond to the Nanobodies against human serum albumin of SEQ ID NO's: 61 to 67, SEQ ID NO's 87 to 89 and SEQ ID NO's 100-104 from applicant's co-pending US provisional application entitled "Improved Nanobodies™ against Tumor Necrosis Factor-alpha" with a filing date of May 18, 2005.

More generally, Nanobodies against serum albumin suitable for use in the invention are described in the International application by applicant entitled "serum albumin binding proteins" with an international filing date of May 17, 2006.

Another embodiment of the present invention is a nucleic acid encoding a polypeptide construct as described above.

Another embodiment of the present invention is a composition comprising a polypeptide construct as described above and at least one thrombolytic agent, for simultaneous, separate or sequential administration to a subject.

Another embodiment of the present invention is a composition as described above wherein said thrombolytic agent is any of staphylokinase, tissue plasminogen activator, streptokinase, single chain streptokinase, urokinase and acyl plasminogen streptokinase complex.

Another embodiment of the present invention is a polypeptide construct as described above, or a nucleic acid as described above, or a composition as described above for use in the treatment, prevention and/or alleviation of disorders relating to platelet-mediate aggregation or dysfunction thereof.

Another embodiment of the present invention is a use of a polypeptide construct as described above, or a nucleic acid as described above, or a composition as described above for the preparation of a medicament for the treatment, prevention and/or alleviation of disorders relating to platelet-mediate aggregation or dysfunction thereof.

Another embodiment of the present invention is a polypeptide construct, nucleic acid or composition as described above or a use of a polypeptide construct, nucleic acid or composition as described above wherein said disorders are any arising from transient cerebral ischemic attack, unstable or stable angina, angina pectoris, cerebral infarction, myocardial infarction, peripheral arterial occlusive disease, restenosis, coronary by-pass graft, or coronary artery valve replacement and coronary interventions such angioplasty, stenting, carotid endarterectomy or atherectomy.

Another embodiment of the present invention is a polypeptide construct, nucleic acid or composition as described above or a use of a polypeptide construct, nucleic acid or composition as described above wherein said disorders are any of the formation of a non-occlusive thrombus, the formation of an occlusive thrombus, arterial thrombus formation, acute coronary occlusion, restenosis, restenosis after PCTA or stenting, thrombus formation in stenosed arteries, hyperplasia after angioplasty, atherectomy or arterial stenting, occlusive syndrome in a vascular system or lack of patency of diseased arteries.

Another embodiment of the present invention is a polypeptide construct, nucleic acid or composition as described above or a use of a polypeptide construct, nucleic acid or composition as described above wherein said disorder is plaque or thrombus formation in high sheer environments.

Another embodiment of the present invention is a polypeptide construct, nucleic acid or composition as described above or a use of a polypeptide construct as described above wherein said polypeptide construct is administered intravenously, subcutaneously, orally, sublingually, topically, nasally, vaginally, rectally or by inhalation.

Another embodiment of the present invention is a composition comprising a polypeptide construct as described above or a nucleic acid encoding said polypeptide construct, or a composition as described above and a pharmaceutically acceptable vehicle.

Another embodiment of the present invention is a method of producing a polypeptide as described above, comprising
(a) culturing host cells comprising nucleic acid capable of encoding a polypeptide as described above under conditions allowing the expression of the polypeptide, and,
(b) recovering the produced polypeptide from the culture.

Another embodiment of the present invention is a method as described above, wherein said host cells are bacterial or yeast.

Another embodiment of the present invention is a method for treating invasive medical devices to prevent platelet-mediate aggregation around the site of invasion comprising the step of coating said device with a polypeptide construct as described above.

Another embodiment of the present invention is an invasive medical device for circumventing platelet-mediate aggregation around the site of invasion, wherein said device is coated with a polypeptide construct as described above.

Another embodiment of the present invention is a method of identifying an agent that modulates platelet-mediated aggregation comprising
(a) contacting a polypeptide construct as described above with a polypeptide corresponding to its target, or a fragment thereof, in the presence and absence of a candidate modulator under conditions permitting binding between said polypeptides, and
(b) measuring the binding between the polypeptides of step (a), wherein a decrease in binding in the presence of said candidate modulator, relative to the binding in the absence of said candidate modulator identified said candidate modulator as an agent that modulate platelet-mediated aggregation.

Another embodiment of the present invention is a kit for screening for agents that modulate platelet-mediated aggregation according to the method as described above.

Another embodiment of the present invention is an unknown agent that modulates platelet-mediated aggregation identified according to the method as described above.

Another embodiment of the present invention is a method of diagnosing a disease or disorder characterised by dysfunction of platelet-mediated aggregation comprising the steps of:
(a) contacting a sample with a polypeptide construct as described above, and
(b) detecting binding of said polypeptide construct to said sample, and
(c) comparing the binding detected in step (b) with a standard, wherein a difference in binding relative to said sample is diagnostic of a disease or disorder characterised by dysfunction of platelet-mediated aggregation.

Another embodiment of the present invention is a kit for screening for diagnosing a disease or disorder characterised by dysfunction of platelet-mediated aggregation according to the method as described above.

Another embodiment of the present invention is a kit as described above comprising a polypeptide construct as described above.

In the polypeptides of the invention, the one or more Nanobodies of the invention which are directed against a target may be of the same sequence. Alternatively they may not all have the same sequence. It is within the scope of the invention that a polypeptide of the invention comprises anti-target Nanobodies of the invention which do not all share the same sequence, but which are directed against the same target, or fragment thereof, one or more antigens thereof.

It is another aspect of the invention that the polypeptide of the invention comprises two or more Nanobodies of the invention, wherein any two Nanobodies of the invention are directed against different epitopes/targets, i.e. against any of vWF, vWF A1 domain, A1 domain of activated vWF, vWF A3 domain.

Another aspect of the invention is a bispecific polypeptide of the invention comprising a Nanobody of the invention directed against vWF A1 domain, A1 domain of activated vWF, and another Nanobody of the invention directed against vWF A3 domain. Said bispecific polypeptide of the invention inhibits the interaction between vWF and collagen, and the interaction between vWF and platelets.

According to an aspect of the present invention a polypeptide of the invention may comprise two or more Nanobodies of the invention which have been joined. The Nanobodies of the invention may be identical in sequence and directed against the same target or antigen. Depending on the number of $V_{HH}$s linked, a multivalent $V_{HH}$ may be bivalent (2 $V_{HH}$s), trivalent (3 $V_{HH}$s), tetravalent (4 $V_{HH}$s) or have a higher valency molecules.

The present invention also relates to the finding that a polypeptide of the invention further comprising one or more Nanobodies of the invention each directed against a serum protein of a subject, surprisingly has significantly prolonged half-life in the circulation of said subject compared with the half-life of the anti-target Nanobody of the invention(ies) when not part of said construct. Furthermore, the said constructs were found to exhibit the same favourable properties of $V_{HH}$s such as high stability remaining intact in mice, extreme pH resistance, high temperature stability and high target affinity.

The serum protein may be any suitable protein found in the serum of subject, or fragment thereof. In one aspect of the invention, the serum protein is serum albumin, serum immunoglobulins, thyroxine-binding protein, transferrin, or fibrinogen. Depending on the intended use such as the required half-life for effective treatment and/or compartmentalisation of the target antigen, the $V_{HH}$-partner can be directed to one of the above serum proteins.

Such constructs are able to circulate in the subject's serum for several days, reducing the frequency of treatment, the inconvenience to the subject and resulting in a decreased cost of treatment. Furthermore, it is an aspect of the invention that the half-life of the polypeptide of the invention disclosed herein may be controlled by the number of anti-serum protein Nanobodies of the invention present in the construct. A controllable half-life is desirable in several circumstances, for example, in the application of a timed dose of a therapeutic polypeptide of the invention.

Another embodiment of the present invention is a polypeptide of the invention as mentioned herein, further comprising a thrombolytic agent.

Said thrombolytic agent may be non-covalently or covalently attached to a Nanobody of the invention via covalent or non-covalent means. Such covalent means are described below. Non-covalent means include via a protein interaction such as biotin/strepavidin, or via an immunoconjugate.

Alternatively, the thrombolytic agent may be administered simultaneous, separate or sequential in respect of a polypeptide of the invention.

Another aspect of the invention is a composition comprising at least one polypeptide of the invention and at least one thrombolytic agent, for simultaneous, separate or sequential administration to a subject.

One aspect of the invention is a method for treating autoimmune disease comprising administering to an individual an effective amount of at least one polypeptide of the invention and at least one thrombolytic agent, simultaneously, separately or sequentially.

Another aspect of the invention is a kit containing at least one polypeptide of the invention and at least one thrombolytic agent for simultaneous, separate or sequential administration to a subject. It is an aspect of the invention that the kit may be used according to the invention. It is an aspect of the invention that the kit may be used to treat the diseases as cited herein.

By simultaneous administration means the polypeptide and thrombolytic agent are administered to a subject at the same time. For example, as a mixture or a composition comprising said components. Examples include, but are not limited to a solution administered intravenously, a tablet, liquid, topical cream, etc., wherein each preparation comprises the components of interest.

By separate administration means polypeptide and thrombolytic agent are administered to a subject at the same time or substantially the same time. The components are present in the kit as separate, unmixed preparations. For example, the polypeptide and thrombolytic agent may be present in the kit as individual tablets. The tablets may be administered to the subject by swallowing both tablets at the same time, or one tablet directly following the other.

By sequential administration means the polypeptide and thrombolytic agent are administered to a subject sequentially. The polypeptide and thrombolytic agent are present in the kit as separate, unmixed preparations. There is a time interval between doses. For example, one component might be administered up to 336, 312, 288, 264, 240, 216, 192, 168, 144, 120, 96, 72, 48, 24, 20, 16, 12, 8, 4, 2, 1, or 0.5 hours after the other component.

In sequential administration, one component may be administered once, or any number of times and in various doses before and/or after administration of another component. Sequential administration may be combined with simultaneous or sequential administration.

The medical uses of the polypeptide of the invention described below, also apply to the composition comprising a polypeptide of the invention and at least one polypeptide thrombolytic agent, for simultaneous, separate or sequential administration to a subject as disclosed here above.

Thrombolytic agents according to the invention may include, for example, staphylokinase, tissue plasminogen activator, streptokinase, single chain streptokinase, urokinase and acyl plasminogen streptokinase complex.

The Nanobodies of the invention may be joined to form any of the polypeptide of the invention disclosed herein comprising more than one Nanobody of the invention using methods known in the art or any future method. For example, they may be fused by chemical cross-linking by reacting amino acid residues with an organic derivatisation agent such as described by Blattler et al, Biochemistry 24, 1517-1524; EP294703. Alternatively, the Nanobody of the invention may be fused genetically at the DNA level i.e. a polynucleotide construct formed which encodes the complete polypeptide of the invention comprising one or more anti-target Nanobodies of the invention and one or more anti-serum protein Nanobodies of the invention. A method for producing bivalent or multivalent $V_{HH}$ polypeptide of the invention is disclosed in PCT patent application WO 96/34103. One way of joining multiple Nanobodies of the invention is via the genetic route by linking Nanobody of the invention coding sequences either directly or via a peptide linker. For example, the C-terminal end of the first Nanobody of the invention may be linked to the N-terminal end of the next Nanobody of the invention. This linking mode can be extended in order to link additional Nanobodies of the invention for the construction and production of tri-, tetra-, etc. functional constructs.

The polypeptide of the invention disclosed herein may be made by the skilled artisan according to methods known in the art or any future method. For example, $V_{HH}$s may be obtained using methods known in the art such as by immunising a camel and obtaining hybridoma's therefrom, or by cloning a library of Nanobodies of the invention using molecular biology techniques known in the art and subsequent selection by using phage display.

Nanobodies have a unique structure that consists of a single variable domain. $V_{HH}$ molecules derived from Camelidae antibodies are among the smallest intact antigen-binding domains known (approximately 15 kDa, or 10 times smaller than a conventional IgG) and hence are well suited towards delivery to dense tissues and for accessing the limited space between macromolecules participating in or starting the process of platelet mediated aggregation.

Despite the small size of nanobodies, and thus advantages for penetration, it is still surprising that such a small molecule can inhibit interactions between large polymers such as vWF (up to 60 monomers) and collagen and with such a high efficiency. It has been described that only the large multimeric forms of vWF are hemostatically active (Furlan, M. 1996, Ann. Hematol. 72:341-348). Binding of multimeric vWF to collagen occurs with ~100-fold higher affinity than binding of monomeric vWF fragments.

The results from the high shear experiments indicate that a lower dose may be administered to patients. Therefore, fewer side effects are expected (such as immunogenicity or bleeding problems).

In another embodiment of the present invention, a polypeptide of the invention comprises one or more Nanobodies of the invention directed to the same target, and further comprises one or more Nanobodies of the invention directed to the same target but to a different epitope in the same domain.

Another embodiment of the present invention is a polypeptide of the invention wherein the number of Nanobodies of the invention directed to the same target is two or more.

In another embodiment of the present invention, a polypeptide of the invention comprises one or more Nanobodies of the invention directed to one domain of the same target, and one or more Nanobodies of the invention directed to the same target but to another domain of the same target. Examples of different domains might be the A1 and A3 domains of vWF It is one non-limiting aspect of the invention that at least one $V_{HH}$ directed to the A1 domain in a heterospecific polypeptide of the invention recognizes the active conformation of vWF. Such polypeptide of the invention may have superior anti-thrombotic effects compared to the monomeric $V_{HH}$'s. Perfusion experiment were performed in a flow chamber, to study platelet aggregation under high shear to study the effects of these polypeptide of the invention.

The discovery of naturally occurring Nanobodies of the invention in llama, dromedary and camel revealed a new class of therapeutic molecules which combine the advantages of monoclonal antibodies for example specificity, low toxicity with the advantages of small molecules for example tissue penetration and stability. Unfortunately, the development of appropriate therapeutic products based on these proteins has the drawback of being Camelidae derived, and thus not human. Non-human proteins contain amino acid residues that can be immunogenic when injected into a human patient. Although studies have shown that Camelidae-derived $V_{HH}$ are not immunogenic when injected in mice, replacing Camelidae residues by human residues is preferable. These humanized polypeptides should be substantially non-immunogenic in humans, but retain the affinity and activity of the wild type polypeptide.

The result of humanisation is preferably that immunogenicity upon administration in human patients is minor or nonexistent. Humanising a polypeptide, according to the present invention, comprises a step of replacing one or more of the Camelidae amino acids by their human counterpart as found in the human consensus sequence, without that polypeptide losing its typical character, i.e. the humanisation does not significantly affect the antigen binding capacity of the resulting polypeptide.

WO 04/062551 and the further description herein describe some preferred, but non-limiting examples of amino acid residues of the antibody variable domain ($V_{HH}$) which may be modified without diminishing the native affinity of the domain for antigen and while reducing its immunogenicity with respect to a heterologous species; the use of $V_{HH}$s having modifications at the identified residues which are useful for administration to heterologous species; and to the $V_{HH}$ so modified. More specifically, the invention also encompasses the preparation of modified $V_{HH}$s, which are modified for administration to humans, the resulting $V_{HH}$ themselves, and the use of such "humanized" $V_{HH}$s in the treatment of diseases in humans.

As mentioned in WO 04/062551 and in the further description herein, humanization of $V_{HH}$ polypeptides requires the introduction and mutagenesis of only a limited number of amino acids in a single polypeptide chain without dramatic loss of binding and/or inhibition activity. This is in contrast to humanization of scFv, Fab, (Fab)2 and IgG, which requires the introduction of amino acid changes in two chains, the light and the heavy chain and the preservation of the assembly of both chains.

A humanisation technique may be performed by a method comprising the replacement of any of the following residues either alone or in combination: FR1 positions 1, 5, 28 and 30, the hallmark amino acid at position 37, 44, 45 and 47 in FR2, FR3 residues 74, 75, 76, 83, 84, 93 and 94 and positions 103, 104, 108 and 111 in FR4; numbering according to the Kabat numbering.

The Nanobodies of the invention have a high degree of homology to human germline VH DP-47. Further humanization may also involve the introduction and mutagenesis of a limited amount of amino acids in a single polypeptide chain. This is in contrast to humanization of scFv, Fab, (Fab)2 and IgG, which requires the introduction of amino acid changes in two chains, the light and the heavy chain and the preservation of the assembly of both chains.

The polypeptides contain human-like residues in FR2. Humanization may also involve mutagenesis of residues in FR1 at position 1 and 5 which were introduced by the primer used for repertoire cloning and do not occur naturally in the llama sequence. Mutagenesis of those residues did not result in loss of binding and/or inhibition activity. Humanization of FR1 also required mutagenesis of position 28 and 30. Mutagenesis of those residues also did not result in-loss of binding and/or inhibition activity.

Humanization may also involve mutagenesis of residues in FR3 at position 74, 75, 76, 83, 84, 93, 94. Mutagenesis of those residues did not result in loss of binding and/or inhibition activity.

Humanization may also involve mutagenesis of residues in FR4 at position 104, 108 and 111. Mutagenesis of Q108L resulted in lower production level in *Escherichia coli*. Position 108 is solvent exposed in camelid $V_{HH}$, while in human antibodies this position is buried at the VH-VL interface (Spinelli, 1996; Nieba, 1997). In isolated $V_H$s position 108 is solvent exposed. The introduction of a non-polar hydrophobic Leu instead of polar uncharged Gln can have a drastic effect on the intrinsic foldability/stability of the molecule.

One embodiment of the present invention is a method for humanizing a $V_{HH}$ comprising the steps of:
(a) replacing of any of the following residues either alone or in combination:
FR1 positions 1, 5, 28 and 30,
the hallmark amino acid at position 37, 44, 45 and 47 in FR2,
FR3 residues 74, 75, 76, 83, 84, 93 and 94,
and positions 103, 104, 108 and 111 in FR4;
numbering according to the Kabat numbering.

Examples of such humanized sequences are given below and in the appended sequence listing.

The use of antibodies derived from sources such as mouse, sheep, goat, rabbit etc., and humanised derivatives thereof as a treatment for conditions which require a modulation of platelet-associated aggregation, is problematic for several reasons. Traditional antibodies are not stable at room temperature, and have to be refrigerated for preparation and storage, requiring necessary refrigerated laboratory equipment, storage and transport, which contribute towards time and expense. Refrigeration is sometimes not feasible in developing countries. The yields of expression of said Fab molecules are very low and the method of production is very labor intensive. Furthermore, the manufacture or small-scale production of said antibodies is expensive because the mammalian cellular systems necessary for the expression of intact and active antibodies require high levels of support in terms of time and equipment, and yields are very low. Furthermore, traditional antibodies have a binding activity which depends upon pH, and hence are unsuitable for use in environments outside the usual physiological pH range such as, for example, in treating gastric bleeding, gastric surgery. Furthermore, traditional antibodies are unstable at low or high pH and hence are not suitable for oral administration. However, it has been demonstrated that camelid antibodies resist harsh conditions, such as extreme pH, denaturing reagents and high temperatures (Ewert S et al, Biochemistry 2002 Mar. 19; 41(11):3628-36), so making them suitable for delivery by oral administration. Furthermore, traditional antibodies have a binding activity which depends upon temperature, and hence are unsuitable for use in assays or kits performed at temperatures outside biologically active-temperature ranges (e.g. 37±20° C.).

The Nanobodies and polypeptides of the invention not only possess the advantageous characteristics of conventional antibodies, such as low toxicity and high selectivity, but they also exhibit additional properties. They are more soluble, meaning they may be stored and/or administered in higher concentrations compared with conventional antibodies. They are stable at room temperature meaning they may be prepared, stored and/or transported without the use of refrigeration equipment, conveying a cost, time and environmental savings. Other advantageous characteristics as compared to conventional antibodies include short half-life in the circulation which may be modulated according to the invention by, for example, albumin-coupling, a bispecific nanobody with one specificity against albumin and the other against the target, Fc coupling, $V_{HH}$ coupling (bivalent $V_{HH}$s) or by pegylation. A short and controllable half-life is desirable for surgical procedures, for example, which require an inhibition of platelet-mediated aggregation for a limited time period. Also, when bleeding problems occur or other complications, dosage can be lowered immediately. The polypeptides of the present invention also retain binding activity at a pH and temperature outside those of usual physiological ranges, which means they may be useful in situations of extreme pH and temperature which require a modulation of platelet-mediated aggregation, such as in gastric surgery, control of gastric bleeding, assays performed at room temperature etc. The polypeptides of the present invention also exhibit a prolonged stability at extremes of pH, meaning they would be suitable for delivery by oral administration. The polypeptides of the present invention may be cost-effectively produced through fermentation in convenient recombinant host organisms such as *Escherichia coli* and yeast; unlike conventional antibodies which also require expensive mammalian cell culture facilities, achievable levels of expression are high. Examples of yields of the polypeptides of the present invention are 1 to 10 mg/ml (*E. coli*) and up to 1 g/l (yeast). The polypeptides of the present invention also exhibit high binding affinity for a broad range of different antigen types, and ability to bind to epitopes not recognised by conventional antibodies; for example they display long CDR-based loop structures with the potential to penetrate into cavities and exhibit enzyme function inhibition. Furthermore, since binding often occurs through the CDR3 loop only, it is envisaged that peptides derived from CDR3 could be used therapeutically (Desmyter et al., J Biol Chem, 2001, 276: 26285-90). The polypeptides of the invention are also able to retain full binding capacity as fusion protein with an enzyme or toxin. Furthermore, it might be expected that the undesirable thrombocytopenia caused by Fc:Fc receptor mediated activation of platelet aggregation and/or F(ab')(2)-mediated crosslinking of platelets which has been observed when using intact IgG or F(ab')(2) therapeutically in vivo (see Cauwenberghs N. et al, Arteriosclerosis, Thrombosis and Vascular biology, 2000, 20: 1347), will be avoided in the use of $V_{HH}$, since $V_{HH}$ contains no Fc and it is not bivalent. Thus the polypeptides of the invention, homologues or functional portions thereof provide a considerable cost and time saving in the treatment and diagnosis of conditions related to platelet-mediated aggregation, and the patient in need of said polypeptides would encounter fewer of the problems associated with conventional agents.

Platelet-mediated aggregation is the process wherein vWF-bound collagen adheres to platelets and/or platelet receptors, ultimately resulting in platelet activation. Platelet activation leads to fibrinogen binding, and finally to platelet aggregation. It is within the scope of the present invention to provide polypeptides which modulate the processes which comprise platelet-mediated aggregation such as vWF-collagen binding, vWF-platelet receptor adhesion, collagen-platelet receptor adhesion, platelet activation, fibrinogen binding and/or platelet aggregation.

According to an aspect of the invention a polypeptide of the invention may be a homologous sequence of a full-length polypeptide of the invention. According to another aspect of the invention, a polypeptide of the invention may be a functional portion of a full-length polypeptide of the invention. According to another aspect of the invention, a polypeptide of the invention may be a homologous sequence of a full length polypeptide of the invention. According to another aspect of the invention, a polypeptide of the invention may be a functional portion of a homologous sequence of a full length polypeptide of the invention. According to an aspect of the invention a polypeptide of the invention may comprise a sequence of a polypeptide of the invention.

According to an aspect of the invention a Nanobody of the invention used to form a polypeptide of the invention may be a complete Nanobody of the invention (e.g. a $V_{HH}$) or a homologous sequence thereof. According to another aspect of the invention, a Nanobody of the invention used to form the polypeptide of the invention may be a functional portion of a complete Nanobody of the invention. According to another aspect of the invention, a Nanobody of the invention used to form the polypeptide of the invention may be a homologous sequence of a complete Nanobody of the invention. According to another aspect of the invention, a Nanobody of the invention used to form the polypeptide of the invention may be a functional portion of a homologous sequence of a complete Nanobody of the invention.

According to another aspect of the invention a polypeptide of the invention may be an homologous sequence of the parent sequence. According to another aspect of the invention, a polypeptide of the invention may be a functional portion parent sequence. According to another aspect of the invention, a polypeptide of the invention may be a functional portion of a homologous sequence of the parent sequence.

As used herein, an homologous sequence may comprise additions, deletions or substitutions of one or more amino acids, which do not substantially alter the functional characteristics of the polypeptide. The number of amino acid deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence according to the present invention includes polypeptides extended by the addition of amino acids to form human heavy chain antibody or human single domain heavy chain antibody, which do not substantially alter the functional characteristics of the unmodified polypeptide.

Where homologous sequence indicates sequence identity, it means a sequence which presents a high sequence identity (more than 70%, 75%, 80%, 85%, 90%, 95% or 98% sequence identity) with the parent sequence, and is preferably characterised by similar properties of the parent sequence, namely affinity, said identity calculated using known methods.

Alternatively, an homologous sequence may also be any amino acid sequence resulting from allowed substitutions at any number of positions of the parent sequence according to the formula below:
Ser substituted by Ser, Thr, Gly, and Asn;
Arg substituted by one of Arg, His, Gln, Lys, and Glu;
Leu substituted by one of Leu, Ile, Phe, Tyr, Met, and Val;
Pro substituted by one of Pro, Gly, Ala, and Thr;
Thr substituted by one of Thr, Pro, Ser, Ala, Gly, His, and Gln;
Ala substituted by one of Ala, Gly, Thr, and Pro;
Val substituted by one of Val, Met, Tyr, Phe, Ile, and Leu;
Gly substituted by one of Gly, Ala, Thr, Pro, and Ser;
Ile substituted by one of Ile, Met, Tyr, Phe, Val, and Leu;
Phe substituted by one of Phe, Trp, Met, Tyr, Ile, Val, and Leu;
Tyr substituted by one of Tyr, Trp, Met, Phe, Ile, Val, and Leu;
His substituted by one of His, Glu, Lys, Gln, Thr, and Arg;
Gln substituted by one of Gln, Glu, Lys, Asn, His, Thr, and Arg;
Asn substituted by one of Asn, Glu, Asp, Gln, and Ser;
Lys substituted by one of Lys, Glu, Gln, His, and Arg;
Asp substituted by one of Asp, Glu, and Asn;
Glu substituted by one of Glu, Asp, Lys, Asn, Gln, His, and Arg;
Met substituted by one of Met, Phe, Ile, Val, Leu, and Tyr.

A homologous according to the present invention may refer to nucleotide sequences of more than 50, 100, 200, 300, 400, 500, 600, 800 or 1000 nucleotides able to hybridize to the reverse-complement of the nucleotide sequence capable of encoding a polypeptide under stringent hybridisation conditions (such as the ones described by SAMBROOK et al., Molecular Cloning, Laboratory Manuel, Cold Spring, Harbor Laboratory press, New York).

As used herein, a functional portion refers to a Nanobody of the invention of sufficient length such that the interaction of interest is maintained with affinity of 1×10−6 M or better.

Alternatively a functional portion of a Nanobody of the invention comprises a partial deletion of the complete amino acid sequence and still maintains the binding site(s) and protein domain(s) necessary for the binding of and interaction with the target.

Alternatively a functional portion of any of Nanobody of the invention is a polypeptide which comprises a partial deletion of the complete amino acid sequence and which still maintains the binding site(s) and protein domain(s) necessary for the inhibition of binding of vWF to collagen.

Alternatively a functional portion of any Nanobody of the invention is a polypeptide which comprises a partial deletion of the complete amino acid sequence and which still maintains the binding site(s) and protein domain(s) necessary for the binding of and interaction with the A1 domain of vWF.

Alternatively a functional portion of any Nanobody of the invention is a polypeptide which comprises a partial deletion of the complete amino acid sequence and which still maintains the binding site(s) and protein domain(s) necessary for the binding of and interaction with collagen.

Alternatively a functional portion comprises a partial deletion of the complete amino acid sequence of a polypeptide and which still maintains the binding site(s) and protein domain(s) necessary for the binding of and interaction with the antigen against which it was raised. It includes, but is not limited to $V_{HH}$ domains.

As used herein, a functional portion as it refers to a polypeptide sequence refers to less than 100% of the sequence (e.g., 99%, 90%, 80%, 70%, 60% 50% etc.), but comprising 5 or more amino acids.

A portion as it refers to a nucleotide sequence encoding a polypeptide sequence refers to less than 100% of the sequence (e.g., 99%, 90%, 80%, 70%, 60% 50% etc.), but comprising 15 or more nucleotides.

An aspect of the present invention is the administration of a polypeptide of the invention according to the invention can avoid the need for injection. Conventional antibody-based therapeutics have significant potential as drugs because they have exquisite specificity to their target and a low inherent toxicity, however, they have one important drawback: they are relatively unstable, and are sensitive to breakdown by proteases. This means that conventional antibody drugs cannot be administered orally, sublingually, topically, nasally, vaginally, rectally or by inhalation because they are not resistant to the low pH at these sites, the action of proteases at these sites and in the blood and/or because of their large size. They have to be administered by injection (intravenously, subcutaneously, etc.) to overcome some of these problems. Administration by injection requires specialist training in order to use a hypodermic syringe or needle correctly and safely. It further requires sterile equipment, a liquid formulation of the therapeutic polypeptide, vial packing of said polypeptide in a sterile and stable form and, of the subject, a suitable site for entry of the needle. Furthermore, subjects commonly experience physical and psychological stress prior to and upon receiving an injection.

An aspect of the present invention overcomes these problems of the prior art, by providing the polypeptides constructs of the present invention. Said constructs are sufficiently small, resistant and stable to be delivered orally, sublingually, topically, nasally, vaginally, rectally or by inhalation substantial without loss of activity. The polypeptides constructs of the present invention avoid the need for injections, are not only cost/time savings, but are also more convenient and more comfortable for the subject.

One embodiment of the present invention is a polypeptide of the invention for use in treating, preventing and/or alleviating the symptoms of disorders susceptible to modulation by a substance that controls platelet mediated aggregation which is able pass through the gastric environment without the substance being inactivated.

As known by persons skilled in the art, once in possession of said polypeptide of the invention, formulation technology may be applied to release a maximum amount of polypeptide in the right location (in the stomach, in the colon, etc.). This method of delivery is important for treating, prevent and/or alleviate the symptoms of disorders whose targets are located in the gut system.

An aspect of the invention is a method for treating, preventing and/or alleviating the symptoms of a disorder susceptible to modulation by a substance that controls platelet mediated aggregation which is able pass through the gastric environment without being inactivated, by orally administering to a subject a polypeptide of the invention.

Another embodiment of the present invention is a use of a Nanobody or polypeptide of the invention for the preparation of a medicament for treating, preventing and/or alleviating the symptoms of disorders susceptible to modulation by a substance that controls platelet mediated aggregation which is able pass through the gastric environment without being inactivated.

An aspect of the invention is a method for delivering a substance that controls platelet mediated aggregation to the gut system without said substance being inactivated, by orally administering to a subject a Nanobody or polypeptide of the invention.

An aspect of the invention is a method for delivering a substance that controls platelet mediated aggregation to the bloodstream of a subject without the substance being inactivated, by orally administering to a subject a Nanobody or polypeptide of the invention.

Another embodiment of the present invention is a Nanobody or polypeptide of the invention for use in treating, preventing and/or alleviating the symptoms or disorders susceptible to modulation by a substance that controls platelet mediated aggregation delivered to the vaginal and/or rectal tract.

In a non-limiting example, a formulation according to the invention comprises a Nanobody or polypeptide of the invention, in the form of a gel, cream, suppository, film, or in the form of a sponge or as a vaginal ring that slowly releases the active ingredient over time (such formulations are described in EP 707473, EP 684814, U.S. Pat. No. 5,629,001).

An aspect of the invention is a method for treating, preventing and/or alleviating the symptoms of disorders susceptible to modulation by a substance that controls platelet mediated aggregation delivered to the vaginal and/or rectal tract, by vaginally and/or rectally administering to a subject a Nanobody or polypeptide of the invention.

Another embodiment of the present invention is a use of a Nanobody or polypeptide of the invention for the preparation of a medicament for treating, preventing and/or alleviating the symptoms of disorders susceptible to modulation by a substance that controls platelet mediated aggregation delivered to the vaginal and/or rectal tract.

An aspect of the invention is a method for delivering a substance that controls platelet mediated aggregation to the vaginal and/or rectal tract without being said substance being inactivated, by administering to the vaginal and/or rectal tract of a subject a Nanobody or polypeptide of the invention.

An aspect of the invention is a method for delivering a substance that controls platelet mediated aggregation to the bloodstream of a subject without said substance being inactivated, by administering to the vaginal and/or rectal tract of a subject a Nanobody or polypeptide of the invention.

Another embodiment of the present invention is a Nanobody or polypeptide of the invention, for use in treating, preventing and/or alleviating the symptoms of disorders susceptible to modulation by a substance that controls platelet mediated aggregation delivered to the nose, upper respiratory tract and/or lung.

In a non-limiting example, a formulation according to the invention, comprises a Nanobody or polypeptide of the invention in the form of a nasal spray (e.g. an aerosol) or inhaler. Since the Nanobody or polypeptide of the invention is small, it can reach its target much more effectively than therapeutic IgG molecules.

An aspect of the invention is a method for treating, preventing and/or alleviating the symptoms of disorders susceptible to modulation by a substance that controls platelet mediated aggregation delivered to the upper respiratory tract and lung, by administering to a subject a Nanobody or polypeptide of the invention, by inhalation through the mouth or nose.

Another embodiment of the present invention is a use of a Nanobody or polypeptide of the invention for the preparation of a medicament for treating, preventing and/or alleviating the symptoms of disorders susceptible to modulation by a substance that controls platelet mediated aggregation delivered to the nose, upper respiratory tract and/or lung, without said polypeptide being inactivated.

An aspect of the invention is a method for delivering a substance that controls platelet mediated aggregation to the nose, upper respiratory tract and lung without inactivation, by administering to the nose, upper respiratory tract and/or lung of a subject a Nanobody or polypeptide of the invention.

An aspect of the invention is a method for delivering a substance that controls platelet mediated aggregation to the bloodstream of a subject without inactivation by administering to the nose, upper respiratory tract and/or lung of a subject a Nanobody or polypeptide of the invention.

One embodiment of the present invention is a Nanobody or polypeptide of the invention for use in treating, preventing and/or alleviating the symptoms of disorders susceptible to modulation by a substance that controls platelet mediated aggregation delivered to the intestinal mucosa, wherein said disorder increases the permeability of the intestinal mucosa. Because of their small size, a Nanobody or polypeptide of the invention can pass through the intestinal mucosa and reach the bloodstream more efficiently in subjects suffering from disorders which cause an increase in the permeability of the intestinal mucosa.

An aspect of the invention is a method for treating, preventing and/or alleviating the symptoms of disorders susceptible to modulation by a substance that controls platelet mediated aggregation delivered to the intestinal mucosa, wherein said disorder increases the permeability of the intestinal mucosa, by orally administering to a subject a Nanobody or polypeptide of the invention.

This process can be even further enhanced by an additional aspect of the present invention—the use of active transport carriers. In this aspect of the invention, $V_{HH}$ is fused to a carrier that enhances the transfer through the intestinal wall into the bloodstream. In a non-limiting example, this "carrier" is a second $V_{HH}$ which is fused to the therapeutic $V_{HH}$. Such fusion constructs are made using methods known in the art. The "carrier" $V_{HH}$ binds specifically to a receptor on the intestinal wall which induces an active transfer through the wall.

Another embodiment of the present invention is a use of a Nanobody or polypeptide of the invention for the preparation of a medicament for treating, preventing and/or alleviating the symptoms of disorders susceptible to modulation by a substance that controls platelet mediated aggregation delivered to the intestinal mucosa, wherein said disorder increases the permeability of the intestinal mucosa.

An aspect of the invention is a method for delivering a substance that controls platelet mediated aggregation to the intestinal mucosa without being inactivated, by administering orally to a subject a Nanobody or polypeptide of the invention.

An aspect of the invention is a method for delivering a substance that controls platelet mediated aggregation to the bloodstream of a subject without being inactivated, by administering orally to a subject a Nanobody or polypeptide of the invention.

This process can be even further enhanced by an additional aspect of the present invention—the use of active transport carriers. In this aspect of the invention, a Nanobody or polypeptide of the invention as described herein is fused to a carrier that enhances the transfer through the intestinal wall into the bloodstream. In a non-limiting example, this "carrier" is a $V_{HH}$ which is fused to said polypeptide. Such fusion constructs made using methods known in the art. The "carrier" $V_{HH}$ binds specifically to a receptor on the intestinal wall which induces an active transfer through the wall.

One embodiment of the present invention is a Nanobody or polypeptide of the invention for use in treating, preventing and/or alleviating the symptoms of disorders susceptible to modulation by a substance that controls platelet mediated aggregation which is able pass through the tissues beneath the tongue effectively. A formulation of said Nanobody or polypeptide of the invention, for example, a tablet, spray, drop is placed under the tongue and adsorbed through the mucus membranes into the capillary network under the tongue.

An aspect of the invention is a method for treating, preventing and/or alleviating the symptoms of disorders susceptible to modulation by a substance that controls platelet mediated aggregation which is able pass through the tissues beneath the tongue effectively, by sublingually administering to a subject a Nanobody or polypeptide of the invention.

Another embodiment of the present invention is a use of a Nanobody or polypeptide of the invention for the preparation of a medicament for treating, preventing and/or alleviating the symptoms of disorders susceptible to modulation by a substance that controls platelet mediated aggregation which is able to pass through the tissues beneath the tongue.

An aspect of the invention is a method for delivering a substance that controls platelet mediated aggregation to the tissues beneath the tongue without being inactivated, by administering sublingually to a subject a Nanobody or polypeptide of the invention.

An aspect of the invention is a method for delivering a substance that controls platelet mediated aggregation to the bloodstream of a subject without being inactivated, by administering orally to a subject a Nanobody or polypeptide of the invention.

One embodiment of the present invention is a Nanobody or polypeptide of the invention for use in treating, preventing and/or alleviating the symptoms of disorders susceptible to modulation by a substance that controls platelet mediated aggregation which is able pass through the skin effectively.

A formulation of said Nanobody or polypeptide of the invention, for example, a cream, film, spray, drop, patch, is placed on the skin and passes through.

An aspect of the invention is a method for treating, preventing and/or alleviating the symptoms of disorders susceptible to modulation by a substance that controls platelet mediated aggregation which is able pass through the skin effectively, by topically administering to a subject a Nanobody or polypeptide of the invention.

Another embodiment of the present invention is a use of a Nanobody or polypeptide of the invention for the preparation of a medicament for treating, preventing and/or alleviating the symptoms of disorders susceptible to modulation by a substance that controls platelet mediated aggregation which is able pass through the skin effectively.

An aspect of the invention is a method for delivering a substance that controls platelet mediated aggregation to the skin without being inactivated, by administering topically to a subject a Nanobody or polypeptide of the invention.

An aspect of the invention is a method for delivering a substance that controls platelet mediated aggregation to the bloodstream of a subject, by administering topically to a subject a Nanobody or polypeptide of the invention.

In another embodiment of the present invention, a Nanobody or polypeptide of the invention further comprises a carrier Nanobody of the invention (e.g. $V_{HH}$) which acts as an active transport carrier for transport of said Nanobody or polypeptide of the invention via the lung lumen to the blood.

A Nanobody or polypeptide of the invention further comprising a carrier that binds specifically to a receptor present on the mucosal surface (bronchial epithelial cells) resulting in the active transport of the polypeptide from the lung lumen to the blood. The carrier Nanobody of the invention may be fused to the Nanobody or polypeptide of the invention. Such fusion constructs made using methods known in the art and are describe herein. The "carrier" Nanobody of the invention binds specifically to a receptor on the mucosal surface which induces an active transfer through the surface.

Another aspect of the present invention is a method to determine which Nanobodies of the invention (e.g. $V_{HH}$s) are actively transported into the bloodstream upon nasal administration. Similarly, a naïve or immune $V_{HH}$ phage library can be administered nasally, and after different time points after administration, blood or organs can be isolated to rescue phages that have been actively transported to the bloodstream. A non-limiting example of a receptor for active transport from the lung lumen to the bloodstream is the Fc receptor N (FcRn). One aspect of the invention includes the $V_{HH}$ molecules identified by the method. Such $V_{HH}$ can then be used as a carrier $V_{HH}$ for the delivery of a therapeutic $V_{HH}$ to the corresponding target in the bloodstream upon nasal administration.

One embodiment of the present invention is a Nanobody or polypeptide of the invention for use in treating, preventing and/or alleviating the symptoms of disorders relating to platelet-mediated aggregation or dysfunction thereof. Said disorders include, thrombotic thrombocytopenic purpura (TTP), transient cerebral ischemic attack, unstable or stable angina pectoris, cerebral infarction, myocardial infarction, peripheral arterial occlusive disease, restenosis. Said disorders further include those arising from coronary by-pass graft, coronary artery valve replacement and coronary interventions such angioplasty, stenting, or atherectomy.

Other disorders are any of the formation of a non-occlusive thrombus, the formation of an occlusive thrombus, arterial thrombus formation, acute coronary occlusion, restenosis, restenosis after PCTA or stenting, thrombus formation in stenosed arteries, hyperplasia after angioplasty, atherectomy or arterial stenting, occlusive syndrome in a vascular system or lack of patency of diseased arteries.

One aspect of the invention is a Nanobody or polypeptide of the invention for use in the treatment, prevention and/or alleviation of disorders or conditions relating to platelet-mediated aggregation or dysfunction thereof, wherein said Nanobody or polypeptide of the invention is administered intravenously, subcutaneously, orally, sublingually, topically, nasally, vaginally, rectally or by inhalation.

Another aspect of the invention is the use of a Nanobody or polypeptide of the invention for the preparation of a medicament for the treatment, prevention and/or alleviation of disorders or conditions relating to platelet-mediated aggregation or dysfunction thereof, wherein said Nanobody or polypeptide of the invention is administered intravenously, subcutaneously, orally, sublingually, topically, nasally, vaginally, rectally or by inhalation.

Another aspect of the invention is a method of treating, preventing and/or alleviating disorders or conditions relating to relating to platelet-mediated aggregation or dysfunction thereof, comprising administering to a subject a Nanobody or polypeptide of the invention, wherein said heterospecific Nanobody or polypeptide of the invention is administered intravenously, subcutaneously, orally, sublingually, topically, nasally, vaginally, rectally or by inhalation.

Another aspect of the invention is a Nanobody or polypeptide of the invention for use in the treatment, prevention and/or alleviation of disorders or conditions relating to platelet-mediated aggregation or dysfunction thereof.

Another aspect of the invention is a use of a polypeptide of the invention for the preparation of a medicament for the treatment, prevention and/or alleviation of disorders or conditions relating to platelet-mediated aggregation or dysfunction thereof.

One can use a Nanobody or polypeptide of the invention of the present invention in order to screen for agents that modulate the binding of the polypeptide to a vWF. When identified in an assay that measures binding or said polypeptide displacement alone, agents will have to be subjected to functional testing to determine whether they act as modulators of platelet-mediated aggregation. Some examples of suitable screening methods are discussed in WO 04/062551. Of course, these methods can easily be applied to screening for candidate modulators which alter the binding between the Nanobody or polypeptide of the invention disclosed herein and vWF.

A cell that is useful according to the invention is preferably selected from the group consisting of bacterial cells such as, for example, *E. coli*, yeast cells such as, for example, *S. cerevisiae, P. pastoris*, insect cells or mammalian cells, e.g. as mentioned above.

A cell that is useful according to the invention can be any cell into which a nucleic acid sequence encoding a Nanobody or polypeptide of the invention can be or has been introduced such that the polypeptide is expressed at natural levels or above natural levels, as defined herein. Preferably a polypeptide of the invention that is expressed in a cell exhibits normal or near normal pharmacology, as defined herein.

According to a preferred embodiment of the present invention, a cell is selected from the group consisting of COS7-cells, a CHO cell, a LM (TK-) cell, a NIH-3T3 cell, HEK-293 cell, K-562 cell or a 1321N1 astrocytoma cell but also other transfectable cell lines.

In general, "therapeutically effective amount", "therapeutically effective dose" and "effective amount" means the amount needed to achieve the desired result or results (treating or preventing platelet aggregation). One of ordinary skill in the art will recognize that the potency and, therefore, an "effective amount" can vary for the various Nanobodies or polypeptides that inhibit platelet-mediated aggregation used in the invention. One skilled in the art can readily assess the potency of the Nanobody or polypeptide.

By "pharmaceutically acceptable" is meant a material that is not biologically or otherwise undesirable, i.e., the material may be administered to an individual along with the Nanobody or polypeptide without causing any undesirable biological effects or interacting in a deleterious manner with any of the other components of the pharmaceutical composition in which it is contained.

The invention disclosed herein is useful for treating or preventing a condition of platelet-mediated aggregation, in a subject and comprising administering a pharmaceutically effective amount of a Nanobody or polypeptide or composition that inhibits BTK and that inhibits platelet-mediated aggregation.

The invention disclosed herein is useful for treating or preventing the first steps of thrombus formation, in a subject and comprising administering a pharmaceutically effective amount of a Nanobody or polypeptide or composition according to the invention.

The invention disclosed herein is useful for treating or preventing restenosis, in a subject and comprising administering a pharmaceutically effective amount of a Nanobody or polypeptide or composition according to the invention.

One aspect of the present invention is the use of Nanobodies or polypeptides of the invention for treating or preventing a condition of platelet-mediated aggregation, in a subject and comprising administering a pharmaceutically effective amount of a Nanobody or polypeptide in combination with another, such as, for example, aspirin.

One aspect of the present invention is the use of Nanobodies or polypeptides of the invention for treating or preventing a condition of platelet-mediated aggregation, in a subject and comprising administering a pharmaceutically effective amount of a Nanobody or polypeptide in combination with another, such as, for example, a thrombolytic agent.

Another aspect of the present invention is a use of a Nanobody or polypeptide of the invention for treating or preventing plaque or thrombus in an individual. Said plaque or thrombus formation may be under conditions of high sheer. In both thrombosis and reocclusion, the reversible adhesion or tethering of the platelets at high shear rate is followed by a firm adhesion through the collagen receptor on platelets resulting in platelet activation; the tethering of platelets by vWF to collagen exposed in the damaged vessel wall is especially important under high shear conditions. The inventors have found that Nanobody or polypeptide of the invention of the present invention unexpected performed well under high sheer conditions.

The present invention is not limited to the administration of formulations comprising a single Nanobody or polypeptide of the invention. It is within the scope of the invention to provide combination treatments wherein a formulation is administered to a patient in need thereof that comprises more than one Nanobody or polypeptide of the invention.

Conditions of platelet-mediated aggregation include, but are not limited to, unstable angina, stable angina, angina pectoris, embolus formation, deep vain thrombosis, hemolytic uremic syndrome, hemolytic anemia, acute renal failure, thrombolytic complications, thrombotic thrombocytopenic purpura, disseminated intravascular comgelopathy, thrombosis, coronary heart disease, thromboembolic complications, myocardial infarction, restenosis, and atrial thrombosis formation in atrial fibrillation, chronic unstable angina, transient ischemic attacks and strokes, peripheral vascular disease, arterial thrombosis, pre-eclampsia, embolism, restenosis and/or thrombosis following angioplasty, carotid endarterectomy, anastomosis of vascular grafts, and chronic exposure to cardiovascular devices. Such conditions may also result from thromboembolism and reocculsion during and after thrombolytic therapy, after angioplasty, and after coronary artery bypass.

It is well known in the art how to determine the inhibition of platelet-mediated aggregation using the standard tests described herein, or using other similar tests. Preferably, the method would result in at least a 10% reduction in platelet-mediated aggregation, including, for example, 15%, 20%, 25%, 30%, 40%, 50%, 60%, 70%, 80%, 90%, 100%, or any amount in between, more preferably by 90%.

Similarly, the method would result in at least a 10% reduction in intracellular calcium mobilisation including, for example, 15%, 20%, 25%, 30%, 40%, 50%, 60%, 70%, 80%, 90%, 100%. Similarly, the method would result in at least a 10% reduction in the level of phosphorylated PLCg 2 including, for example, 15%, 20%, 25%, 30%, 40%, 50%, 60%, 70%, 80%, 90%, 100%.

The reduction can be measured, for example, by comparing the optical impedence in a chronology platelet aggregometer. Any other known measurement method may also be used. For example, (1) upon collagen stimulation, the level of collagen-induced intracellular calcium mobilization increases over time and so the measurement may include measuring the level of collagen-induced intracellular calcium or (2) upon collagen stimulation, the level of phosphorylated PLCg 2 increases over time and so the measurement may include measuring the level of phosphorylated PLCg 2.

The cells can be contacted in vitro, for example, by adding a Nanobody or polypeptide of the invention to the culture medium (by continuous infusion, by bolus delivery, or by changing the medium to a medium that contains the Nanobody or polypeptide) or by adding the Nanobody or polypeptide to the extracellular fluid in vivo (by local delivery, systemic delivery, inhalation, intravenous injection, bolus delivery, or continuous infusion). The duration of "contact" with a cell or population of cells is determined by the time the Nanobody or polypeptide is present at physiologically effective levels or at presumed physiologically effective levels in the medium or extracellular fluid bathing the cell or cells. Preferably, the duration of contact is 1-96 hours, and more preferably, for 24 hours, but such time would vary based on the half life of the Nanobody or polypeptide and could be optimized by one skilled in the art using routine experimentation.

The Nanobody or polypeptide useful in the present invention can be formulated as pharmaceutical compositions and administered to a mammalian host, such as a human patient or a domestic animal in a variety of forms adapted to the chosen route of administration, i.e., orally or parenterally, by intranasally by inhalation, intravenous, intramuscular, topical or subcutaneous routes.

The Nanobody or polypeptide of the present invention can also be administered using gene therapy methods of delivery. See, e.g., U.S. Pat. No. 5,399,346, which is incorporated by reference in its entirety. Using a gene therapy method of delivery, primary cells transfected with the gene for the Nanobody or polypeptide of the present invention can additionally be transfected with tissue specific promoters to target specific organs, tissue, grafts, tumors, or cells.

Thus, the present Nanobody or polypeptide may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the Nanobody or polypeptide may be combined with one or more excipients and used in the form of ingestible tablets, buccal tablets, troches, capsules, elixirs, suspensions, syrups, wafers, and the like. Such compositions and preparations should contain at least 0.1% of the Nanobody or polypeptide. The percentage of the compositions and preparations may, of course, be varied and may conveniently be between about 2 to about 60% of the weight of a given unit dosage form. The amount of the Nanobody or polypeptide in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the Nanobody or polypeptide, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the Nanobody or polypeptide may be incorporated into sustained-release preparations and devices.

The Nanobody or polypeptide may also be administered intravenously or intraperitoneally by infusion or injection. Solutions of the Nanobody or polypeptide can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the Nanobody or polypeptide in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present Nanobody or polypeptide may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present Nanobody or polypeptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the Nanobody or polypeptide to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the Nanobody or polypeptide can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the Nanobody or polypeptide in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the Nanobody or polypeptide required for use in treatment will vary with the route of administration, the nature of the condition being treated and the age and condition of the patient and will be ultimately at the discretion of the attendant physician or clinician. Also the dosage of the Nanobody or polypeptide varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention provides for an agent that is a modulator of platelet-mediated aggregation.

The candidate agent may be a synthetic agent, or a mixture of agents, or may be a natural product (e.g. a plant extract or culture supernatant). A candidate agent according to the invention includes a small molecule that can be synthesized, a natural extract, peptides, proteins, carbohydrates, lipids etc.

Candidate modulator agents from large libraries of synthetic or natural agents can be screened. Numerous means are currently used for random and directed synthesis of saccharide, peptide, and nucleic acid based agents. Synthetic agent libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural agents in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and agents are readily modified through conventional chemical, physical, and biochemical means.

Useful agents may be found within numerous chemical classes. Useful agents may be organic agents, or small organic agents. Small organic agents have a molecular weight of more than 50 yet less than about 2,500 daltons, preferably less than about 750, more preferably less than about 350 daltons. Exemplary classes include heterocycles, peptides, saccharides, steroids, and the like. The agents may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate agent according to the invention is from about 10 mM to about 100 µM or more (i.e. 1 mM, 10 mM, 100 mM, 1 M etc.). The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

A high throughput screening kit according to the invention comprises all the necessary means and media for performing the detection of an agent that modulates platelet-mediated aggregation by interacting with a target of the invention, such as for example vWF, or fragment thereof in the presence of a polypeptide, preferably at a concentration in the range of 1 µM to 1 mM. The kit comprises the following. Recombinant cells of the invention, comprising and expressing the nucleotide sequence encoding vWF, or fragment thereof, which are grown according to the kit on a solid support, such as a microtiter plate, more preferably a 96 well microtiter plate, according to methods well known to the person skilled in the art especially as described in WO 00/02045. Alternatively vWF, or fragment thereof is supplied in a purified form to be immobilized on, for example, a 96 well microtiter plate by the person skilled in the art. Alternatively vWF, or fragment thereof is supplied in the kit pre-immobilized on, for example, a 96 well microtiter plate. Modulator agents according to the invention, at concentrations from about 1 µM to 1 mM or more, are added to defined wells in the presence of an appropriate concentration of Nanobody or polypeptide of the invention said concentration of said polypeptide preferably in the range of 1 µM to 1 mM. Kits may contain more than one polypeptide Binding assays are performed as according to the methods already disclosed herein and the results are compared to the baseline level of, for example vWF, or fragment thereof binding to a polypeptide of the invention, but in the absence of added modulator agent. Wells showing at least 2 fold, preferably 5 fold, more preferably 10 fold and most preferably a 100 fold or more increase or decrease in vWF-polypeptide binding (for example) as compared to the level of activity in the absence of modulator, are selected for further analysis.

The invention provides for kits useful for screening for modulators of platelet-mediated aggregation, as well as kits useful for diagnosis of diseases or disorders characterised by dysregulation platelet-mediated aggregation. Kits useful according to the invention can include an isolated vWF, or fragment thereof. Alternatively, or in addition, a kit can comprise cells transformed to express vWF, or fragment thereof. In a further embodiment, a kit according to the invention can comprise a polynucleotide encoding vWF, or fragment thereof. In a still further embodiment, a kit according to the invention may comprise the specific primers useful for amplification of vWF, or fragment thereof. Kits useful according to the invention can comprise a Nanobody or polypeptide of the invention. A kit according to the invention can comprise cells transformed to express said polypeptide. Kits may contain more than one polypeptide. In a further embodiment, a kit according to the invention can comprise a polynucleotide encoding a macromolecule, for example, vWF, or fragment thereof. In a still further embodiment, a kit according to the invention may comprise the specific primers useful for amplification of a macromolecule such as, for example, vWF, or fragment thereof. All kits according to the invention will comprise the stated items or combinations of items and packaging materials therefore. Kits will also include instructions for use.

The invention also provides for invasive medical devices coated with a Nanobody or polypeptide of the invention or an agent resulting from a screening method of the invention for use in devices requiring the same. Non-limiting examples of devices include surgical tubing, occlusion devices, prosthetic devices. Application for said devices include surgical procedures which require a modulation of platelet-mediated aggregation around the site of invasion.

One embodiment of the present is a method for treating invasive medical devices to prevent platelet-mediate aggregation around the site of invasion comprising the step of coating said device with a Nanobody or polypeptide of the invention or agent according to the invention.

Another embodiment of the present is a invasive medical devices that circumvents platelet-mediate aggregation around the site of invasion, wherein said device is coated with a Nanobody or polypeptide of the invention or agent according to the invention.

In another aspect, the invention relates to a method for the prevention and/or treatment of at least one aggregation-mediated disorder (as described herein), said method comprising administering, to a subject in need thereof, a pharmaceutically active amount of a Nanobody of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

The invention also relates to a method for the prevention and/or treatment of at least one disease or disorder that can be prevented and/or treated by administering a Nanobody or polypeptide of the invention to a patient, said method comprising administering, to a subject in need thereof, a pharmaceutically active amount of a Nanobody of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of a Nanobody of the invention, of a polypeptide of the invention, and/or of a pharmaceutical composition comprising the same.

In another embodiment, the invention relates to a method for immunotherapy, and in particular for passive immunotherapy, which method comprises administering, to a subject suffering from or at risk of the diseases and disorders mentioned herein, a pharmaceutically active amount of a Nanobody of the invention, of a polypeptide of the invention, and/or of a pharmaceutical composition comprising the same.

In the above methods, the Nanobodies and/or polypeptides of the invention and/or the compositions comprising the same can be administered in any suitable manner, depending on the specific pharmaceutical formulation or composition to be used. Thus, the Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

As mentioned herein and as will be clear to the skilled person, for acute conditions and complications (i.e. as may occur with some of the aggregation-mediated disorders mentioned herein), usually administration directly into the blood stream such by infusion or injection or any other suitable means will be preferred.

The Nanobodies and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more Nanobodies and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific Nanobody and polypeptide of the invention to be used, the specific route of administration and the specific pharmaceutical formulation or composition used, the Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single Nanobody or polypeptide of the invention will be used. It is however within the scope of the invention to use two or more Nanobodies and/or polypeptides of the invention in combination.

The Nanobodies and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the Nanobodies and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician, and for example include, but are not limited to heparin, aspirin (e.g. Aspegic®), Plavix and/or Reopro.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are administered to be simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

The invention also relates to the use of a Nanobody or polypeptide of the invention in the preparation of a pharmaceutical composition for the prevention and/or treatment of at least one disease or disorder (e.g. an aggregation disorder as mentioned herein) that can be prevented and/or treated by administering a Nanobody or polypeptide of the invention to a patient.

Generally, the treatment regimen will be followed until the desired therapeutic effect is achieved and/or for as long as the desired therapeutic effect is to be maintained. Again, this can be determined by the clinician.

Finally, it will also be clear to the skilled person that it may be possible to "graft" one or more of the CDR's mentioned above for the Nanobodies of the invention onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2): 184-199; Kettleborough et al., Protein Eng. 1991 October; 4(7): 773-783; O'Brien and Jones, Methods Mol. Biol. 2003: 207:81-100; and Skerra, J. Mol. Recognit. 2000:13:167-187, and Saerens et al., J. Mol. Biol. 2005 Sep. 23; 352(3):597-607, and the further references cited therein; and also include for example the framework regions of other (single) domain antibodies. For example, techniques known per se for grafting mouse or rat CDR's onto human frameworks and scaffolds can be used in an analogous manner to provide chimeric proteins comprising one or more of the CDR's of the Nanobodies of the invention and one or human framework regions or sequences.

Thus, in another embodiment, the invention comprises a chimeric polypeptide comprising at least one CDR sequence chosen from the group consisting of CDR1 sequences, CDR2 sequences and CDR3 sequences mentioned herein for the Nanobodies of the invention. Preferably, such a chimeric polypeptide comprises at least one CDR sequence chosen from the group consisting of the CDR3 sequences mentioned herein for the Nanobodies of the invention, and optionally also at least one CDR sequence chosen from the group consisting of the CDR1 sequences and CDR2 sequences mentioned herein for the Nanobodies of the invention. For example, such a chimeric polypeptide may comprise one CDR sequence chosen from the group consisting of the CDR3 sequences mentioned herein for the Nanobodies of the invention, one CDR sequence chosen from the group consisting of the CDR1 sequences mentioned herein for the Nanobodies of the invention and one CDR sequence chosen from the group consisting of the CDR1 sequences and CDR2 sequences mentioned herein for the Nanobodies of the invention. The combinations of CDR's that are mentioned herein as being preferred for the Nanobodies of the invention will usually also be preferred for these chimeric polypeptides.

In said chimeric polypeptides, the CDR's may be linked to further amino acid sequences and/or may be linked to each other via amino acid sequences, in which said amino acid sequences are preferably framework sequences or are amino acid sequences that act as framework sequences, or together form a scaffold for presenting the CDR's. Reference is again made to the prior art mentioned in the last paragraph. According to one preferred embodiment, the amino acid sequences are human framework sequences, for example $V_H3$ framework sequences. However, non-human, synthetic, semi-synthetic or non-immunoglobulin framework sequences may also be used. Preferably, the framework sequences used are such that (1) the chimeric polypeptide is capable of binding xxxx, i.e. with an affinity that is at least 1%, preferably at least 5%, more preferably at least 10%, such as at least 25% and up to 50% or 90% or more of the affinity of the corresponding Nanobody of the invention; (2) the chimeric polypeptide is suitable for pharmaceutical use; and (3) the chimeric polypeptide is preferably essentially non-immunogenic under the intended conditions for pharmaceutical use (i.e. indication, mode of administration, dosis and treatment regimen) thereof (which may be essentially analogous to the conditions described herein for the use of the Nanobodies of the invention).

According to one non-limiting embodiment, the chimeric polypeptide comprises at least two CDR sequences (as mentioned above) linked via at least one framework sequence, in which preferably at least one of the two CDR sequences is a CDR3 sequence, with the other CDR sequence being a CDR1 or CDR2 sequence. According to a preferred, but non-limiting embodiment, the chimeric polypeptide comprises at least two CDR sequences (as mentioned above) linked at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the chimeric polypeptides have the structure FR1'-CDR1-FR2'-CDR2-FR3'-CDR3-FR4', in which CDR1, CDR2 and CDR3 are as defined herein for the CDR's of the Nanobodies of the invention, and FR1', FR2', FR3' and FR4' are framework sequences. FR1', FR2', FR3' and FR4' may in particular be Framework 1, Framework 2, Framework 3 and Framework 4 sequences, respectively, of a human antibody (such as $V_H3$ sequences) and/or parts or fragments of such Framework sequences. It is also possible to use parts or fragments of a chimeric polypeptide with the structure FR1'-CDR1-FR2'-CDR2-FR3'-CDR3-FR4. Preferably, such parts or fragments are such that they meet the criteria set out in the preceding paragraph.

Figures 1, 12:
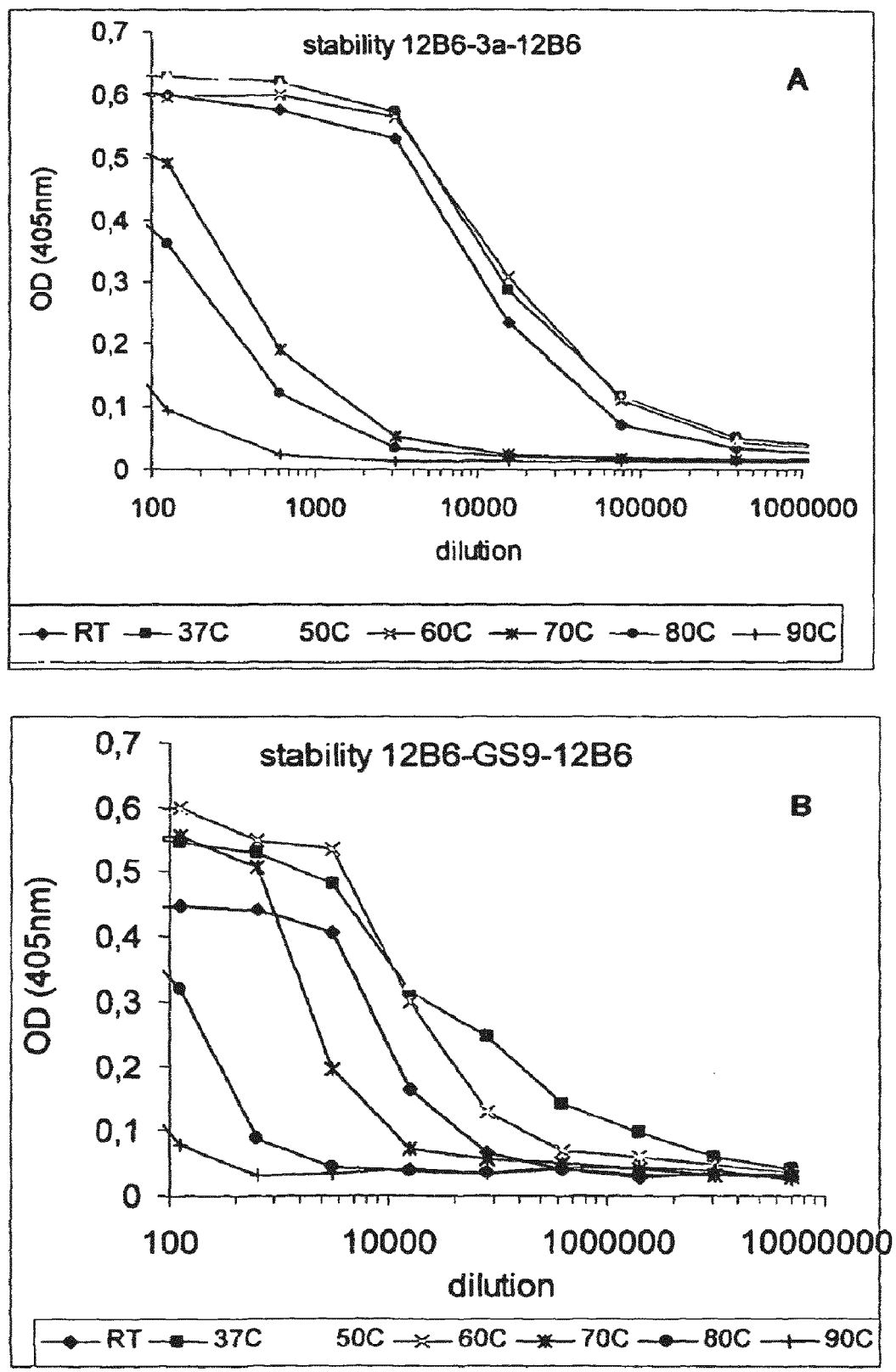

The invention will now be further described by means of the following non-limiting examples and figures, in which the Figures show:

FIG. 1: Binding of nanobodies to vWF in ELISA

Figures 2, 12:
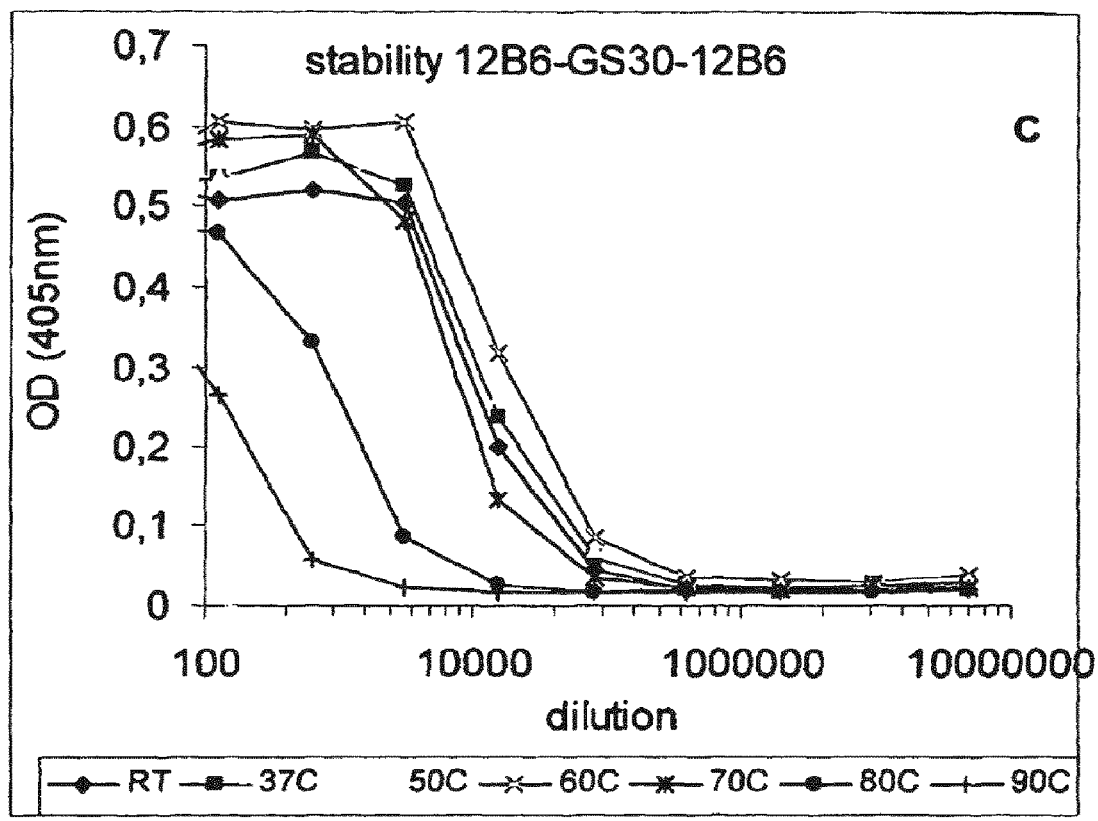

FIG. 2: Alignment of 12A5 homologue nanobody sequences (12A5, SEQ ID NO:60; 12B4, SEQ ID NO:67; 12E8, SEQ ID NO:68; 12A6, SEQ ID NO:69; 12D8, SEQ ID NO:70)

FIG. 3: Alignment of 12B6 homologue nanobody sequences (12B6, SEQ ID NO:62; 12A2, SEQ ID NO:71; 12F2, SEQ ID NO:72; 14H10, SEQ ID NO:73)

FIG. 4: Binding of 12A5 homologue nanobodies to vWF in BIACORE

Figure 5:
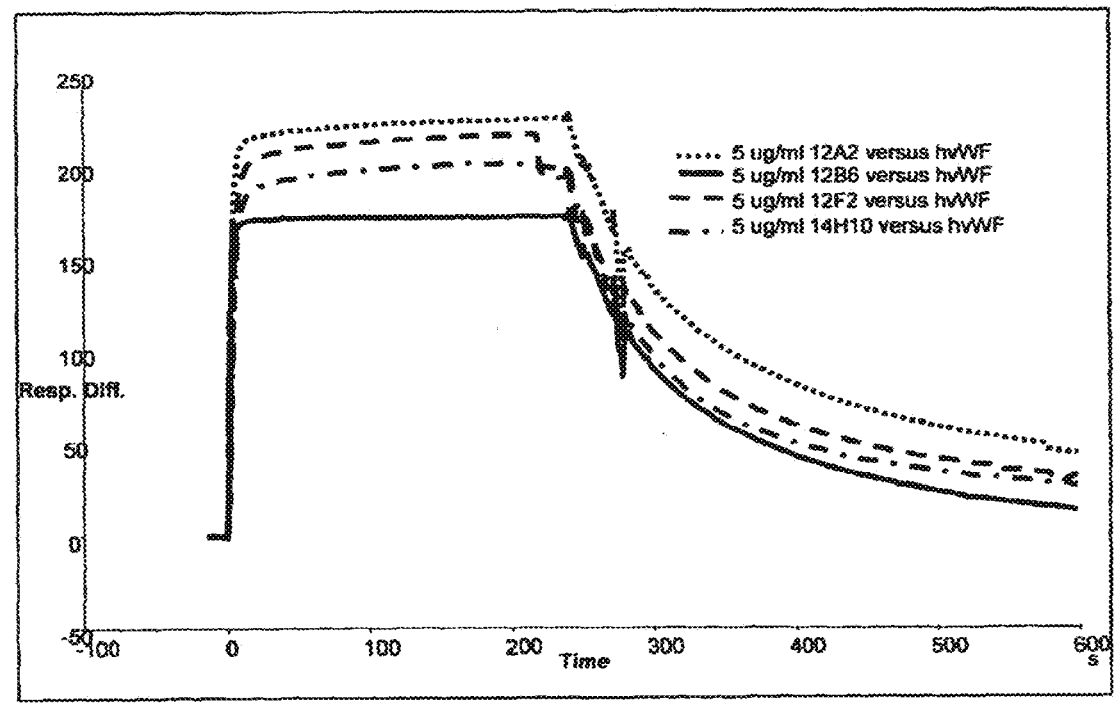

FIG. 5: Binding of 12B6 homologue nanobodies to vWF in BIACORE

Figure 6:
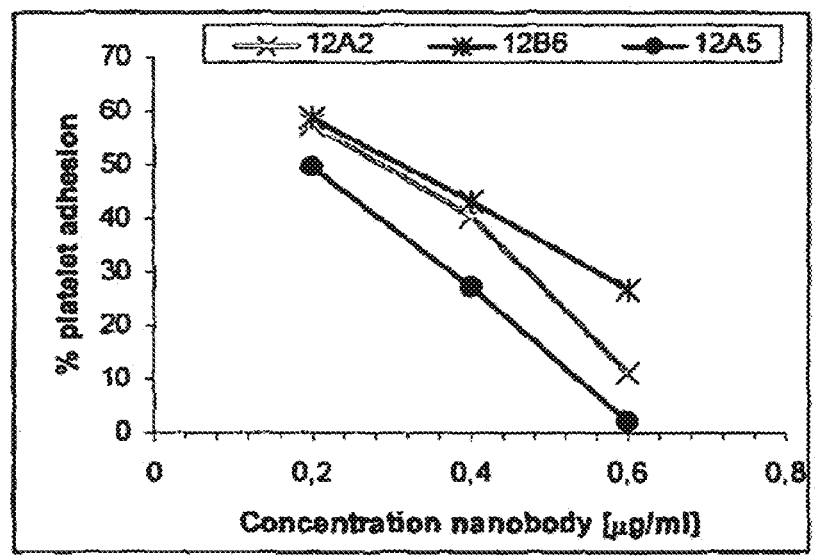
Figure 9:
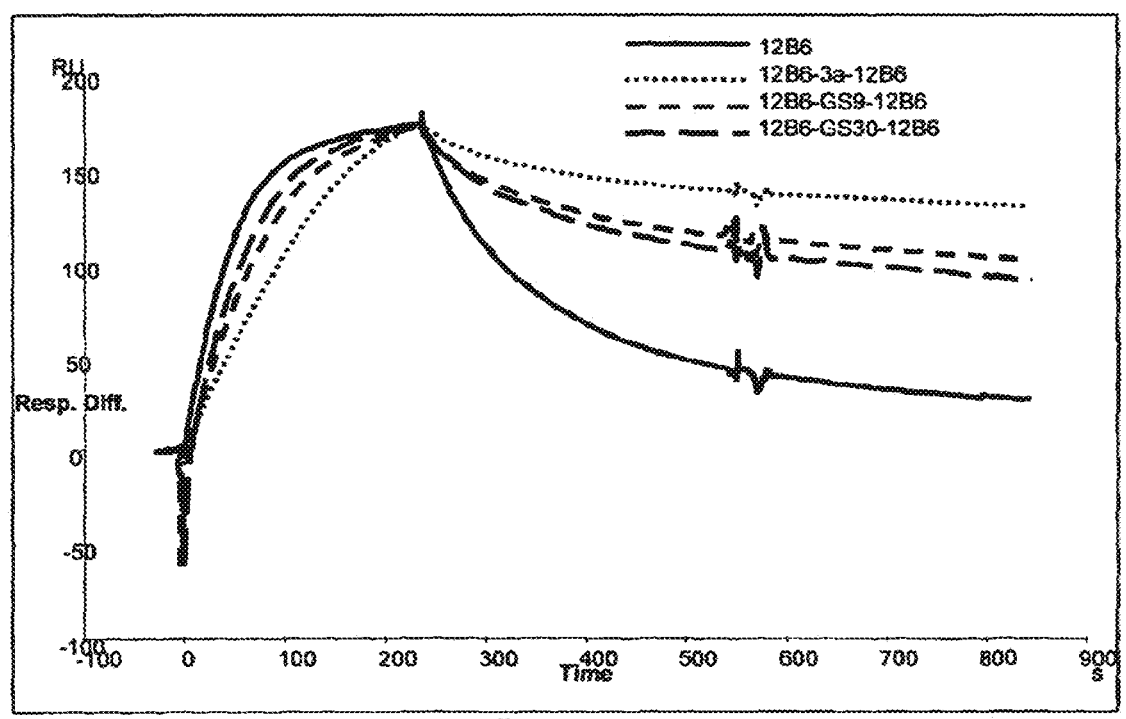
Figure 10:
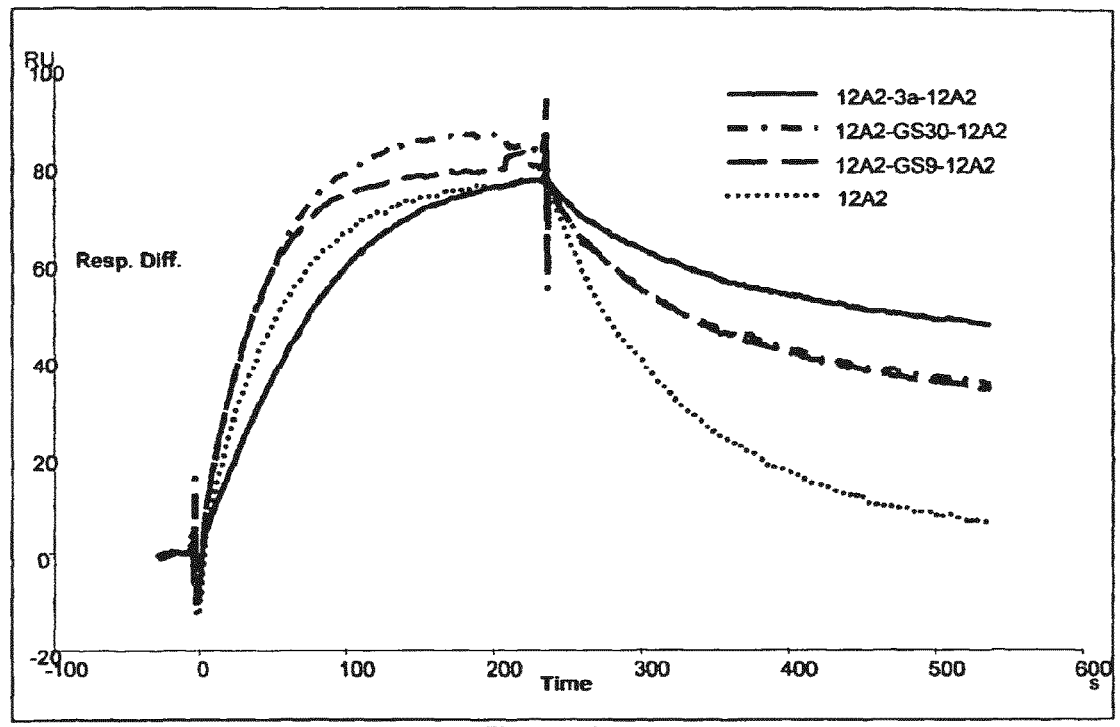
Figure 11:
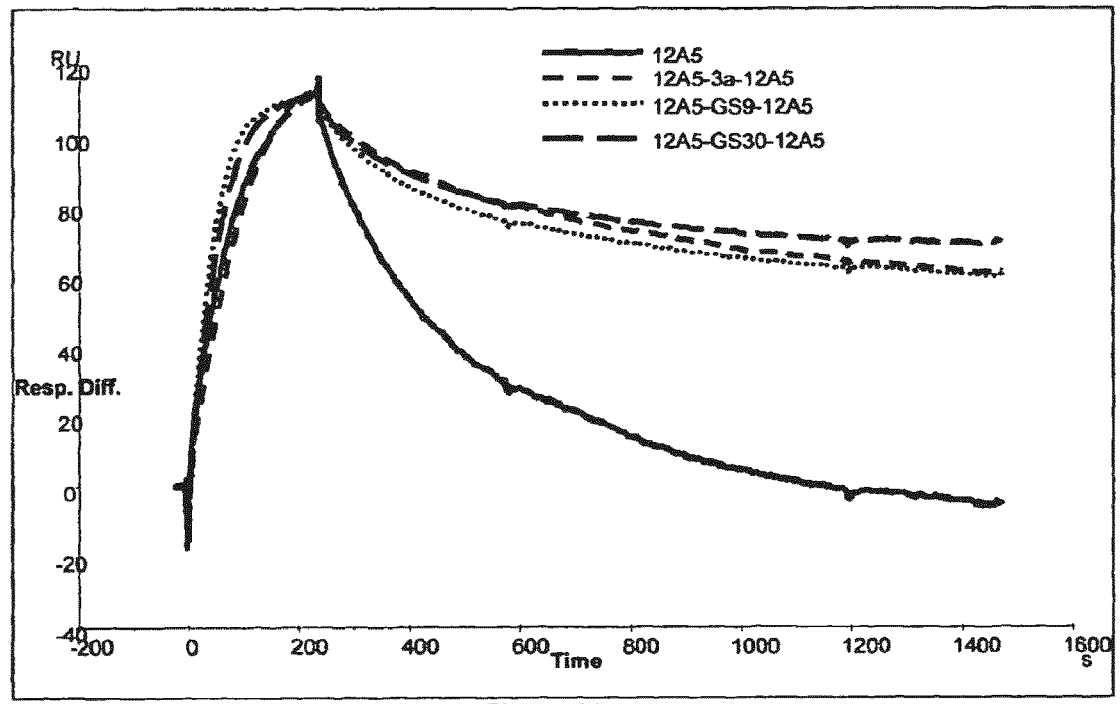
Figures 1, 13:
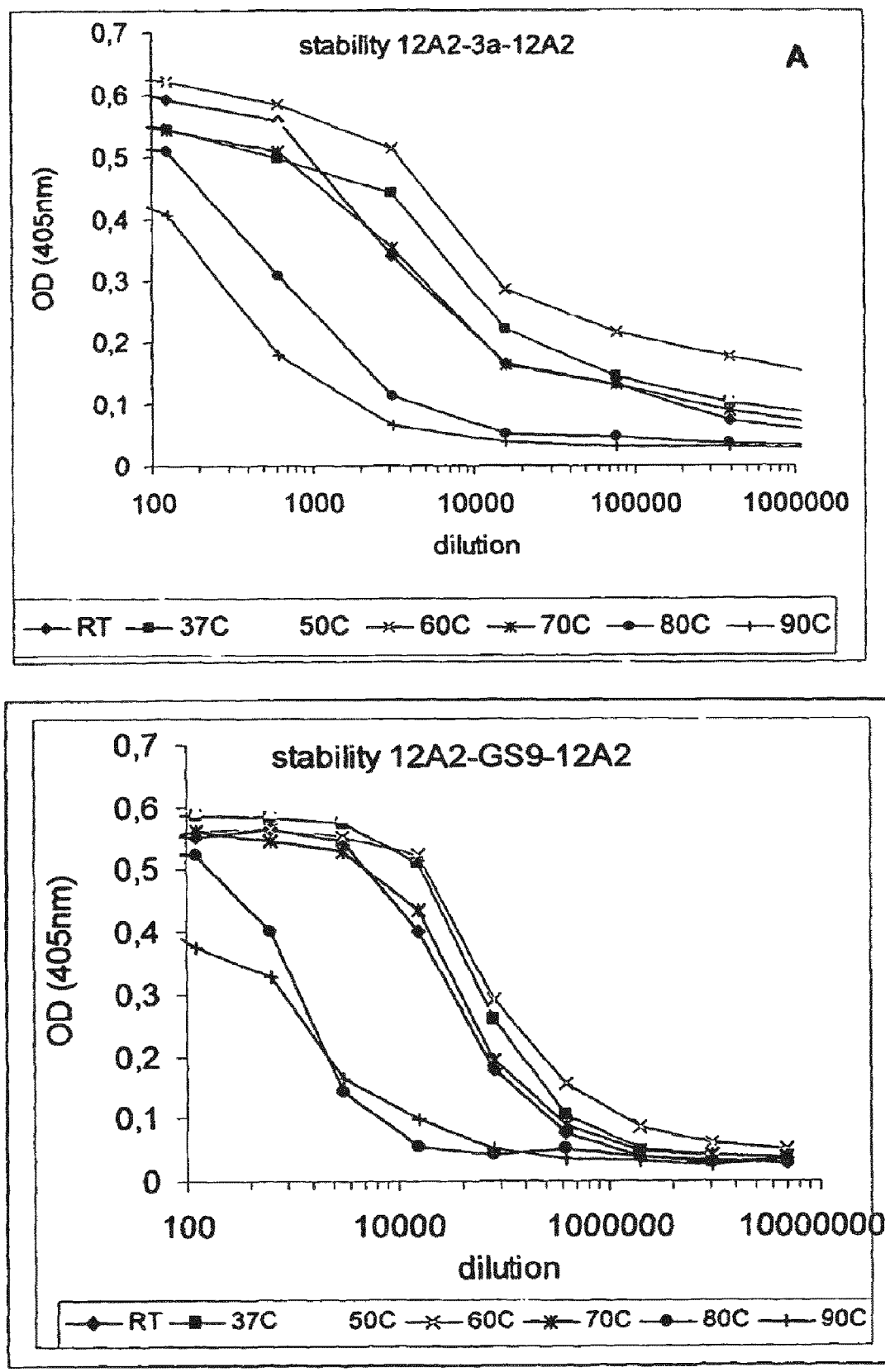
Figures 2, 13:
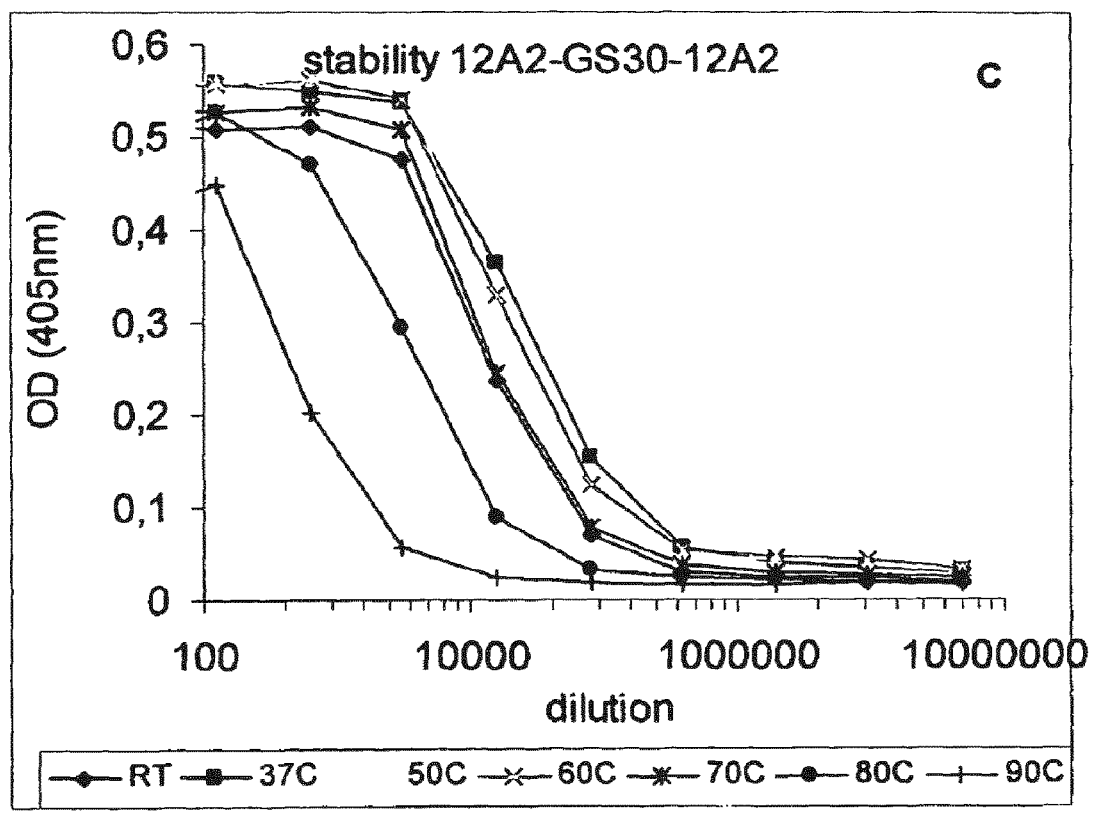
Figures 1, 14:
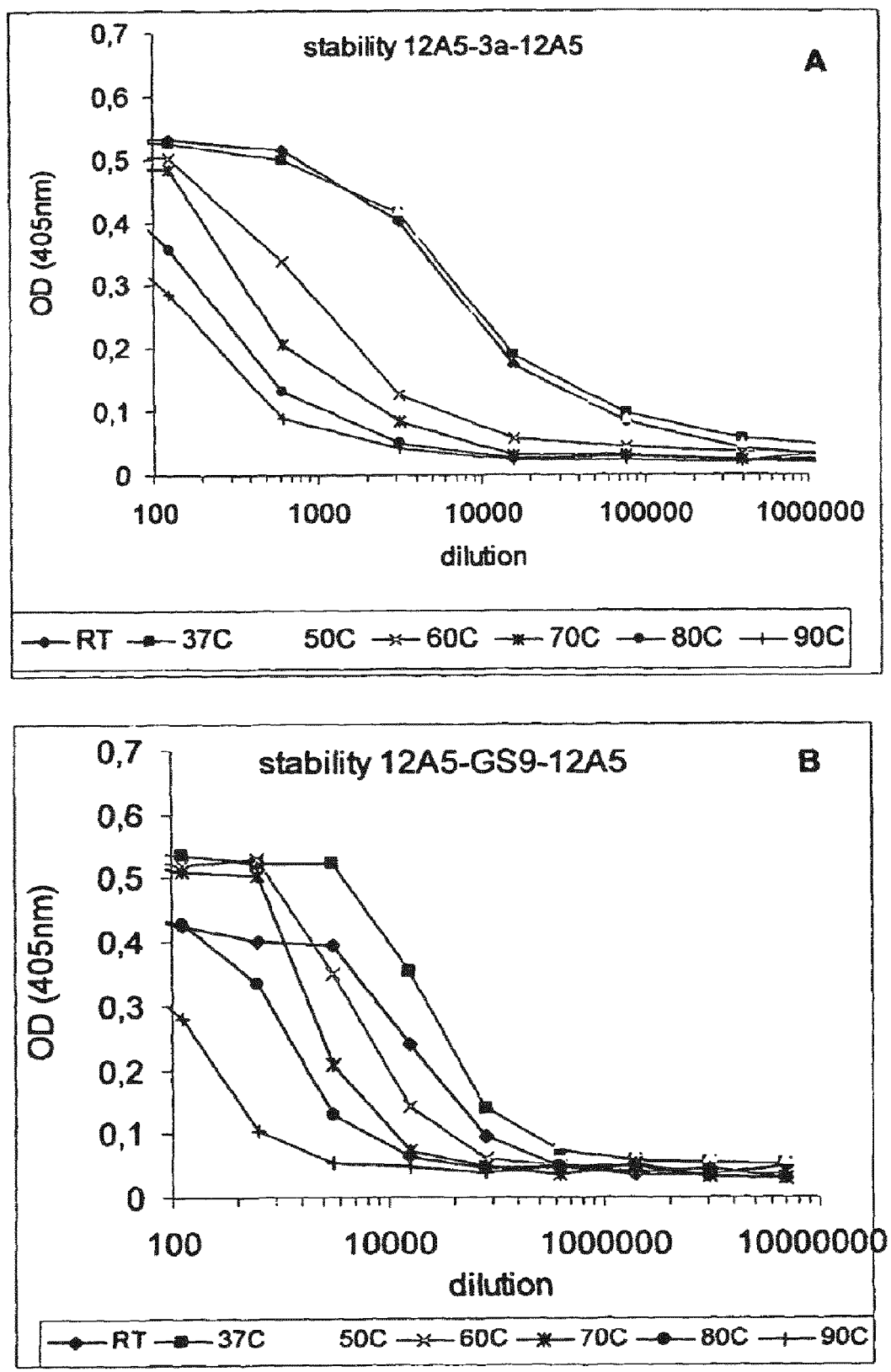
Figures 2, 14:
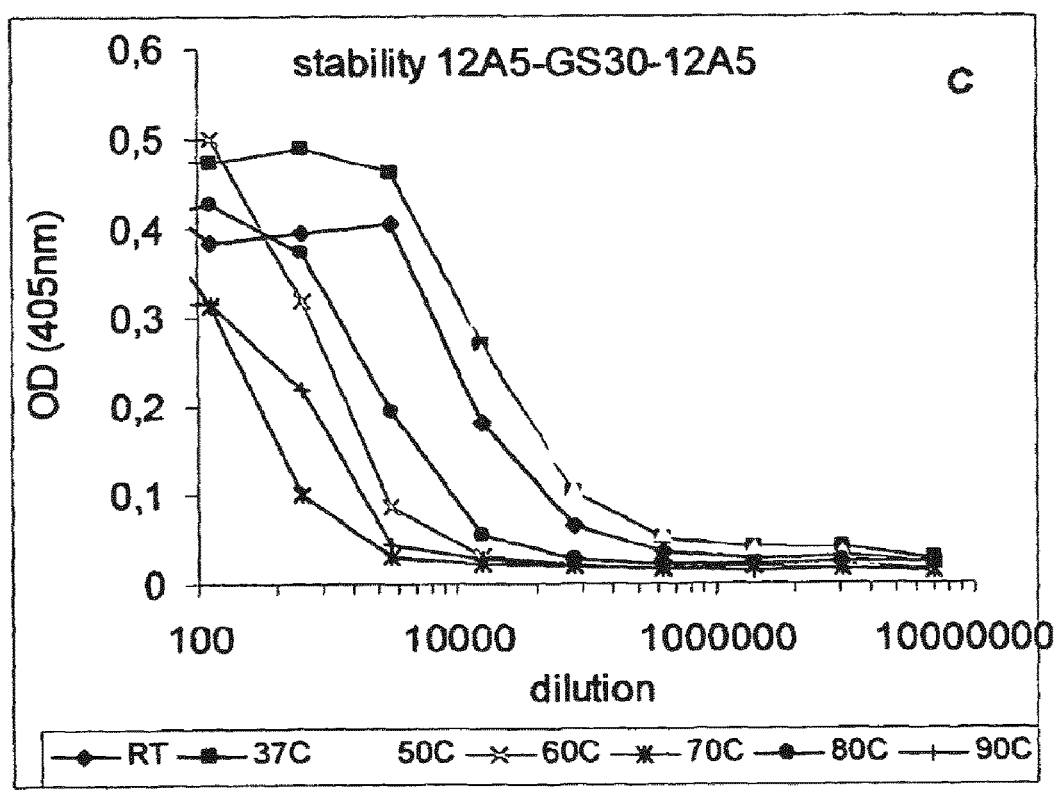

FIG. 6: Platelet adhesion at different concentrations of 12B6, 12A2 and 12A5 nanobodies FIG. 7a: Binding in ELISA to vWF for 12B6 nanobody after heating at increasing temperatures FIG. 7b: Binding in ELISA to vWF for 12A2 nanobody after heating at increasing temperatures FIG. 7c: Binding in ELISA to vWF for 12A5 nanobody after heating at increasing temperatures FIG. 8a: Binding of vWF from different species to 12B6 nanobody in ELISA FIG. 8b: Binding of vWF from different species to 12A2 nanobody in ELISA FIG. 8c: Binding of vWF from different species to 12A5 nanobody in ELISA FIG. 9: Binding of bivalent 12B6 nanobodies to vWF in BIACORE FIG. 10: Binding of bivalent 12A2 nanobodies to vWF in BIACORE FIG. 11: Binding of bivalent 12A5 nanobodies to vWF in BIACORE FIG. 12: Binding in ELISA to vWF of bivalent 12B6 nanobodies after heating at increasing temperatures FIG. 13: Binding in ELISA to vWF of bivalent 12A2 nanobodies after heating at increasing temperatures FIG. 14: Binding in ELISA to vWF of bivalent 12A5 nanobodies after heating at increasing temperatures FIG. 15: Alignment of humanised 12B6 nanobody sequences (12B6, SEQ ID NO:62; 12B6H1, SEQ ID NO:86; 12B6H2, SEQ ID NO:87; 12B6H3, SEQ ID NO:88; 12B6H4, SEQ ID NO:89)

FIG. 16: Binding in ELISA to vWF of wild type and humanised 12B6 nanobody

FIG. 17: Alignment of humanised 12A2 nanobody sequences (12A2, SEQ ID NO:71, 12A2H1, SEQ ID NO:90, 12A2H3, SEQ ID NO:91; 12A2H4, SEQ ID NO:92; 12A2H11, SEQ ID NO:93; 12A2H13, SEQ ID NO:94)

Figure 18:
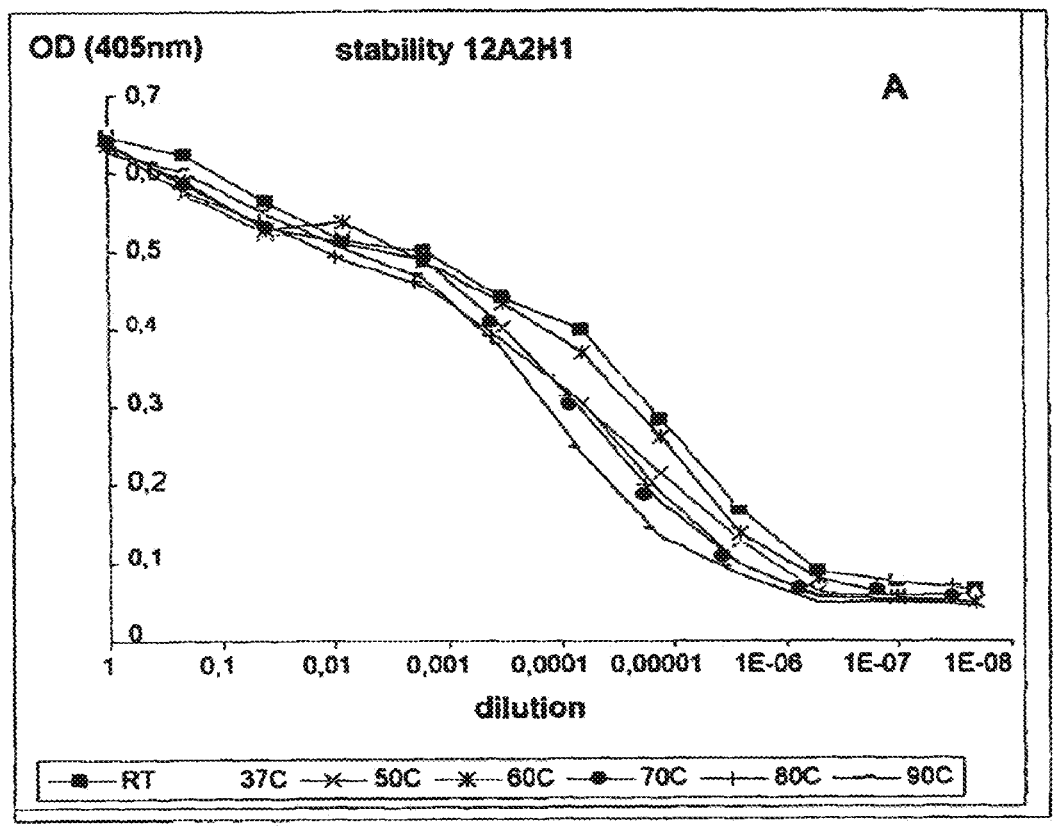
Figure 1:
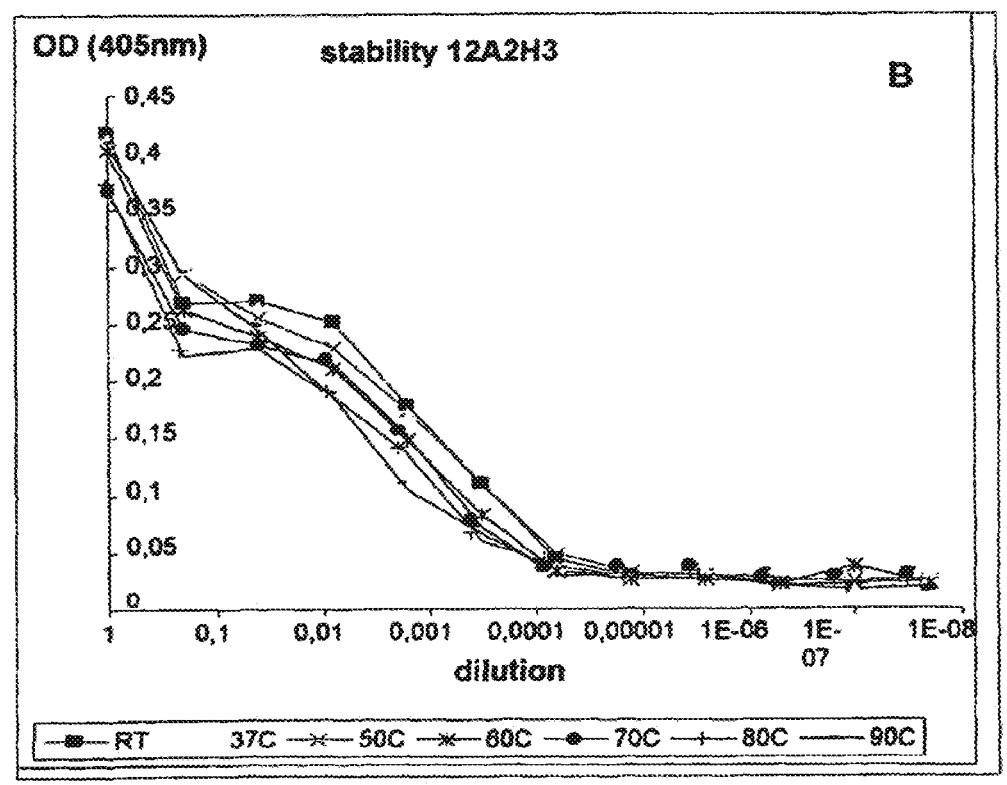
Figures 2, 18:
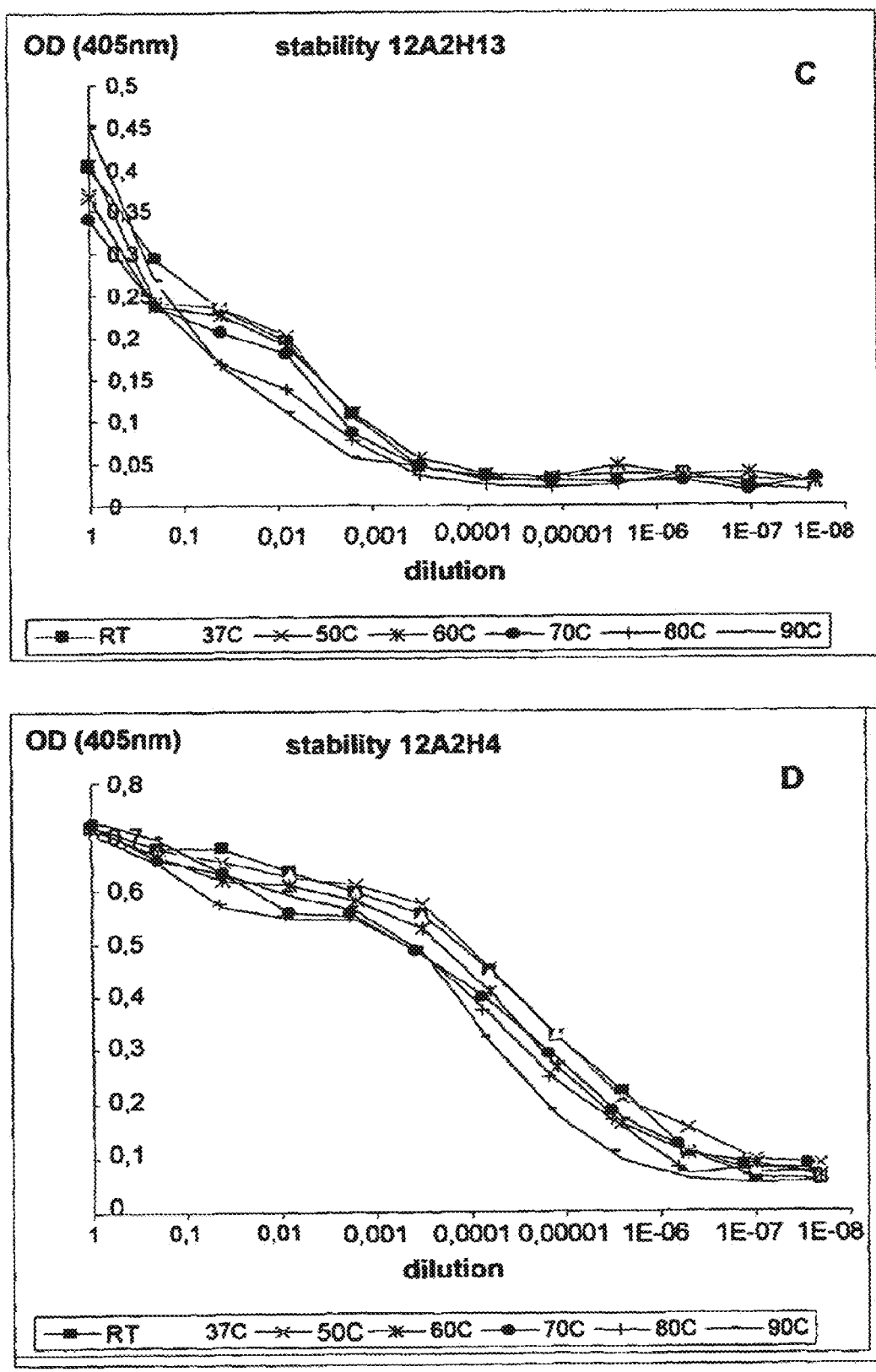

FIG. 18: Binding in ELISA to vWF of humanised 12A2 nanobodies, after heating at increasing temperatures FIG. 19: Binding in ELISA to vWF of humanised 12A2 nanobodies FIG. 20: Alignment of humanised 12A5 nanobody sequences (12A5, SEQ ID NO:60; 12A5H1, SEQ ID NO:95; 12A5H2, SEQ ID NO:96; 12A5H3, SEQ ID NO:97)

FIG. 21: Binding in ELISA to vWF of wild type and humanised 12A5 nanobody

FIG. 22: Alignment of nanobodies selected for bivalent form (12A2H1, SEQ ID NO:90; 12A2H4, SEQ ID NO:92; 12B6H2, SEQ ID NO:87)

Figure 23:
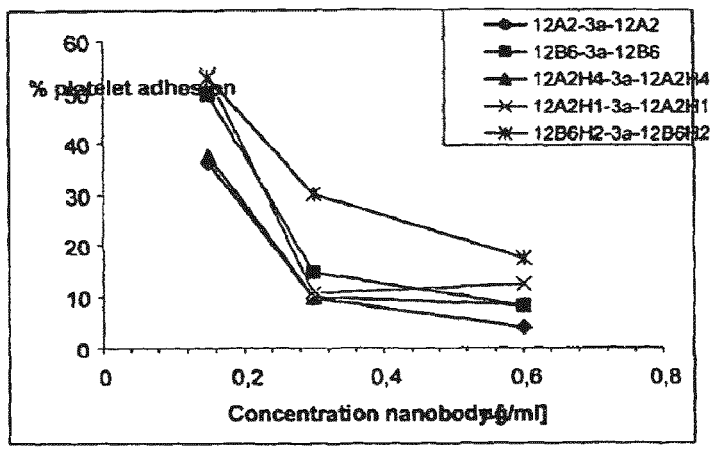

FIG. 23: Platelet adhesion at different concentrations of bivalent (humanised) nanobodies FIG. 24: Blood flow pattern for Folts model in baboons FIG. 25: Experimental setup for Folts model in baboons FIG. 26: Folts study of baboon control group. The blood flow in function of time is shown, indicating the CFRs (representative of 2 independent experiments)

Figure 27:
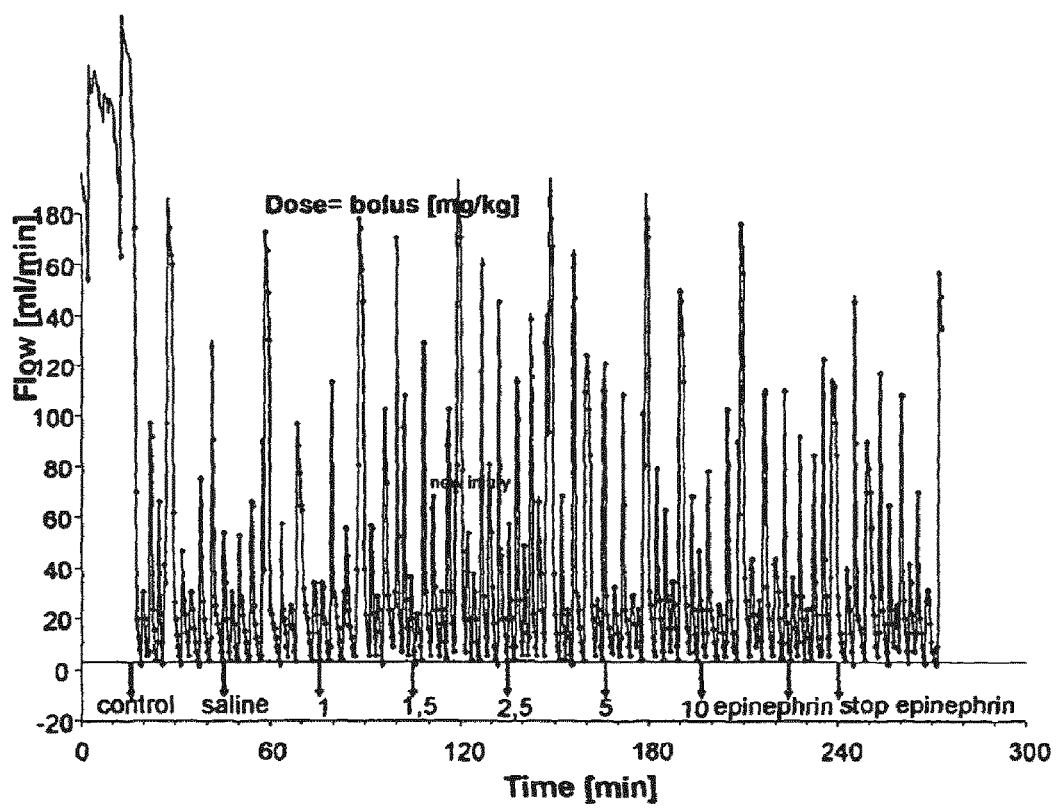

FIG. 27: Folts study of baboon group treated with Aspegic. The blood flow in function of time is shown, indicating the CFRs (representative of 3 independent experiments)

Figure 28:
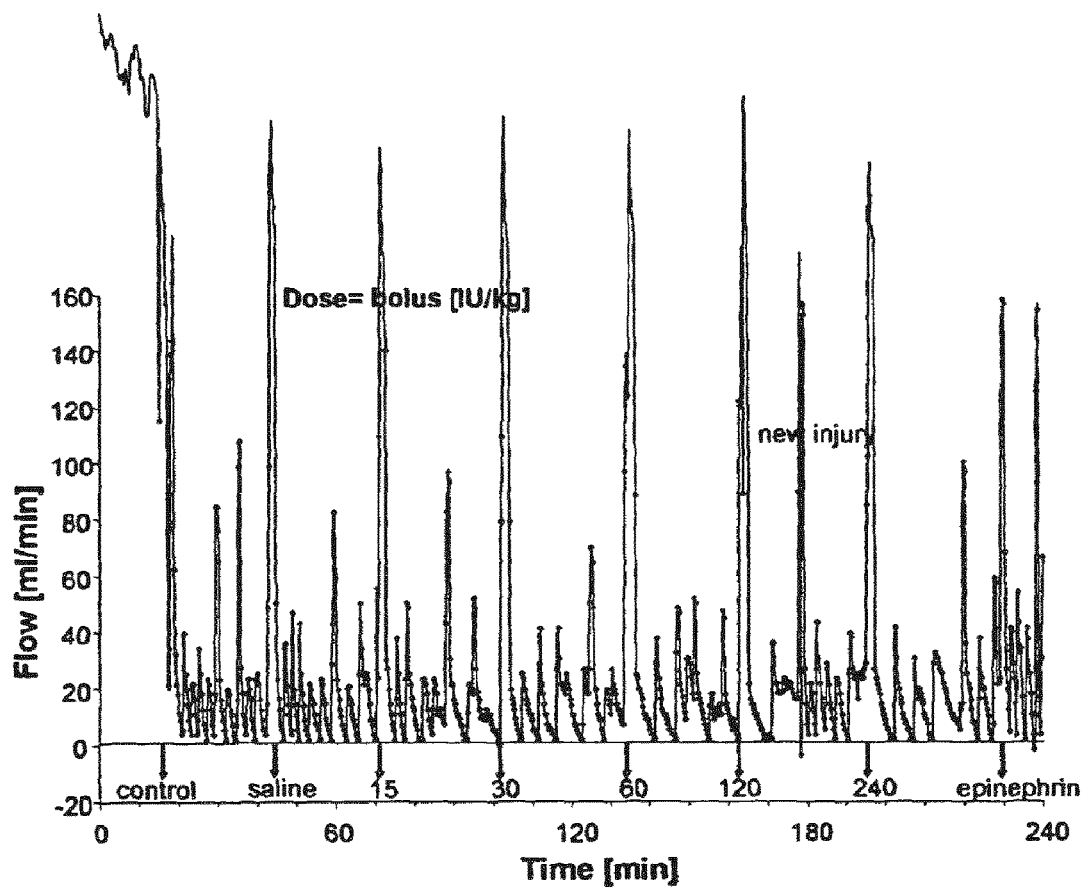

FIG. 28: study of baboon group treated with Heparin. The blood flow in function of time is shown, indicating the CFRs (representative of 3 independent experiments)

Figure 29:
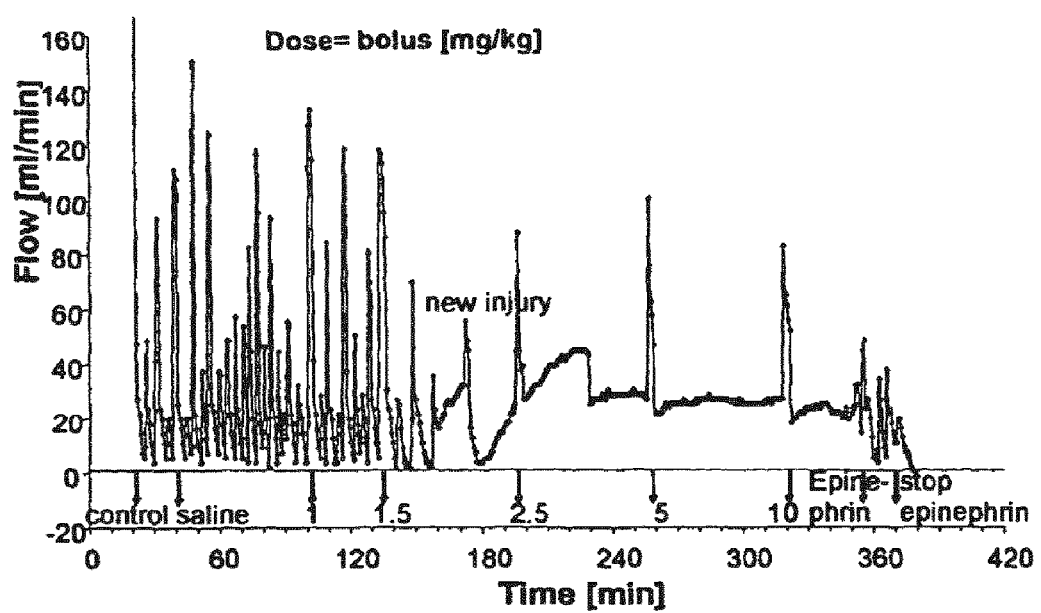

FIG. 29: Folts study of baboon group treated with Plavix. The blood flow in function of time is shown, indicating the CFRs (representative of 4 independent experiments)

Figure 30:
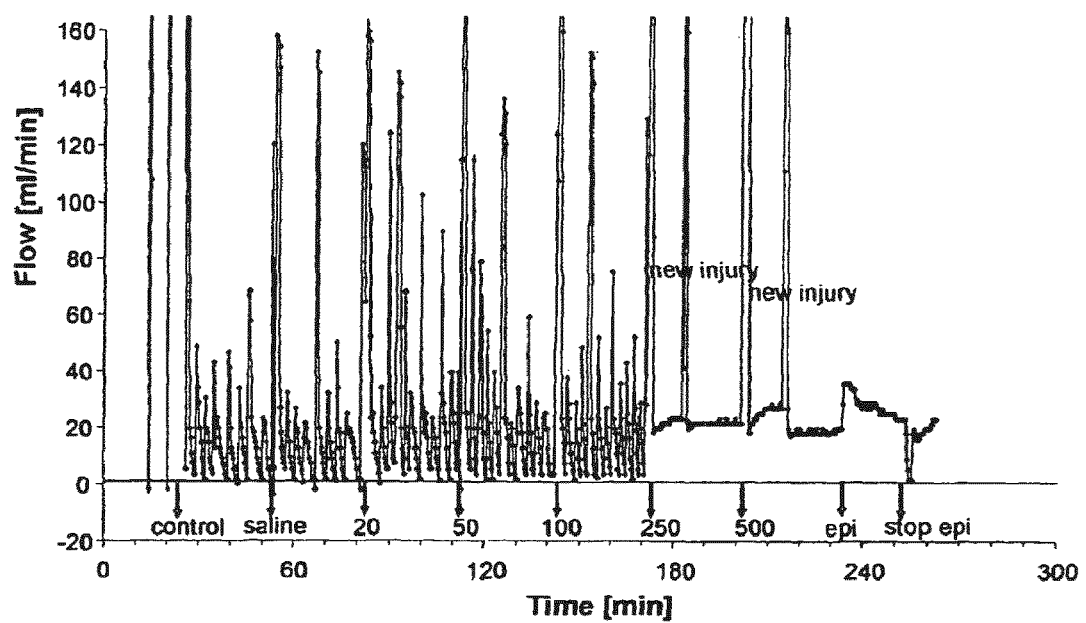

FIG. 30: Folts study of baboon group treated with Reopro. The blood flow in function of time is shown, indicating the CFRs (representative of 3 independent experiments)

Figure 31:
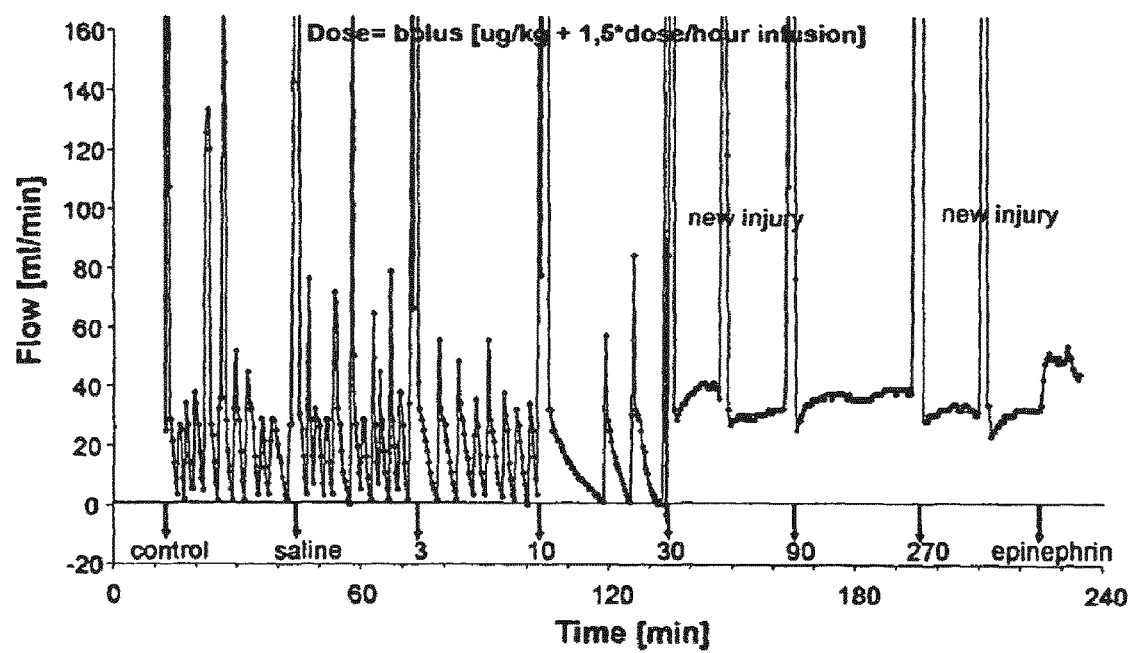

FIG. 31: Folts study of baboon group treated with ALX-0081 (SEQ ID NO:98). The blood flow in function of time is shown, indicating the CFRs (representative of 8 independent experiments)

Figure 32:
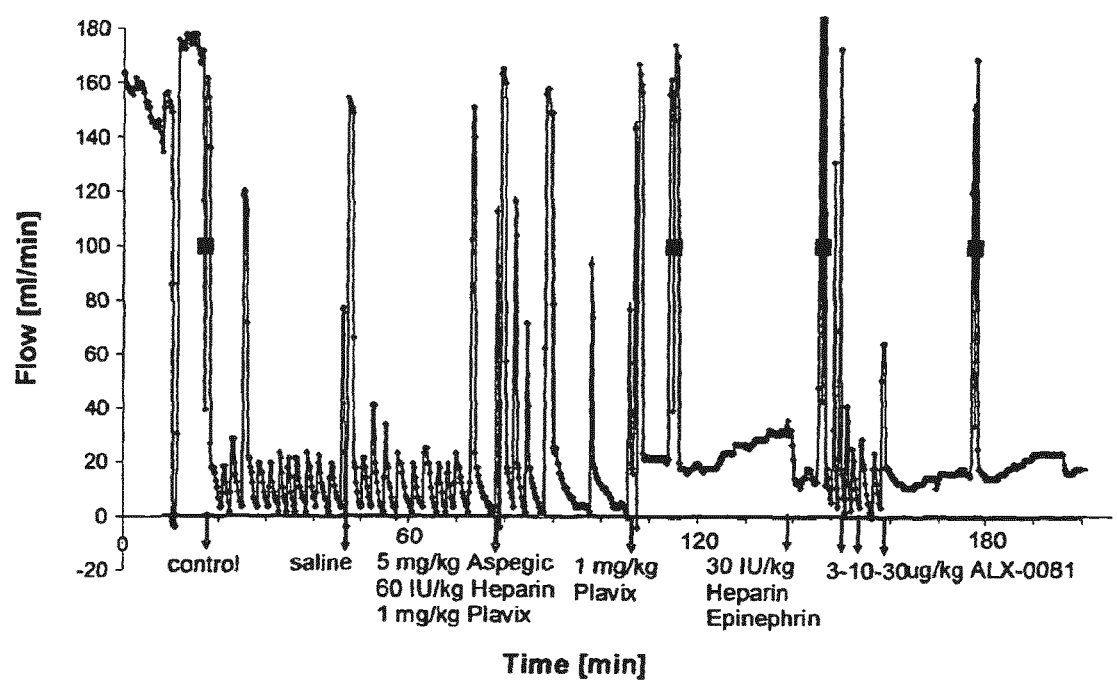

FIG. 32: Flow read out from baboon ID 6 treated with a combination of Aspegic, Heparin, Plavix and ALX-0081

Figure 33:
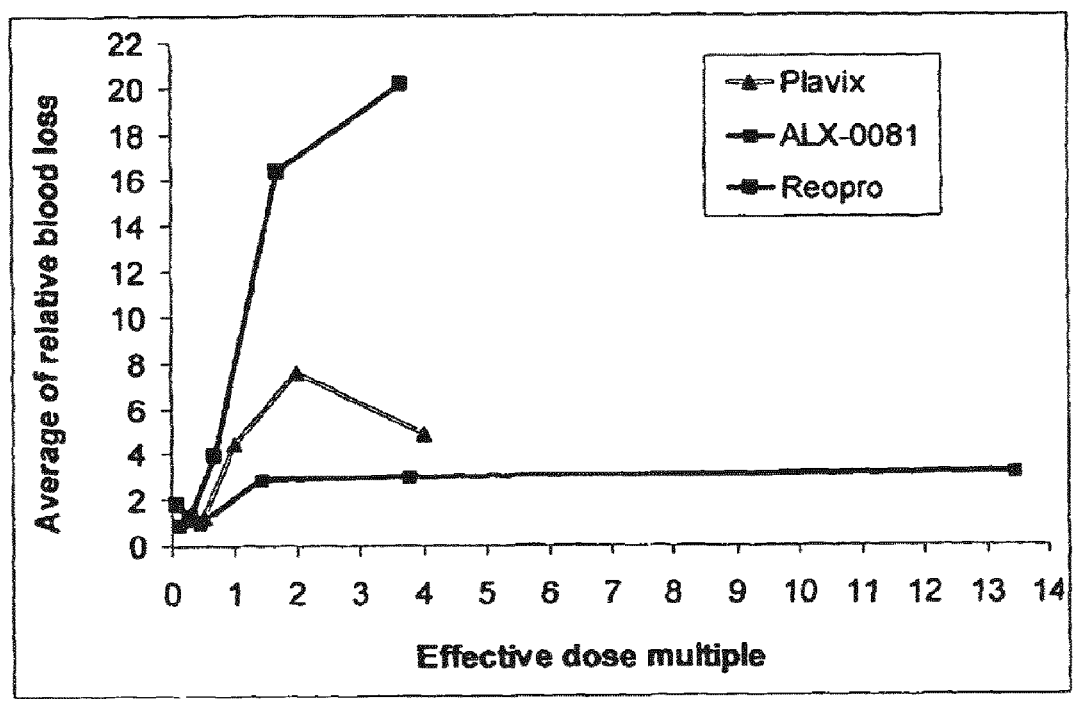

FIG. 33: Averages of relative blood loss in function of different doses of Plavix, Reopro and ALX-0081

Figure 34:
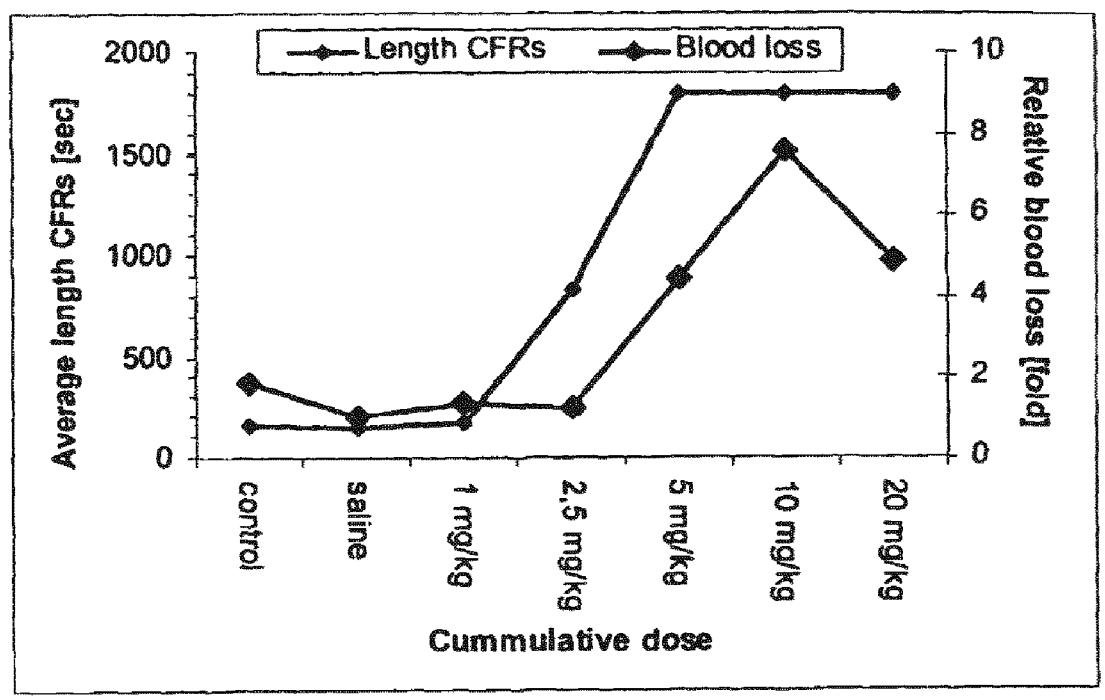

FIG. 34: Average length of CFRs and average relative amount of blood loss for animals treated with Plavix in function of increasing drug dose.

Figure 35:
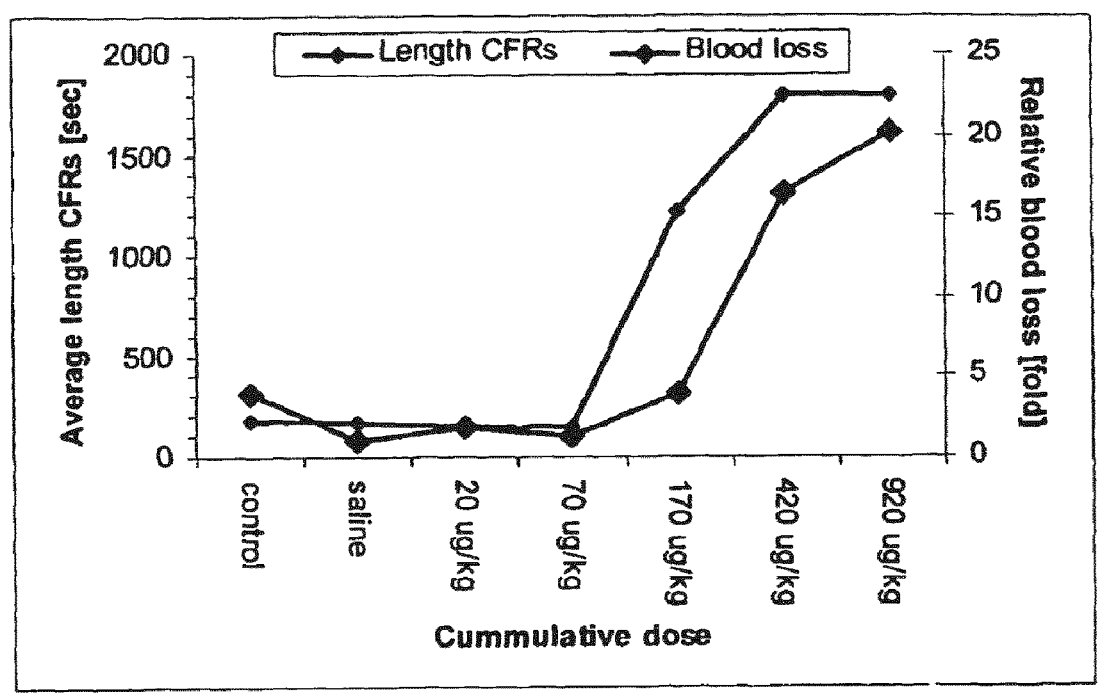

FIG. 35: Average length of CFRs and average relative amount of blood loss for animals treated with Reopro in function of increasing drug dose FIG. 36: Average length of CFRs and average relative amount of blood loss for animals treated with ALX-0081 in function of increasing drug dose FIG. 37: ristocetin-induced aggregation (%, ■) and length of CFRs (s, ♦) for each baboon treated with ALX-0081 in function of all doses FIG. 38: Concentration of ALX-0081 in plasma versus the length of CFRs for all baboons treated with ALX-0081

Figure 39:
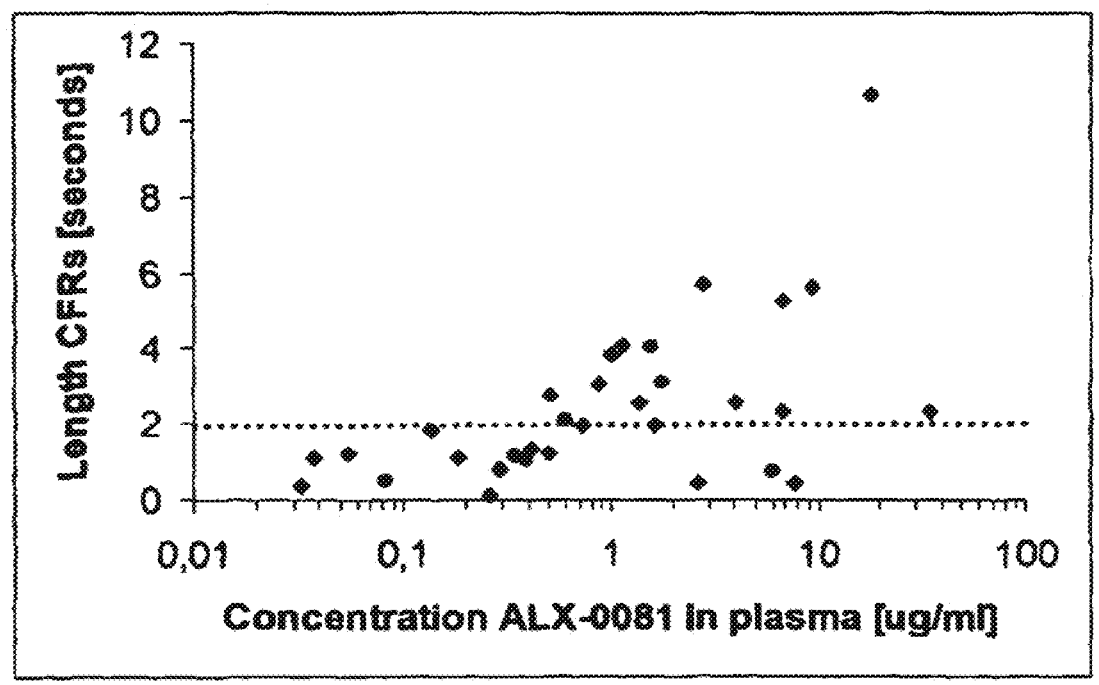

FIG. 39: Concentration of ALX-0081 in plasma versus relative amount of blood loss from the gauzes FIG. 40: Folts study of baboon 1 treated with ALX-0081 and vWF. The blood flow in function of time is shown, indicating the CFRs FIG. 41: strings (arrows) of adhered platelets on ULvWF secreted from stimulated endothelial cells FIG. 42: Absence of strings when platelets are perfused over ULvWF in the presence of ALX-0081

Figure 43:

FIG. 43: Control perfusion experiment: ULvWF strings before (panel A, indicated with red arrows) and during (panel B) perfusion with normal plasma. In panel B, ULvWF strings being cleaved by ADAMTS-13 are indicated with a blue and red arrow for a piece of an ULvWF string moving away or for largely cleaved ULvWF strings respectively FIG. 44: Perfusion experiment in presence of ALX-0081. Microscopic image of a field before (panel A) and of the same field after (panel B) perfusion with normal plasma. An UlvWF string is indicated in panel A with a red arrow which is absent in panel B due to cleavage of the ULvWF by ADAMTS-13.

Figure 45:
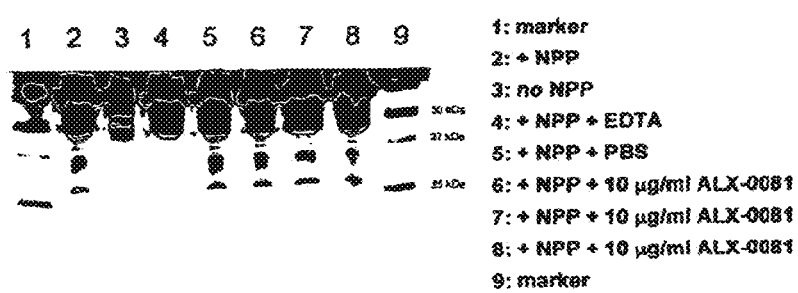

FIG. 45: cleavage of A1-A2-A3 by ADAMTS-13 present in normal pool plasma (NPP) in the absence and presence of ALX-0081 and in which the Tables, which form an integral part of the present description, are as follows:

Table 8: Sequence listing of anti-vWF nanobodies
Table 9: Expression yields of anti-vWF nanobodies
Table 10: Platelet adhesion in perfusion chamber of anti-vWF nanobodies Table 11: Sequence listing of 12B6 and 12A5 homologue nanobodies
Table 12: Estimated K-on, K-off and KD values for 12A5 homologue nanobodies
Table 13: Estimated K-on, K-off and KD values for 12B6 homologue nanobodies
Table 14: Real KD value of 12B6, 12A2 and 12A5 nanobodies
Table 15: Platelet adhesion in perfusion chamber of 12B6, 12A2 and 12A5 nanobodies
Table 16: Concentration of 12B6, 12A2 and 12A5 nanobodies after heating at increasing temperatures
Table 17: Sequence listing of bivalent nanobodies
Table 18: Sequence listing of linker sequences
Table 19: Expression yields of bivalent 12B6, 12A2 and 12A5 nanobodies
Table 20: Concentration of 12B6 bivalent nanobodies after heating at increasing temperatures
Table 21: Concentration of 12A2 bivalent nanobodies after heating at increasing temperatures
Table 22: Concentration of 12A5 bivalent nanobodies after heating at increasing temperatures
Table 23: Platelet adhesion in perfusion chamber of 12A2 bivalent nanobodies
Table 24: Sequence listing of humanised 12B6 nanobodies
Table 25: Expression yields of wild type and humanised 12B6 nanobodies
Table 26: Concentration of wild type and humanised 12B6 nanobodies after heating at increasing temperatures
Table 27: KD values for wild type and humanised 12B6 nanobodies
Table 28: Sequence listing of humanised 12A2 nanobodies
Table 29: Expression yields of wild type and humanised 12A2 nanobodies
Table 30: Concentration of wild type and humanised 12A2 nanobodies after heating at increasing temperatures
Table 31: Platelet adhesion of wild type and humanised 12A2 nanobodies in perfusion chamber at 0.7 and 1.5 ug/ml
Table 32: Platelet adhesion of wild type and humanised 12A2 nanobodies in perfusion chamber at 0.5, 1 and 2 ug/ml
Table 33: KD values for wild type and humanised 12A2 nanobodies
Table 34: Sequence listing of humanised 12A5 nanobodies
Table 35: Expression yields of wild type and humanised 12A5 nanobodies
Table 36: Concentration of wild type and humanised 12A5 nanobodies after heating at increasing temperatures
Table 37: KD values for wild type and humanised 12A5 nanobodies
Table 38: Sequence listing of humanised bivalent nanobodies
Table 39: Expression yields of humanised bivalent nanobodies
Table 40: Concentration of humanised bivalent nanobody after heating at increasing temperatures
Table 41: Platelet adhesion of wild type and humanised bivalent nanobodies
Table 42: baboons used with the different test compounds in the Folts study
Table 43: Length of CFRs (s) for control animals (ND=not done)
Table 44: Length of CFRs (s) for animals treated with Aspegic™ (ND=not done)
Table 45: Length of CFRs (s) for animals treated with Heparin™ (ND=not done)
Table 46: Length of CFRs (s) for animals treated with Plavix™ (ND=not done)
Table 47: Length of CFRs (s) for animals treated with Reopro™ (ND=not done)
Table 48: Length of CFRs (s) for animals treated with ALX-0081 (ND=not done)
Table 49: baboons used with the different test compounds in the Folts study
Table 50: Inhibition of CFRs in the Folts model for the different drugs tested. The number of experiments in which an inhibition of CFRs was observed in the mentioned different conditions is shown as a function of the total number of independent repeats of that condition.
Table 51: Length of CFRs (seconds) for each baboon and each dose of Aspegic, Heparin, Plavix and ALX-0081. The effective dose is indicated in yellow
Table 52: Blood loss relative to the second control gauze for animals treated with Plavix™ in function of final dose (STD=standard deviation)
Table 53: Blood loss relative to the second control gauze for animals treated with Reopro™ in function of final dose (STD=standard deviation)
Table 54: Blood loss relative to the second control gauze for animals treated with ALX-0081 in function of final dose (STD=standard deviation)
Table 55: The average of the total amount of blood loss (=sum of blood loss from the first five doses of test compound) as relative to the second control gauze
Table 56: Blood loss in gauzes relative to the second control gauze for each baboon treated with Aspegic, Heparin, Plavix and ALX-0081 in function of drug dose. The effective drug dose in which a complete inhibition of CFRs was observed, is indicated in yellow
Table 57: % ristocetin-induced platelet aggregation for each baboon treated with Aspegic, Heparin, Plavix and ALX-0081 in function of drug dose
Table 58: concentration of ALX-0081 [µg/ml] in blood samples obtained at 10 minutes after administration
Table 59: Length of CFRs [seconds] for baboons treated with ALX-0081 and with vWF
Table 60: Volumes [α] to prepare the different mixtures for study of cleavage of A1A2A3 by ADAMTS13.

EXAMPLES

A. Selection and Screening of Nanobodies Specific for vWF and Inhibiting Platelet Adhesion Example 1

Antigen Specific Monovalent Nanobodies

The nanobodies represented in Table 8 SEQ ID Nos: 60 to 66 are obtained from llamas immunized with human vWF or with recombinant A1 domain of vWF. The nanobodies bind to the A1 domain of vWF and inhibit the interaction between vWF and gpIb on the platelets.

Example 2

Expression and Purification of Nanobodies

Plasmid was prepared (QIAGEN, according to the manufacturers instructions) and was transformed into WK6 or TG1 electro-competent cells. A single colony was used to start an overnight culture in LB containing 2% glucose and 100 µg/ml ampicillin. This overnight culture was diluted 100-fold in 2×300 ml TB medium containing 100 µg/ml ampicillin, and incubated at 37° C. until OD600 nm=0.5. 1 mM IPTG was added and the culture was incubated for 3 more hours at 37° C. or overnight at 28° C.

Cultures were centrifuged for 20 minutes at 10000 rpm at 4° C. The pellet was frozen overnight or for 1 hour at −20° C. Next, the pellet was thawed at room temperature for 40 minutes, resuspended in 20 ml peri buffer (50 mM $NaH_2PO_4$ and 300 mM NaCl) and shaken at room temperature for 1 hour. Periplasmic fraction was isolated by centrifugation for 20 minutes at 4° C. at 20000 rpm. The nanobodies were purified on a Nickel column (TALON, Clonetech) as described by the manufacturer and expression yields were calculated as represented in Table 9.

Example 3

Binding of nanobodies to vWF in ELISA

The nanobodies of Example 1 were tested for binding to vWF in ELISA. Therefore, a microtiterplate (Nunc, Maxisorb) was coated with vWF (Red Cross) at a 200-fold dilution and pre-warmed for 15 minutes at 37° C. The plate was coated overnight at 4° C. The plate was then washed with PBS-Tween and blocked for two hours at room temperature with PBS-1% casein. After washing, the samples were applied at a concentration of 10 µg/ml and 3-fold dilutions were made in PBS. After a two hours incubation period, the plates were washed and mouse monoclonal anti-myc antibody at a 1000-fold dilution was applied for 1 hour at room temperature. The plates were washed and polyclonal anti-mouse-HRP (DAKO) was applied at a 1000-fold dilution for one hour at room temperature. The plates were washed and ABTS/$H_2O_2$ substrate was applied. The OD 405 nm was measured. Results are shown in FIG. 1.

Example 4

Inhibition of Platelet Adhesion by Nanobodies in a Flow Chamber

The protein samples were analysed in a perfusion chamber. Thermanox coverslips (Nunc) were soaked overnight in 80% ethanol, rinsed thoroughly with distilled water and air-dried. Human placental collagen type III (Sigma) was solubilized in 0.05 mol/l acetic acid and sprayed on the coverslips at a final density of 30 µg/$cm^2$ with a retouching airbrush. After spraying the coverslips were blocked with 1% human albumin solution in PBS for at least 1 hour at RT. Perfusions were performed with a single-pass perfusion chamber under non-pulsatile flow conditions using a modified small perfusion chamber with a slit height of 0.1 mm and a slit width of 2 mm. Blood was obtained by venipuncture from healthy volunteers and anti-coagulated with Penta/PPACK. Triplicate coverslips were inserted into the chamber. Five milliliters of blood was pre-warmed at 37° C. for 5 minutes with or without addition of 2 microgram/ml nanobody and then circulated through the chamber for 5 minutes at a wall shear rate of 1600 $s^{-1}$ using an infusion pump. After a perfusion run, the coverslip was taken from the chamber, rinsed in Hepes buffered saline (10 mM Hepes, 150 mM NaCL, ph 7.4), fixed in 0.5% glutaraldehyde in PBS, dehydrated in methanol and stained with May-Grün-wald and Giemsa (Riedel de Haen). Platelet deposition was evaluated as platelet surface coverage using light microscopy and computer-assisted analysis. Results are shown in Table 10. Nanobodies 12B6 and 12A5 clearly inhibit platelet adhesion to collagen type III in the perfusion chamber at high shear rate.

Example 5

Analysis in BIACORE for Binding to vWF for Homologues Nanobodies

Nanobodies 12B6 and 12A5 inhibit platelet adhesion in the perfusion chamber. Homologue sequences were obtained from the llama comprising the amino acid differences as shown in Table 11 SEQ ID Nos 67 to 73. FIGS. 2 and 3 represent the alignment of the 12A5 and 12B6 homologue nanobody sequences.

vWF was covalently bound to the sensor chip surface via amine coupling. The CM5 surface of the chip was activated by the injection of EDC/NHS (1:1 mix of 0.4 M 1-ethyl-3-(3-dimethylaminopropyl)-carbodiimide and 0.1 M N-hydroxysuccinimide in water) for 7 minutes. Upon activation vWF was injected until an increase of 6000 response units was detected. The excess of reactive groups was deactivated with 1 M Ethanolamine-HCl (pH 8.5) for 7 minutes. The flowrate was kept constant during the immobilization procedure at 5 ul/min. The eluent buffer was 0.01 M HEPES (pH 7.4) with 0.15 M NaCl, 3 mM EDTA and 0.005% Surfactant P20.

The nanobodies 12B6 and 12A5 and their homologue proteins were analysed in BIACORE on vWF at a concentration of the nanobody of 5 µg/ml as shown in FIGS. 4 and 5. Estimated kon, K-off and KD values are represented in Table 12 and 13. Nanobodies 12A5 and 12B5 have the best K-on and K-off rates. Nanobodies 12A2 and 12B6 have the best K-on rate, the K-off rates are very comparable for all nanobodies tested.

Table 14 shows the real KD value for vWF on BIACORE using a range of concentrations of the nanobodies. From the set of curves that were generated for each nanobody, only those curves where equilibrium was reached, were used to derive the KD value via steady state affinity.

For the treatment of acute events, the fast inhibition of vWF is very important, and thus a fast K-on rate is preferred. The K-on rate determines how fast a nanobody binds its target (vWF) when injected into human or animals.

Example 6

Compare Inhibiting Nanobodies for Potency in the Perfusion Chamber

To compare the potency for inhibition of platelet adhesion, the nanobodies 12A2, 12B6 and 12A5 were tested in the perfusion chamber at 0.2, 0.4 and 0.6 µg/ml. The experiment was performed using the same donor for all nanobodies. Results are shown in Table 15 and FIG. 6. The nanobodies show a very comparable inhibiting capacity in the perfusion chamber, with full inhibition of platelet adhesion at a concentration of 0.6 µg/ml nanobody.

Example 7

Stability of Nanobodies at Elevated Temperatures

A stock solution of nanobodies at a concentration of 200 µg/ml in PBS was prepared and divided into several tubes. Each tube containing nanobody was incubated at different temperatures for 1 hour, then cooled at room temperature for 2 hours and put at 4° C. overnight. The next day, the samples were centrifuged for 30 minutes at 13000 rpm, and the supernatant was tested for OD280 nm. The concentration of supernatants were measured spectophotometrically and expressed as a percentage of the concentration at room temperature. The results are summarized in Table 16.

Figure 7A:
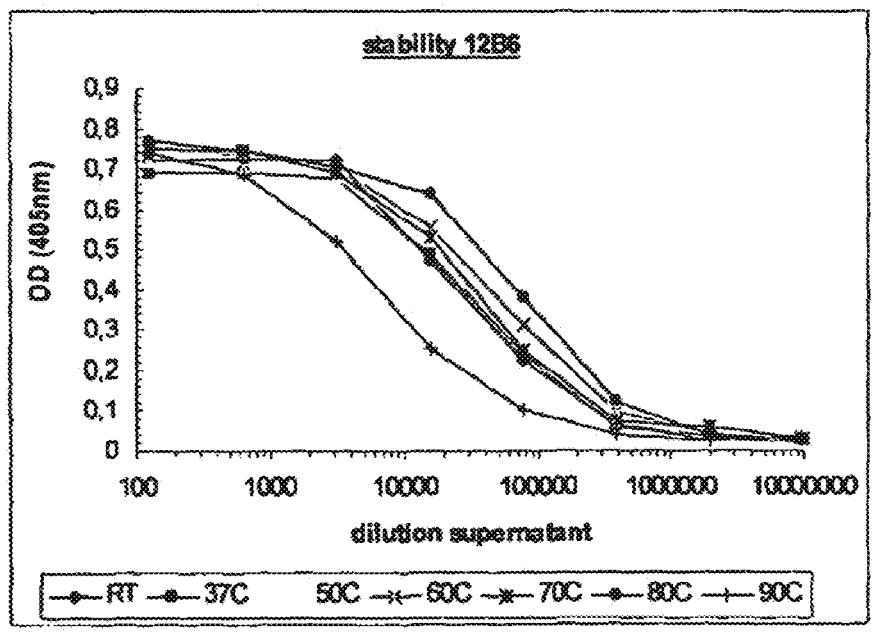
Figure 7B:
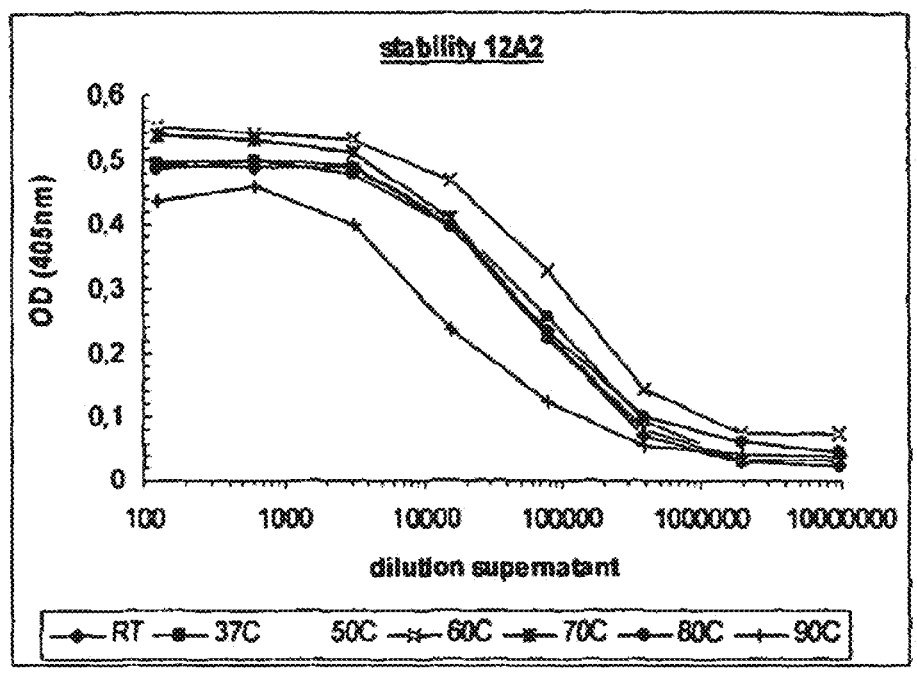
Figure 7C:
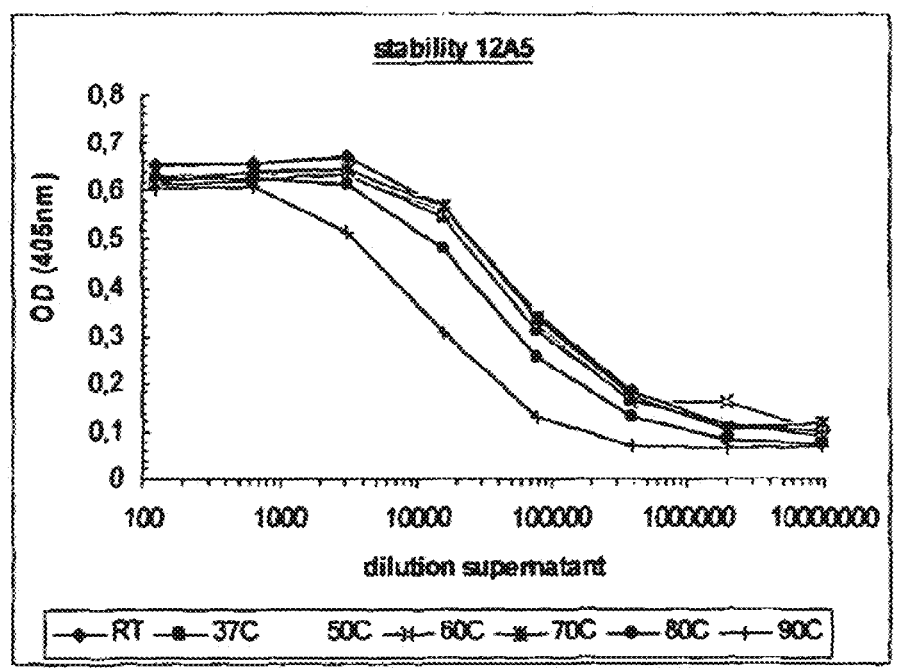

The supernatants were also tested in ELISA for binding to vWF as described above in Example 3. As shown in FIG. 7a (12B6), 7b (12A2) and 7c (12A5), the nanobodies are very stable at elevated temperatures.

Example 8

Cross-Reactivity of the Nanobodies with vWF from Other Species

A microtiterplate was coated with mouse anti-myc at 1/1000 overnight at 4° C. The plate was washed with PBS-Tween and blocked for two hours at room temperature with PBS-1% casein. After washing, the nanobodies were applied at a concentration of 10 µg/ml in PBS. After a one hour incubation period, the plates were washed and plasma (dog, pig, human, baboon and cynomologues monkey) was applied starting at a five-fold dilution and making further two-fold dilutions in PBS. The plates were incubated for 1 hour at room temperature. The plates were washed and polyclonal anti-vWF-HRP (DAKO) was applied at a 2000-fold dilution for one hour at room temperature. The plates were washed and ABTS/$H_2O_2$ substrate was applied. The OD 405 nm was measured.

Figure 8A:
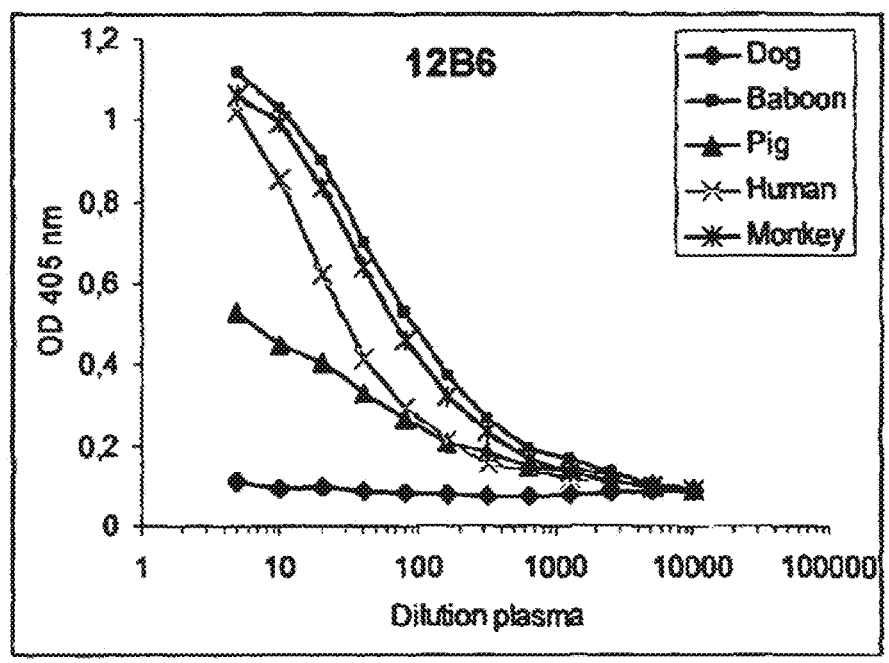
Figure 8B:
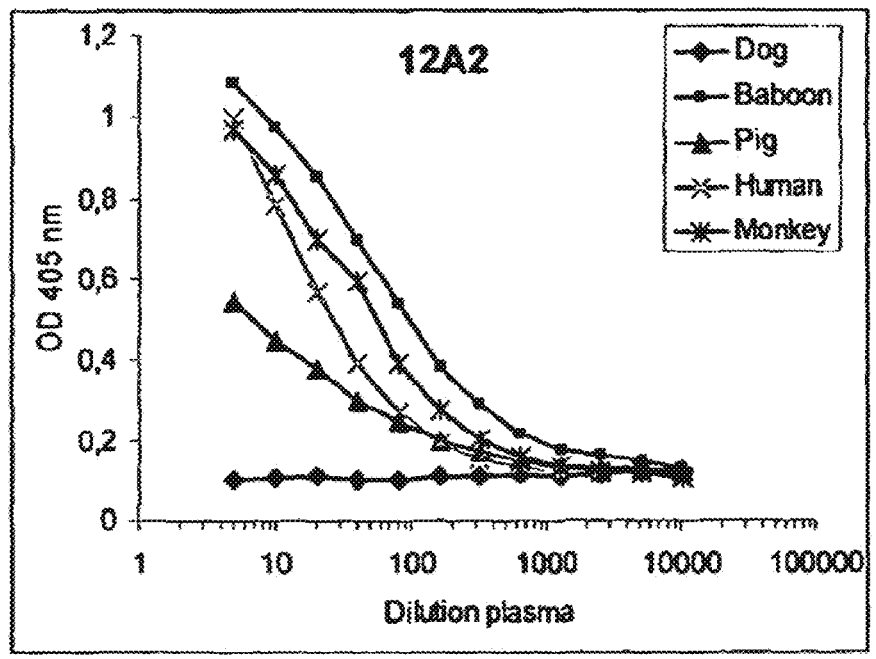
Figure 8C:
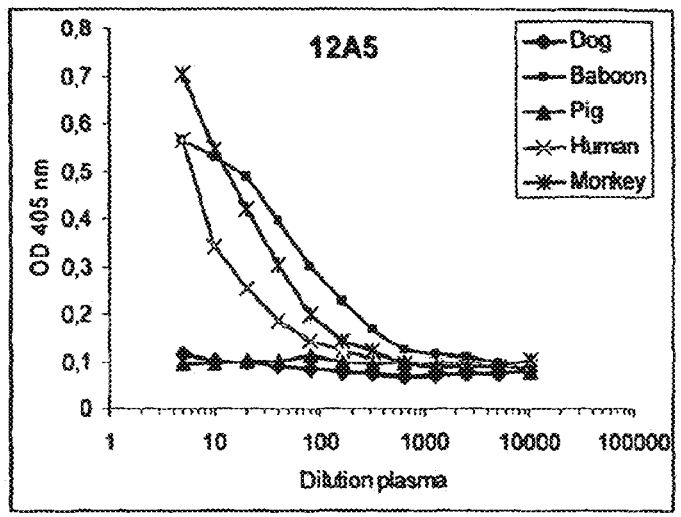

As shown in FIG. 8a (12B6), 8b (12A2) and 8c (12A5), nanobodies 12A5, 12A2 and 12B6 are cross-reactive with human, baboon and cynomologues monkey vWF. The nanobodies 12A2 and 12B6 are also cross-reactive with pig vWF. These nanobodies can therefore be tested for efficacy and safety in pigs. None of the nanobodies is cross-reactive with dog vWF.

B. Construction of Bivalent Nanobodies Specific for vWF and Inhibiting Platelet Adhesion

Example 9

Amino Acid Sequences of the Bivalent Nanobodies

Table 17 SEQ ID Nos 74 to 82 represents bivalent nanobodies constructed for 12B6, 12A2 and 12A5. The nanobodies were linked with the linkers represented in Table 18 SEQ ID Nos 83 to 85.

Example 10

Expression and Purification of the Bivalent Nanobodies

Expressions were performed as described above in Example 2. Expression yields are summarized in Table 19.

Example 11

Analysis of the Bivalent Nanobodies in BIACORE

The bivalent nanobodies of Example 9 were analyzed in BIACORE at 1.3 nM as described above in Example 5 to compare the affinities for vWF versus the monovalent nanobody. The bivalent nanobodies 12B6 (FIG. 9), 12A2 (FIG. 10) and 12A5 (FIG. 11) have an improved affinity for vWF when compared to the monovalent nanobody.

Example 12

Stability of the Bivalent Nanobodies at Elevated Temperatures

Stability of the bivalent nanobodies was measured as described above in Example 7. The concentration (µg/ml) of the supernatants was measured and expressed as a percentage of the concentration at room temperature. The results are summarized in Table 20 (bivalent 12B6), Table 21 (bivalent 12A2) and Table 22 (bivalent 12A5).

The supernatants were tested in ELISA for binding to vWF as described above in Example 3. The supernatants were applied starting at a 1/100 dilution and 1/5 dilutions were made in PBS. Results are shown in FIG. 12 (12B6), FIG. 13 (12A2) and FIG. 14 (12A5).

Example 13

Analysis of Monovalent and Bivalent 12A2 in the Flow Chamber

Nanobody 12A2 (monovalent and bivalent forms) was tested in the perfusion chamber as described above in Example 4. The experiment was performed using the same donor for all nanobodies. Results are summarized in Table 23. The bivalent nanobodies inhibit platelet adhesion more efficiently then the monovalent form.

C. Humanisation of Nanobodies Specific for vWF and Inhibiting Platelet Adhesion

Example 14

Humanisation of 12B6 Nanobody

Table 24 SEQ ID Nos: 86 to 89 represents four humanised 12B6 nanobodies. Table II lists the amino acid changes that were performed to achieve these sequences. FIG. 15 represents the alignment of the humanised sequences for 12B6.

TABLE II

| | non-limiting humanizing substitutions | | | | | | | | | |
|---|---|---|---|---|---|---|---|---|---|---|
| | Q1E | A14P | A17S | E44G | D46E | R76N | M77S | A82bS | K83R | P84A |
| 12B6H1 | X | X | X | X | | | | X | X | X |
| 12B6H2 | X | X | X | X | X | | | X | X | X |
| 12B6H3 | X | X | X | X | | X | | X | X | X |
| 12B6H4 | X | X | X | X | | | X | X | X | X |

Expressions were performed as described in Example 2. Expression yields are summarized in Table 25.

The stability of the humanised nanobodies was measured as described in Example 7. Table 26 summarizes the OD280 nm concentrations (µg/ml) of the supernatants expressed as a percentage of the concentration at room temperature.

FIG. 16 shows the binding of humanised 12B6 nanobodies to vWF in ELISA performed as described in Example 3.

The affinity of humanised 12B6 nanobodies for vWF was determined in BIACORE. KD values are summarized in Table 27.

Example 15

Humanisation of 12A2 Nanobody

Table 28 SEQ ID Nos: 90 to 94 represents five humanised 12A2 nanobodies. Tables III and IV list the following amino acid changes that were performed to achieve these sequences. FIG. 17 represents the alignment of the humanised sequences for 12A2.

TABLE III

| non-limiting humanizing substitutions: | | | | | | | |
|---|---|---|---|---|---|---|---|
| | Q1E | K3Q | E5V | A14P | A17S | R27F | E44G | D46E |
| 12A2H1 | X | X | X | X | X | | X | X |
| 12A2H3 | X | X | X | X | X | | X | X |
| 12A2H4 | X | X | X | X | X | | X | X |
| 12A2H11 | X | X | X | X | X | X | X | X |
| 12A2H13 | X | X | X | X | X | X | X | X |

TABLE IV

| | R76N | M77S | N82bS | K83R | P84A | Q108L |
|---|---|---|---|---|---|---|
| 12A2H1 | | | X | X | X | |
| 12A2H3 | X | | X | X | X | |
| 12A2H4 | | X | X | X | X | |
| 12A2H11 | | | X | X | X | |
| 12A2H13 | X | X | X | X | X | X |

Expressions were performed as described in Example 2. Expression yields are summarized in Table 29.

Stability of the humanised nanobodies was measured as described in Example 7. Table 30 summarizes the OD280 nm concentrations (µg/ml) of the supernatants expressed as a percentage of the concentration at room temperature. All humanised 12A2 nanobodies are very stable upon heating at increasing temperatures.

The ELISA of FIGS. 18 and 19 was performed as described in Example 3. 12A2H1 and 12A2H4 bind very well to vWF in ELISA.

The nanobodies were tested in the flow chamber at a concentration of 0.7 µg/ml and 1.5 µg/ml. The same donor was used for all the experiments. The experiment was performed as described in Example 4. Results are summarized in Table 31 and 32.

The affinity of humanised 12A2 nanobodies for vWF was determined in BIACORE. KD values are summarized in Table 33.

Example 16

Humanisation of 12A5 Nanobody

Table 34 SEQ ID Nos: 95 to 97 represents three humanised 12A5 nanobodies. Table V lists the amino acid changes that were performed to achieve these sequences. FIG. 20 represents the alignment of the humanised sequences for 12A5.

TABLE V

| non-limiting humanizing substitutions: | | | | | | | |
|---|---|---|---|---|---|---|---|
| | A1E | L23A | Q44G | G73N | P74A | K83R | P84A |
| 12A5H1 | X | X | X | | | X | X |
| 12A5H2 | X | X | X | | X | X | X |
| 12A5H3 | X | X | X | X | X | X | X |

Expressions were performed as described above in Example 2. Expression yields after TALON purification are summarized in Table 35 for each humanised 12A5 nanobody.

Stability of the humanised 12A5 nanobodies was measured as described above in Example 7. The OD280 of the supernatants was measured and expressed as percentage of the OD280 at room temperature. The results are summarized in Table 36. All humanised 12A5 nanobodies are comparably stable upon heating at increasing temperatures to the wild type.

ELISA was performed as described in Example 3. FIG. 21 illustrates the binding activity for vWF in ELISA.

The affinity of humanised 12A5 nanobodies for vWF was determined in BIACORE. KD values are summarized in Table 37.

Example 17

Bivalent Humanised Nanobodies

Three humanised nanobodies 12A2H1, 12A2H4 and 12B6H2 were selected for bivalent form with the 3a linker. The sequences of these 3 nanobodies differ only by a few amino acids as shown in FIG. 22. Table 38 SEQ ID Nos 98 to 100 lists the sequences of the bivalent nanobodies. Table 38 SEQ ID Nos 101- to 106 lists the sequences of humanised bivalent nanobodies linked with the GS9 and GS30 linker, respectively.

Expressions were performed as described in Example 2. The nanobodies containing a $(His)_6$-tag were purified on a Nickel column (TALON, Clonetech) as described by the manufacturer. The tag-sequence is EQKLISEEDLNGAA$_{HHHHHH}$. Nanobodies without tags were purified on protein A. Expression yields were calculated and are summarized in Table 39.

Stability of the humanised bivalent nanobodies was measured as described in Example 7. OD280 of the supernatants was measured and expressed as percentage of the OD280 at room temperature. The results are summarized in Table 40.

The nanobodies (humanised but also wild type) were tested in the flow chamber at a concentration of 0.15 µg/ml, 0.3 µg/ml and 0.6 µg/ml. The same donor was used for all the experiments. The experiment was performed as described in Example 4. FIG. 23 shows the platelet adhesion at different concentrations of bivalent nanobodies. Table 41 lists platelet adhesion of wild type and humanised bivalent nanobodies.

D. Effect of (Bivalent) Nanobody on Arterial Thrombosis in a Baboon Folts Model

Example 18

Baboon FOLTS Model with ALX-0081

In this study the efficacy and safety of ALX-0081 was evaluated in a Folts thrombosis model in baboons.

Also, the efficacy and safety of ALX-0081 in a Folts thrombosis model in baboons was compared to other drugs currently used in the clinic, such as Reopro, Plavix, Aspegic, Heparin and Epinephrin. All these were diluted in 0.9% sodium chloride and administered as intravenous bolus injections. This study was as well designed to determine the effective dose for each of these compounds.

Finally, the efficacy in a Folts thrombosis model in baboons of a combination of drugs that is currently used in the clinic in a percutaneous coronary intervention (PCI) setting was tested: Aspegic, Heparin, and Plavix. We furthermore evaluated if ALX-0081 can improve the efficacy of this combination when added on top.

We looked at safety parameters such as induction of bleeding, vWF and factor VIII levels, and platelet count, PT, and aPTT.

Study Protocol

The study protocol that was applied is the original Folts model and some modifications described below (Folts J D, et al, Circulation. 1976; 54:365-370).

Healthy male or female baboons (*Papio ursinus*) were used. The animals were 8-17 kg of weight and were disease-free for at least 2 weeks prior to use. The baboons were fed with dry standard food only. The baboons were used at different time points. The weight of the baboons are summarized in table 42 (efficacy study ALX-0081 and comparison with individual drugs) and table 50 (efficacy of a combination of drugs and ALX-0081 on top of this combination).

Animals were anaesthetized and body temperature is maintained at 37° C. with a heating table. A segment of a femoral artery was dissected free from surrounding tissue. A shunt was placed between the femoral vein and femoral artery to obtain high shear rates. The mean and phasic blood flow was recorded continuously throughout the experiment. Baseline flow was recorded for 20 minutes. The proximal dissection site of the femoral artery was then injured by applying two overlapping occlusions of the artery for 1 second using a forceps. A clamp was placed over the injured site to create an external stenosis.

Figure 24:
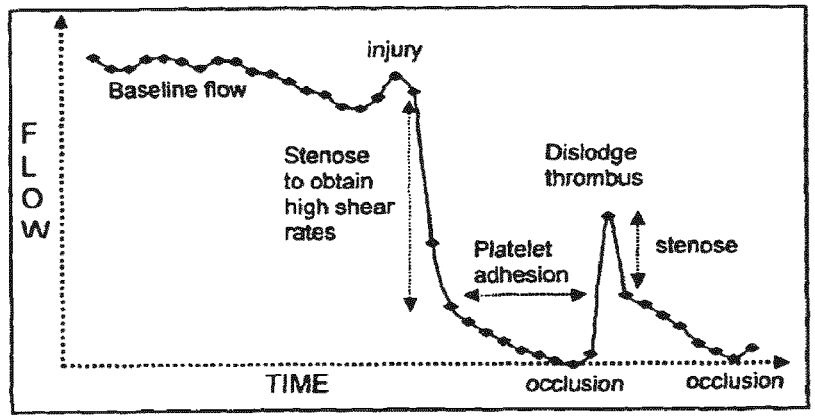

A gradual decline in blood flow due to platelet adhesion and aggregation was observed. When flow was reduced to zero, blood flow was restored by opening the clamp to dislodge the platelet-rich thrombus. This repetitive pattern of decreasing blood flow following mechanical restoration is referred to as cyclic flow reductions (CFRs). Additional endothelial injury was repeated if needed to finally obtain stable CFRs in these baboons. The number of times the thrombus needed to be dislodged determines the number of CFRs. FIG. 24 illustrates blood flow pattern during the Folts model in baboons.

After a 30-minute control period of reproducible CFRs, the vehicle was administered as an internal control and CFRs were followed up for 30 more minutes. After this period, test agents (saline (n=2), Reopro (n=3), Aspegic (n=3), Plavix (n=4), Heparin (n=3) or ALX-0081 Nanobody™ (n=9)) were provided via an intravenous bolus injection (followed by a continuous infusion for ALX-0081) and monitoring was continued up to 30 minutes after drug administration. This procedure was repeated for several times with escalating doses of the test substance. The anti-thrombotic effect was quantified by comparing the length of CFRs before and after drug administration. When full inhibition of CFRs was observed, a new injury was applied in order to confirm that the inhibition was an effect of the treatment but not of a natural healing phenomenon. At the end of the experiments, Epinephrin (2.2 µg/kg/min) was injected in order to distinguish between a weak and a strong inhibition of the CFRs. Indeed, it has been demonstrated before that CFRs reappear in the presence of Epinephrin when aspirin (a weak anti-platelet drug) is used in the same model.

Figure 25:
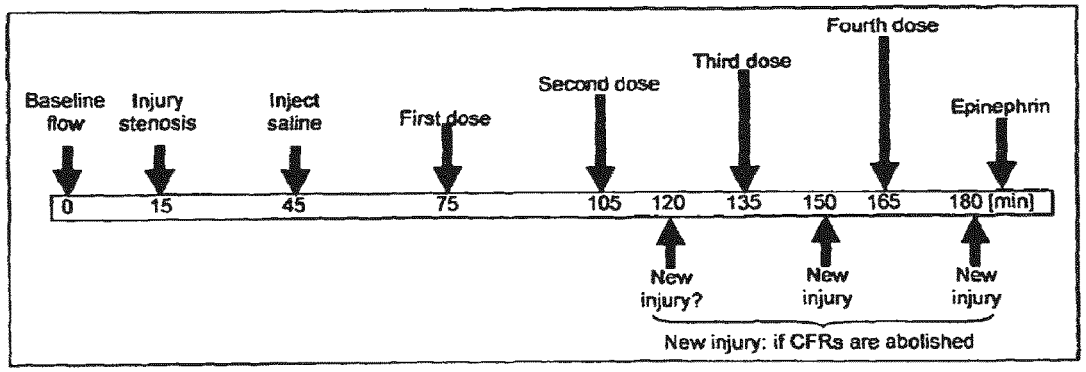

The setup of the experiment is illustrated FIG. 25.

The length of the CFRs, after each dose of test compound are summarized in tables 43-48. Doses at which full inhibition of CFRs is obtained are shaded.

A representative read out of the blood flow during the Folts model experiments is shown in FIGS. 26-31.

Figure 26:
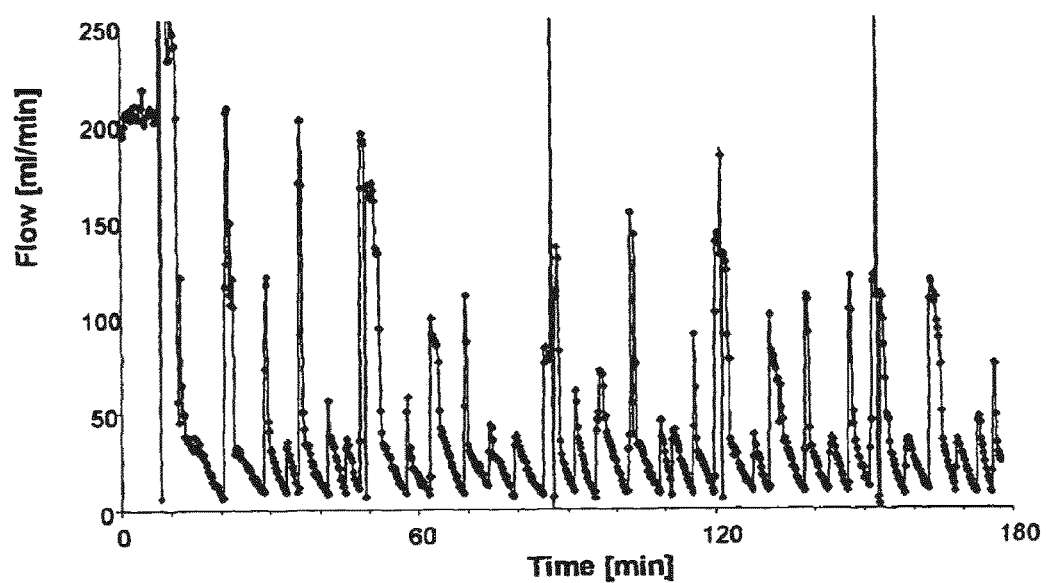

The results demonstrate that CFRs can be obtained in the control animals for at least 3 hours, without the need for a new injury in between. The mean length of the CFRs is 2-5 minutes and there is no effect on the length of the CFRs by injection of saline (FIG. 26, table 43).

Aspegic

Three animals were injected with Aspegic (injectable Aspirin) and looked for inhibition of CFRs. In the clinic, a bolus injection of 250 mg (±3-5 mg/kg) is administered to the patient, just before the start of a percutaneous coronary intervention (PCI) procedure. In two animals (baboon 3 and 5) no inhibition of CFRs could be obtained at doses as high as 80 and 40 mg/kg Aspegic respectively (FIG. 27, table 44). In baboon 4, it was very difficult to establish a stable repetitive pattern of CFRs in the control phase. After several new injuries were made (this is at the time we injected saline), stable CFRs were obtained. Full inhibition of CFRs was obtained at the dose of 5 mg/kg Aspegic, but at higher doses and upon new injury, the CFRs returned, although the mean length of the CFRs was 3-4 times longer than before administration of Aspegic. After infusion of Epinephrin, the CFRs returned immediately and completely (table 44).

Heparin

Three animals were injected with unfractionated Heparin and looked for inhibition of CFRs. In the clinic, a bolus injection of 60-70 IU/kg is administered to the patient, and the aPTT (activated partial thromboplastin time) is monitored every 30 minutes. Extra Heparin is administered if the aPTT is <250 seconds. In baboons 7 and 8, no inhibition of the CFRs could be obtained even not at doses as high as 240 IU/kg (FIG. 28, table 45). In baboon 6, full inhibition of the CFRs was obtained at the first dose of 15 IU/kg and at higher doses, but when we made a new injury the CFRs returned each time. At the highest dose of 240 IU/kg, CFRs were inhibited even after a new injury, but the flow was decreasing and upon infusion of Epinephrine, the CFRs returned immediately.

Plavix

Four baboons were treated with Plavix and used for the Folts study. We used Plavix as injectable drug by re-suspending tablets in methanol. Therefore, we were able to perform a dose escalation experiment as for the other drugs. In patients, 300-600 mg Plavix is administered orally, inhibition of platelet aggregation can be seen 2 hours after single oral doses of Plavix. Already at the 2.5 mg/kg final dose in the baboons, an effect on the length of the CFRs could be demonstrated, but this inhibitory effect started only 10 minutes after injection (FIG. 29, table 46). In baboon 12, full inhibition of the CFRs was obtained at this dose of 2.5 mg/kg. In the other three baboons full inhibition of CFRs was obtained at the 5 mg/kg final dose. CFRs remained inhibited when a new injury was made, but returned after infusion of Epinephrin. When Epinephrin infusion was stopped, the CFRs remained for another 5 minutes, but then again full inhibition was obtained (FIG. 29).

Reopro

Reopro was tested for efficacy in the Folts model in three baboons. In the clinic, patients receive a dose of 250 µg/kg followed by a continuous infusion of 7.5 µg/kg/hour. This is also the dose which we needed in baboons 13, 14 and 15 to obtain full inhibition of the CFRs (final dose of 170-420 µg/kg (FIG. 30, table 47). We administered to the baboons a bolus injection only. When a new injury was applied, complete inhibition of the CFRs was retained and infusion of Epinephrin could not reverse this inhibition (FIG. 30).

ALX-0081

Nine baboons received ALX-0081 and were used in the Folts model. In all baboons full inhibition of CFRs was obtained at the dose of 30 µg/kg+45 µg/kg/hour (final dose of 43 µg/kg). In 2 baboons, full inhibition was already obtained at the 10 µg/kg+15 µg/kg/hour (baboons 17 and 22). Inhibition was retained upon a new injury and after infusion of Epinephrin in all nine baboons (FIG. 31, table 48).

Aspegic-Heparin-Plavix-ALX-0081 (Asp/Hep/Plav/ALX) Combinations

Seven baboons received a bolus injection of 5 mg/kg Aspirin, 60 IU/kg Heparin and increasing doses of Plavix. Extra Heparin was administered at different time points to sustain a certain level (aPTT should be at least doubled versus control). CFRs were monitored for 30 minutes after each dose of test compounds. We started at a dose of 1 mg/kg Plavix and added 1 mg/kg after 30 minutes. The anti-thrombotic effect was quantified by comparing the length of CFRs before and after drug administration. When full inhibition of CFRs was observed, a new injury was applied. Epinephrin was injected and continued till the end of the experiment. If CFRs did not return, a new injury was applied. After 2-3 CFRs increasing doses of ALX-0081 were added: (1), 3, 10 or 30 µg/kg. We waited after each dose of ALX-0081 for 2 CFRs and increased the dose until full inhibition of CFRs was obtained. At full inhibition of the CFRs, continuous infusion was started of 1.5 times dose ALX-0081/kg/hour for 30 minutes and epinephrine infusion was continued. A new injury was applied after 10-15 minutes. The specifications of the baboons that were used in this study are represented in table 49.

The results from these studies for each test compound individually are summarized in table 50. A clear superior anti-thrombotic effect in the Folts thrombosis baboon model is observed for ALX-0081 and Reopro when compared to Aspirin, Heparin or Plavix: upon new injury and after infusion of Epinephrin, the CFRs do not return in the Folts model in the ALX-0081 and Reopro treated baboons in contrast to the model in Aspegic, Heparin or Plavix treated animals. The dose of ALX-0081 required for full inhibition of CFRs is approximately 10-fold lower than the dose needed for Reopro. Therefore, it is concluded that ALX-0081 is more potent than Reopro.

After administration of a combination of 5 mg/kg Aspirin, 60 IU/kg Heparin and increasing doses of Plavix, in all seven baboon full inhibition of CFRs was obtained at this final dose. The dose of Plavix required for full inhibition is 2.5-fold lower than the dose needed when Plavix alone is administered. For all baboons tested, CFRs did not return when a new injury was made (FIG. 32). However, upon injection of Epinephrin, CFRs returned spontaneously in baboons 5, 8, 9 and 10 and upon a new injury in baboons 4, 6 and 7. Extra Heparin was injected at the same time as epinephrin. After 2 CFRs, increasing doses of ALX-0081 were administered while continuing the infusion of Epinephrin. The dose of ALX-0081 was increased from 1 over 3-10 to 30 µg/kg. When full inhibition of CFRs was obtained, a continuous infusion of ALX-0081 was started at 1.5 times the effective dose/kg/hour. In all seven baboons, full inhibition of the CFRs was obtained at the 30 µg/kg dose. This effective dose of ALX-0081 is the same as required for complete inhibition of CFRs in the Folts model when ALX-0081 is administered alone.

Therefore, we can conclude that the efficacy of ALX-0081 is not increased by simultaneous infusion of Plavix, Heparin and Aspegic. This observation is completely in line with our hypothesis: ALX-0081 inhibits the very first interaction between platelets and the exposed collagen in the damaged arterial wall. Plavix and Aspegic on the other hand inhibit further downstream in the cascade leading to the development of a thrombus. Therefore, Plavix and Aspirin do not contribute to better efficacy as ALX-0081 interferes already with the first step in thrombus formation. Moreover, when a new injury was applied at the effective dose of ALX-0081, the CFRs did not return, demonstrating a potent antithrombotic effect of this Nanobody™. The results are summarized in table 51.

Measurements

The following parameters were measured: a) bleeding analysis, b) vWF concentration, Factor VIII levels, and platelet count, PT and aPTT c) ristocetin-induced platelet aggregation d) ALX-0081 concentration, and e) analysis of arterial sections for restenosis, f) immunogenicity of ALX-0081 a) Bleeding Analysis

To analyze bleeding, an incision was made with a scalpel in the groin. This was done at 15 minutes after recording baseline flow, when the injury was made in the artery. Gauzes were inserted in the wound and replaced every 30 minutes just before each new dose of test compound. The amount of blood loss after each dose of test compound was determined by weighing the gauzes. Blood loss is expressed relative to the amount of blood loss in the second control gauze (during the saline injection) (tables 52-54).

For all baboons treated with Plavix and Reopro, blood loss is high (up to 9-40 fold respectively at the highest dose), starting from the effective dose on. For animals treated with ALX-0081 bleeding is lower than in the Plavix treated animals, and much lower when compared to Reopro treated animals.

In order to determine the safety versus efficacy level of Plavix, Reopro and ALX-0081 as antithrombotic drugs, the averages of blood loss relative to the second control gauze are shown for these drugs in function of the drug dose as multiple of the effective dose (FIG. 33). The effective dose for Plavix is 5 mg/kg, for Reopro 250 µg/kg and for ALX-0081 30 µg/kg (table 46-48). These results nicely demonstrate the superior safety of ALX-0081 when compared to Reopro and Plavix: the window in which ALX-0081 could be administered without a major increase in bleeding is much wider compared to Plavix and Reopro.

Figure 36:
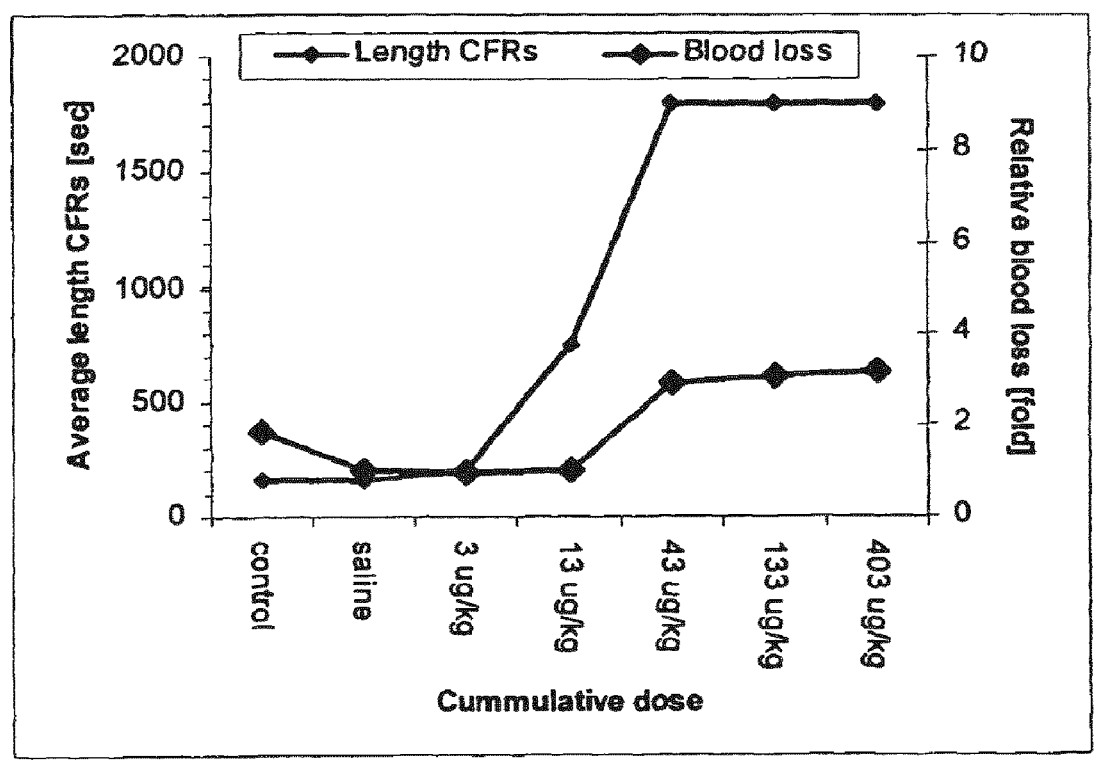
Figure 37A:
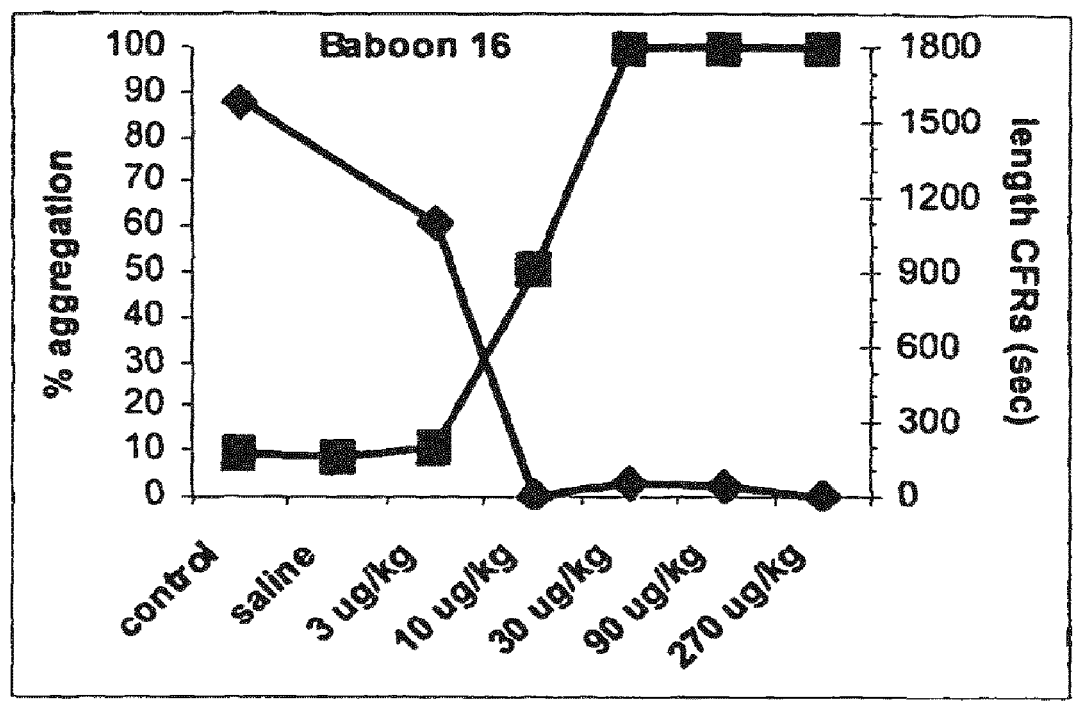
Figure 37B:
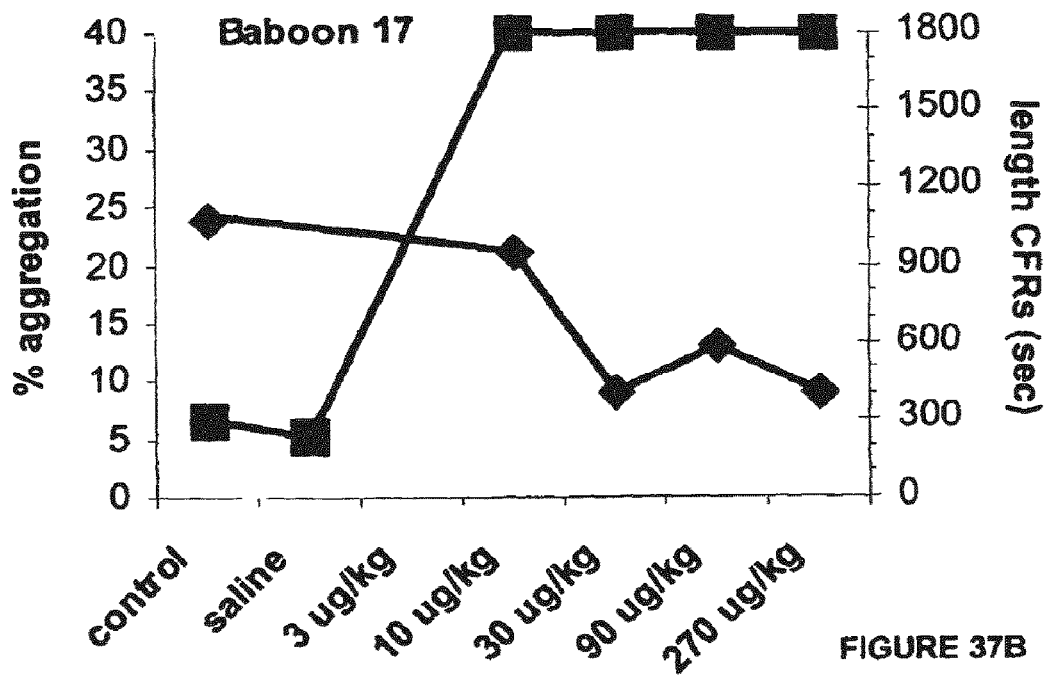
Figure 37C:
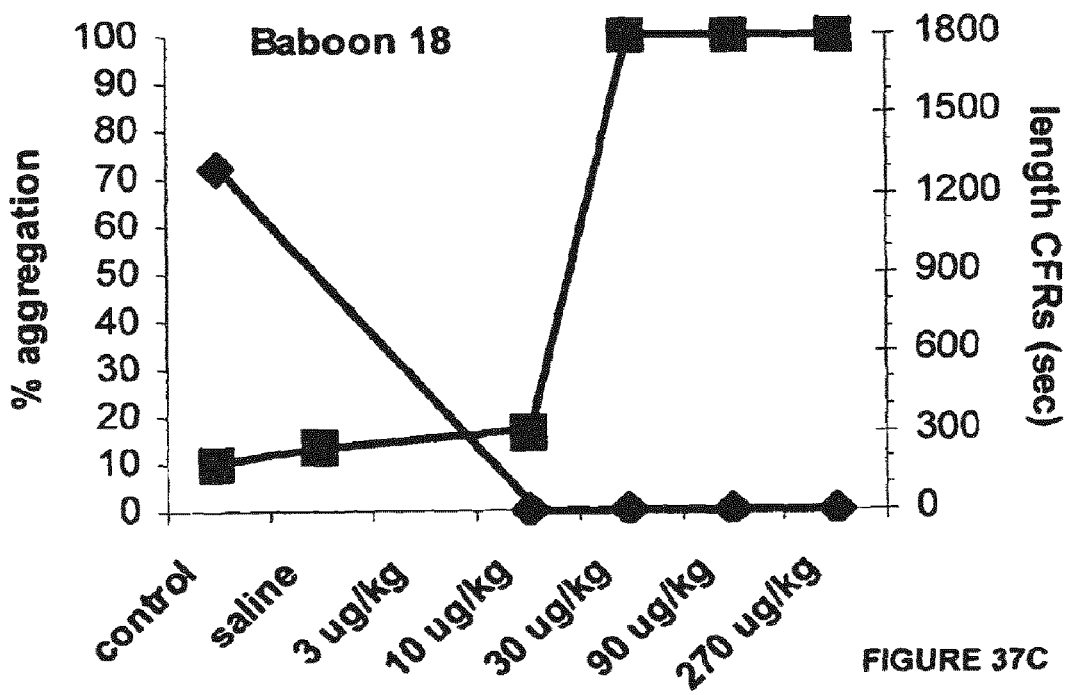
Figure 37D:
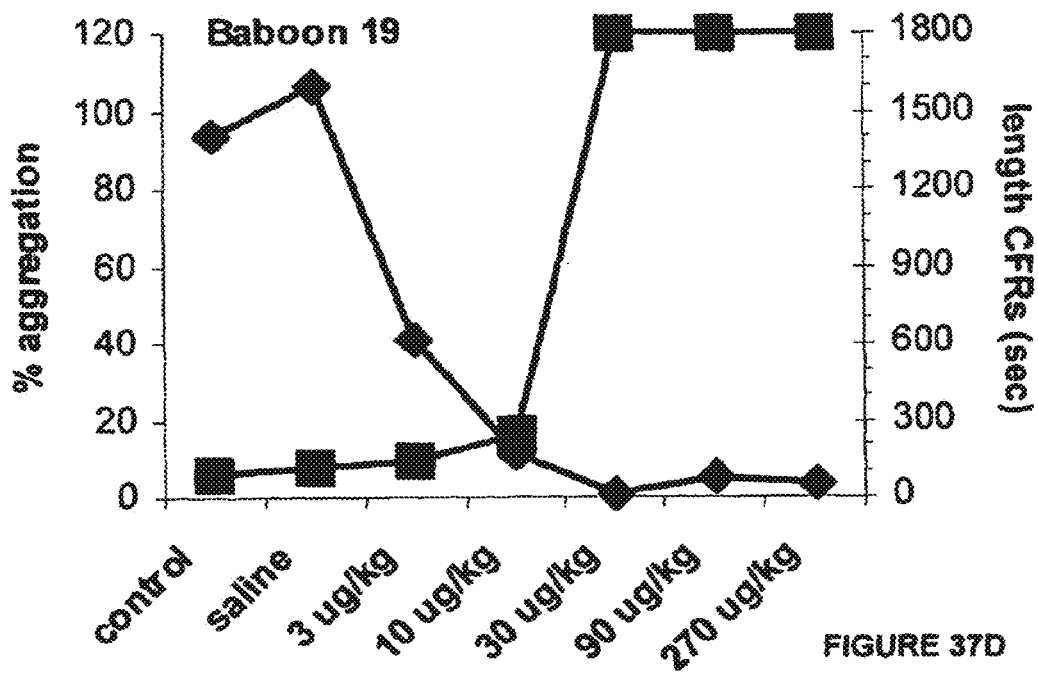
Figure 37E:
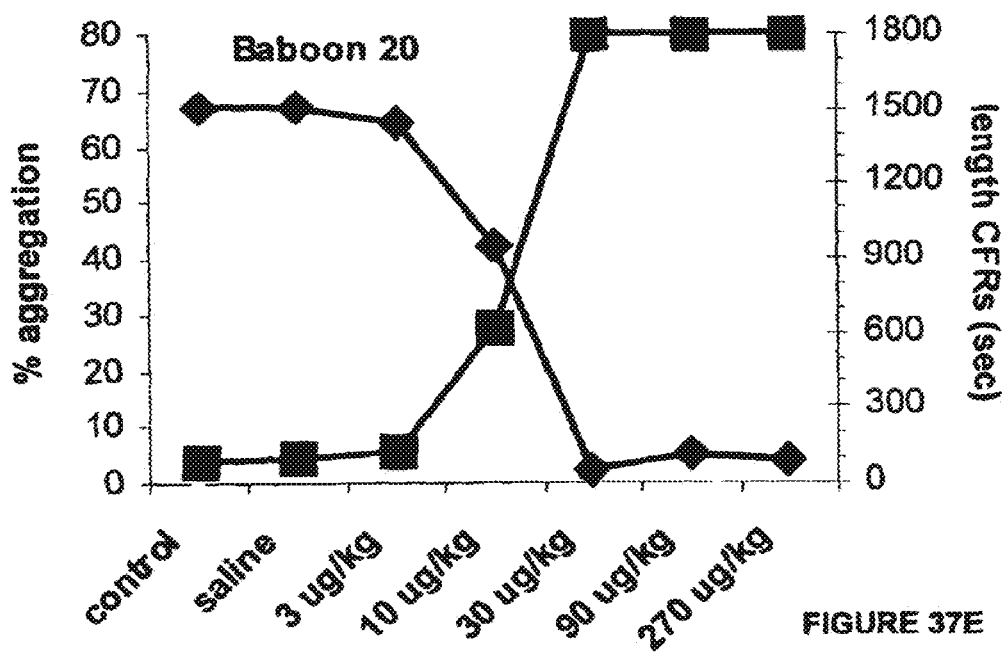
Figure 37F:
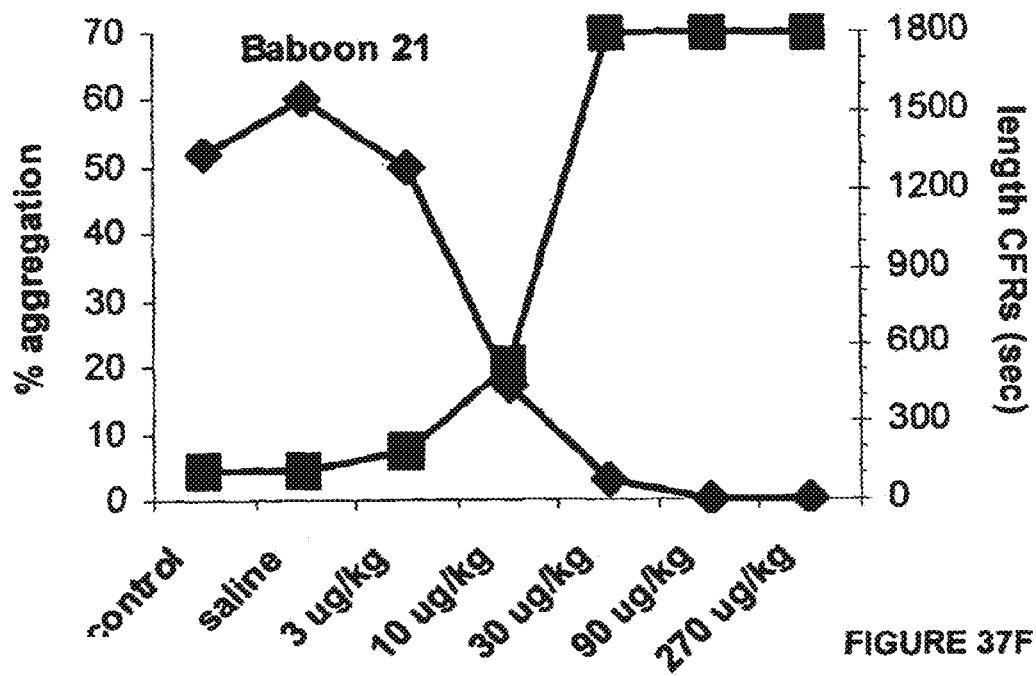
Figure 37G:
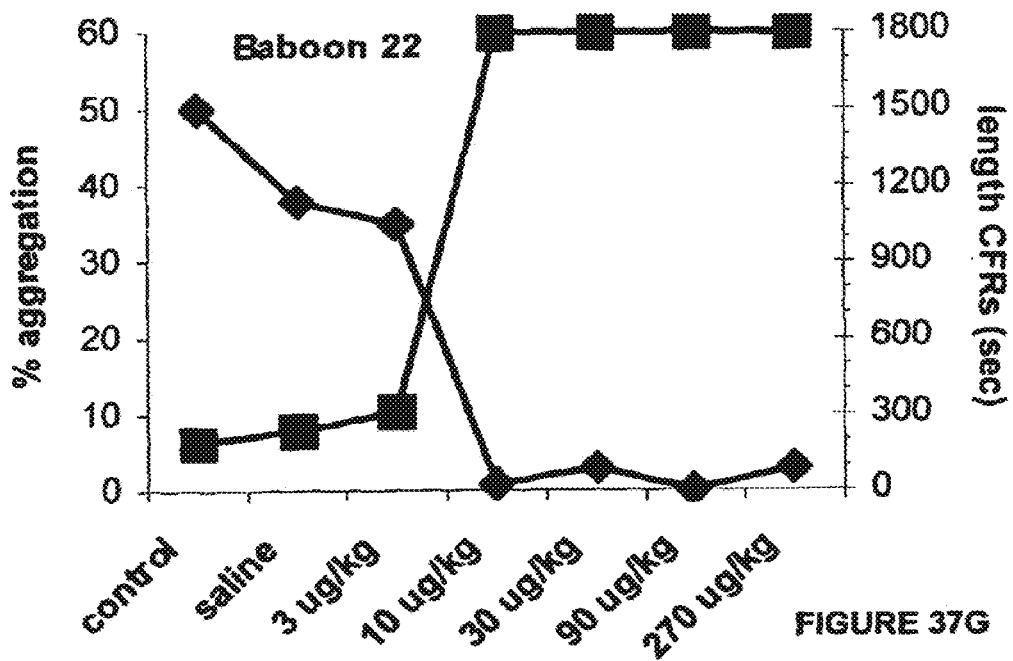
Figure 37H:
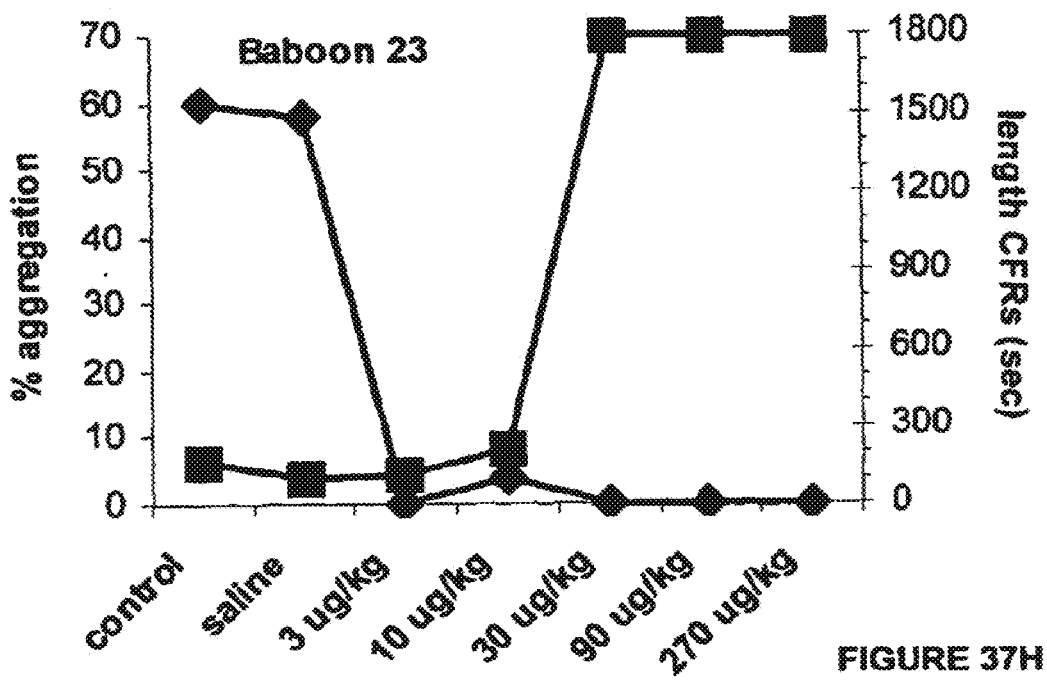
Figure 37I:
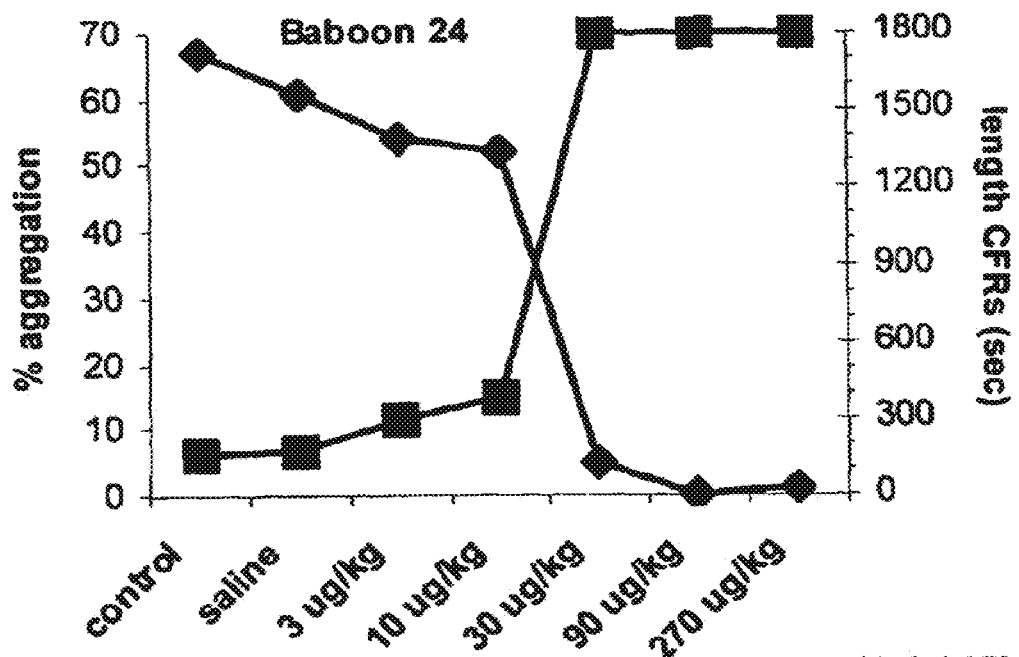

The results from the averages of blood loss in the gauzes (if available) were combined with the averages of the lengths of the CFRs in the FIGS. 34-36.

A broad therapeutic window was observed for ALX-0081 in the Folts model: a strong antithrombotic effect could be demonstrated without any major bleedings for cumulative doses ranging from 43 µg/kg up to 403 µg/kg (FIG. 36). In contrast however, the therapeutic window for Reopro and Plavix in the same model was much more narrow compared to ALX-0081, combining an effective antithrombotic effect with a high blood loss (FIG. 34-35).

The average of the total amount of blood loss (=sum of blood loss from the gauzes of the first five doses of test compound) as relative to the second control gauze are summarized in table 55. In this table we also indicate the final dose as multiple of the effective dose (=sum of the five doses divided by the effective dose). As mentioned before, the effective dose for Plavix is 5 mg/kg, for Reopro 250 µg/kg and for ALX-0081 30 µg/kg.

The results shown in table 55 clearly show that total blood loss is significantly increased in the animals treated with Plavix and to an even higher extent in the animals treated with Reopro. Blood loss in animals receiving ALX-0081 is 2-fold and 4 fold less than in Plavix or Reopro treated animals, respectively. This again clearly demonstrates that ALX-0081 is safer than Plavix and Reopro in terms of bleeding risk, although doses of more than 10-fold the effective dose were used.

The effective combination of Aspegic, Heparin and Plavix results in an increase in blood loss of up to 14 fold when compared to the control gauze (table 56). Addition of ALX-0081 on top of the combination of Aspegic, Heparin and Plavix does not result in increased bleeding except for baboons 4 and 7. In baboon 7, bleeding was much increased after administration of epinephrine, extra heparin and non effective doses of ALX-0081, but was lower again after administration of the effective dose of ALX-0081. These results demonstrated that ALX-0081 is safe when added on top of the combination of drugs that is currently used in a clinical setting.

b) vWF Concentration, Factor VIII Level, Platelet Count, PT and aPTT vWF

The vWF levels in the platelet rich plasma (PRP) of blood samples taken after administration of the different doses of the drugs in the Folts model were determined using an immunosorbent assay and expressed as a percentage of the human standard (WHO $5^{th}$ International Standard for factor VIII and VWF)

The results clearly demonstrate that the different drugs used in the model have no major effect on the vWF level.

Factor VIII

The factor VIII levels in the PRP of blood samples taken after administration of the different doses of the drugs in the Folts model were determined using the aPTT test. We did not test the plasma samples of the baboons treated with Heparin, as we demonstrated that Heparin prolongs the aPTT time. The FVIII levels were expressed as percentage of the first control sample, taken 10 minutes after injury of the femoral artery. We do not see any effect of the treatments on the aPTT test.

Platelet Count, PT and aPTT

The platelet count measurements during the Folts model experiments were performed. The data showed that baboon 15 has a very low platelet count when compared to the other animals. The platelet counts for all kind of treatments, except for the Plavix treatment, are very comparable to what we see in the control animals and are fairly constant over time.

The PT values demonstrate no effect of the test compounds on the PT time, except for baboons treated with the 240 IU/kg dose of Heparin where a minor increase in PT was observed.

The aPTT values observed during the Folts model studies are summarized. These results indicate that the test compounds have no effect on the aPTT values, except for the baboons treated with Heparin. In these animals, aPTT values are prolonged from the 30-60 IU/kg dose on, as is also observed in patients. Heparin acts as an anticoagulant by forming a complex with antithrombin and catalyzing the inhibition of activated blood coagulation factors such as XIa, IXa, Xa and thrombin (factor IIa). These factors are all involved in the intrinsic coagulation cascade of which its functionality is measured in the aPTT test.

c) Measurement of Ristocetin-Induced Platelet Aggregation in Blood Obtained from Baboons Treated with ALX-0081

Blood obtained from baboons treated with ALX-0081 was analyzed for inhibition of platelet aggregation. Platelet aggregations were performed on a Chronolog whole blood and optical Aggregometer (Model 560CA, Chronolog, USA). PRP was prepared (collected on 0.38 mol/L citrate), by centrifuging the whole blood at 1200 rpm for 5 minutes. The upper fraction containing the PRP was carefully removed. The lower fraction was further centrifuged at 3000 rpm for 10 minutes to prepare platelet poor plasma (PPP). Platelets were counted in PRP and diluted in PPP to a final concentration of 200.000 platelets per microliter. 3 mg/ml ristocetin (DAKO) was added and aggregation was measured.

The ex vivo platelet aggregation is measured in the blood samples taken during the Folts experiment in the baboons treated with ALX-0081. The GPIb-IX-V dependent platelet aggregation through vWF is measured using ristocetin as a modulator. The % aggregation is measured at each time point and at each dose. The control sample is taken at 10 minutes after arterial injury.

Results from the RIPA test are compared to the inhibition of the CFRs for each baboon treated with ALX-0081 (FIG. 37). As shown in FIG. 37, an inverse relation between the RIPA and the length of the CFRs is observed. Moreover, these results demonstrate that full inhibition in the RIPA test is obtained at lower doses than full inhibition of CFRs in baboons 16, 18, 19 and 23. For baboons 20, 21, 22 and 24 the results with RIPA compare very well with the results for efficacy in the Folts model.

d) Concentration of ALX-0081

Microtiterplates are coated with mouse polyclonal anti-myc overnight at 4° C. at a 1000-fold dilution. The plates are washed with PBS-Tween and blocked for 2 hours at RT with PBS-1% casein. Samples are diluted in a non-coated microtiterplate in 25% reference baboon plasma. The standard curve is prepared by diluting the nanobody in the same reference baboon plasma sample. Samples are applied on the anti-myc coated plates and allowed to bind for 2 hours at RT. The plates are washed 5 times with PBS-Tween. Rabbit anti-vWF-HRP (DAKO) is applied at a 3000-fold dilution for one hour at RT. For measuring OD405 nm, samples are washed 5 times with PBS-Tween and ABTS/$H_2O_2$ substrate is added.

We determined the concentration of ALX-0081 in plasma samples taken at 10 minutes after each bolus injection. The bolus injection was immediately followed by a continuous infusion. The concentrations (µg/ml) are summarized in table 58.

For all baboons an increasing level of ALX-0081 in the plasma samples was measured by ELISA after dose-escalation of ALX-0081. For baboon 16, consistently higher amounts of ALX-0081 were determined in the plasma sample taken after the 10 µg/kg dose compared to the sample taken after 30 µg/kg. The ALX-0081 level in that sample is also substantially higher than what is noted for all other baboons given the same dosing schedule of ALX-0081. As the levels of ALX-0081 for baboon 16 after the higher doses are in line of the expectations, we assume that an unknown abnormality during blood sampling accounts for this outlier.

The concentration of ALX-0081 for each dose in the different baboons is variable. For the 3 µg/kg dose, the concentration ranges between 0.03 and 0.14 µg/ml for 10 µg/kg between 0.18 and 1.23 µg/ml, for 30 µg/kg between 0.51 and 1.14 µg/ml, for 90 µg/kg between 1.38 and 6.77 µg/ml and for 270 µg/kg between 4.03 and 35.14 µg/ml.

Figure 38:
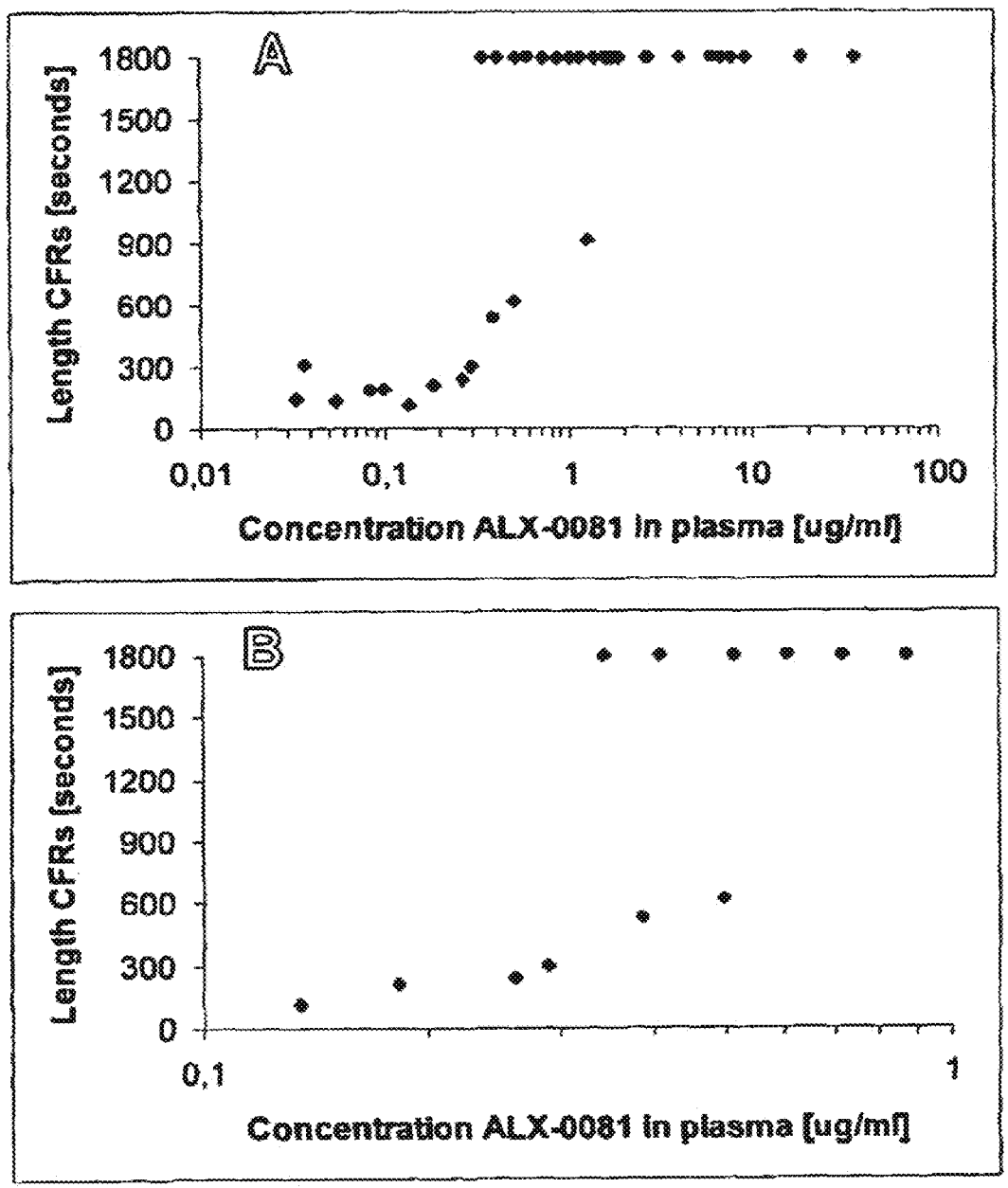

In FIG. 38, we plot the concentration of ALX-0081 in plasma versus the length of the CFRs.

The concentration of ALX-0081 required for full inhibition of CFRs is between 0.3 and 0.5 µg/ml, which is in full agreement with the concentration required to inhibit platelet adhesion to collagen in the flow chamber at high shear rate, when ALX-0081 is spiked in human blood. In blue (FIG. 38, panel B) we indicated the concentration range of ALX-0081 where inhibition starts (leaving out the 10 µg/kg dose in baboon 16).

When we plot the concentration of ALX-0081 versus the relative amount of blood loss from the gauzes, we observe a more than 2-fold increase in bleeding at doses above 1 µg/ml (FIG. 39). A 10-fold increase in blood loss was observed when the ALX-0081 concentration is 19 µg/ml, which is 40-60-fold the effective concentration.

e) Analysis of Arterial Sections for Restenosis

Four weeks after treatment of the second artery, the arteries are dissected free from surrounding tissue. The artery is tied at the upper and low site of the endothelial injury including the site where the shunt was placed. A section is removed of 2 centimeter, cut in a lower (shunt site) and upper part (stenosed and injured site) and stored in 10% formaldehyde. The baboons are then sacrificed by euthanasia injection. The arteries are marked according to origin and cut into rings of 2 mm each. The rings are placed into marked cassettes suitable for histology processing. The cassettes are then placed overnight in an automated VIP Tissue Tek processor following the overnight processing schedule as described in Bancroft (Bancroft, John D., Stevens Alan (1990). Theory and Practice of Histological Techniques. Third Edition).

After processing, the arteries are embedded in marked paraffin wax blocks and cooled on a freeze plate. The wax blocks are cut in series sections of 4 micron each on a rotary microtome. Sections are picked up on glass slides and stained for histological evaluation. Haematoxylin and Eosin as well as Verhoeff's method for elastic fibers stains are performed on each of the arteries (Bancroft, John D., Stevens Alan (1990). Theory and Practice of Histological Techniques. Third Edition). After staining, the slides are dehydrated, cleared, mounted and labelled. Blind analysis of the sections is performed.

f) Immunogenicity Analysis

The presence of ALX-0081 immunoglobulins in plasma of three baboons was evaluated by two methods, respectively an ELISA method and a SPR-based method on Biacore. The baboons were treated for 8 weeks with increasing doses of ALX-0081 (starting from 10 µg/kg). During said 8 weeks, no immunogenic response could be observed upon injection of ALX-0081. The half-life of ALX-0081 ranged between 7 and 9 hours.

Example 20

Use of vWF as an Antidote for ALX-0081

Despite the proven safety of ALX-0081 in baboons, and the rapid clearance of the Nanobody™, we decided to evaluate the use of vWF as an antidote for ALX-0081. This was tested in a Folts model in baboons where we evaluated if the inhibitory effect of ALX-0081 on arterial thrombus formation can be reversed by injection of vWF.

The experimental procedure followed the original Folts model with the modifications as described in the previous example 18.

Healthy male baboons (*Papio ursinus*) were used in this study. The animals were 9-12 kg of weight and were disease-free for at least 2 weeks prior to use. The baboons were fed with dry standard food only.

Three baboons were used in this study, the length of the CFRs during the control phase, after administration saline, ALX-0081 and vWF is summarized in table 59.

Figure 40:
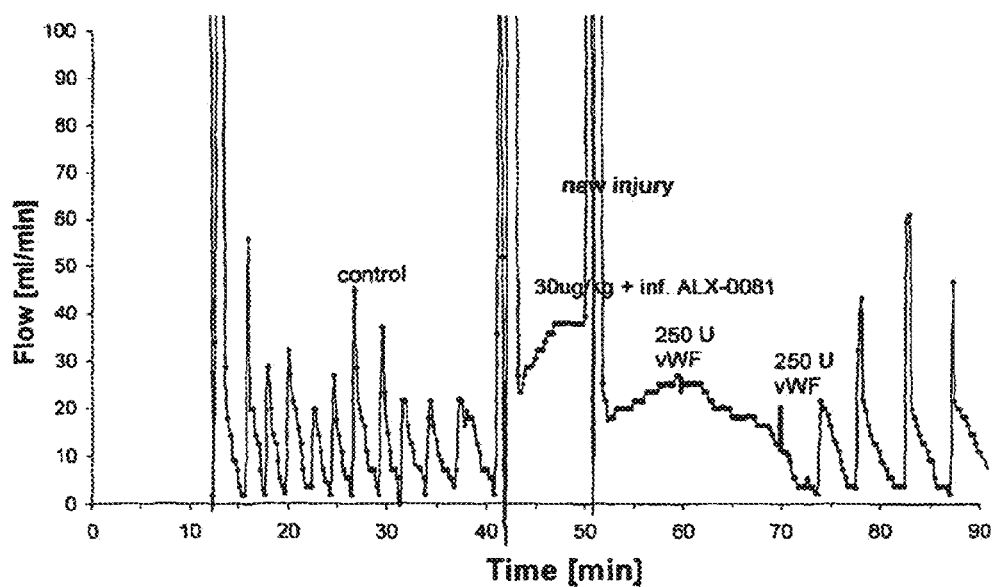

The blood flow as a function of time for each baboon and experiment is shown in FIG. 40.

In all three baboons, full inhibition of CFRs was obtained at the 30 µg/kg+45 µg/kg/hour dose of ALX-0081, even when a new injury was applied, the CFRs did not return. Upon injection of the first dose of vWF (250 IU), the flow gradually decreased, but CFRs did not return until an extra dose of 250 IU of vWF was administered. This result demonstrated nicely that the activity of ALX-0081 can be reversed by administration of vWF, and that therefore, vWF would be a good antidote for this Nanobody™.

Thus, another aspect of the invention relates to the use of vWF, of a suitable fragment thereof, of DDAVP (desmopressinor) or a suitable fragment thereof, or of a pharmaceutical composition comprising any of the foregoing, as an antidote for complications or undesired side effects associated with the use of a Nanobody, protein or polypeptide against vWF, in particular a Nanobody, protein or polypeptide as described herein.

Example 21

Effects of ALX-0081 on Platelet Adhesion to Endothelial Cell-Derived UlvWF and on the Activity of ADAMTS-13

This study serves as a proof of concept for the use of ALX-0081 as a drug in TTP patients. Perfusions of platelets reconstituted in TTP plasma (no ADAMTS13) are performed on endothelial cells secreting ULvWF, in the absence and presence of ALX-0081. In a separate experiment we test if ALX-0081, which binds to the A1 domain of vWF, interferes with the ADAMTS-13 activity. ADAMTS-13 binds to and cleaves the A2 domain of vWF.

Endothelial cells were obtained from human umbilical cord veins by the method of Maruyama (Z. Zellforsch. Mikrosk. A4nat. 60:69; 1963). Endothelial cells were activated with 100 µM histamine (Sigma-Aldrich, St Louis, Mo.) for 15 minutes at room temperature before the perfusion experiments.

Blood was drawn from healthy volunteers who denied ingestion of aspirin or other nonsteroidal anti-inflammatory drugs (NSAIDs) for the preceding 10 days into one-tenth volume 3.4% sodium citrate. Platelet-rich plasma (PRP) was prepared from whole blood by centrifugation (10 minutes at 200 g at room temperature). The PRP was acidified by addition of one-tenth volume of ACD (2.5% trisodium citrate, 1.5% citric acid, and 2% D-glucose), and the platelets were spun down (500 g, 15 minutes). The platelet pellet was resuspended in HEPES (N-2-hydroxyethylpiperazine-N'-2-ethanesulfonic acid)-Tyrode buffer (10 mM HEPES, 137 mM NaCl, 2.68 mM KCl, 0.42 mM $NaH_2PO_4$, 1.7 mM $MgCl_2$, 5 mM D-glucose, pH 6.5). Prostacyclin ($PGI_2$, 10 ng/mL) was added to prevent platelet activation during the subsequent washing step. Platelets were spun down and resuspended in a small volume of HEPES-Tyrode buffer. This platelet suspension was diluted in HEPES buffer at pH 7.4, or in TTP plasma.

Perfusions were performed in a single-pass perfusion chamber as described previously. The experiment was followed by real-time videomicroscopy.

In a second type of experiment, different reaction mixtures were prepared as summarized in table 60, however, without the addition of the A1A2A3 construct. The A1A2A3 construct is a recombinant fragment consisting out of the A1, A2 and A3 domain of vWF. Mixtures were pre-incubated for 5 minutes at 37° C. after which the A1A2A3 fragment is added and the mixture is incubated in a waterbath overnight at 37° C. The next day a reducing SDS-PAGE is run on the samples (12%, and using as marker the Precision Plus Protein Standards from BioRad) and blotted on Immobilon-FL (Millipore). The blot was blocked for 2 hours at room temperature with blockbuffer (1:1 Odyssey blockbuffer in 1xTBS pH=7.4) and incubated with Rabbit polyclonal anti-vWF (DAKO). Alexa Fluor 680 goat anti-rabbit was used for detection. Scanning was done on the ODYSSEY to detect the degradation products.

Control Experiment: Binding of Platelets to ULvWF

Figure 41:
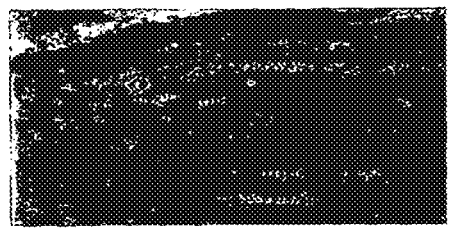

Endothelial cells were isolated from freshly obtained human umbilical cords by collagenase digestion of the interior of the umbilical vein. The cells were grown in tissue culture as a homogeneous population. Cultured human endothelial cells grow as monolayers of closely opposed, polygonal large cells and they contain cytoplasmic inclusions (Weibel-Palade bodies). Histamine-stimulated endothelial cells isolated from human umbilical cords express ultra-large von Willebrand factor (ULvWF) on their surface. Perfusion of these stimulated cells with isolated blood platelets, which are suspended into either buffer or plasma from a patient with acquired TTP, results in deposition of platelets onto the ULvWF (8). These ULvWF-adhered platelets appear as so-called 'strings', which are visible when the perfusion experiment is monitored by real-time video microscopy (FIG. 41).
Inhibition by ALX-0081 for the Generation of Platelet Strings Platelets were resuspended in buffer or in TTP plasma and the concentrations of ALX-0081 used in this experiment were 0.2, 2 and 10 µg/ml. Histamine-stimulated endothelial cells isolated from human umbilical cords are perfused with these platelet suspensions as described above.

Figure 42:

Addition of ALX-0081 to platelets resuspended in buffer or in plasma from a TTP patient results in a complete inhibition of string formation under all conditions tested (FIG. 42). Perfusion experiments were performed at a shear stress of 2.5 dyn/cm2 for 4 minutes. During this 4 minute perfusion at least 20 microscopic fields were examined, and in the presence of the Nanobody™, no strings could be demonstrated at all conditions tested (FIG. 42).

Cleavage of ULvWF by ADAMTS-13

ADAMTS-13 reduces the size of large and ultralarge VWF multimers to smaller forms by specifically cleaving the Y842/M843 peptide bond in the VWF A2 domain. Two types of assays were used to evaluate the effect of ALX-0081 on the cleavage of ULvWF by ADAMTS-13: i.e. a perfusion assay and an assay observing the cleavage of a recombinant vWF fragment.

In a first experiment, strings were generated by a 4 minute perfusion of washed platelets resuspended in buffer over histamine-stimulated endothelial cells. Subsequently, the non-adhered platelets were washed away by a 4 minute perfusion of buffer. After that, buffer was perfused for an other 4 minutes, followed by a 4 minute perfusion of pooled normal plasma containing ADAMTS-13. Detachment of the platelet strings was observed after perfusion of pooled normal plasma (FIG. 43). More than 95% of the strings were cleaved after the 4 minute perfusion.

Figure 44:
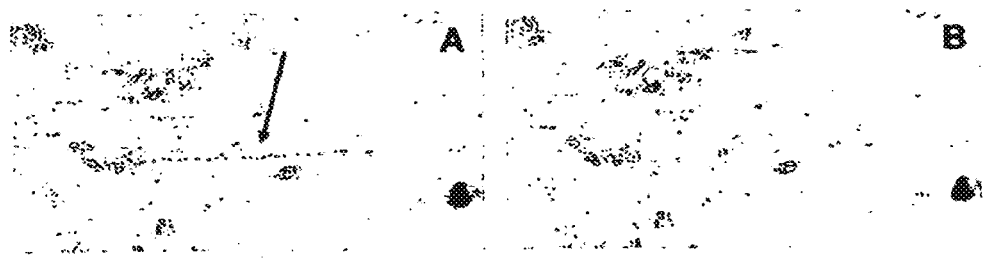

In a next experiment, strings were generated by a 4 minute perfusion of washed platelets resuspended in buffer over histamine-stimulated endothelial cells and the non-adhered platelets were washed away by a 4 minute perfusion of buffer as above. After that, ALX-0081 (10 µg/ml in buffer) was perfused for 4 minutes, followed by a 4 minute perfusion of pooled normal plasma containing ALX-0081 (10 µg/ml=10-fold molar excess over vWF) and ADAMTS-13. We could clearly demonstrate detachment of the platelet strings and 95% of the strings were cleaved after the 4 minute perfusion (FIG. 44)

These results clearly demonstrate that ALX-0081 does not have an effect on the cleavage of ULvWF strings by ADAMTS-13.

In a second assay, a recombinant fragment containing the A1-A2-A3 domain of vWF was mixed with normal pool plasma (NPP) containing ADAMTS-13, resulting in proteolytic cleavage of the fragment which was observed by a Western Blot analysis. ADAMTS-13 activity was tested in the absence and presence of 10 µg/ml ALX-0081. As indicated in FIG. 45 ALX-0081 has no effect on the cleavage of the vWF fragment (lanes 6-7-8).

In order to demonstrate that the observed cleavage is specific for ADAMTS-13, a control experiment in the presence of EDTA was performed as EDTA inhibits the activity of ADAMTS-13. As expected, the presence of EDTA in NPP resulted in inhibition of cleavage of the fragment (FIG. 45 lane 4).

This experiment again proves that ALX-0081 has no effect on the ADAMTS-13 activity.

TABLE 8

Sequence listing of anti-vWF nanobodies

| Name | SEQ ID NO | Sequence |
|---|---|---|
| 12A5 | 60 | AVQLVESGGGLVQPGGSLRLSCLASGRIFSIGAMGMYRQAPGKQRELVATITSGGSTN YADPVKGRFTISRDGPKNTVYLQMNSLKPEDTAVYYCYANLKQGSYGYRFNDYWGQGT QVTVSS |
| 12B1 | 61 | QVQLVESGGGLVQAGGSLRLSCAASGRTFSNYGMGWFRQAPGKEREFVTSISWSGTYT AYSDNVKGRFTISRDNAKNTVYLQMDSLKPEDTAVYYCAAQSRYRSNYYDHDDKYAYW GQGTQVTVSS |
| 12B6 | 62 | QVQLVESGGGLVQAGGALRLSCAASGRTFSYNPMGWFRQAPGKERDVVAAISRTGGST YYARSVEGRFTISRDNAKRMVYLQMNALKPEDTAVYYCAAAGVRAEDGRVRTLPSEYN FWGQGTQVTVSS |
| 12D11 | 63 | AVQLVDSGGGLVQAGGSLRLSCTASERTTFSSYTLGWFRQAPGKEREFVGGISWSGVS TDYAEFAKGRFTISRDHAANTVYLEMNSLKPEDTAVYYCAALGRYRSNWRNIGQYDYW GQGTQVTVSS |
| 12E3 | 64 | EVQLVESGGGLVQAGGSLRLSCAASGRTFNNYGMGWFRQAPGKEREFVTSISWSGSYT AYADNVKGRFTISRDNAKNTVYLQMDSLKPGDTAVYYCAAQSRYSSNYYDHDDKYAYW GQGTQVTVSS |
| 12C9 | 65 | AVQLVESGGGLVQPGGSLKLSCATSGSIFSSSAMAWYRQASGKQRELVATITSGGRTS YADSVKGRFTISRDNAKNTVYLQMNSLKPEDTAVYDCNFVVDGKRAPWGQGTQVTVSS |
| 14F8 | 66 | AVQLVESGGGLVQAGESLRLSCTSSGRAFSYYNTGWFRQAPGKEREFVAAISWSGGLT YYADSVKGRFTISRDNAKDMVYLQMASLKPEDTAVYYCAANRRQKTVQMGERAYDYWG QGTQVTVSS |

TABLE 9

Expression yields of anti-vWF nanobodies

| Nanobody | Yield (mg/l) after TALON |
|---|---|
| 12A5 | 13 |
| 12B1 | 6 |
| 12B6 | 16 |
| 12D11 | 8 |
| 12E3 | 4 |
| 12C9 | 25 |
| 14F8 | 48 |

TABLE 10

Platelet adhesion in perfusion chamber of anti-vWF nanobodies

| Nanobody | Control | % Platelet adhesion at 2 µg/ml |
|---|---|---|
| 12A5 | 60 ± 7 | 10 ± 3 |
| 12B1 | 60 ± 7 | 56 ± 3 |
| 12B6 | 60 ± 7 | 19 ± 5 |
| 12D11 | 60 ± 7 | 61 ± 7 |
| 12E3 | 60 ± 7 | 54 ± 1 |
| 12C9 | 71 ± 3 | 68 ± 8 |
| 14F8 | 71 ± 3 | 51 ± 10 |

TABLE 12

Estimated K-on, K-off and KD values for 12A5 homologue nanobodies

| Nanobody | Koff (×10$^{-3}$/s) | Kon (×10$^6$ 1/Ms) | KD (nM) |
|---|---|---|---|
| 12A5 | 2.51 | 0.629 | 3.98 |
| 12B4 | 2.2 | 0.544 | 4.05 |
| 12E8 | 2.93 | 0.171 | 17.1 |
| 12A6 | 4.72 | 0.188 | 25.1 |
| 12D8 | 5.84 | 0.139 | 41.9 |

TABLE 13

Estimated K-on, K-off and KD values for 12B6 homologue nanobodies

| Nanobody | Koff (×10$^{-3}$/s) | Kon (×10$^6$ 1/Ms) | KD (nM) |
|---|---|---|---|
| 12B6 | 5.97 | 2.55 | 2.33 |
| 12A2 | 3.49 | 1.11 | 3.13 |
| 12F2 | 4.04 | 6.41 | 6.3 |
| 14H10 | 3.97 | 6.84 | 5.81 |

TABLE 11

Sequence listing of 12B6 and 12A5 homologue nanobodies

| Name | SEQ ID NO | Sequence |
|---|---|---|
| | | 12A5 homologue sequences |
| 12B4 | 67 | QVQLVESGGGLVQPGGSLRLSCLASGRIFSIGAMGLYRQAPGKQRELVATITSGGSTNYADSVKGRFTISRDGPKNTVYLQMNSLKPEDTAVYYCYANLKQGSYGYRFNDYWGQGTQVTVSS |
| 12E8 | 68 | AVQLEESGGGLVQPGGSLRLSCLASGRIFSIGAMGLYRQAPGKQRELVATITSGGSTNYADSVKGRFTISRDGAKNTVYLQMNSLKPEDTAVYYCYANLKQGDYGYRFNDYWGQGTQVTVSS |
| 12A6 | 69 | QVQLVESGGGLVQPGGSLRLSCLASGRIFSIGTMGLYRQAPGKQRELVATITSGGSTNYADSVKGRFTISRDGAKNTVYLQMNSLRPEDTAVYYCYANLKQGDYGYRFNDYWGQGTQVTVSS |
| 12D8 | 70 | AVQLVESGGGLVQPGGSLRLSCLASGRIFSIGTMGLYRQAPGKQRELVATITSGGSTNYADSVKGRFTISRDGAKNTVYLQMNSLRPEDTAVYYCYANLKQGDYGYRFNDYWGQGTQVTVSS |
| | | 12B6 homologue sequences |
| 12A2 | 71 | QVKLEESGGGLVQAGGALRLSCAASGRTFSYNPMGWFRQAPGKERDLVAAISRTGGSTYYPDSVEGRFTISRDNAKRMVYLQMNNLKPEDTAVYYCAAAGVRAEDGRVRTLPSEYTFWGQGTQVTVSS |
| 12F2 | 72 | QVKLVESGGGLVQAGGALRLSCAASGRTFSYNPMGWFRQAPGRERDVVAAISRTGGSTYYPDSVEGRFTISRDNAKRMVYLQMNNLKPEDTAVYYCAAAGVRAEDGRVRSLPSEYTFWGQGTQVTVSS |
| 14H10 | 73 | QVKLEESGGGLVQAGGALRLSCAASGRTFSYNPMGWFRQAPGKERDVVAAISRTGGSTYYPDSVEGRFTISRDNAKRMVYLEMNNLKPDDTAVYYCAAAGVRAEDGRVRTLPSEYTFWGQGTQVTVSS |

TABLE 14

Real KD value of 12B6, 12A2 and 12A5 nanobodies

| Nanobody | Koff (×10⁻³/s) | Kon (×10⁶ 1/Ms) | KD (nM) |
|---|---|---|---|
| 12B6 | 10.03 | 2.28 | 4.5 |
| 12A2 | 9.9 | 2.24 | 4.4 |
| 12A5 | 3.3 | 1.22 | 2.7 |

TABLE 15

Platelet adhesion in perfusion chamber of 12B6, 12A2 and 12A5 nanobodies

| | % Platelet adhesion | | | |
|---|---|---|---|---|
| Nanobody | 0 µg/ml | 0.2 µg/ml | 0.4 µg/ml | 0.6 µg/ml |
| Control | 71 ± 3 | — | — | — |
| 12B6 | — | 59 ± 6 | 43 ± 7 | 27 ± 8 |
| 12A2 | — | 58 ± 8 | 40 ± 10 | 11 ± 8 |
| 12A5 | — | 50 ± 7 | 27 ± 10 | 2 ± 2 |

TABLE 16

Concentration of 12B6, 12A2 and 12A5 nanobodies after heating at increasing temperatures

| Nanobody | RT | 37° C. | 50° C. | 60° C. | 70° C. | 80° C. | 90° C. |
|---|---|---|---|---|---|---|---|
| 12B6 | 100 | 97 | 100 | 104 | 94 | 91 | 68 |
| 12A2 | 100 | 106 | 104 | 100 | 93 | 87 | 90 |
| 12A5 | 100 | 108 | 107 | 98 | 83 | 75 | 66 |

TABLE 17

Sequence listing of bivalent nanobodies

| Name | SEQ ID NO | Sequence |
|---|---|---|
| 12A2-3a-12A2 | 74 | QVKLEESGGGLVQAGGALRLSCAASGRTFSYNPMGWFRQAPGKERDLVAAISRTGGSTYYPDSVEGRFTISRDNAKRMVYLQMNNLKPEDTAVYYCAAAGVRAEDGRVRTLPSEYTFWGQGTQVTVSSAAAEVQLVESGGGLVQAGGALRLSCAASGRTFSYNPMGWFRQAPGKERDLVAAISRTGGSTYYPDSVEGRFTISRDNAKRMVYLQMNNLKPEDTAVYYCAAAGVRAEDGRVRTLPSEYTFWGQGTQVTVSS |
| 12A2-GS9-12A2 | 75 | QVKLEESGGGLVQAGGALRLSCAASGRTFSYNPMGWFRQAPGKERDLVAAISRTGGSTYYPDSVEGRFTISRDNAKRMVYLQMNNLKPEDTAVYYCAAAGVRAEDGRVRTLPSEYTFWGQGTQVTVSSGGGGSGGGSEVQLVESGGGLVQAGGALRLSCAASGRTFSYNPMGWFRQAPGKERDLVAAISRTGGSTYYPDSVEGRFTISRDNAKRMVYLQMNNLKPEDTAVYYCAAAGVRAEDGRVRTLPSEYTFWGQGTQVTVSS |
| 12A2-GS30-12A2 | 76 | QVKLEESGGGLVQAGGALRLSCAASGRTFSYNPMGWFRQAPGKERDLVAAISRTGGSTYYPDSVEGRFTISRDNAKRMVYLQMNNLKPEDTAVYYCAAAGVRAEDGRVRTLPSEYTFWGQGTQVTVSSGGGGSGGGGSGGGGSGGGGSGGGGSGGGGSEVQLVESGGGLVQAGGALRLSCAASGRTFSYNPMGWFRQAPGKERDLVAAISRTGGSTYYPDSVEGRFTISRDNAKRMVYLQMNNLKPEGTAVYYCAAAGVRAEDGRVRTLPSEYTFWGQGTQVTVSS |
| 12A5-3a-12A5 | 77 | AVQLVESGGGLVQPGGSLRLSCLASGRIFSIGAMGMYRQAPGKQRELVATITSGGSTNYADPVKGRFTISRDGPKNTVYLQMNSLKPEDTAVYYCYANLKQGSYGYRFNDYWGQGTQVTVSSAAAEVQLVESGGGLVQPGGSLRLSCLASGRIFSIGAMGMYRQAPGKQRELVATITSGGSTNYADPVKGRFTISRDGPKNTVYLQMNSLKPEDTAVYYCYANLKQGSYGYRFNDYWGQGTQVTVSS |
| 12A5-GS9-12A5 | 78 | AVQLVESGGGLVQPGGSLRLSCLASGRIFSIGAMGMYRQAPGKQRELVATITSGGSTNYADPVKGRFTISRDGPKNTVYLQMNSLKPEDTAVYYCYANLKQGSYGYRFNDYWGQGTQVTVSSGGGGSGGGSEVQLVESGGGLVQPGGSLRLSCLASGRIFSIGAMGMYRQAPGKQRELVATITSGGSTNYADPVKGRFTISRDGPKNTVYLQMNSLKPEDTAVYYCYANLKQGSYGYRFNDYWGQGTQVTVSS |

TABLE 17-continued

Sequence listing of bivalent nanobodies

| Name | SEQ ID NO | Sequence |
|---|---|---|
| 12A5-GS30-12A5 | 79 | AVQLVESGGGLVQPGGSLRLSCLASGRIFSIGAMGMYRQAPGKQRELVA TITSGGSTNYADPVKGRFTISRDGPKNTVYLQMNSLKPEDTAVYYCYAN LKQGSYGYRFNDYWGQGTQVTVSSGGGGSGGGGSGGGGSGGGGSGGGGS GGGGSEVQLVESGGGLVQPGGSLRLSCLASGRIFSIGAMGMYRQAPGKQ RELVATITSGGSTNYADPVKGRFTISRDGPKNTVYLQMNSLKPEDTAVY YCYANLKQGSYGYRFNDYWGQGTQVTVSS |
| 12B6-3a-12B6 | 80 | QVQLVESGGGLVQAGGALRLSCAASGRTFSYNPMGWFRQAPGKERDVVA AISRTGGSTYYARSVEGRFTISRDNAKRMVYLQMNALKPEDTAVYYCAA AGVRAEDGRVRTLPSEYNFWGQGTQVTVSSAAAEVQLVESGGGLVQAGG ALRLSCAASGRTFSYNPMGWFRQAPGKERDVVAAISRTGGSTYYARSVE GRFTISRDNAKRMVYLQMNALKPEDTAVYYCAAAGVRAEDGRVRTLPSE YNFWGQGTQVTVSS |
| 12B6-GS9-12B6 | 81 | QVQLVESGGGLVQAGGALRLSCAASGRTFSYNPMGWFRQAPGKERDVVA AISRTGGSTYYARSVEGRFTISRDNAKRMVYLQMNALKPEDTAVYYCAA AGVRAEDGRVRTLPSEYNFWGQGTQVTVSSGGGGSGGGSEVQLVESGGG LVQAGGALRLSCAASGRTFSYNPMGWFRQAPGKERDVVAAISRTGGSTY YARSVEGRFTISRDNAKRMVYLQMNALKPEDTAVYYCAAAGVRAEDGRV RTLPSEYNFWGQGTQVTVSS |
| 12B6-GS30-12B6 | 82 | QVQLVESGGGLVQAGGALRLSCAASGRTFSYNPMGWFRQAPGKERDVVA AISRTGGSTYYARSVEGRFTISRDNAKRMVYLQMNALKPEDTAVYYCAA AGVRAEDGRVRTLPSEYNFWGQGTQVTVSSGGGGSGGGGSGGGGSGGGG SGGGGSGGGGSEVQLVESGGGLVQAGGALRLSCAASGRTFSYNPMGWFR QAPGKERDVVAAISRTGGSTYYARSVEGRFTISRDNAKRMVYLQMNALK PEDTAVYYCAAAGVRAEDGRVRTLPSEYNFWGQGTQVTVSS |

TABLE 18

Sequence listing of linker sequences

| Name | SEQ ID NO | Sequence |
|---|---|---|
| 3a | 83 | AAA |
| GS9 | 84 | GGGGSGGGS |
| GS30 | 85 | GGGGSGGGGSGGGGSGGGGSGGGGSGGGGS |

TABLE 19

Expression yields of bivalent 12B6, 12A2 and 12A5 nanobodies

| Nanobody | Yield (mg/l) after TALON or other purification |
|---|---|
| 12B6 | 16 |
| 12B6-3a-12B6 | 9 |
| 12B6-GS9-12B6 | 16 |
| 12B6-GS30-12B6 | 17 |
| 12A2 | 18 |
| 12A2-3a-12A2 | 45 |
| 12A2-GS9-12A2 | 22 |
| 12A2-GS30-12A2 | 11 |
| 12A5 | 13 |
| 12A5-3a-12A5 | 10 |
| 12A5-GS9-12A5 | 11 |
| 12A5-GS30-12A5 | 18 |

TABLE 20

Concentration of 12B6 bivalent nanobodies after heating at increasing temperatures

| Nanobody | RT | 37° C. | 50° C. | 60° C. | 70° C. | 80° C. | 90° C. |
|---|---|---|---|---|---|---|---|
| 12B6 | 100 | 97 | 100 | 104 | 94 | 91 | 68 |
| 12B6-3a-12B6 | 100 | 103 | 96 | 87 | 9 | 8 | 6 |
| 12B6-GS9-12B6 | 100 | 103 | 94 | 88 | 19 | 8 | 7 |
| 12B6-GS30-12B6 | 100 | 100 | 100 | 98 | 46 | 14 | 11 |

TABLE 21

Concentration of 12A2 bivalent nanobodies after heating at increasing temperatures

| Nanobody | RT | 37° C. | 50° C. | 60° C. | 70° C. | 80° C. | 90° C. |
|---|---|---|---|---|---|---|---|
| 12A2 | 100 | 106 | 104 | 100 | 93 | 87 | 90 |
| 12A2-3a-12A2 | 100 | 87 | 88 | 91 | 55 | 50 | 43 |
| 12A2-GS9-12A2 | 100 | 102 | 113 | 138 | 91 | 13 | 15 |
| 12A2-GS30-12A2 | 100 | 115 | 93 | 116 | 81 | 49 | 34 |

TABLE 22

Concentration of 12A5 bivalent nanobodies after heating at increasing temperatures

| Nanobody | RT | 37° C. | 50° C. | 60° C. | 70° C. | 80° C. | 90° C. |
|---|---|---|---|---|---|---|---|
| 12A5 | 100 | 108 | 107 | 98 | 83 | 75 | 66 |
| 12A5-3a-12A5 | 100 | 101 | 114 | 29 | 6 | 4 | 6 |
| 12A5-GS9-12A5 | 100 | 104 | 115 | 32 | 13 | 14 | 10 |
| 12A5-GS30-12A5 | 100 | 104 | 87 | 7 | 6 | 35 | 21 |

TABLE 23

Platelet adhesion in perfusion chamber of 12A2 bivalent nanobodies

| | % Platelet adhesion | | | |
|---|---|---|---|---|
| Nanobody | 0 µg/ml | 0.1 µg/ml | 0.2 µg/ml | 0.4 µg/ml |
| Control | 81 ± 5 | — | — | — |
| 12A2 | — | 78 ± 2 | 72 ± 6 | 61 ± 8 |
| 12A2-3a-12A2 | — | 74 ± 5 | 50 ± 3 | 33 ± 0 |
| 12A2-GS9-12A2 | — | 81 ± 1 | 73 ± 1 | 40 ± 2 |
| 12A2-GS30-12A2 | — | 81 ± 3 | 73 ± 3 | 37 ± 1 |

TABLE 24

Sequence listing of humanised 12B6 nanobodies

| Name | SEQ ID NO | Sequence |
|---|---|---|
| 12B6H1 | 86 | EVQLVESGGGLVQPGGSLRLSCAASGRTFSYNPMGWFRQAPGKGRDVVAAISRTGGST YYARSVEGRFTISRDNAKRMVYLQMNSLRAEDTAVYYCAAAGVRAEDGRVRTLPSEYN FWGQGTQVTVSS |
| 12B6H2 | 87 | EVQLVESGGGLVQPGGSLRLSCAASGRTFSYNPMGWFRQAPGKGREVVAAISRTGGST YYARSVEGRFTISRDNAKRMVYLQMNSLRAEDTAVYYCAAAGVRAEDGRVRTLPSEYN FWGQGTQVTVSS |
| 12B6H3 | 88 | EVQLVESGGGLVQPGGSLRLSCAASGRTFSYNPMGWFRQAPGKGRDVVAAISRTGGST YYARSVEGRFTISRDNAKNMVYLQMNSLRAEDTAVYYCAAAGVRAEDGRVRTLPSEYN FWGQGTQVTVSS |
| 12B6H4 | 89 | EVQLVESGGGLVQPGGSLRLSCAASGRTFSYNPMGWFRQAPGKGRDVVAAISRTGGST YYARSVEGRFTISRDNAKRSVYLQMNSLRAEDTAVYYCAAAGVRAEDGRVRTLPSEYN FWGQGTQVTVSS |

TABLE 25

Expression yields of wild type and humanised 12B6 nanobodies

| Nanobody | Yield (mg/l) after TALON or other purification |
|---|---|
| 12B6 | 16 |
| 12B6H1 | 3 |
| 12B6H2 | 9 |
| 12B6H3 | 8 |
| 12B6H4 | 3 |

TABLE 26

Concentration of wild type and humanised 12B6 nanobodies after heating at increasing temperatures

| Nanobody | RT | 37° C. | 50° C. | 60° C. | 70° C. | 80° C. | 90° C. |
|---|---|---|---|---|---|---|---|
| 12B6 | 100 | 97 | 100 | 104 | 94 | 91 | 68 |
| 12B6H1 | 100 | 101 | 100 | 97 | 45 | 58 | 54 |
| 12B6H2 | 100 | 97 | 96 | 96 | 83 | 46 | 53 |

TABLE 26-continued

Concentration of wild type and humanised 12B6 nanobodies after heating at increasing temperatures

| Nanobody | RT | 37° C. | 50° C. | 60° C. | 70° C. | 80° C. | 90° C. |
|---|---|---|---|---|---|---|---|
| 12B6H3 | 100 | 101 | 98 | 97 | 74 | 73 | 65 |
| 12B6H4 | 100 | 101 | 100 | 93 | 41 | 66 | 54 |

TABLE 27

KD values for wild type and humanised 12B6 nanobodies

| Nanobody | KD (nM) |
|---|---|
| 12B6 | 4.4 |
| 12B6H1 | 4.4 |
| 12B6H2 | 3.5 |
| 12B6H3 | 9 |
| 12B6H4 | 7.3 |

TABLE 28

Sequence listing of humanised 12A2 nanobodies

| Name | SEQ ID NO | Sequence |
|---|---|---|
| 12A2H1 | 90 | EVQLVESGGGLVQPGGSLRLSCAASGRTFSYNPMGWFRQAPGKGRELVAAISRTGG STYYPDSVEGRFTISRDNAKRMVYLQMNSLRAEDTAVYYCAAAGVRAEDGRVRTLP SEYTFWGQGTQVTVSS |
| 12A2H3 | 91 | EVQLVESGGGLVQPGGSLRLSCAASGRTFSYNPMGWFRQAPGKGRELVAAISRTGG STYYPDSVEGRFTISRDNAKNMVYLQMNSLRAEDTAVYYCAAAGVRAEDGRVRTLP SEYTFWGQGTQVTVSS |
| 12A2H4 | 92 | EVQLVESGGGLVQPGGSLRLSCAASGRTFSYNPMGWFRQAPGKGRELVAAISRTGG STYYPDSVEGRFTISRDNAKRSVYLQMNSLRAEDTAVYYCAAAGVRAEDGRVRTLP SEYTFWGQGTQVTVSS |
| 12A2H11 | 93 | EVQLVESGGGLVQPGGSLRLSCAASGFTFSYNPMGWFRQAPGKGRELVAAISRTGG STYYPDSVEGRFTISRDNAKRMVYLQMNSLRAEDTAVYYCAAAGVRAEDGRVRTLP SEYTFWGQGTQVTVSS |
| 12A2H13 | 94 | EVQLVESGGGLVQPGGSLRLSCAASGFTFSYNPMGWFRQAPGKGRELVAAISRTGG STYYPDSVEGRFTISRDNAKNSVYLQMNSLRAEDTAVYYCAAAGVRAEDGRVRTLP SEYTFWGQGTLVTVSS |

TABLE 29

Expression yields of wild type and humanised 12A2 nanobodies

| Nanobody | Yield (mg/l) after TALON or other purification |
|---|---|
| 12A2 | 18 |
| 12A2H1 | 11 |
| 12A2H3 | 11 |
| 12A2H4 | 11 |
| 12A2H11 | 15 |
| 12A2H13 | 11 |

TABLE 30

Concentration of wild type and humanised 12A2 nanobodies after heating at increasing temperatures

| Nanobody | RT | 37° C. | 50° C. | 60° C. | 70° C. | 80° C. | 90° C. |
|---|---|---|---|---|---|---|---|
| 12A2 | 100 | 106 | 104 | 100 | 93 | 87 | 90 |
| 12A2H1 | 100 | 99 | 99 | 99 | 100 | 89 | 80 |
| 12A2H3 | 100 | 102 | 101 | 102 | 102 | 90 | 89 |
| 12A2H4 | 100 | 100 | 101 | 100 | 99 | 90 | 83 |
| 12A2H11 | 100 | 111 | 113 | 107 | 103 | 85 | 67 |
| 12A2H13 | 100 | 104 | 103 | 103 | 100 | 90 | 81 |

TABLE 31

Platelet adhesion of wild type and humanised 12A2 nanobodies in perfusion chamber at 0.7 and 1.5 ug/ml

| | % Platelet adhesion | | |
|---|---|---|---|
| Nanobody | 0 μg/ml | 0.7 μg/ml | 1.5 μg/ml |
| Control | 73 ± 4 | — | — |
| 12A2 | — | 36 ± 3 | 34 ± 5 |
| 12A2H1 | — | 49 ± 1 | 47 ± 3 |
| 12A2H3 | — | 62 ± 4 | 63 ± 1 |
| 12A2H4 | — | 55 ± 1 | 54 ± 1 |
| 12A2H11 | — | 57 ± 1 | 52 ± 1 |
| 12A2H13 | — | 67 ± 4 | 67 ± 4 |

TABLE 32

Platelet adhesion of wild type and humanised 12A2 nanobodies in perfusion chamber at 0.5, 1 and 2 ug/ml

| | % Platelet adhesion | | |
|---|---|---|---|
| Nanobody | 0 μg/ml | 0.5 μg/ml | 1 μg/ml | 2 μg/ml |
| Control | 72 ± 1 | — | — | — |
| 12A2 | — | 33 ± 10 | 35 ± 11 | 10 ± 10 |
| 12A2H1 | — | 40 ± 9 | 43 ± 3 | 38 ± 5 |
| 12A2H4 | — | 61 ± 1 | 57 ± 1 | 46 ± 5 |

TABLE 33

KD values for wild type and humanised 12A2 nanobodies

| Nanobody | KD (nM) |
|---|---|
| 12A2 | 3.1 |
| 12A2 H3 | 14.6 |
| 12A2 H11 | 10.6 |
| 12A2 H13 | 38.8 |

TABLE 34

Sequence listing of humanised 12A5 nanobodies

| Name | SEQ ID NO | Sequence |
|---|---|---|
| 12A5H1 | 95 | EVQLVESGGGLVQPGGSLRLSCAASGRIFSIGAMGMYRQAPGKGRELVATITSGGS TNYADPVKGRFTISRDGPKNTVYLQMNSLRAEDTAVYYCYANLKQGSYGYRFNDYW GQGTQVTVSS |
| 12A5H2 | 96 | EVQLVESGGGLVQPGGSLRLSCAASGRIFSIGAMGMYRQAPGKGRELVATITSGGS TNYADPVKGRFTISRDGAKNTVYLQMNSLRAEDTAVYYCYANLKQGSYGYRFNDYW GQGTQVTVSS |
| 12A5H3 | 97 | EVQLVESGGGLVQPGGSLRLSCAASGRIFSIGAMGMYRQAPGKGRELVATITSGGS TNYADPVKGRFTISRDNAKNTVYLQMNSLRAEDTAVYYCYANLKQGSYGYRFNDYW GQGTQVTVSS |

TABLE 35

Expression yields of wild type and humanised 12A5 nanobodies

| Nanobody | Yield (mg/l) after TALON |
|---|---|
| 12A5 | 13 |
| 12A5H1 | 8 |
| 12A5H2 | 9 |
| 12A5H3 | 11 |

TABLE 36

Concentration of wild type and humanised 12A5 nanobodies after heating at increasing temperatures

| Nanobody | 37° C. | 50° C. | 60° C. | 70° C. | 80° C. | 90° C. |
|---|---|---|---|---|---|---|
| 12A5 | 108 | 107 | 98 | 83 | 75 | 66 |
| 12A5H1 | 99 | 91 | 86 | 60 | 69 | 63 |
| 12A5H2 | 99 | 108 | 90 | 58 | 67 | 60 |
| 12A5H3 | 101 | 97 | 97 | 67 | 73 | 64 |

TABLE 37

KD values for wild type and humanised 12A5 nanobodies

| Nanobody | KD (nM) |
|---|---|
| 12A5 | 1.6 |
| 12A5H1 | 1.8 |
| 12A5H2 | 12.8 |
| 12A5H3 | ND |

TABLE 38

Sequence listing of humanised bivalent nanobodies

| Name | SEQ ID NO | Sequence |
|---|---|---|
| 12A2H1-3a-12A2H1 | 98 | EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSS<u>AAA</u>EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSS |
| 12A2H4-3a-12A2H4 | 99 | EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSS<u>AAA</u>EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSS |
| 12B6H2-3a-12B6H2 | 100 | EVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSS<u>AAA</u>EVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSS |
| 12A2H1-GS9-12A2H1 | 101 | EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSS<u>GGGGSGGGS</u>EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSS |
| 12A2H4-GS9-12A2H4 | 102 | EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSS<u>GGGGSGGGS</u>EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSS |
| 12B6H2-GS9-12B6H2 | 103 | EVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSS<u>GGGGSGGGS</u>EVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSS |
| 12A2H1-GS30-12A2H1 | 104 | EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSSGGGGS<u>GGGGSGGGGSGGGGSGGGGSGGGGS</u>EVQLVESGGGLVQPGGSLRLSCAASGRTFSYNPMGWFRQAPGKGRELVAAISRTGGSTYYPDSVEGRFTISRDNAKRMVYLQMNSLRAEDTAVYYCAAAGVRAEDGRVRTLPSEYTFWGQGTQVTVSS |
| 12A2H4-GS30-12A2H4 | 105 | EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSSGGGGS<u>GGGGSGGGGSGGGGSGGGGSGGGGS</u>EVQLVESGGGLVQPGGSLRLSCAASGRTFSYNPMGWFRQAPGKGRELVAAISRTGGSTYYPDSVEGRFTISRDNAKRSVYLQMNSLRAEDTAVYYCAAAGVRAEDGRVRTLPSEYTFWGQGTQVTVSS |
| 12B6H2-GS30-12B6H2 | 106 | EVQLVESGGGLVQPGGSLRLSCAASGRTFSYNPMGWFRQAPGKGREVVAAISRTGGSTYYARSVEGRFTISRDNAKRMVYLQMNSLRAEDTAVYYCAAAGVRAEDGRVRTLPSEYNFWGQGTQVTVSS<u>GGGGSGGGGSGGGGSGGGG</u> |

TABLE 38-continued

Sequence listing of humanised bivalent nanobodies

| Name | SEQ ID NO | Sequence |
|------|-----------|----------|
|  |  | SGGGGSGGGGSEVQLVESGGGLVQPGGSLRLSCAASGRTFSYNPMGWFR QAPGKGREVVAAISRTGGSTYYARSVEGRFTISRDNAKRMVYLQMNSLR AEDTAVYYCAAAGVRAEDGRVRTLPSEYNFWGQGTQVTVSS |

TABLE 39

Expression yields of humanised bivalent nanobodies

| Nanobody | Tags | Yield (mg/l) |
|---|---|---|
| 12A2H1-3a-12A2H1 | Yes | 5 |
| 12A2H1-3a-12A2H1 | No | 6 |
| 12A2H4-3a-12A2H4 | Yes | 10 |
| 12A2H4-3a-12A2H4 | No | 7 |
| 12B6H2-3a-12B6H2 | Yes | 10 |
| 12B6H2-3a-12B6H2 | No | 2 |

TABLE 40

Concentration of humanised bivalent nanobody after heating at increasing temperatures

| Nanobody | Tags | 37° C. | 50° C. | 60° C. | 70° C. | 80° C. | 90° C. |
|---|---|---|---|---|---|---|---|
| 12A2H1-3a-12A2H1 | Yes | 98 | 96 | 93 | 63 | 8 | 9 |
| 12A2H1-3a-12A2H1 | No | 100 | 99 | 100 | 77 | 14 | 15 |
| 12A2H4-3a-12A2H4 | Yes | 100 | 99 | 95 | 9 | 6 | 9 |
| 12A2H4-3a-12A2H4 | No | 98 | 98 | 98 | 18 | 17 | 26 |
| 12B6H2-3a-12B6H2 | Yes | 100 | 91 | 85 | 7 | 6 | 7 |
| 12B6H2-3a-12B6H2 | No | 100 | 99 | 99 | 28 | 13 | 18 |

TABLE 41

Platelet adhesion of wild type and humanised bivalent nanobodies

| Nanobody | % Platelet adhesion | | | |
|---|---|---|---|---|
|  | 0 µg/ml | 0.15 µg/ml | 0.3 µg/ml | 0.6 µg/ml |
| Control | 65 ± 8 | — | — | — |
| 12B6-3a-12B6 | — | 50 ± 5 | 15 ± 6 | 8 ± 6 |
| 12B6H2-3a-12B6H2 | — | 53 ± 4 | 30 ± 16 | 17 ± 6 |
| 12A2-3a-12A2 | — | 36 ± 8 | 10 ± 8 | 4 ± 3 |
| 12A2H1-3a-12A2H1 | — | 54 ± 4 | 10 ± 11 | 12 ± 7 |
| 12A2H4-3a-12A2H4 | — | 38 ± 2 | 10 ± 6 | 8 ± 4 |

TABLE 42 baboons used with the different test compounds in the Folts study

| Baboon ID | Sex | Weight [kg] | Left leg | Right leg |
|---|---|---|---|---|
| 1 | male | 9.8 |  | Control |
| 2 | male | 10.0 |  | Control |
| 13 | male | 12.4 |  | Reopro |
| 14 | male | 9.5 |  | Reopro |
| 15 | male | 10.8 |  | Reopro |
| 16 | male |  | ALX-0081 |  |
| 17 | male | 15.6 |  | ALX-0081 |
| 18 | male | 17.2 |  | ALX-0081 |
| 20/22 | male | 12.7 | ALX-0081 | ALX-0081 |
| 21 | female | 8.0 |  | ALX-0081 |
| 23 | male |  |  | ALX-0081 |
| 24 | male | 9.4 | ALX-0081 |  |
| 3/19 | male | 15.2 | Aspegic | ALX-0081 |
| 4 | female | 13.6 | Aspegic |  |
| 5 | male | 17.4 | Aspegic |  |
| 9 | male | 13.2 |  | Plavix |
| 6/10 | male | 10.2 | Heparin | Plavix |
| 7/11 | male | 9.4 | Heparin | Plavix |
| 8/12 | male | 10.5 | Heparin | Plavix |

TABLE 43

Length of CFRs (s) for control animals

| Control | | Baboon ID | |
|---|---|---|---|
| Final dose | Dose | 1 | 2 |
| 0 | control | 291 | 249 |
| 0 | saline | 294 | 278 |
| 0 | saline | 427 | 185 |
| 0 | saline | 285 | 203 |
| 0 | saline | 438 | 175 |

(ND = not done)

TABLE 44

Length of CFRs (s) for animals treated with Aspegic ™

| Aspegic | | Baboon ID | | |
|---|---|---|---|---|
| Final dose | Dose | 3 | 4 | 5 |
| 0 | control | 88 | no CFRs | 148 |
| 0 | saline | 147 | 204 | 184 |
| 1 mg/kg | 1 mg/kg | 149 | 164 | 135 |
| 2.5 mg/kg | 1.5 mg/kg | 102 | 325 | 115 |
| 5 mg/kg | 2.5 mg/kg | 102 | >1800 | 245 |
| 10 mg/kg | 5 mg/kg | 113 | 905 | 156 |
| 20 mg/kg | 10 mg/kg | 125 | 657 | 169 |
| 40 mg/kg | 20 mg/kg | 110 | ND | 145 |
| 80 mg/kg | 40 mg/kg | 129 | ND | ND |
| Epinephrin | | ND | 161 | ND |

(ND = not done)

TABLE 47

Length of CFRs (s) for animals treated with Reopro ™

| Reopro | | Baboon ID | | |
|---|---|---|---|---|
| Final dose | Dose | 13 | 14 | 15 |
| 0 | control | 144 | 90 | 308 |
| 0 | saline | 141 | 103 | 268 |
| 20 µg/kg | 20 µg/kg | 98 | 82 | 254 |
| 70 µg/kg | 50 µg/kg | 90 | 90 | 248 |
| 170 µg/kg | 100 µg/kg | 90 | >1800 | >1800 |
| 420 µg/kg | 250 µg/kg | >1800 | >1800 | >1800 |
| 920 µg/kg | 500 g/kg | >1800 | >1800 | >1800 |
| Epinephrin | | >1200 | >1200 | >1200 |

(ND = not done)

TABLE 48

Length of CFRs (s) for animals teated with ALX-0081

| ALX-0081 | | Baboon ID | | | | | | | | |
|---|---|---|---|---|---|---|---|---|---|---|
| Final dose | Dose | 16 | 17 | 18 | 19 | 20 | 21 | 22 | 23 | 24 |
| 0 | control | 168 | 293 | 185 | 90 | 94 | 117 | 188 | 164 | 161 |
| 0 | saline | 151 | 236 | 242 | 117 | 98 | 107 | 233 | 105 | 178 |
| 3 µg/kg | 3 microgram/kg | 193 | ND | ND | 144 | 133 | 183 | 312 | 112 | 295 |
| 13 µg/kg | 10 microgram/kg | 913 | >1800 | 298 | 237 | 620 | 525 | >1800 | 213 | 380 |
| 43 µg/kg | 30 microgram/kg | >1800 | >1800 | >1800 | >1800 | >1800 | >1800 | >1800 | >1800 | >1800 |
| 133 µg/kg | 90 microgram/kg | >1800 | >1800 | >1800 | >1800 | >1800 | >1800 | >1800 | >1800 | >1800 |
| 403 µg/kg | 270 microgram/kg | >1800 | >1800 | >1800 | >1800 | >1800 | >1800 | >1800 | >1800 | >1800 |
| Epinephrin | | >1200 | >1200 | >900 | >900 | >900 | >900 | >900 | >900 | >900 |

(ND = not done)

TABLE 45

Length of CFRs (s) for animals treated with Heparin ™

| Heparin | | Baboon ID | | |
|---|---|---|---|---|
| Final dose | Dose | 6 | 7 | 8 |
| 0 | control | 232 | 113 | 166 |
| 0 | saline | 298 | 131 | 246 |
| 15 IU/kg | 15 IU/kg | 630 | 208 | 255 |
| 30 IU/kg | 30 IU/kg | 355 | 241 | 320 |
| 60 IU/kg | 60 IU/kg | 432 | 246 | 332 |
| 120 IU/kg | 120 IU/kg | 610 | 160 | 206 |
| 240 IU/kg | 240 IU/kg | >1800 | 221 | 169 |
| Epinephrin | | 109 | 65 | ND |

(ND = not done)

TABLE 46

Length of CFRs (s) for animals treated with Plavix ™

| Plavix | | Baboon ID | | | |
|---|---|---|---|---|---|
| Final dose | Dose | 9 | 10 | 11 | 12 |
| 0 | control | 215 | 178 | 84 | 144 |
| 0 | saline | 168 | 160 | 88 | 189 |
| 1 mg/kg | 1 mg/kg | 189 | ND | 132 | 179 |
| 2.5 mg/kg | 2.5 mg/kg | 883 | 400 | 258 | >1800 |
| 5 mg/kg | 2.5 mg/kg | >1800 | >1800 | >1800 | >1800 |
| 10 mg/kg | 5 mg/kg | >1800 | >1800 | >1800 | >1800 |
| 20 mg/kg | 10 mg/kg | >1800 | >1800 | >1800 | >1800 |
| Epinephrin | | 241 | 91 | 83 | 66 |

(ND = not done)

TABLE 49 baboons used with the different test compounds in the Folts study

| Baboon ID | Sex | Weight [kg] | Mix |
|---|---|---|---|
| 1 | Male | 9.8 | Asp/Hep/Plav/ALX |
| 2 | Female | 13.6 | Asp/Hep/Plav/ALX |
| 3 | Female | 7.8 | Asp/Hep/Plav/ALX |
| 4 | Male | 12.1 | Asp/Hep/Plav/ALX |
| 5 | Male | 11.4 | Asp/Hep/Plav/ALX |
| 6 | Male | 11.4 | Asp/Hep/Plav/ALX |
| 7 | Male | 14.0 | Asp/Hep/Plav/ALX |

TABLE 50

Inhibition of CFRs in the Folts model for the different drugs tested. The number of experiments in which an inhibition of CFRs was observed in the mentioned different conditions is shown as a function of the total number of independent repeats of that condition.

| Test compound | Inhibition of CFRs | Inhibition of CFRs after new injury | Inhibition of CFRs after administration of Epinephrin | Effective dose |
|---|---|---|---|---|
| Control | 0/2 | ND | ND | — |
| Aspegic | 0/3 | 0/3 | 0/1 | — |

TABLE 50-continued

Inhibition of CFRs in the Folts model for the different drugs tested. The number of experiments in which an inhibition of CFRs was observed in the mentioned different conditions is shown as a function of the total number of independent repeats of that condition.

| Test compound | Inhibition of CFRs | Inhibition of CFRs after new injury | Inhibition of CFRs after administration of Epinephrin | Effective dose |
|---|---|---|---|---|
| Heparin | 1/3 | 1/3 | 0/2 | — |
| Plavix | 4/4 | 4/4 | 0/4 | 5 mg/kg |
| Reopro | 3/3 | 3/3 | 3/3 | 170-420 µg/kg |
| ALX-0081 | 9/9 | 9/9 | 9/9 | 13-43 µg/kg + 1.5 × dose/kg/hour |

TABLE 51

Length of CFRs (seconds) for each baboon and each dose of Aspegic, Heparin, Plavix and ALX-0081. The effective dose is indicated in yellow

|  | 4 | 5 | 6 | 7 | 8 | 9 | 10 |
|---|---|---|---|---|---|---|---|
| control | 82 | 99 | 109 | 95 | 113 | 142 | 113 |
| saline | 113 | 119 | 108 | 114 | 131 | 168 | 92 |
| 5 mg/kg Aspegic + 60 IU/kg Heparin + 1 mg/kg Plavix | 153 | 135 | 272 | 742 | 146 | 219 | 223 |
| +1 mg/kg Plavix | >1800 | >1800 | >1800 | >1800 | >1800 | >1800 | >1800 |
| Epinephrin + non effective doses ALX-0081 + Heparin | 250 | 72 | 87 | 95 | 106 | 105 | 105 |
| Epinephrin + effective dose ALX-0081 | >1800 | >1800 | >1800 | >1800 | >1800 | >1800 | >1800 |

TABLE 52

Blood loss relative to the second control gauze for animals treated with Plavix™ in function of final dose

| Plavix | | Baboon ID | | | | | |
|---|---|---|---|---|---|---|---|
| Final dose | Dose | 9 | 10 | 11 | 12 | Average | STD |
| 1 mg/kg | 1 mg/kg | 0.6 | 1.3 | 1.6 | 1.2 | 1.4 | 0.2 |
| 2.5 mg/kg | 1.5 mg/kg | 1.5 | 1.4 | 1.1 | 1.0 | 1.2 | 0.2 |
| 5 mg/kg | 2.5 mg/kg | 5.1 | 4.7 | 1.4 | 6.6 | 4.5 | 2.2 |
| 10 mg/kg | 5 mg/kg | 6.5 | 4.5 | 5.8 | 13.6 | 7.6 | 4.1 |
| 20 mg/kg | 10 mg/kg | 3.7 | 4.1 | 9.1 | 2.6 | 4.9 | 2.9 |

(STD = standard deviation)

TABLE 53

Blood loss relative to the second control gauze for animals treated with Reopro™ in function of final dose

| Reopro | | Baboon ID | | | | |
|---|---|---|---|---|---|---|
| Final dose | Dose | 13 | 14 | 15 | Average | STD |
| 20 µg/kg | 20 µg/kg | 2.7 | 0.6 | 2.1 | 1.8 | 1 |
| 70 µg/kg | 50 µg/kg | 1.2 | 2.1 | 0.4 | 1.2 | 1 |
| 170 µg/kg | 100 µg/kg | 1.2 | 6.0 | 4.7 | 4.0 | 2 |
| 420 µg/kg | 250 µg/kg | 28.3 | 7.1 | 13.9 | 16.4 | 11 |
| 920 µg/kg | 500 µg/kg | 39.8 | 14.5 | 6.3 | 20.2 | 17 |

(STD = standard deviation)

TABLE 54

Blood loss relative to the second control gauze for animals treated with ALX-0081 in function of final dose

| ALX-0081 | | Baboon ID | | | | | | | | Average | STD |
|---|---|---|---|---|---|---|---|---|---|---|---|
| Final dose | Dose | 17 | 18 | 19 | 20 | 21 | 22 | 23 | 24 | | |
| 3 µg/kg | 3 µg/kg | ND | ND | 0.4 | 1.2 | 0.5 | 1.1 | 1.8 | 0.8 | 1.0 | 0.5 |
| 13 µg/kg | 10 µg/kg | 1.2 | 0.8 | 0.1 | 1.2 | 1.1 | 1.3 | 1.1 | 1.1 | 1.0 | 0.4 |
| 43 µg/kg | 30 µg/kg | 2.8 | 2.0 | 4.1 | 3.9 | 2.1 | 3.8 | 3.0 | 1.6 | 2.9 | 1.0 |
| 133 µg/kg | 90 µg/kg | 2.5 | 3.1 | 2.0 | 0.4 | 4.0 | 5.3 | 5.6 | 1.4 | 3.0 | 1.8 |
| 403 µg/kg | 270 µg/kg | 2.6 | 2.3 | 2.3 | 0.4 | 0.8 | 5.6 | 10.7 | 0.9 | 3.2 | 3.4 |

(STD = standard deviation)

TABLE 55

The average of the total amount of blood loss
(=sum of blood loss from the first five doses
of test compound) as relative to the second control gauze

| Test compound | Total dose as multiple of effective dose | Average of total blood loss | Standard deviation of blood loss |
|---|---|---|---|
| Plavix | 4 | 19.4 | 4.0 |
| Reopro | 3.5 | 44 | 26 |
| ALX-0081 | 13 | 10.8 | 5.7 |

TABLE 56

Blood loss in gauzes relative to the second control gauze for each baboon treated with Aspegic, Heparin, Plavix and ALX-0081 in function of drug dose. The effective drug dose in which a complete inhibition of CFRs was observed, is indicated in yellow

|  | 4 | 5 | 6 | 7 | 8 | 9 | 10 | median ± STD |
|---|---|---|---|---|---|---|---|---|
| 5 mg/kg Aspegic + 60 IU/kg Heparin + 1 mg/kg Plavix | 2.6 | 1 | 4.6 | 12.1 | 1.3 | 1.4 | 1.8 | 1.8 ± 3.5 |
| +1 mg/kg Plavix |  | 3.7 | 13.9 | 4.8 | 13.1 | 1.4 | 4.3 | 5.6 | 4.8 ± 6.7 |
| Epinephrin + non effective doses ALX-0081 + Heparin | 9.4 | 2.7 | 2.7 | 67 | 0.3 | 4.8 | 9.2 | 4.8 ± 13.7 |
| Epinephrin + effective dose ALX-0081 | 23.4 | 2.0 | 1 | 39.4 | 1.3 | 4.5 | 0.8 | 2.0 ± 10.3 |

TABLE 57

% ristocetin-induced platelet aggregation for each baboon treated with Aspegic, Heparin, Plavix and ALX-0081 in function of drug dose

|  | 4 | 5 | 6 | 7 | 8 | 9 | 10 |
|---|---|---|---|---|---|---|---|
| control | 75 | 78 | 79 | 70 | 46 | 70 | 46 |
| saline | 48 | 78 | 74 | 24 | 45 | 65 | 47 |
| 5 mg/kg Aspegic + 60 IU/kg Heparin + 1 mg/kg Plavix | 62 | 65 | 89 | 64 | 66 | 68 | 55 |
| 1 mg/kg Plavix +1 mg/kg Plavix | 42 | 63 | 66 | 83 | 59 | 76 | 60 |
| Epinephrin + effective dose ALX-0081 | 0 | 24 | 24 | 6 | 17 | 7 | 8 |

TABLE 58 concentration of ALX-0081 [µg/ml] in blood samples obtained at 10 minutes after administration

| ALX-0081 | | Baboon ID | | | | | | | |
|---|---|---|---|---|---|---|---|---|---|
| Final dose | Dose | 16 | 17 | 18 | 19 | 20 | 21 | 22 | 23 | 24 |
| 3 µg/kg | 3 µg/kg | 0.10 |  |  | 0.03 | 0.05 | 0.08 | 0.04 | 0.14 | 0.08 |
| 13 µg/kg | 10 µg/kg | 1.23 | 0.34 | 0.29 | 0.26 | 0.50 | 0.39 | 0.41 | 0.18 | 0.42 |
| 43 µg/kg | 30 µg/kg | 1.00 | 0.51 | 0.72 | 1.14 | 1.01 | 0.61 | 1.01 | 0.87 | 1.21 |
| 133 µg/kg | 90 µg/kg | 1.87 | 1.38 | 1.77 | 1.61 | 2.64 | 1.60 | 6.77 | 2.75 | 5.01 |
| 403 µg/kg | 270 µg/kg | 6.77 | 4.03 | 6.73 | 35.14 | 7.66 | 6.01 | 9.24 | 18.56 | 16.62 |

TABLE 59

Length of CFRs [seconds] for baboons treated with ALX-0081 and with vWF

|  | Baboon ID | | |
|---|---|---|---|
| Dose | 1 | 2 | 3 |
| Control | 119 | 140 | 111 |
| Saline | ND | 158 | 158 |
| 30 µg/kg + 45 µg/kg/hour ALX-0081 | >1800 | >1800 | >1800 |
| 250 IU vWF | >420 | >1800 | >1800 |
| 250 IU vWF | 246 | 256 | 230 |

TABLE 60

Volumes [µl] to prepare the different mixtures for study of cleavage of A1A2A3 by ADAMTS13

|  | NPP | NPP + EDTA | NPP + ALX-0081 | PBS |
|---|---|---|---|---|
| Tris (100 mM) | 5 | 5 | 5 | 5 |
| BaCl$_2$ (10 mM) | 5 | 5 | 5 | 5 |
| Pefablock (100 mM) | 1.3 | 1.3 | 1.3 | 1.3 |
| Plasma | 3.3 | 3.3 | 3.3 | 3.3 |
| ALX 0081 (2.48 mg/ml) | — | — | 4 | — |
| PBS | — | — | — | 4 |
| EDTA (0.35M) pH = 8.3 | — | 2.6 | — | — |
| H$_2$O | 81.9 | 79.3 | 77.9 | 77.9 |
| A1A2A3 (460 µg/ml) | 3.5 | 3.5 | 3.5 | 3.5 |

The invention claimed is:

1. Nanobody against Von Willebrand Factor (vWF), said Nanobody consisting of 4 framework regions (FR1 to FR4 respectively) and 3 complementarity determining regions (CDR1 to CDR3 respectively), wherein
   a) CDR1 comprises the amino acid sequence YNPMG [SEQ ID NO: 22]; and
   b) CDR2 comprises the amino acid sequence AISRTGGSTYYPDSVEG [SEQ ID NO: 32] or the amino acid sequence AISRTGGSTYYARSVEG [SEQ ID NO: 31]; and
   c) CDR3 comprises the amino acid sequence AGVRAEDGRVRTLPSEYTF [SEQ ID NO: 42], the amino acid sequence AGVRAEDGRVRTLPSEYNF [SEQ ID NO: 41] or the amino acid sequence AGVRAEDGRVRSLPSEYTF [SEQ ID NO: 43].

2. Nanobody according to claim 1, in which CDR1 comprises the amino acid sequence YNPMG [SEQ ID NO: 22]; CDR2 comprises the amino acid sequence AISRTGGSTYYPDSVEG [SEQ ID NO: 32] and CDR3 comprises the amino acid sequence AGVRAEDGRVRTLPSEYTF [SEQ ID NO: 42].

3. Nanobody according to claim 1, wherein the Nanobody is a KERE-class Nanobody.

4. Humanized variant of the Nanobody of claim 1.

5. Nanobody 12A2H1 (SEQ ID NO:90).

6. A polypeptide which comprises the Nanobody of claim 1.

7. A polypeptide which comprises at least two Nanobodies of claim 1.

8. The polypeptide according to claim 7, wherein the at least two Nanobodies are linked to each other via a linker.

9. Pharmaceutical composition comprising the Nanobody of claim 1 and a pharmaceutically acceptable carrier.

10. Pharmaceutical composition comprising the polypeptide of claim 6 and a pharmaceutically acceptable carrier.

11. A method of treating a disease or disorder related to platelet-mediated aggregation, the method comprising:
administering the pharmaceutical composition of claim 9 to treat the disease or disorder related to platelet-mediated aggregation.

12. A method of treating a disease or disorder related to platelet-mediated aggregation, the method comprising:
administering the pharmaceutical composition of claim 10 to treat the disease or disorder related to platelet-mediated aggregation.

* * * * *